Figure 1:
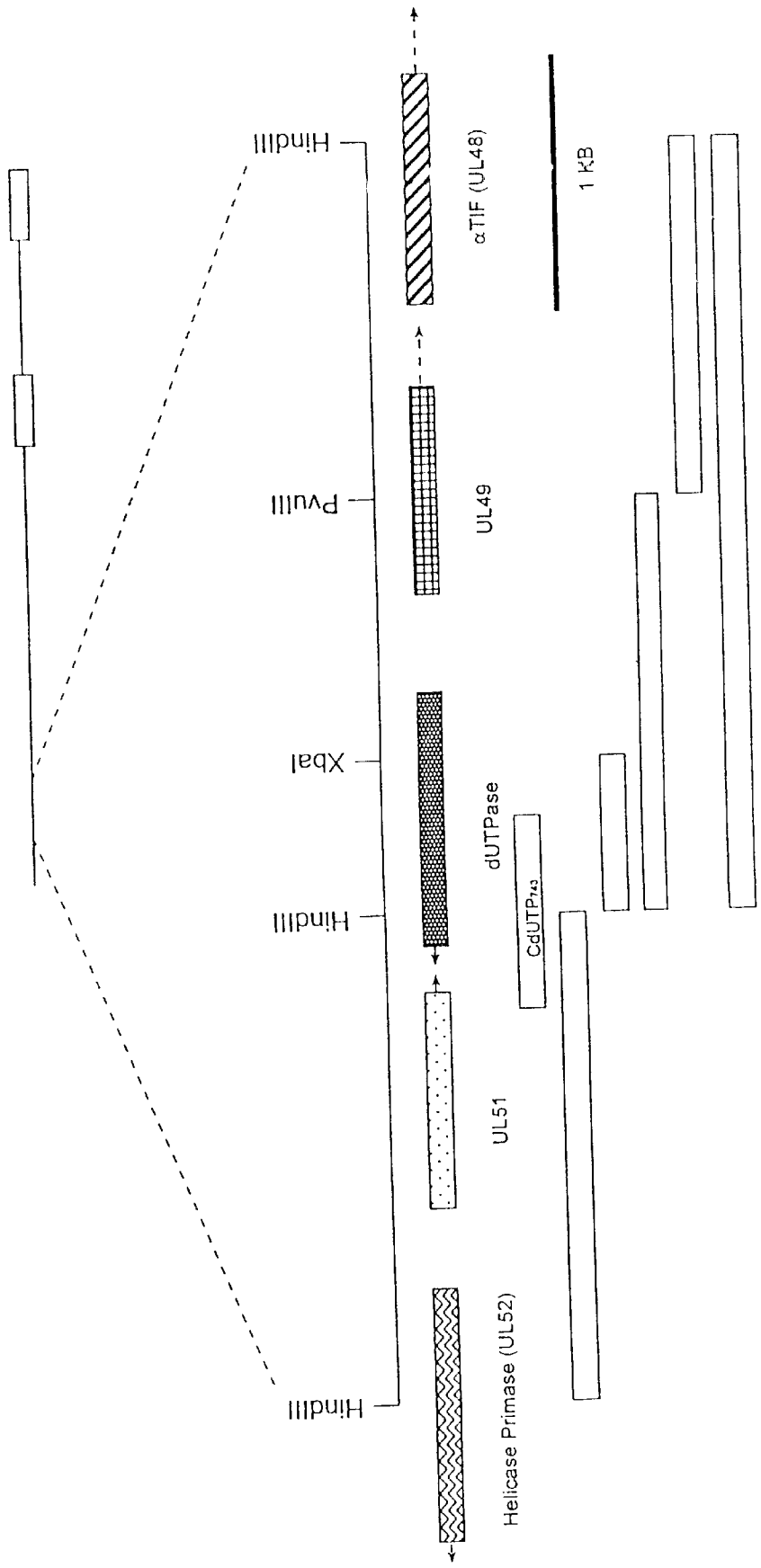

United States Patent [19]
Haanes et al.

[11] Patent Number: 5,804,197
[45] Date of Patent: Sep. 8, 1998

[54] RECOMBINANT CANINE HERPESVIRUSES

[75] Inventors: Elizabeth J. Haanes, Berthoud; Rexann S. Frank, Wellington, both of Colo.

[73] Assignee: Heska Corporation, Ft. Collins, Colo.

[21] Appl. No.: 680,726

[22] Filed: Jul. 12, 1996

Related U.S. Application Data

[63] Continuation-in-part of Ser. No. 602,010, Feb. 15, 1996.

[51] Int. Cl.$^6$ .................. A61K 39/245; A61K 39/00; C12N 7/01; C12N 15/00
[52] U.S. Cl. .................. 424/229.1; 424/199.1; 435/235.1; 435/320.1
[58] Field of Search .................. 424/229.1, 199.1; 435/235.1, 320.1

[56] References Cited

U.S. PATENT DOCUMENTS

| | | | |
|---|---|---|---|
| 5,223,424 | 6/1993 | Cochran et al. | 435/236 |
| 5,266,489 | 11/1993 | Rey-Senelonge et al. | 435/320.1 |
| 5,310,668 | 5/1994 | Ellis et al. | 435/172.3 |
| 5,324,664 | 6/1994 | Nunberg et al. | 435/320.1 |

FOREIGN PATENT DOCUMENTS

WO 95/26751  10/1995  WIPO.

OTHER PUBLICATIONS

Binn, et al., "Viruses Recovered from Laboratory Dogs with Respiratory Disease," pp. 140–145, P.S.E.B.M., v. 126.

Breeden, et al., "Identification and Transcriptional Mapping of Genes Encoded at the IR/Us Junction of Equine Herpesvirus Type 1," pp. 649–660, *Virology*, 191 (1992).

Carmichael, "*Herpesvirus canis*: Aspects of Pathogenesis and Immune Response," pp. 1714–1721, J.A.V.M.A., vol. 156 (Jun. 15, 1970).

de Wind, et al., "Ribonucleotide reductase–deficient mutants of pseudorabies virus are avirulent for pigs and induce partial protective immunity," pp. 351–359, *Journal of General Virology*, 74 (1993).

Elton, et al., "Sequence analysis of the 4.7–kb Bam-HI–EcoRI fragment of the equine herpesvirus type–1 short unique region," pp. 203–208, Elsevier Science Publishers B.V. 0378–119/91 (1991).

Graham, et al., "A New Technique for the Assay of Infectivity of Human Adenovirus 5 DNA", pp. 456–467, *Virology*, 52 (1973).

Holliday, et al., "Inhibition of herpes simplex virus types 1 and 2 replication in vitro by mercurithio analogs of deoxyuridine," pp. 197–203, *Antiviral Research*, 16 (1991).

Kit, et al., "Nucleotide Sequence Changes in Thymidine Kinase Gene of Herpes Simplex Virus Type 2 Clones from an Isolate of a Patient Treated with Acyclovir," pp. 1483–1490, *Antimicrobial Agents and Chemotherapy*, vol. 31, No. 10 (Oct. 1987).

Kit, et al., "Thymidine Kinase (TK) Induction after Infection of TK–Deficient Rabbit Cell Mutants with Bovine Herpesvirus Type 1 (BHV–1): Isolation of TK$^-$BHV–1 Mutants," pp. 381–389, *Virology*, 130 (1983).

Lees, et al., "The Epstein–Barr Virus Candidate Vaccine Antigen gp340/220 is Highly Conserved between Virus Types A and B," pp. 578–586, *Virology*, 195 (1993).

Liang, et al., "Identification and Deletion Mutagenesis of the Bovine Herpesvirus 1 dUTPase Gene and a Gene Homologous to Herpes Simplex Virus UL49.5," pp. 42–50, *Virology*, 195 (1993).

Limbach, et al., "Nucleotide sequence of the genes encoding the canine herpesvirus gB, gC and gC homologues," pp. 2029–2039, *Journal of General Virology*, 75 (1994).

McGeoch, et al., The Complete DNA Sequence of the Long Unique Region in the Genome of Herpes Simplex Virus Type 1, pp. 1531–1574, *Journal of General Virology*, 69 (1988).

McGeoch, et al., "Sequence Determination and Genetic Content of the Short Unique Region in the Genome of Herpes Simplex Virus Type 1," pp. 1–13, 1985 Academic Press Inc. (London) Ltd.

Meignier, et al., "Virulence of and Establishment of Latency by Genetically Engineered Deletion Mutants of Herpes Simplex Virus 1," pp. 251–254, *Virology*, 162 (1988).

Meinkoth, et al., "Hybridization of Nucleic Acids Immobilized on Solid Supports," pp. 267–284, *Analytical Biochemistry*, 138 (1984).

Nunberg, et al., "Identification of the Thymidine Kinase Gene of Feline Herpes virus: Use of Degenerate Oligonucleotides in the Polymerase Chain Reaction to Isolate Herpevirus Gene Homologs," pp. 3240–3249, *Journal of Virology*, vol. 63, No. 8 (Aug. 1989).

Peterson, et al., "Propagation and Quantitation of Animal Herpesviruses in Eight Cell Culture Systems," pp. 93–98, *Comp. Immun. Microbiol. Infect. Dis.*, vol. 11, No. 2 (1988).

(List continued on next page.)

*Primary Examiner*—Ponnathapura Achutamurthy
*Assistant Examiner*—Phuong T. Nui
*Attorney, Agent, or Firm*—Sheridan Ross P.C.

[57] ABSTRACT

The present invention includes novel recombinant canine herpes virus (CHV) and novel recombinant CHV genomes, and particularly to those CHV and CHV genomes that contain heterologous nucleic acid molecules. The present invention also relates to the use of such genomes and viruses in a variety of applications, including as therapeutic compositions to protect animals from disease. The present invention also relates to novel isolated CHV nucleic acid molecules, to CHV proteins encoded by such nucleic acid molecules, and to antibodies raised against such CHV proteins as well as to the use of such CHV nucleic acid molecules, proteins and antibodies as therapeutic compositions to protect an animal from CHV. The present invention also includes constructs comprising CHV nucleic acid molecules that include heterologous nucleic acid molecules, to recombinant vectors including such constructs, and to the use of such constructs and vectors in the production of recombinant CHV and recombinant CHV genomes.

51 Claims, 5 Drawing Sheets

OTHER PUBLICATIONS

Rémond, et al., "Gene organization in th $U_L$ region and inverted repeats of the canine herpesvirus genome," pp. 37–48, *Journal of General Virology*, 77 (1996).

Rémond, et al., "Sequence of the canine herpesvirus thymidine kinase gene: taxon–preferred amino acid residues in the alphaherpesviral thymidine kinases," pp. 341–354, *Virus Research*, 39 (1995).

Riggio, et al., "DNA sequence of a gene cluster in the equine herpesvirus–4 genome which contains a newly identified herpesvirus gene encoding a membrane protein," pp. 171–178, *Archives of Virology*, 133 (1993).

Robertson, et al., Evolution of the herpes thymidine kinase: identification and comparison of the equine Herpes virus 1 thymidine kinase gene reveals similarity to a cell–encoded thymidylate kinase, pp. 11303–11317, *Nucleic Acids Research*, vol. 16, No. 23 (1988).

Simard, et al., "Sequencing and 5'–and 3'–end Transcript Mapping of the Gene Encoding the Small Subunit of Ribonucleotide Reductase from Bovine Herpesvirus Type–1," pp. 689–701, *Virology*, 190 (1992).

Spatz, et al., "Identification of the feline herpesvirus type 1 (FHV–1) genes encoding glycoproteins G, D, I and E: expression of FHV–1 glycoprotein D in vaccinia and raccoon proxviruses," pp. 1235–1244, *Journal of General Virology*, 75 (1994).

Tack, et al., The Complete DNA Sequence and the Genetic Organization of the Short Unique Region (U) of the Bovine Herpesvirus Type 1 (ST Strain), pp. 409–421, *Virology*, 199 (1994).

Telford, et al., "The DNA Sequence of Equine Herpesvirus–1," pp. 304, 316, *Virology*, 189 (1992).

van Zijl, et al., "Regeneration of Herpesviruses from Molecularly Cloned Subgenomic Fragments," pp. 2191–2195, *Journal of Virology*, vol. 61, No. 6 (Jun. 1988).

Walboomers, et al., "A New Method for the Isolation of Herpes Simplex Virus Type 2 DNA," pp. 256–258, *Virology*, 74 (1976).

Wolff, et al., "Detect Gene Transfer into Mouse Muscle in Vivo," pp. 1465–1468, *Science*, vol. 247 (23 Mar. 1990).

Pyles et al., *J. Virol.*, 68(7):4514–4524, Jul. 1994.

*Fields Virology* vol. 2, Chap 72, 1996, p. 2248–2249.

Pyles et al. J. Virol. 66(11), 1992, p. 6706–6713.

RECOMBINANT CANINE HERPESVIRUSES

CROSS-REFERENCE TO RELATED APPLICATIONS

The present application is a continuation-in-part of pending U.S. patent application Ser. No. 08/602,010, entitled "Recombinant Canine Herpesviruses", filed Feb. 15, 1996, and which is incorporated by reference herein in its entirety.

FIELD OF THE INVENTION

The present invention relates to canine herpesvirus (CHV), and particularly to novel recombinant CHV and recombinant CHV genomes, including those that contain heterologous nucleic acid molecules. The present invention also relates to the use of such genomes and viruses in a variety of applications, including as therapeutic compositions to protect animals from disease. The present invention also relates to novel isolated CHV nucleic acid molecules, to proteins encoded by such nucleic acid molecules, and to use of such CHV nucleic acid molecules to insert heterologous nucleic acid molecules into CHV genomes.

BACKGROUND OF THE INVENTION

Dogs and other canids are affected by a number of diseases against which it would be desirable to develop protective vaccines. Live vaccines, and particularly live viral vector vaccines, are attractive vaccine vector candidates as they appear to be associated with longer-lasting immunity than inactivated virus vaccines or subunit vaccines. One disadvantage of live vaccines, however, has been that attenuated virus strains often revert to virulence. Another disadvantage has been the host range of a number of viral vaccines. In an attempt to deliver genes to an animal, several viral and bacterial systems, such as poxviruses, adenoviruses, Salmonella, and BCG (Bacillus Calmette-Guerin), have been genetically manipulated to generate vectors containing heterologous antigen genes in order to immunize a host with a vaccine in which the antigens are presented in a "live" configuration. See, for example, the following two review articles: Esposito et al., pp. 195–247, 1989, Advances in Veterinary Science and Comparative Medicine, Vol. 33; Dougan et al., pp. 271–300, 1989, Advances in Veterinary Science and Comparative Medicine, Vol. 33.

Several herpes virus vaccines, such as those based on bovine herpes virus (BHV), cytomegalovirus (CMV), Epstein Barr virus (EBV), equine herpes virus (EHV), feline herpes virus (FHV), herpes simplex virus (HSV), Marek's disease virus (MDV), pseudorabies virus (PRV), turkey herpes virus (HVT), and varicella zoster virus (VZV) have been developed and several have shown at least some efficacy as vaccines against the virus per se or as vectors carrying other genes in certain indications. The listed herpes viruses, however, also have the drawback that even if attenuated, they are subject to reversion.

Canine herpes virus (CHV) infection is a relatively benign infection except in newborn puppies. A few vaccines to protect against CHV infection have been reported including a small-plaque variant CHV vaccine disclosed in U.S. Pat. No. 4,213,965, by Carmichael, issued Jul. 22, 1980. The nucleotide sequences of CHV genes encoding gB, gC, gD and UL45 homologs have been reported by Limbach et al., 1994, J. Gen. Virol. 75, 2029–2039, but these proteins, while proposed as vaccine candidates against CHV, were not tested as such by Limbach et al., ibid.

The inventors are not aware of any reports which describe the use of CHV as a vaccine vector, either with respect to inactivating genes in the CHV genome using recombinant DNA techniques, and/or to delivering protective compounds to a canid, in spite of the need to develop safe and efficacious delivery systems to protect canids, and especially dogs, from disease. Two U.S. patents (i.e., U.S. Pat. No. 5,266,489, by Rey-Senelonge et al., issued Nov. 30, 1993; and U.S. Pat. No. 5,223,424, by Cochran et al., issued Jun. 29, 1993) at best speculate on the insertion of genes into certain CHV loci, but neither claims CHV vectors or vaccines, nor provides data supporting such speculations. U.S. Pat. No. 5,266,489, ibid., claimed HVT having a foreign gene inserted into the ribonucleotide reductase (RR) small subunit gene of the HVT genome, but also disclosed without support the insertion of foreign genes into the RR small subunit genes of BHV, CHV, CMV, duck herpes virus, EBV, EHV, FHV, HSV, PRV and VZV. The inventors, however, have demonstrated the inaccuracy of this disclosure in that the inventors have found, and disclosed in the present application, that the CHV genome lacks the RR small subunit gene. That is, the CHV RR small subunit gene does not exist to provide a target for the insertion of foreign genes.

U.S. Pat. No. 5,223,424, ibid., claimed specific hybrid PRV constructs having deletions in the TK, repeat, or and/or gX regions and heterologous sequences inserted into the repeat and/or gX regions, but also proposed without data the ability to insert foreign genes into the repeat region of the CHV genome, even though that genome had not yet been mapped. Also disclosed were certain BHV and HVT constructs and proposals, without data, to delete and insert genes in other herpesviruses, such as EHV and FHV, HSV and MDV. It is also of note that a patent application (now U.S. Pat. No. 5,273,876, by Hock et al, issued Dec. 28, 1993) that was filed significantly later than U.S. Pat. No. 5,223,424, ibid., and shares two co-inventors with U.S. Pat. No. 5,223,424, ibid., states in column 2, lines 57–61, "Among the herpesviruses, only four herpesviruses (herpes simplex of humans, herpes saimiri of monkeys, pseudorabies virus and varicella-zoster virus) have been engineered to contain foreign DNA sequences previous to this disclosure," thereby indicating the lack of CHV, or a number of other, herpes virus vectors.

Thus, there remains a need for new and improved methods to vaccinate canids to protect them from diseases, such as those caused by genetic or metabolic disorders as well as those caused by infectious agents such as protozoan parasites, helminth parasites, ectoparasites, fungi, bacteria, and viruses.

SUMMARY OF THE INVENTION

The present invention relates to a new method to protect animals from disease using a recombinant virus or virus genome. When a recombinant CHV of the present invention is administered to an animal, the virus is able to infect cells within the animal. Infected cells are able to express nucleic acid sequences present on the recombinant CHV genome to produce protective compounds, such as proteins and RNAs, capable of protecting the animal from a variety of diseases. Using methods taught in the present invention, vaccines can be generated that are capable of protecting an animal from any disease for which a protective compound can be produced. As such, the present invention is of extremely broad scope and includes a wide variety of vaccines that have a variety of applications.

The present invention includes a recombinant CHV that comprises a recombinant CHV genome. The invention also includes recombinant CHV genomes. In one embodiment, a recombinant CHV has an inactive gene within its genome, with a preferred recombinant CHV in this embodiment being a CdUTPase negative CHV, a CgC negative CHV, a CgE negative CHV, a CgG negative CHV, a CgI negative CHV, a CPK negative CHV, a CTK negative CHV, a CIR6 negative CHV, a CUS2 negative CHV, a CUS9 negative CHV, a CUL49 negative CHV, a CUL51 negative CHV, a CUL45 negative CHV, a CgD negative CHV, a CgB negative CHV, a CUL48 negative CHV, a CUL52 negative CHV, a CgL negative CHV, a CUL49.5 negative CHV, a CICP0 negative CHV, a CICP4 negative CHV, and/or a CUS8.5 negative CHV. In the case of the CUS8.5 negative CHV, a CUS8.5 negative CHV refers to a CHV in which the CUS8.5 open reading frame is disrupted.

The present invention also includes a recombinant CHV genome that comprises a heterologous nucleic acid molecule, which preferably encodes a protective compound that protects a canid from disease. Such a heterologous nucleic acid molecule can be located in an essential gene, a nonessential gene, and/or in an intergenic region. Insertion of a heterologous nucleic acid into a CHV genome can, but need not, inactivate a gene within that genome. Also included in the present invention are methods to produce a recombinant CHV and a recombinant CHV genome, as well as a canine cell line that complements a defect in a gene essential to CHV reproduction in vitro.

One embodiment of the present invention is a method to increase recombinant CHV plaque forming efficiency. Such a method can include the steps of introducing a recombinant CHV genome into a canine cell expressing CHV alpha transinducing factor and culturing the cell to produce recombinant CHV. In another embodiment, the method includes the steps of co-introducing a recombinant CHV genome and a CHV alpha transinducing factor gene into a canine cell and culturing the cell to produce recombinant CHV. The present invention also includes a canine cell line comprising a CHV alpha transinducing factor gene.

One embodiment of the present invention is a therapeutic composition that includes a recombinant CHV, a recombinant CHV genome, or a mixture thereof. The present invention also includes a method to protect an animal from disease by administering such a therapeutic composition to the animal.

The present invention also includes an isolated CHV nucleic acid molecule that hybridizes under stringent hybridization conditions with at least one of the following nucleic acid regions: a CdUTPase gene, a CgE gene, a CgG gene, a CgI gene, a CPK gene, a CTK gene, a CIR6 gene, a CUS2 gene, a CUS9 gene, a CUL49 gene, a CUL51 gene, a CUL48 gene, a CUL52 gene, a CgL gene, a CUL49.5 gene, a CICP4 gene, a CUS8.5 open reading frame, and/or a region of the CHV genome spanning from about the 3' end of the coding region of the CUL41 gene through about the 3' end of the coding region of the CUL38 gene. Also included are recombinant molecules, recombinant viruses, recombinant vectors, and recombinant cells that include such CHV nucleic acid molecules. The present invention also includes CHV proteins encoded by such CHV nucleic acid molecules and antibodies that selectively bind to such CHV proteins, as well as methods to produce such CHV nucleic acid molecules, recombinant molecules, recombinant viruses, recombinant vectors, recombinant cells, CHV proteins and antibodies. Also included in the present invention are therapeutic compositions including such CHV nucleic acid molecules, CHV proteins and antibodies, as well as methods to use such compositions to protect an animal from disease.

BRIEF DESCRIPTION OF THE FIGURES

FIG. 1 depicts a schematic map of two contiguous HindIII fragments that include at least portions of CHV UL48 UL49, dUTPase, UL1 and UL52 genes.

FIG. 2 depicts a schematic map of the AscI fragment that includes the unique short region of CHV.

FIG. 3 depicts a schematic map of the AscI/blunt fragment that includes the terminal inverted repeat region of CHV.

FIG. 4 depicts a schematic map of a region of the CHV genome spanning at least from the CUS9 gene through the CIR6 gene.

FIG. 5 depicts a schematic map of a region of the CHV genome spanning at least from a portion of the CUL52 gene through at least a portion of the CUL48 gene.

DETAILED DESCRIPTION OF THE INVENTION

The present invention relates to canine herpesviruses (CHV), and particularly to recombinant CHV and recombinant CHV genomes as well as to methods to produce and use such viruses and genomes. The present invention also includes identification of regions of the CHV genome that are preferred targets for deletion and/or for insertion of heterologous nucleic acid molecules. As used herein, the term "canine" refers to "of the family Canidae" and, as such, includes reference to dogs (including wild and domesticated dogs), foxes, wolves, jackals, coyotes, and other members of the family Canidae. Similarly, a "canid" is any member of the family Canidae. As used herein, the term CHV refers to any herpesvirus endogenous to the family Canidae. A particularly preferred CHV of the present invention is a recombinant CHV that infects dogs.

One embodiment of the present invention is the use of a recombinant CHV, and particularly of a CHV having a recombinant CHV genome that includes a (i.e., one or more than one) heterologous nucleic acid molecule, as a live CHV-based therapeutic composition, or vaccine, to protect an animal from a disease against which the heterologous nucleic acid molecule is targeted. Live vaccines are advantageous because they are believed to confer more vigorous and longer-lasting immunity than subunit or killed vaccines. While not being bound by theory, it is believed that such advantages are due to the ability of the genetic information carried by the virus to enter cells of the treated animal, replicate itself, and direct the expression of a protective compound, such as a protective protein or a protective RNA, for extended periods of time. Thus, the therapeutic composition need not be administered frequently and, at least in some embodiments, the virus vaccine can function as a self-booster.

CHV is particularly useful as a delivery vehicle for a heterologous nucleic acid molecule to protect canids from a disease for a variety of reasons, including, but not limited to, CHV's limited host range and pathogenicity. CHV, to the inventors' knowledge, has the most limited host range of any herpesvirus, including FHV, in that CHV's host range appears to be substantially limited to canine cells. As far as the inventors are aware, the only report of CHV infection of a cell type other than canine cells is limited infection of mink lung cells; see, for example, Peterson et al, 1988, *Comp. Immunol. Microbiol. Infect. Diseases* 11, 93–98. This limited host range illustrates the safety of CHV in that the virus apparently cannot be transmitted to a variety of species unrelated to canids.

Furthermore, CHV exhibits only limited pathogenicity. Although the virus has been shown to cause a fatal hemorrhagic disease in hypothermic neonatal pups (i.e., essentially all pups experimentally infected with CHV and maintained at room temperature (i.e., from about 25° C. to 27° C. ) within a week of birth die from the infection), CHV causes insignificant respiratory infection in adult dogs; see, for example, Carmichael, 1970, *J. Am. Vet. Med. Assn.* 156, 1714–1721. Moreover, prolonged survival or recovery of experimentally infected neonatal pups maintained at 38.4° C. to 39.5° C. was observed. Adult dogs exposed to CHV do, however, become infected since virus shedding has been shown to occur for at least two weeks post-inoculation; and latency is postulated to occur, since CHV has been isolated from primary cultured cells of normal healthy dogs; see, for example, Carmichael, ibid. Furthermore, maternal antibody, or passive transfer of antibody from seropositive dogs has been shown to protect puppies from an otherwise fatal CHV challenge; see, for example, Carmichael, ibid. Due to its limited pathogenicity, CHV apparently need not be attenuated to the extent required for other viruses used as live vaccine vectors. In addition, vaccination of a dam with CHV can lead to passive protection in her pups.

Another advantage of CHV is its limited temperature range. CHV grows well at temperatures ranging from about 34° C. to about 36° C., with optimal growth occurring at about 35° C. CHV, however, does not grow well at temperatures less than or equal to about 33° C. or at temperatures greater than or equal to about 37° C. As such CHV is significantly more temperature sensitive than any other known wild type herpesvirus, including FHV.

Yet another advantage of CHV is its potential for use as a single, multivalent therapeutic composition against a variety of canine pathogens. That is, the CHV genome can be manipulated to incorporate multiple heterologous nucleic acid molecules without disrupting the ability of the genome to be packaged (i.e., assembled) into a live virus. Examples of multivalent therapeutic compositions are described below.

As far as the inventors are aware, this application is the first report of the genetic engineering of a CHV genome, particularly for the development of efficacious canid vaccines, in spite of a long felt need for efficacious vaccines against canine pathogens. The inventors have developed methods to identify CHV genes and intergenic regions, particularly those having utility as targets for the insertion of heterologous nucleic acid molecules, despite the difficulty of using known herpesvirus sequences to identify such regions due to the AT-rich nature of the CHV genome. The CHV genome contains about 70% adenosine and thymidine residues, compared to other known herpesvirus genomes which, on the average, contain from about 30% to about 58% adenosine and thymidine residues (e.g., HSV, BHV, and PRV contain about 30%, EHV about 54%, and FHV about 58%, adenosine and thymidine residues). As such, it is very difficult to design primers or probes using known herpesvirus sequences to identify CHV analogs.

One embodiment of the present invention is a recombinant CHV. As used herein, a recombinant CHV is a CHV that comprises (i.e., has or includes) a genome that has been genetically engineered (i.e., subjected to recombinant nucleic acid (i.e., DNA or RNA) techniques, such as those disclosed in Sambrook et al., 1989, *Molecular Cloning: A Laboratory Manual*, Cold Spring Harbor Labs Press; Sambrook et al., ibid., is incorporated by reference herein in its entirety) to differ from the genome of a natural CHV isolate (i.e., a herpesvirus endogenous to the family Canidae). Such a genetically engineered genome is referred to herein as a recombinant CHV genome and is described in more detail below.

A recombinant CHV of the present invention includes not only a recombinant CHV genome but also an envelope and capsid in which the genome is packaged. The viral envelope and capsid are preferably a CHV envelope and a CHV capsid, encoded at least in part by CHV genes, thereby imparting to the recombinant CHV the host range of a natural CHV isolate. It is to be noted, however, that the present invention also includes recombinant CHV having envelopes and/or capsids that have been modified to, for example, alter (e.g., broaden, narrow, or completely change) the host range of the recombinant CHV genome. Such modifications can be accomplished by one skilled in the art by, for example, modifying CHV envelope and/or capsid genes and/or replacing such genes with those of another virus. Altered genes can be located on the CHV genome itself and/or in the genome of the cell in which the recombinant virus is produced.

A recombinant CHV genome of the present invention is a CHV genome in which nucleotides have been deleted, inserted, substituted or inverted using recombinant techniques known to those skilled in the art such that the recombinant CHV genome is no longer the same as a natural CHV genome. A recombinant CHV genome of the present invention is capable of effecting expression (e.g., transcription, translation) of coding regions that are operatively linked to regulatory sequences within the genome. As used herein, a coding region is a stretch of nucleotides that encodes an RNA molecule and/or a protein. Coding regions can be endogenous to CHV or can be heterologous nucleic acid molecules of the present invention, which are described in more detail below. The phrase operatively linked refers to the positioning of a coding region in the CHV genome such that the coding region is able to be expressed when the genome is inside a cell. Regulatory sequences include transcription control sequences, translation control sequences, and other regulatory sequences that control the expression of coding regions. Transcription control sequences are sequences which control the initiation, elongation, and termination of transcription. Particularly important transcription control sequences are those which control transcription initiation, such as promoter, enhancer, operator and repressor sequences. Suitable regulatory sequences include any regulatory sequence that can function in the present invention. Preferred regulatory sequences are disclosed herein.

A recombinant CHV genome of the present invention can include a gene that has been inactivated. As used herein, a gene includes a coding region as well as the regulatory sequences involved in expression of that coding region. An inactive gene refers to a gene that no longer exhibits the function of its natural counterpart. Methods to inactivate a gene include, but are not limited to, deletion of one or more nucleotides within the gene, insertion of one or more nucleotides into the gene, replacement of one or more nucleotides within the gene by other nucleotides (i.e., nucleotide substitution), and/or inversion of nucleotides within the gene such that the resulting gene no longer has the function of the corresponding natural gene. Such alterations can be effected anywhere within the gene, such as within the coding region, within the regulatory sequences and/or in regions surrounding the coding region or regulatory sequences such that the alteration(s) cause gene inactivation. In one embodiment, an entire gene or the coding region and/or regulatory sequences thereof can be deleted or replaced.

One embodiment of the present invention is an attenuated recombinant CHV. As used herein, an attenuated CHV is a CHV that does not cause 100% mortality if used to infect canid neonates less than 1 week old that are maintained in room temperature. A preferred attenuated CHV of the present invention causes less than about 90% and preferably less than about 70% mortality when used to infect canid neonates less than 1 week of age maintained at room temperature.

An attenuated recombinant CHV can be produced by inactivating a CHV gene that, due to that gene's inactivation, results in an attenuated virus. Methods to inactivate a gene are disclosed above. An attenuated CHV can be identified by exposing pups less than 1 week old to the recombinant virus to be tested and determining the percentage of exposed pups that die; such an exposure method is disclosed, for example, in Carmichael, ibid. If less than 100% percent of the pups die, the virus being tested is attenuated in accordance with the present invention. Suitable CHV genes to inactivate in order to produce an attenuated CHV include any gene that when inactivated leads to an attenuated virus, as determined using an assay as disclosed above. A preferred attenuated recombinant CHV of the present invention is a CHV having a recombinant genome in which a heterologous nucleic acid molecule is inserted into a gene, the insertion resulting in an attenuated virus.

An attenuated recombinant CHV has utility, for example, as a therapeutic composition to protect an animal from CHV infection and/or as a live CHV-based vaccine carrying a heterologous nucleic acid molecule. It is to be noted, however, that, as disclosed above, it is believed that CHV need not be attenuated for use as a live vaccine vector due to the low pathogenicity of natural CHV, particularly as compared to that of other herpesviruses.

One embodiment of the present invention is a recombinant CHV that can reproduce (i.e., grow) in tissue culture; that is, the virus is a reproduction competent CHV. A reproduction competent CHV is a CHV that upon in vitro infection of an appropriate host cell is able to use host cell machinery, as well as its own regulatory control regions and/or encoded enzymes, to effect self-reproduction, i.e., to form infectious virus.

Reproduction competent recombinant CHV genomes can have gene alterations in one or more genes non-essential for growth in vitro. Suitable gene targets (i.e., genes to alter) include any non-essential CHV gene. A non-essential CHV gene can be identified by altering a CHV gene within a CHV genome (e.g., by genetic engineering or classical mutagenesis) and demonstrating that the altered genome is capable of effecting self-reproduction in tissue culture. Preferred non-essential CHV genes to target include, but are not limited to, a CHV deoxyuridine triphosphate pyrophosphatase (CdUTPase) gene, a CHV glycoprotein C (CgC) gene, a CHV glycoprotein E (CgE) gene, a CHV glycoprotein G (CgG) gene, a CHV glycoprotein I (CgI) gene, a CHV serine-threonine protein kinase US3 (CPK) gene, a CHV thymidine kinase (CTK) gene, a CHV IR6 (CIR6) gene, a CHV US2 (CUS2) gene, a CHV tegument phosphoprotein US9 (CUS9) gene, a CHV membrane protein UL49 (CUL49) gene, a CHV membrane protein CHV UL49.5 (CUL49.5) gene, a CHV regulatory protein ICP0 (CICP0) gene, a CHV membrane protein UL51 (CUL51) gene, and a CHV membrane protein UL45 (CUL45) gene. Particularly preferred non-essential genes to target include a CdUTPase gene, a CgC gene, a CgE gene, a CgG gene, a CgI gene, a CUS2 gene and a CUS9 gene. It is to be noted that CHV regions and genes disclosed herein are named in accordance with herpesvirus nomenclature in that the names include "C" for canine and the rest of the name indicating the corresponding herpes simplex virus (HSV) homolog (e.g., "dUTPase"). For example, the CHV unique short region (CUS) is the shorter region of the CHV genome that has unique sequences, analogous to the US region of HSV; the CHV unique long region (CUL) is the longer region of CHV that has unique sequences, analogous to the UL region of HSV; and the CHV inverted repeat regions (CIRs) are analogous to the HSV IR regions. CUS genes are CHV genes that are homologs of (i.e., genes that share some degree of similarity with) HSV genes located in the US region of the HSV genome. CUL genes are CHV genes that are homologs of HSV genes located in the UL region of the HSV genome. CIR genes are CHV genes that are homologs of HSV genes located in the IR regions of the HSV or EHV genome. It is also to be noted that although the UL, US, and IR designations refer to the respective genes' locations in the HSV genome, they do not necessarily refer to the respective genes' locations in the CHV genome. For example, while CUS2 is partially in the IR region of CHV, HSV US2 is entirely in the U.S. region of HSV.

Another embodiment of the present invention is a recombinant CHV that is defective for reproduction in tissue culture. A reproduction defective CHV is a CHV that when inserted into an appropriate host cell is unable to form infectious virus. Such a defective CHV has at least one inactive gene that encodes a protein essential for reproduction, including, but not limited to proteins essential for viral entry, immediate early or early gene expression, DNA replication, capsid assembly, and viral egress. Suitable gene targets include any essential CHV gene, with preferred targets being genes encoding proteins involved in viral entry and/or egress. CHV defective in viral entry and/or egress are easy to complement and are advantageous over most other reproduction defective mutants in that such virus are able to undergo one round of viral replication. An essential CHV gene can be identified by altering a CHV gene within a CHV genome and demonstrating (a) that the altered genome is not capable of effecting self-reproduction in tissue culture under wild type conditions or, if a temperature sensitive mutant, at a non-permissive temperature; and (b) that the altered genome can reproduce in a complementing cell line that expresses an active protein corresponding to the essential gene defect on the CHV genome (assuming the defect can be complemented in trans), or at a permissive temperature. Preferred essential CHV genes to target include, but are not limited to, a CHV glycoprotein D (CgD) gene, a CHV glycoprotein B (CgB) gene, a CHV alpha trans-inducing factor UL48 (CUL48) gene, a CHV helicase/primase UL52 (CUL52) gene, a CHV glycoprotein L (CgL) gene and a CHV ICP4 (cICP4) gene. Particularly preferred essential genes to target include a CgD gene and a CgB gene.

The present invention also includes cell lines that complement replication defective CHVs and use of such cell lines to produce replication defective viruses. As such, the present invention includes canine cell lines that complement, or supplement, a CHV defect in a gene encoding CgD, CgB, CUL48, or CUL52, and/or CgL. Such cell lines can be produced by a variety of means known to those skilled in the art. For example, a cell capable of complementing a CgD negative, or CgD−, CHV (i.e., a virus with a CHV genome having an inactive CgD gene), can be produced by stable integration of an active CgD gene into the cellular genome or by co-transfection of the CgD− CHV with a nucleic acid molecule capable of complementing the defective CgD gene. Such a nucleic acid molecule can be a nucleic acid containing an active CgD gene operatively linked to regulatory sequences to enable expression of the CgD gene in the transfected cell. In another embodiment, such a nucleic acid molecule can be incorporated into a virus that is co-infected with the CgD− CHV. Such methods can also be used to produce cell lines complementing other replication defective CHVs of the present invention. Any canine cell line that CHV can infect and that expresses the complementary active protein can be used in the production of reproduction-defective CHV. Examples include, but are not limited to, the following cell lines available from American Type Culture Collection (ATCC), Rockville, Md.: ATCC CRL-1542 A-72 (Tumor, canine), ATCC CRL-1430 Cf2Th (Thymus, canine, Canis familiaris), ATCC CRL-10389 DH82 (Monocyte-macrophage, canine), ATCC CRL-8468 D17 (Osteogenic sarcoma, canine), ATCC CCL-183 D-17 (Primary osteogenic sarcoma, canine, Canis familiaris), ATCC CCL-34.1 DoC11 (S+L−) (Kidney, canine, Canis familiaris), ATCC CCL-34 MDCK (NBL-2) (Kidney, canine, Canis familiaris), and ATCC CCL-34.2 MDCK/SF (Kidney, canine, Canis familiaris), such cell lines expressing, preferably in a stable manner, the desired essential gene(s) for complementation. Particularly preferred complementing cell lines include MDCK cells that stably express CgD, CgB, CUL48, CUL52 and/or CgL.

An additional preferred CHV open reading frame to inactivate, or disrupt, includes a CUS8.5 open reading frame.

While not being bound by theory, it is believed that a reproduction defective virus-based vaccine may be safer than a reproduction competent virus-based vaccine. On the other hand, a reproduction competent virus-based vaccine may be more efficacious than a reproduction defective virus-based vaccine. Since CHV, as disclosed above, exhibits low pathogenicity, a reproduction competent recombinant CHV is a preferred embodiment of the present invention.

As heretofore disclosed, one embodiment of the present invention is a recombinant CHV having one or more inactive genes. Preferred recombinant CHV of the present invention include genomes in which one or more of the following CHV genes have been inactivated, preferably using recombinant techniques: a CdUTPase gene, a CgC gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CgB gene, a CUL48 gene, and a CUL52 gene, a CgL gene, a CUL49.5 gene, a CICP0 gene, a CICP4 gene, and a CUS8.5 open reading frame. Other than the genes encoding CgD, CgB, CUL48, CUL52, CgL and CICP4, the preferred genes to inactivate are nonessential genes. Each of the preferred genes to inactivate is a preferred target for the insertion of heterologous nucleic acid molecules; such insertion is a preferred method to inactivate these genes. More preferred recombinant CHV include genomes in which one or more of the following CHV genes have been inactivated, preferably using recombinant techniques: a CdUTPase gene, a CgC gene, a CgE gene, a CgG gene, a CgI gene, a CUS2 gene, a CUS9 gene, a CgD gene, and/or a CgB gene being more preferred. Also preferred are the corresponding recombinant CHV genomes.

Particularly preferred recombinant CHV of this embodiment include a CdUTPase negative CHV, a CgC negative CHV, a CgE negative CHV, a CgG negative CHV, a CgI negative CHV, a CPK negative CHV, a CTK negative CHV, a CIR6 negative CHV, a CUS2 negative CHV, a CUS9 negative CHV, a CUL49 negative CHV, a CUL51 negative CHV, a CUL45 negative CHV, a CgD negative CHV, a CgB negative CHV, a CUL48 negative CHV, a CUL52 negative CHV, a CgL negative CHV, a CUL49.5 negative CHV, a CICP0 negative CHV, a CICP4 negative CHV, and a CUS8.5 negative CHV. Particularly preferred recombinant CHV include a CdUTPase negative CHV, a CgC negative CHV, a CgE negative CHV, a CgG negative CHV, a CgI negative CHV, a CUS2 negative CHV, a CUS9 negative CHV, a CgD negative CHV, and a CgB negative CHV. Also preferred are the corresponding recombinant CHV genomes, as well as recombinant CHV and CHV genomes having more than one of these preferred genes inactivated. Examples of such CHV include, but are not limited to: a CUS2 negative, CdUTPase negative CHV; a CUS2 negative, CdUTPase negative, CgG negative CHV; and a CUS2 negative, CdUTPase negative, CgG negative, CgC negative CHV, a CUL49.5, CdUTPase negative CHV.

One embodiment of the present invention includes a recombinant CHV comprising a recombinant CHV genome comprising a heterologous nucleic acid molecule; i.e., the recombinant CHV genome includes one or more heterologous nucleic acid molecule(s) located, or positioned, in the CHV genome. The present invention also includes a recombinant CHV genome having a heterologous nucleic acid molecule in the genome. Also included is the use of such a CHV and/or CHV genome as a therapeutic composition as well as in the production of a compound encoded by the heterologous nucleic acid molecule(s).

As used herein, a heterologous nucleic acid molecule is a nucleic acid molecule that is not derived from CHV; that is, a heterologous nucleic acid molecule is isolated from a source other than CHV. An isolated nucleic acid molecule of the present invention can be obtained from its natural source, can be produced using recombinant DNA technology (e.g., by amplification, such as by polymerase chain reaction (PCR) amplification and/or cloning) or can be produced by chemical synthesis.

In accordance with the present invention, a heterologous nucleic acid molecule can be inserted into a CHV genome simply to inactivate a CHV gene. A heterologous nucleic acid molecule can also be inserted into a CHV genome to serve as a target for the insertion of a second heterologous nucleic acid molecule, such as to introduce a restriction enzyme site or a recombination site otherwise not present in the CHV genome. For example, CHV strain D 004 (available from ATCC), which does not contain a Sse83871, I-Sce-I, or NotI restriction enzyme site, can be genetically engineered to include one or more sites by inserting into the genome a heterologous nucleic acid molecule containing a Sse83871, I-Sce-I, and/or NotI site(s). Such a heterologous nucleic acid molecule is a good target for the insertion of another heterologous nucleic acid molecule. Other restriction enzyme sites lacking in CHV can be identified using techniques known to those skilled in the art. Without being bound by theory, it is believed that CHV is more likely to lack GC-rich restriction enzyme sites than AT-rich sites, since the CHV genome is AT-rich, as disclosed above.

Another example of a heterologous nucleic acid molecule to insert into a CHV genome is a gene encoding a selectable marker, such as, but not limited to, an *E. colil* lacZ gene, a green fluorescent protein gene, a chloramphenicol transacetylase gene, a xanthine-guanine phosphoribosyl transferase gene, a β-glucuronidase gene, a neomycin resistance gene, an *E. coli* hygromycin resistance gene, and a heterologous thymidine kinase gene (e.g., HSV, FHV; assuming the CHV genome is a CTK negative genome). The presence of such a gene in a CHV genome allows for the selection of recombinant CHV having such a marker gene, and includes the ability to distinguish recombinant CHV from natural CHV isolates. In addition, a second heterologous nucleic acid molecule can be inserted into such a selectable marker gene, thereby inactivating the protein encoded by the marker gene, allowing for yet another method to select for CHV having a desirable heterologous nucleic acid molecule. Methods to select CHV having selectable marker genes, as well as for the inactivation of such markers, is known to those skilled in the art.

A preferred embodiment of the present invention is a recombinant CHV genome, and corresponding virus, in which the genome contains a heterologous nucleic acid molecule operatively linked to a transcription control sequence. As such, the heterologous nucleic acid molecule can be transcribed when transfected into a cell. A heterologous nucleic acid molecule can be joined to CHV transcription control sequences, can be joined to its own or other homologous transcription control sequences, and/or can be joined to transcription control sequences heterologous to both the heterologous nucleic acid molecule and CHV. The heterologous nucleic acid molecule can also be operatively linked to other regulatory sequences. Suitable regulatory sequences include any regulatory sequence that can function in the present invention. Preferred transcription control sequences include those sequences that can function in canine cells, including, but not limited to: mammalian, preferably canine; viral; or natural (i.e., endogenous to the heterologous nucleic acid molecule) transcription control sequences. Examples of transcription control sequences include antibiotic resistance gene, baculovirus, *Heliothis zea* insect virus, vaccinia virus, herpesvirus, poxvirus, adenovirus, simian virus 40, retrovirus, actin, Rous sarcoma virus, heat shock, and mammalian hormone transcription control sequences. Additional suitable transcription control sequences include tissue-specific promoters and enhancers as well as lymphokine-inducible promoters (e.g., promoters inducible by interferons or interleukins). In one embodiment, expression of a heterologous nucleic acid molecule inserted into a CHV genome is mediated, at least in part, by a human cytomegalovirus (CMV) immediate early promoter and a bovine growth hormone polyadenylation site.

A heterologous nucleic acid molecule of the present invention can be located in any region of the CHV genome (i.e., in the UL, US, and/or IR regions), including, but not limited to, in an essential gene, in a non-essential gene, or in an intergenic region. As such, a heterologous nucleic acid molecule can be located in a coding region, a regulatory region, an intron, an untranslated region, or a non-transcribed region of a gene. A heterologous nucleic acid molecule can also be located in a direct or inverted repeat, including direct and/or inverted repeats within the IR, US or UL regions of CHV. For example, a heterologous nucleic acid molecule can be located in one or more CHV origins of replication (Cori), such as in CoriS.

In one embodiment, a heterologous nucleic acid molecule is located in a CHV genome such that a gene is inactivated. Suitable and preferred gene targets are as disclosed above, with non-essential gene targets being preferred.

In another embodiment, a heterologous nucleic acid molecule is located in a region of the CHV genome spanning from about the 3' end of the coding region of the CUL41 gene through about the 3' end of the coding region of the CUL38 gene. CUL41 gene refers to the CHV homolog of the HSV virion host shutoff protein UL41 gene. CUL38 gene refers to the CHV homolog of the HSV capsid protein VP19C UL38 gene. In most herpesviruses analyzed by cloning and sequencing techniques to date, the region between UL41 and UL38 contains genes encoding the large and small subunits of ribonucleotide reductase. The inventors have found, however, that the ribonucleotide reductase genes appear to be at least partially deleted in CHV in such a manner that there is an intergenic target in that region for heterologous nucleic acid molecule insertion.

A preferred recombinant CHV genome of the present invention comprises a heterologous nucleic acid molecule located in a region of the genome such that the heterologous nucleic acid molecule-containing CHV genome can be easily distinguished from a CHV genome not containing the heterologous nucleic acid molecule; that is, the heterologous nucleic acid molecule is inserted into a selectable region of the genome. Suitable selectable regions include any region of the CHV genome that, upon introduction of a heterologous nucleic acid molecule, leads to a detectable (e.g., growth-related, biochemical, or molecular) change in the CHV genome or CHV containing the genome. Examples of such selectable regions include, but are not limited to, a CTK gene and a CdUTPase gene. CHV genomes in which a heterologous nucleic acid molecule is inserted into a CTK gene or a CdUTPase gene can be selected using methods known to those skilled in the art; see for example, Kit et al, 1983, *Virology* 130, 381–389; and Holliday et al, 1991, *Antiviral Research* 16, 197–203.

Additional examples of selectable regions include restriction endonuclease sites, such as the HindIII site or XbaI site in the CdUTPase gene and the AscI site in the CUS2 gene. The AscI site is particularly preferred as there are no other AscI sites in the CHV genome. As such, a particularly preferred CHV of the present invention is a recombinant CHV having a CHV genome including a heterologous nucleic acid molecule in an AscI site in the CHV genome. Even more preferred is recombinant CHV strain D 004 having a heterologous nucleic acid molecule in an AscI site in the CHV genome. Also preferred are the corresponding genomes. Examples of methods to insert a heterologous nucleic acid molecule into a genome, including into restriction endonuclease site(s) in the genome, are disclosed herein. Such methods are known to those skilled in the art.

One embodiment of the present invention is a recombinant CHV genome having a heterologous nucleic acid molecule in one of the following regions of the CHV genome: a region spanning the 9,300 nucleotide AscI restriction endonuclease fragment, denoted herein as $nCAsc_{9300}$, that apparently includes the entire U.S. region; a region spanning the 10,000 nucleotide fragment from AscI to the end of the genome, denoted herein as $nCAsc_{10000}$, that apparently essentially comprises an IR region, including the CIR6 gene; a region spanning the 3,000 nucleotide HindIII fragment, denoted herein as $nCHin_{3000}$, that spans from a portion of CUL48 through a portion of the CdUTPase gene; a region spanning the 1,900 nucleotide HindIII fragment, denoted herein as $nCHin_{1900}$, that includes the remainder of the CdUTPase gene through a portion of CUL52; a region spanning the 5,500 nucleotide HindIII fragment, denoted herein as $nCHin_{5500}$, that includes at least a portion of CgL, CICP0, and CICP4; and/or a region spanning the 8,500 nucleotide HindIII fragment, denoted herein as $nCHin_{8500}$, that includes a portion of CUL48, CUL45 and CgC. Details regarding the production of these and certain other nucleic acid molecules of the present invention are provided in the Examples section.

Also included in the present invention is a recombinant CHV genome having a heterologous nucleic acid molecule in a region of the genome spanning at least one of the following:
a CHV U.S. region comprising $nCUS_{5495}$, a CHV UL region comprising $nCgC/CUL45_{2100}$, a CgE gene comprising $nCgE_{750}$, a CgI gene comprising $nCgI_{161}$, a CUS9 gene comprising $nCUS9_{579}$, a CHV UL region comprising $nCdUTP/CUL51_{743}$, a CTK gene comprising $nCTK_{280}$, a CUL48 gene comprising $nCUL48_{294}$, a CUL49 gene included in $nCHin_{3000}$, a CUL52 gene comprising $nCUL52_{146}$, a CHV UL region comprising $nCUL_{1823}$, a CHV UL region comprising $nCUL49/CUL48_{2044}$, a CHV IR region comprising $nCICP4_{626}$, a CHV UL region comprising $nCgL_{655}$, a CHV UL region comprising $nCUL52_{749}$, a CHV UL region comprising $nCdUTP_{3}200$, as well as allelic variants of such (i.e., said, any of these) regions. As such, the present invention also includes a recombinant CHV genome having a heterologous nucleic acid molecule in a region of the genome spanning at least one of the following: a CIR6 gene including $nCIR6_{552}$, a CUS2 gene including $nCUS2_{1176}$, a CPK gene including $nCPK_{1203}$, a CgG gene including $nCgG_{1248}$, a CgD gene including $nCgD_{357}$, a CdUTPase gene including $nCdUTP_{459}$, a CUL51 gene including $nCUL51_{261}$, a CgD gene including $nCgD_{1038}$, a CgI gene including $nCgI_{1095}$, a CgE gene including $nCgE_{1569}$, a CUS8.5 open reading frame including $nCUS8.5_{237}$, a CUS9 gene including $nCUS9_{360}$, a CUL49 gene including $nCUL49_{420}$, a CUL48 gene including $nCUL48_{1269}$, a CICP4 gene including $nCICP4_{626}$, a CgL gene including $nCgL_{655}$, a CdUTPase gene including $nCdUTP_{918}$, a CUL49 gene including $nCUL49_{255}$, a CUL49.5 gene including $nCUL49.5_{261}$, and a CUL52 gene including $nCUL52_{749}$, as well as allelic variants of such regions.

As used herein, an allelic variant of a nucleic acid molecule, or region, for which nucleic acid sequence is provided herein is a nucleic acid molecule, or region, that occurs at essentially the same locus in another CHV genome as the nucleic acid molecule in CHV strain D 004, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions. Allelic variants are well known to those skilled in the art and would be expected to be found among the family of canine herpesviruses.

The present invention also includes a recombinant CHV genome having a heterologous nucleic acid molecule in a region of the genome spanning at least one of the following nucleic acid molecules: $nCUS_{5495}$ (and, as such, $nCIR6_{552}$, $nCUS2_{1176}$, $nCPK_{1203}$, $nCgG_{1248}$, and/or $nCgD_{357}$), $nCgC/CUL45_{2100}$, $nCgE_{750}$, $nCgI_{161}$, $nCUS9_{579}$, $nCdUTP/CUL51_{743}$ (and, as such, $nCdUTP_{459}$ and $nCUL51_{261}$), $nCTK_{280}$, $nCUL48_{294}$, $nCUL52_{146}$, $nCUS_{10592}$ $nCgD_{1038}$, $nCgI_{1095}$, $nCgE_{1569}$, nCUS8. 5237, $nCUS9_{360}$ nCUL49/CUL482044, nCUL49420, nCUL481269, $nCICP4_{626}$, $nCgL_{6551}$ $nCUL_{1823}$, $nCdUTP_{918}$, $nCUL49.5_{261}$, $nCUL49_{255}$, $nCUL52_{749}$, and/or $nCdUTP_{3200}$, as well as allelic variants of such regions.

A particularly preferred CHV genome of the present invention includes a heterologous nucleic acid molecule located in a region of the CHV genome comprising (e.g., including, represented by, or identified by) at least one of the following nucleic acid sequences: SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:53, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and/or SEQ ID NO:87, as well as complements of such regions and allelic variants of such regions. The relationships between certain nucleic acid molecules and nucleic acid sequences of the present invention are detailed below. It should be noted that since nucleic acid sequencing technology is not entirely error-free, the sequences represented by the SEQ ID NOs in the present invention at best represent apparent nucleic acid or amino acid sequences of CHV nucleic acid molecules or proteins of the present invention. It is also to be noted that a double-stranded nucleic acid molecule of the present invention for which a nucleic acid sequence has been determined for one strand that is represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

The present invention includes a recombinant CHV genome that includes a heterologous nucleic acid molecule that encodes a protective compound; the present invention also includes a recombinant CHV containing such a genome. As used herein, a protective compound is a compound that when administered to an animal protects that animal from a disease corresponding to that compound. For example, a compound derived from *Dirofilaria immitis* protects an animal from heartworm and other related infections, whereas a compound derived from a virus protects an animal from disease caused by that and related viruses. As used herein, the ability of a compound to protect an animal from a disease refers to the ability of that protective compound to treat, ameliorate and/or prevent the disease.

A protective compound of the present invention includes, but is not limited to, a protective protein and a protective RNA species. Essentially any heterologous nucleic acid molecule that encodes a protective protein or RNA can be used in the present invention. A protective protein of the present invention can be, for example, an immunogen that elicits an immune response which will protect an animal from the corresponding disease or some other compound (e.g., an immunomodulator, a toxin, an enzyme, an antibody, or other binding protein) that neutralizes and/or reduces the disease. A protective RNA of the present invention can be, for example, an RNA-based drug, a ribozyme, a molecule capable of triple helix formation, or an antisense RNA that effectively prevents the expression of a detrimental protein, thereby protecting an animal from disease.

It is within the scope of the present invention to produce therapeutic compositions against a variety of diseases, including infectious diseases, genetic diseases, and other metabolic diseases, including diseases that lead to abnormal cell growth, degenerative processes, and/or immunological defects. Therapeutic compositions of the present invention can protect animals from a variety of diseases including, but not limited to, allergies, autoimmune diseases, cancers, cardiovascular diseases, graft rejection, hematopoietic disorders, immunodeficiency diseases, immunoproliferative diseases, immunosuppressive disorders, infectious diseases, inflammatory diseases, jaundice, septic shock, other immunological defects, as well as other genetic or metabolic defects.

One preferred embodiment of the present invention is a recombinant CHV having a heterologous nucleic acid molecule within its genome that encodes a compound that protects a canid, or other animal susceptible to CHV infection, from infectious disease. Such disease can be caused by a variety of infectious agents, including, but not limited to, helminth parasites, protozoan parasites, ectoparasites, fungi (including yeast), bacteria and/or viruses. It should also be noted that although some infectious agents have not been definitively classified into one of these groups, such infectious agents are also included in the present invention. A preferred protective compound is derived from (e.g., obtained from natural source or produced using recombinant or synthetic chemistry techniques) an infectious agent.

Preferred helminth infectious agents to target include nematodes, cestodes and trematodes, with filariid, ascarid, capillarid, strongylid, strongyloides, trichostrongyle, and trichurid, parasitic helminths being more preferred, and filariid nematodes being even more preferred. More preferred parasitic helminths to target include the following: Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria (e.g., *D. immitis*), Dracunculus, Echinococcus, Enterobius, Filaroides, Haemonchus, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirometra, Spirocera, Stephanofilaria, Strongyloides, Strongylus, Taenia, Thelazia, Toxascaris, Toxocara, Trichinella, Trichostrongylus, Trichuris. Uncinaria, and Wuchereria . More preferred helminths to target, particularly with respect to being canine pathogens include Ancylostoma, Angiostrongylus, Brugia, Capillaria, Crenosoma, Dioctophyme, Dipetalonema, Diphyllobothrium, Diplydium, Dirofilaria, Echinococcus, Filaroides, Nanophyetus, Opisthorchis, Paragonimus, Physaloptera, Spirometra, Spirocera, Strongyloides, Taenia, Toxascaris, Toxocara, Trichinella, Trichuris, and Uncinaria.

Preferred protozoal infectious agents to target include Acetospora, Apicoplexa, Ciliophora, Labyrinthomorphorpha, Microspora, Myxozoa and Sarcomastigophora, with Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, being more preferred. More preferred protozoans to target, particularly with respect to being canine pathogens, include Babesia, Balantidium, Besnoitia, Cryptosporidium, Encephalitozoon, Entamoeba, Giardia, Hammondia, Hepatozoon, Isospora, Leishmania, Microsporidia, Neospora, Pentatrichomonas, Pneumocystis, Sarcocystis, Schistosoma, Toxoplasma, and Trypanosoma.

Preferred ectoparasite infectious agents to target include fleas, flies, mosquitoes, ticks, mites, lice, spiders, ants and true bugs, with fleas being more preferred. More preferred are fleas of the genera Ctenocephalides, Ctopsyllus, Diamanus, Echidnophaga Nosopsyllus, Pulex, Tunga, and Xenopsylla, with *Ctenocephalides canis* and *Ctenocephalides felis* fleas being particularly preferred.

Preferred fungal agents include Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha.

Preferred bacterial infectious agents to target include Actinomyces, Bacillus, Bacteroides, Bordetella, Bartonella (e.g., *B. henselae*), Borrelia (e.g., *B. burgdorferi*), Brucella, Campylobacter, Capnocytophaga, Clostridium, Corynebacterium, Coxiella, Dermatophilus, Enterococcus, Ehrlichia (e.g., *E. canis*), Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia (e.g., *Y. pestis*).

Preferred virus infectious agents to target include adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses.

A preferred recombinant CHV of the present invention includes a recombinant CHV genome having a heterologous nucleic acid molecule encoding a protective compound that elicits an immune response. As used herein, a protective compound that elicits an immune response refers to a compound that when administered to an animal in an appropriate manner, known to those skilled in the art, leads to the production of an immune response in that animal against the protective compound. The immune response, which can include humoral and/or cell-mediated components, preferably protects the immunized animal against the disease(s) targeted by the protective compound. As such, preferred protective compounds include, but are not limited to, antigens associated with diseases, as disclosed herein. Particularly preferred protective compounds of the present invention include *Dirofilaria immitis* antigens, *Toxoplasma gondii* antigens, Sarcocystis antigens, *Bartonella henselae* antigens, *Yersinia pestis* antigens, flea antigens, flea allergens, viral antigens, and cancer antigens. Even more preferred protective compounds are those disclosed in the following patent applications and patent publications, which are incorporated by reference herein in their entireties: U.S. Pat. No. 5,356,622, issued Oct. 18, 1994; U.S. Pat. No. 5,399,485, issued Mar. 21, 1995; U.S. Pat. No. 5,418,137, issued May 23, 1995; PCT Publication No. WO 92/13560, published Aug. 20, 1992; PCT Publication No. WO 93/10225, published May 27, 1993; PCT Publication No. WO 93/23077, published Nov. 25, 1993; PCT Publication No. WO 94/15593, published Jul. 21, 1994; PCT Publication No. WO 94/17813, published Aug. 18, 1994; PCT Publication No. WO 94/17824, published Aug. 18, 1994; PCT Publication No. WO 95/24198, published September 14, 1995; PCT Publication No. WO 95/32988, published Dec. 7, 1995; U.S. Ser. No. 08/401,509, filed Mar. 9, 1995; U.S. Ser. No. 08/415,365, filed Mar. 30, 1995; U.S. Ser. No. 08/450,944, filed May 23, 1995; U.S. Ser. No. 08/473,034, filed Jun. 6, 1995; U.S. Ser. No. 08/482,304, filed Jun. 7, 1995; U.S. Ser. No. 08/485,434, filed Jun. 7, 1995; U.S. Ser. No. 08/486,036, filed Jun. 7, 1995; U.S. Ser. No. 08/558,735 filed Nov. 16, 1995; PCT Ser. No. PCT/US95/13200, filed Oct. 6, 1995; PCT Ser. No. PCT/US95/14442, filed Oct. 18, 1995; U.S. Ser. No. 08/630,822, filed Apr. 10, 1996; U.S. Ser. No. 08/602,262, filed Feb. 15, 1996; PCT Ser. No.: PCT/US96/03133, filed Mar. 8, 1996; U.S. Ser. No. 08/639,075, filed Apr. 24, 1996; PCT Ser. No. PCT/US96/07709, filed May 23, 1996; and PCT Ser. No. PCT/US96/09848, filed Jun. 7, 1996, and related filings.

Another preferred protective compound of the present invention is an immunomodulator. Suitable immunomodulators include compounds that enhance the immune response as well as compounds that suppress the immune response. Compounds that enhance the immune response include compounds that preferentially enhance humoral immunity as well as compounds that preferentially enhance cell-mediated immunity. Suitable compounds can be selected depending on the disease being targeted. Suitable immunomodulators include, but are not limited to, cytokines, chemokines, superantigens, and other immunomodulators as well as compounds that induce the production of cytokines, chemokines and other immunomodulators. Examples of such protective compounds include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), and Leishmania elongation initiating factor (LEIF).

One preferred embodiment of the present invention is a recombinant CHV having more than one heterologous nucleic acid molecule included in the CHV genome. Such a CHV can include two or more heterologous nucleic acid molecules encoding two or more protective compounds to protect an animal from a given disease (e.g., two or more heartworm antigens), or can include two or more heterologous nucleic acid molecules encoding protective compounds each targeted against a different disease (e.g., a compound to protect an animal against heartworm and a compound to protect an animals against a viral infection). A preferred multivalent CHV can also include an heterologous nucleic acid molecule encoding a protective compound that elicits an immune response as well as an heterologous nucleic acid molecule encoding an immunomodulator to enhance the desired immune response. Also included in the present invention are protective compounds that are fusion, or multivalent, proteins comprising more than one functional domain.

The present invention also includes recombinant CHV genomes. As such, the invention includes any CHV genome disclosed herein, including those included in recombinant CHV of the present invention. Also included in the present invention are cells comprising recombinant CHV genomes of the present invention. As used herein, a cell comprising a recombinant CHV genome is a cell into which a recombinant CHV genome has been introduced. Such introduction can be accomplished by any method by which a nucleic acid molecule can be inserted into a cell. Such methods, known to those skilled in the art, include, but are not limited to, infection (i.e., with a virus comprising the genome), transfection, transformation, electroporation, microinjection, lipofection, adsorption, and protoplast fusion. A preferred cell comprises a recombinant CHV having a heterologous nucleic acid molecule, which preferably is operatively linked to a transcription control sequence. Cells containing CHV genomes are useful in the production of recombinant CHV. Methods to produce recombinant CHV are disclosed herein.

The present invention also includes isolated CHV nucleic acid molecules. As used herein, a CHV nucleic acid molecule is a nucleic acid molecule that is derived from CHV. As such, the nucleic acid molecule can be produced, for example, by recovery of such a nucleic acid molecule directly from a CHV genome, by recombinant DNA techniques, or by chemical synthesis. That the CHV nucleic acid molecule is isolated indicates that the molecule is removed from its natural milieu. An isolated CHV nucleic acid molecule can include DNA, RNA, or derivatives of either DNA or RNA.

A preferred CHV nucleic acid molecule of the present invention is a CHV nucleic acid molecule that hybridizes under stringent hybridization conditions with at least one of the following: with a CdUTPase gene, a CgC gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CUL48 gene, a CgL gene, a CUL49.5 gene, a CICP4 gene, a CUS8.5 open reading frame, and/or a CUL52 gene; with other regions of a CUS; and/or with a region of the CHV genome spanning from about the 3' end of the coding region of the CUL41 gene through about the 3' end of the coding region of the CUL38 gene. The identifying characteristics of such regions, including the CHV genes listed, are heretofore described.

As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mis-match between two nucleic acid molecules are disclosed, for example, in Meinkoth et al, 1984, *Anal. Biochem* 138, 267–284; Meinkoth et al, ibid, is incorporated by reference herein in its entirety. An example of such conditions includes, but is not limited to, the following: Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 2× SSPE, 1% Sarkosyl, 5× Denhardts and 0.1 mg/ml denatured salmon sperm DNA at a temperature as calculated using the formulae of Meinkoth et al., ibid. for about 2 to about 12 hours. The filters are then washed 3 times in a wash solution containing 2× SSPE, 1% Sarkosyl at about 55° C. for about 15 minutes each. The filters can be further washed in a wash solution containing 2× SSPE, 1% Sarkosyl at about 55° C. for about 15 minutes per wash.

A CHV nucleic acid molecule of the present invention can include an isolated natural CHV gene or a homolog thereof, the latter of which is described in more detail below. A CHV nucleic acid molecule of the present invention can include one or more regulatory regions, full-length or partial coding regions, or combinations thereof. The minimal size of a CHV nucleic acid molecule of the present invention is the minimal size that can form a stable hybrid with one of the aforementioned CHV genes and other regions under stringent hybridization conditions.

Isolated CHV nucleic acid molecules include natural nucleic acid molecules and homologs thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a CHV protein of the present invention or to form stable hybrids under stringent conditions with natural gene isolates.

A CHV nucleic acid molecule homolog can be produced using a number of methods known to those skilled in the art (see, for example, Sambrook et al., ibid.). CHV nucleic acid molecule homologs can be selected from a mixture of modified nucleic acids by screening for the function of the protein encoded by the nucleic acid molecule and/or by hybridization with a CHV region as defined above.

An isolated CHV nucleic acid molecule of the present invention can include a nucleic acid sequence that encodes at least one CHV protein of the present invention; such proteins are discussed in further detail below. Although the phrase "nucleic acid molecule" primarily refers to the physical nucleic acid molecule and the phrase "nucleic acid sequence", primarily refers to the sequence of nucleotides on the nucleic acid molecule, the two phrases can be used interchangeably, especially with respect to a nucleic acid molecule, or a nucleic acid sequence, being capable of encoding a CHV protein.

One embodiment of the present invention is a CHV nucleic acid molecule that, when administered to an animal, is capable of protecting that animal from CHV infection. Such a CHV nucleic acid molecule can be, or encode, an antisense RNA, a molecule capable of triple helix formation, a ribozyme, or other nucleic acid-based drug compound. In an additional embodiment, a CHV nucleic acid molecule of the present invention can encode a protective protein, the nucleic acid molecule being delivered to the animal by direct injection (i.e, as a naked nucleic acid) or in a vehicle such as a recombinant virus vaccine or a recombinant cell vaccine.

One embodiment of the present invention is a CHV nucleic acid molecule that hybridizes under stringent hybridization conditions with $nCUS_{5495}$, $nCgC/CUL45_{2100}$, $nCgE_{750}$, $nCgI_{161}$, $nCUS9_{579}$, $nCdUTP/CUL51_{743}$, $nCTK_{280}$, $nCUL48_{294}$, a nCUL49 included in $nCHin_{3000}$, $nCUL52_{146}$, $nCgI_{1095}$, $nCgE_{1569}$, $nCUS8.5_{237}$, $ncUS9_{360}$, $nCUL49/CUL48_{2044}$, $nCUL49_{420}$, $nCUL48_{1269}$, $nCICP4_{626}$, $nCgL_{655}$, $nCUL_{1823}$, $nCdUTP_{918}$, nCUL49.5261, $nCUL49_{255}$, and/or $nCUL52_{749}$. Such a CHV nucleic acid molecule can also hybridize under stringent hybridization conditions with $nCAsc_{9300}$, $nCAsc_{10000}$, $nCHin_{3000}$, $nCHin_{1900}$, $nCHin_{5500}$, $nCHin_{8500}$, $nCIR6_{552}$, $nCUS2_{1176}$, $nCPK_{1203}$, $nCgG_{1248}$, $nCgD_{357}$, $nCdUTP_{459}$, $nCTK_{279}$, $nCUS9_{450}$, $nCUL48_{291}$, $nCUL5l_{261}$, $nCUL52_{144}$, $nCgI,_{159}$, $nCUS,_{10592}$, $nCICP4_{624}$, $nCgL_{516}$, $nCUL52_{747}$, $nCdUTP_{858}$, and/or $nCdUTP_{3200}$. At least some of such CHV nucleic acid molecules can hybridize under stringent hybridization conditions with a nucleic acid molecule having nucleic acid sequence SEQ ID NO:1, SEQ ID NO:2, SEQ ID NO:13, SEQ ID NO:14, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:35, SEQ ID NO:37, SEQ ID NO:51, SEQ ID NO:52, SEQ ID NO:63, SEQ ID NO:64, SEQ ID NO:69, SEQ ID NO:70, SEQ ID NO:71, SEQ ID NO:73, SEQ ID NO:74, SEQ ID NO:77, SEQ ID NO:78, SEQ ID NO:85, SEQ ID NO:86, and/or SEQ ID NO:87, as well as complements of such sequences.

SEQ ID NO:1 and SEQ ID NO:2 represent the deduced nucleic acid sequences of the two complementary strands of $nCUS_{5495}$. Translation of SEQ ID NO:1 and SEQ ID NO:2 indicates that nucleic acid molecule $nCUS_{5495}$ encodes CIR6, CUS2, CPK and CgG proteins as well as a portion of a CgD protein. Specifically, SEQ ID NO:2 includes: a coding region for a CIR6 protein of about 183 amino acids, denoted herein as $nCIR6_{552}$ and represented by SEQ ID NO:3, assuming a start codon spanning about nucleotides 4566–4568 and a stop codon spanning about nucleotides 5115–5117 of SEQ ID NO:2; and a coding region for a CUS2 protein of about 391 amino acids, denoted herein as $nCUS2_{1176}$ and represented by SEQ ID NO:5, assuming a start codon spanning about nucleotides 3232–3234 and a stop codon spanning about nucleotides 4405–4407 of SEQ ID NO:2. The amino acid sequences of the respective encoded proteins $PCIR6_{183}$ and $PCUS2_{391}$ are represented by SEQ ID NO:4 and SEQ ID NO:6. SEQ ID NO:1 includes: a coding region for a CPK protein of about 400 amino acids, denoted herein as $nCPK_{1203}$ and represented by SEQ ID NO:7, assuming a start codon spanning about nucleotides 2384–2386 and a stop codon spanning about nucleotides 3584–3586 of SEQ ID NO:1; a coding region for a CgG protein of about 415 amino acids, denoted herein as $nCgG_{1248}$ and represented by SEQ ID NO:9, assuming a start codon spanning about nucleotides 3698–3700 and a stop codon spanning about nucleotides 4943–4945 of SEQ ID NO:1; and a partial coding region for a CgD protein of about 119 amino acids, denoted herein as $nCgD_{357}$ and represented by SEQ ID NO:11, assuming a start codon spanning about nucleotides 5137–5139. The amino acid sequences of the respective encoded proteins $PCPK_{400}$, $PCgG_{415}$, and $PCgD_{119}$ are represented by SEQ ID NO:8, SEQ ID NO:10 and SEQ ID NO:12.

SEQ ID NO:13 and SEQ ID NO:14 represent the deduced nucleic acid sequences of the two complementary strands of $nCdUTP/CUL51_{743}$. SEQ ID NO:13 includes a partial coding region for a CdUTPase protein of about 152 amino acids, denoted herein as $nCdUTP_{459}$ and represented by SEQ ID NO:15, assuming a first in-frame codon spanning about nucleotides 3–5, and a stop codon spanning about nucleotides 459–461 of SEQ ID NO:13. The amino acid sequence of the encoded protein $PCdUTP_{152}$ is represented by SEQ ID NO:16. SEQ ID NO:14 includes a partial coding region for a CUL51 protein of about 86 amino acids, denoted herein as $nCUL51_{261}$ and represented by SEQ ID NO:33, assuming a first in-frame codon spanning about nucleotides 1–3, and a stop codon spanning about nucleotides 259–261 of SEQ ID NO:14. The amino acid sequence of the encoded protein $PCUL51._{6}$ is represented by SEQ ID NO:34.

SEQ ID NO:17 and SEQ ID NO:19 represent the deduced nucleic acid sequences of the two complementary strands of $nCUS9_{579}$. SEQ ID NO:17 includes a coding region for a CUS9 protein of about 149 amino acids, denoted herein as $nCUS9_{450}$ and represented by SEQ ID NO:20, assuming a start codon spanning about nucleotides 54–56 and a stop codon spanning about nucleotides 501–503 of SEQ ID NO:17. The amino acid sequence of the encoded protein $PCUS9_{149}$ is represented by SEQ ID NO:18.

SEQ ID NO:21 and SEQ ID NO:23 represent the deduced nucleic acid sequences of the two complementary strands of nCUL48$_{294}$. SEQ ID NO:21 includes a partial coding region for a CUL48 protein of about 97 amino acids, denoted herein as nCUL48$_{291}$ and represented by SEQ ID NO:24, assuming a first in-frame codon spanning about nucleotides 3–5 of SEQ ID NO:21. The amino acid sequence of the encoded protein PCUL48$_{97}$ is represented by SEQ ID NO:22.

SEQ ID NO:25 and SEQ ID NO:27 represent the deduced nucleic acid sequences of the two complementary strands of nCUL52$_{146}$. SEQ ID NO:25 includes a partial coding region for a CUL52 protein of about 48 amino acids, denoted herein as nCUL52$_{144}$ and represented by SEQ ID NO:28, assuming a first in-frame codon spanning about nucleotides 1–3 of SEQ ID NO:25. The amino acid sequence of the encoded protein PCUL52$_{48}$ is represented by SEQ ID NO:26.

SEQ ID NO:29 and SEQ ID NO:31 represent the deduced nucleic acid sequences of the two complementary strands of nCgI$_{161}$. SEQ ID NO:29 includes a partial coding region for a CgI protein of about 53 amino acids, denoted herein as nCgI$_{159}$ and represented by SEQ ID NO:32, assuming a first in-frame codon spanning about nucleotides 3–5 of SEQ ID NO:29. The amino acid sequence of the encoded protein PCgI$_{53}$ is represented by SEQ ID NO:30.

SEQ ID NO:35 and SEQ ID NO:37 represent the deduced nucleic acid sequences of the two complementary strands of nCTK$_{280}$. SEQ ID NO:35 includes a partial coding region for a CTK protein of about 93 amino acids, denoted herein as nCTK$_{279}$ and represented by SEQ ID NO:38, assuming a first in-frame codon spanning about nucleotides 2–4 of SEQ ID NO:35. The amino acid sequence of the encoded protein PCTK$_{93}$ is represented by SEQ ID NO:36.

The identities of additional nucleic acid molecules, nucleic acid sequences, proteins, and amino acid sequences are presented in the Examples.

Comparison of the CHV nucleic acid sequences SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and SEQ ID NO:87 with known sequences indicates that none of these CHV nucleic acid sequences share more than about 70% identity (many, if not all, sharing significantly less identity) with a known nucleic acid sequence. As such, a preferred CHV nucleic acid molecule has a nucleic acid sequence that is at least about 80%, preferably at least about 85%, more preferably at least about 90%, even more preferably at least about 95%, and even more preferably at least about 99% identical to nucleic acid sequence SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and/or SEQ ID NO:87, as well as complements of such sequences.

A more preferred CHV nucleic acid molecule of the present invention includes at least a portion of CHV nucleic acid molecule nCAsc$_{9300}$, nCAsc$_{10000}$, nCHin$_{3000}$, nCHin$_{1900}$, nCHin$_{5500}$, nCHin$_{8500}$, nCUS$_{5495}$, nCIR6$_{552}$, nCUS2$_{1176}$, nCPK$_{1203}$, nCgG$_{1248}$, nCdUTP/CUL51$_{743}$, nCdUTP$_{459}$, nCUS9$_{579}$, nCUS9$_{450}$, nCUL48$_{294}$, nCUL48$_{291}$, nCUL52$_{146}$, nCUL52$_{144}$, nCgI$_{161}$, nCgI$_{159}$, nCgE$_{750}$, nCTK$_{280}$, nCTK$_{279}$, nCUL51$_{261}$, nCUS$_{10592}$, nCgI$_{1095}$, nCgE$_{1569}$, nCUS8.5$_{237}$, nCUS9$_{360}$, nCUL49/CUL48$_{2044}$, nCUL49$_{420}$, nCUL48$_{1269}$, nCICP4$_{626}$, nCICP4$_{624}$, nCgL$_{655}$, nCgL$_{516}$, nCUL$_{1823}$, nCdUTP$_{918}$, nCUL49.5$_{261}$, nCUL49$_{255}$, nCUL52$_{749}$, nCUL52$_{747}$, nCdUTP$_{858}$, and/or nCdUTP$_{3200}$, as well as allelic variants of those CHV nucleic acid molecules. Such CHV nucleic acid molecules can include nucleotides in addition to those included in the defined fragments; examples of such CHV nucleic acid molecules include full-length genes, full-length coding regions, or nucleic acid molecules encoding multivalent proteins. Particularly preferred CHV nucleic acid molecules are nCAsc$_{9300}$, nCAsc$_{10000}$, nCHin$_{3000}$, nCHin$_{1900}$, nCHin$_{5500}$, nCHin$_{8500}$, nCUS$_{5495}$, nCIR6$_{552}$, nCUS2$_{1176}$, nCPK$_{1203}$, nCgG$_{1248}$, nCdUTP/CUL51$_{743}$, nCdUTP$_{459}$, nCUS9$_{579}$, nCUS9$_{450}$, nCUL48$_{294}$, nCUL48$_{291}$, nCUL52$_{146}$, nCUL52$_{144}$, nCgI$_{161}$, nCgI$_{159}$, nCgE$_{750}$, nCTK$_{280}$, nCTK$_{279}$, nCUL51$_{261}$, nCUS$_{10592}$, nCgI$_{1095}$, nCgE$_{1569}$, nCUS8.5$_{237}$, nCUS9$_{360}$, nCUL49/CUL48$_{2044}$, nCUL49$_{420}$, nCUL48$_{1269}$, nCICP4$_{626}$, nCICP4$_{624}$, nCgL$_{655}$, nCgL$_{516}$, nCUL$_{1823}$, nCdUTP$_{918}$, nCUL49.5$_{261}$, nCUL49$_{255}$, nCUL52$_{749}$, nCUL52$_{747}$, nCdUTP$_{858}$, and/or nCdUTP$_{3200}$.

Similarly, a preferred CHV nucleic acid molecule of the present invention includes at least a portion of nucleic acid sequence SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and/or SEQ ID NO:87; or a complement of SEQ ID NO:3, SEQ ID NO:5, SEQ ID NO:7, SEQ ID NO:9, SEQ ID NO:15, SEQ ID NO:20, SEQ ID NO:24, SEQ ID NO:28, SEQ ID NO:32, SEQ ID NO:33, SEQ ID NO:38, SEQ ID NO:55, SEQ ID NO:57, SEQ ID NO:59, SEQ ID NO:61, SEQ ID NO:65, SEQ ID NO:67, SEQ ID NO:71, SEQ ID NO:75, SEQ ID NO:79, SEQ ID NO:81, SEQ ID NO:83, and/or SEQ ID NO:87; as well as allelic variants of such nucleic acid molecules. More preferred is a nucleic acid molecule that includes at least one of the following nucleic acid sequences: SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and/or SEQ ID NO:87; or a complement of SEQ ID NO:3, SEQ ID NO:5, SEQ ID NO:7, SEQ ID NO:9, SEQ ID NO:15, SEQ ID NO:20, SEQ ID NO:24, SEQ ID NO:28, SEQ ID NO:32, SEQ ID NO:33, SEQ ID NO:38, SEQ ID NO:55, SEQ ID NO:57, SEQ ID NO:59, SEQ ID NO:61, SEQ ID NO:65, SEQ ID NO:67, SEQ ID NO:71, SEQ ID NO:75, SEQ ID NO:79, SEQ ID NO:81, SEQ ID NO:83, and/or SEQ ID NO:87; also included are nucleic acid molecules that are allelic variants of nucleic acid molecules having those nucleic acid sequences. Such nucleic acid molecules can include nucleotides in addition to those included in the SEQ ID NOs.

The present invention also includes CHV nucleic acid molecules encoding a protein, including nucleic acid molecules that have been modified to accommodate codon usage properties of the cells in which such nucleic acid molecules are to be expressed. CHV proteins of the present invention are described in more detail below. Particularly preferred nucleic acid molecules are those that encode a protein having at least one of the following amino acid sequences: SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and/or SEQ ID NO:88.

The present invention also includes CHV nucleic acid molecules that are oligonucleotides capable of hybridizing, under stringent hybridization conditions, with complementary regions of other, preferably longer, CHV nucleic acid molecules of the present invention. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. oligonucleotides of the present invention can be used in a variety of applications including, but not limited to, as probes to identify additional nucleic acid molecules, as primers to amplify or extend nucleic acid molecules or in therapeutic applications to inhibit CHV infection as disclosed herein.

The present invention also includes an isolated CHV protein encoded by a CHV nucleic acid molecule of the present invention. As such, the present invention includes a CHV protein encoded by a CHV nucleic acid molecule that hybridizes under stringent hybridization conditions with at least one of the following: a CdUTPase gene, a CgC gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CUL48 gene, and/or a CUL52 gene; and/or with other portions of a CUS region; and/or with a CgL gene, a CUL49.5 gene, a CICP4 gene, and/or a CUS8.5 open reading frame.

According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis. As used herein, a CHV protein can be a full-length protein or any homolog of such a protein. Examples of CHV homologs include CHV proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog retains a desired activity of the natural protein, such as, but not limited to, enzymatic activity, activity important for viral growth, and/or ability to elicit an immune response. These activities can be measured using techniques known to those skilled in the art.

CHV protein homologs can be the result of natural allelic variation or natural mutation. CHV protein homologs of the present invention can also be produced using techniques known in the art including, but not limited to, direct modifications to the protein or modifications to the gene encoding the protein using, for example, classic or recombinant DNA techniques to effect random or targeted mutagenesis.

The minimal size of a CHV protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a CHV protein homolog of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a CHV protein homolog of the present invention is from about 4 to about 6 amino acids in length, with preferred sizes depending on whether full-length, fusion, or other functional portions of such proteins are desired.

One embodiment of the present invention is a CHV protein that can protect an animal from disease, preferably by eliciting an immune response against CHV, and/or can detect CHV infection in an animal. The minimum size of such a protein is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

The present invention also includes mimetopes of CHV proteins that can be used in accordance with methods as disclosed for CHV proteins of the present invention. As used herein, a mimetope of a CHV protein of the present invention refers to any compound that is able to mimic the activity of such a CHV protein, often because the mimetope has a structure that mimics the CHV protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the present invention is a fusion, or multivalent, protein that includes a CHV protein-containing domain attached to another functional domain. Such a domain can be an entire protein, or function portion thereof. Examples of such domains include not only protective compounds as disclosed above, but also domains that enhance a protein's stability (e.g., during production, storage and/or use) or that aid in protein purification.

A preferred isolated protein of the present invention is a protein encoded by a nucleic acid molecule that hybridizes under stringent hybridization conditions with $nCIR6_{552}$, $nCUS2_{1176}$, $nCPK_{1203}$, $nCgG_{1248}$, $nCgD_{357}$, $nCgC/CUL45_{2100}$, $nCdUTP_{459}$, $nCUS9_{450}$, $nCUL48_{291}$, $nCUL52_{144}$, $nCgI_{159}$, $nCgE_{750}$, $NCTK_{279}$, $nCUL51_{261}$, $nCgI,_{1095}$, $nCgE_{1569}$, $nCUS8.5_{237}$, $nCUS9_{360}$, $nCUL49/CUL48_{2044}$, $nCUL49_{420}$, $nCUL48_{1269}$, $nCICP4_{626}$, $nCgL_{655}$, $nCUL_{1823}$, $nCdUTP_{918}$, $nCUL49.5_{261}$, $nCUL49_{255}$, and/or $nCUL52_{749}$. Also included is a protein that hybridizes under stringent hybridization conditions with $nCAsc_{9300}$, $nCAsc_{10000}$, $nCHin_{3000}$, $nCHin_{1900}$, $nCHin_{5500}$, and/or $nCHin_{8500}$. A further preferred isolated protein is encoded by a nucleic acid molecule that hybridizes under stringent hybridization conditions with a nucleic acid molecule having the complement of nucleic acid sequence SEQ ID NO:3, SEQ ID NO:5, SEQ ID NO:7, SEQ ID NO:9, SEQ ID NO:11, SEQ ID NO:15, SEQ ID NO:20, SEQ ID NO:24, SEQ ID NO:28, SEQ ID NO:32, SEQ ID NO:33, SEQ ID NO:38, SEQ ID NO:55, SEQ ID NO:57, SEQ ID NO:59, SEQ ID NO:61, SEQ ID NO:65, SEQ ID NO:67, SEQ ID NO:71, SEQ ID NO:75, SEQ ID NO:79, SEQ ID NO:81, SEQ ID NO:83, and/or SEQ ID NO:87, or by an allelic variant of any of such nucleic acid molecules. Proteins encoded by nucleic acid sequences SEQ ID NO:3, SEQ ID NO:5, SEQ ID NO:7, SEQ ID NO:9, SEQ ID NO:11, SEQ ID NO:15, SEQ ID NO:20, SEQ ID NO:24, SEQ ID NO:28, SEQ ID NO:32, SEQ ID NO:33, SEQ ID NO:38, SEQ ID NO:55, SEQ ID NO:57, SEQ ID NO:59, SEQ ID NO:61, SEQ ID NO:65, SEQ ID NO:67, SEQ ID NO:71, SEQ ID NO:75, SEQ ID NO:79, SEQ ID NO:81, SEQ ID NO:83, and SEQ ID NO:87 have amino acid sequences SEQ ID NO:4, SEQ ID NO:6, SEQ ID NO:8, SEQ ID NO:10, SEQ ID NO:12, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and SEQ ID NO:88, respectively.

Comparison of the CHV amino acid sequences SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and SEQ ID NO:88 with known sequences indicates that none of these CHV amino acid sequences share more than about 75% identity (many, if not all, sharing significantly less identity) with a known amino acid sequence.

A preferred CHV protein has an amino acid sequence that is at least about 80%, preferably at least about 85%, more preferably at least about 90%, even more preferably at least about 95%, and even more preferably at least about 99% identical to amino acid sequence SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and/or SEQ ID NO:88.

A more preferred CHV protein includes at least a portion of $PCIR6_{183}$, $PCUS2_{391}$, $PCPK_{400}$, $PCgG_{415}$, $PCdUTP_{152}$, $PCUS9_{149}$, $PCUL48_{97}$, $PCUL52_{48}$, $PCUL51_{86}$, $PCgI_{53}$, $PCTK_{93}$, $PCgI_{364}$, $PCgE_{522}$, $PCUS8.5_{78}$, $PCUS9_{119}$, $PCUL49_{139}$, $PCUL48_{422}$, $PCICP4_{208}$, $PCgL_{171}$, $PCdUTP_{305}$, $PCUL49.5_{86}$, $PCUL49_{85}$, and/or $PCUL52_{249}$, as well as proteins encoded by allelic variants of the nucleic acid molecules encoding such proteins. Also preferred are proteins including at least a portion of CgE and/or CUL49 proteins. A particularly preferred CHV protein includes $PCIR6_{183}$, $PCUS2_{391}$, $PCPK_{400}$, $PCgG_{415}$, $PCdUTP_{152}$, $PCUS9_{149}$, $PCUL48_{97}$, $PCUL52_{48}$, $PCUL51_{86}$, $PCgI_{53}$, $PCTK_{93}$, $PCgI_{364}$, $PcgE_{522}$, $PCUS8.5_{78}$, $PCUS9_{119}$, $PCUL49_{139}$, $PCUL48^{422}$, $PCICP4_{208}$, $PCgL_{171}$, $PCdUTP_{305}$, $PCUL49.5_{86}$, $PCUL49_{85}$, and/or $PCUL52_{249}$ (including, but not limited to the encoded proteins, full-length proteins, processed proteins, multivalent proteins).

Similarly, a preferred CHV protein of the present invention includes at least a portion of SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and/or SEQ ID NO:88. A particularly preferred CHV protein includes SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and/or SEQ ID NO:88. Also included are proteins encoded by allelic variants of the nucleic acid molecules encoding such proteins.

The present invention also includes a recombinant vector, which includes at least one isolated CHV nucleic acid molecule inserted into any vector capable of delivering the CHV nucleic acid molecule into a host cell. The vector can be either RNA or DNA, either prokaryotic or eukaryotic, and typically is a virus or a plasmid. Recombinant vectors can be used in the cloning, sequencing, and/or otherwise manipulating of CHV nucleic acid molecules of the present invention. Suitable and preferred CHV nucleic acid molecules to include in a recombinant vector are disclosed herein.

One embodiment of the present invention is a recombinant vector comprising an inactive CHV gene. Such a recombinant vector, also referred to as a transfer vector, can be used to produce a CHV comprising a CHV genome having an inactive gene by, for example, co-transfecting such a transfer vector with a CHV genome into a host cell and selecting for a CHV comprising a recombinant CHV genome having an inactive gene. Such a recombinant CHV genome is produced in the host cell by homologous recombination between the inactive gene on the transfer vector and the corresponding active gene on the transfected CHV genome. Transfection, culturing and purification methods to obtain recombinant CHV and CHV genomes are known to the art; see, for example, Graham et al., 1973, *Virology* 52:456–467; Graham et al, ibid. is incorporated by reference herein in its entirety.

Another embodiment of the present invention is a recombinant vector comprising a CHV nucleic acid molecule that includes a heterologous nucleic acid molecule (i.e., a heterologous nucleic acid molecule is located within a CHV nucleic acid molecule). Suitable and preferred heterologous nucleic acid molecules are disclosed herein. Such a heterologous nucleic acid molecule can be operatively linked to a transcription control sequence, as disclosed above. A recombinant vector comprising a CHV nucleic acid molecule into which a heterologous nucleic acid molecule is inserted is also a transfer vector. Such a transfer vector can be co-transfected with a CHV genome into a host cell to produce a recombinant CHV having a CHV genome including a heterologous nucleic acid molecule, using methods as described above. Recombinant CHV can be selected by identifying those CHV that have the heterologous nucleic acid molecule. If the recombinant vector comprises a selectable marker into which the heterologous nucleic acid molecule is inserted, selection methods as disclosed herein can also be used to identify recombinant CHV. A preferred embodiment is a recombinant vector comprising a CHV nucleic acid molecule having a heterologous nucleic acid molecule in which a majority of the CHV nucleic acid molecule is deleted; a sufficient size of the CHV nucleic acid molecule is retained to allow homologous recombination to occur with the corresponding target gene on the CHV genome. Examples of insertion of a heterologous nucleic acid molecule into a CHV genomic restriction site and into a CHV gene, as well as use of a selectable marker are provided in the Examples section.

Transfer vectors of the present invention are preferably able to replicate in bacterial, and particularly *E. coli*, hosts, thereby enabling easy manipulation of the CHV nucleic acid molecules, and, if included, heterologous nucleic acid molecules, prior to insertion of such CHV nucleic acid molecules into a CHV genome. Such manipulations, including culturing of *E. coli* comprising such vectors, is described, for example, in Sambrook et al, ibid.

In one embodiment, recombinant CHV are produced by co-transfection of a set of overlapping cosmid clones comprising the entire viral CHV genome, at least one of the cosmid clones having been genetically engineered to, for example, contain an inactive CHV gene and/or a heterologous nucleic acid molecule. Details of such a method are presented in the Examples.

Any canid host cell is suitable for recombinant CHV production. Examples of suitable and preferred host cells are provided herein. After transfection, transfected cells are cultured in an effective medium, using techniques such as those described in Graham et al, ibid. As used herein, an effective medium refers to any medium in which the transfected cells can produce recombinant CHV. An effective medium is typically an aqueous medium comprising assimilable carbohydrate, nitrogen and phosphate sources, as well as appropriate salts, minerals, metals and other nutrients, such as vitamins, growth factors and hormones. Culturing is carried out at a temperature, pH and oxygen content appropriate for the transfected cell. Such culturing conditions are well within the expertise of one of ordinary skill in the art.

Recombinant CHV can be recovered from the cultured transfected cells using a combination of standard techniques such as, but not limited to, freeze/thaw cycles, sonication, sucrose gradient centrifugation, and/or high speed centrifugation. Recombinant CHV genomes can be recovered from the cultured transfected cells using a combination of standard techniques such as, but not limited to, those described by Walboomers et al, 1976*, Virology* 74, 256–258.

Preferably, a recombinant CHV or recombinant CHV genome of the present invention is recovered in "substantially pure" form. As used herein, "substantially pure" refers to a purity that allows for the effective use of the recombinant CHV or CHV genome as a vaccine without substantial negative side effects.

The present invention also includes a method to increase recombinant CHV plaque forming efficiency, thereby facilitating the production of recombinant CHV and CHV genomes. The phrase to increase recombinant CHV plaque forming efficiency refers to the ability to increase, or enhance, the production of CHV above the frequency of plaque forming units produced when a CHV genome is transfected into a cell in the absence of additional factors. The method includes the step of expressing the CHV alpha transinducing factor gene (i.e., CUL48 gene, also called the CHV alpha-tif gene) when a CHV genome is introduced into a canine cell.

Herpesviruses studied to date carry into infected cells a transcriptional activator called alpha transinducing factor (also called VP16 or Vmw65); see, for example, Batterson et al., 1983*, J. Virol*., 46:371–377. This transactivator protein interacts, along with cellular proteins, with a cis-acting sequence element present in the upstream regulatory regions of herpesvirus immediate early genes. Since purified herpesvirus DNA is infectious in the absence of alpha-tif, it is not absolutely required for expression of immediate early genes, but its presence in stably transfected cell lines has been shown to enhance infectivity of herpes simplex virus type-1 viral DNA; see, for example, Werstuck et al., 1990*, J. Virol*., 64:984–991.

Expression of the CHV alpha-tif gene can be accomplished in a variety of ways, including, but not limited to, the following. In one embodiment, a recombinant CHV genome is introduced into a canine cell expressing CHV alpha transinducing factor and the cells are cultured to produce recombinant CHV. A canine cell expressing CHV alpha-tif is a canine cell that has been genetically engineered to produce CHV alpha-tif in either a stable or transient manner. Such a canine cell can be produced by introducing a CUL48 nucleic acid molecule of the present invention into a canine cell line in such a manner that the CUL48 nucleic acid molecule can direct the expression of active alpha-tif. An example of a useful CUL48 nucleic acid molecule is such $nCUL48_{1269}$. Details regarding the production of an alpha-tif-expressing canine cell and the use such a cell in the production of recombinant CHV and CHV genomes is present in the Examples.

In another embodiment, recombinant CHV plaque forming efficiency is increased by co-introducing a recombinant CHV genome and a CHV alpha transinducing factor gene into a canine cell and culturing the cell to produce recombinant CHV. The CHV alpha transinducing factor gene can be introduced as part of a recombinant molecule of the present invention. Details regarding this method are also presented in the Examples.

The present invention also includes canine cell lines that include a CHV alpha-tif gene; such cell lines are able to express alpha-tif, thereby facilitating CHV production. One example of such a cell line is a canine cell line transfected with CHV nucleic acid molecule nCUL48$_{1269}$.

One embodiment of the present invention is a recombinant molecule that includes a CHV nucleic acid molecule operatively linked to a transcription control sequence. Such a recombinant molecule, when introduced into a host cell, can direct the expression of the CHV nucleic acid molecule(s), thereby leading to the production of one or more CHV protein of the present invention. Such a recombinant molecule preferably is replication competent. Suitable and preferred CHV nucleic acid molecules to include in such a recombinant molecule are as disclosed herein for suitable and preferred CHV nucleic acid molecules per se.

Isolated CHV proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing one or more CHV proteins, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred CHV nucleic acid molecules with which to transform a cell are as disclosed herein for suitable and preferred CHV nucleic acid molecules per se.

Suitable host cells to transform include any cell that can be transformed with a CHV nucleic acid molecule of the present invention. Host cells can be either untransformed cells or cells that are already transformed with at least one nucleic acid molecule. Host cells of the present invention either can be endogenously (i.e., naturally) capable of producing CHV proteins of the present invention or can be capable of producing such proteins after being transformed with at least one CHV nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, yeast, insect and mammalian cells. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $P_L$ and lambda $P_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus, phosphate-regulated and nitrate-regulated transcription control sequences as well as other sequences capable of controlling gene expression in prokaryotic or eukaryotic cells, including those disclosed herein for expression of heterologous nucleic acid molecules, including endogenous CHV transcription control regions.

Recombinant cells of the present invention can be used to produce one or more proteins by culturing such cells under conditions effective to produce such a protein, and recovering the protein. Effective conditions to produce a protein include, but are not limited to, appropriate media, bioreactor, temperature, pH and oxygen conditions that permit protein production. Such culturing conditions are well within the expertise of one of ordinary skill in the art.

Depending on the vector and host system used for production, resultant CHV proteins may either remain within the recombinant cell; be secreted into the fermentation medium; be secreted into a space between two cellular membranes, such as the periplasmic space in $E.$ $coli$; or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a CHV protein of the present invention or to a mimetope thereof. Such antibodies are also referred to herein as anti-CHV antibodies. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce CHV proteins of the present invention. Antibodies raised against defined proteins or mimetopes can be advantageous because such antibodies are not substantially contaminated with antibodies against other substances that might otherwise cause interference in a diagnostic assay or an assay to monitor recombinant CHV administration, or side effects if used in a therapeutic composition.

Antibodies of the present invention have a variety of potential uses that are within the scope of the present invention. For example, such antibodies can be used (a) as compounds to monitor recombinant CHV or recombinant CHV genome administration, (b) as therapeutic compounds to passively immunize an animal in order to protect the animal from CHV infection, and/or (c) as reagents in assays to detect CHV infection.

One embodiment of the present invention is a therapeutic composition that includes a recombinant CHV, a recombinant CHV genome, or a mixture (i.e., combination) of one or more recombinant CHVs and/or recombinant CHV genomes. As used herein, a therapeutic composition, or vaccine, is a formulation that, when administered to an animal in an effective manner, is capable of protecting that animal from a disease against which the therapeutic composition is targeted. Some therapeutic compositions of the present invention can modulate (i.e., either elicit or suppress) an immune response to protect an animal from disease, whereas other therapeutic compositions can protect an animal in other ways, as disclosed herein. A therapeutic composition of the present invention can be used to prevent and/or treat a disease depending on whether the composition is administered as a prophylactic or after the animal has the disease.

A therapeutic composition of the present invention, when administered to an animal in an effective manner, can infect the cells of the animal (in a manner essentially harmless to the animal) and direct the production of a protective compound able to protect the animal from a disease targeted by the therapeutic composition. If a recombinant CHV includes a protective compound in its envelope and/or capsid, the CHV can function as an immunogen per se.

As disclosed herein, therapeutic compositions can be designed to target a variety of diseases, depending on the nature of the heterologous nucleic acid molecule(s) included in such recombinant CHV and recombinant CHV genomes. Examples of such diseases, and the nature of the corresponding heterologous nucleic acid molecules, are disclosed herein. Furthermore, therapeutic compositions of the present invention can comprise multivalent vaccines. For example, a CHV genome can encode a variety of protective compounds, and/or more than one recombinant CHV genome and/or recombinant CHV can be administered. The present invention also includes the use of a recombinant CHV or recombinant CHV genome to protect an animal against CHV infection. Such a therapeutic composition can, but need not, include a heterologous nucleic acid molecule.

A therapeutic composition of the present invention is preferably administered to a canid, due to the host range specificity of CHV. Suitable canids include dogs (including domesticated and wild dogs), foxes, wolves, jackals, coyotes, and other members of the family Canidae. Particularly preferred canids to treat include domesticated dogs.

It is, however, also within the scope of the present invention to administer therapeutic compositions to other animals. Recombinant CHV can be administered to any animal susceptible to such therapy. Without being bound by theory, it is believed that sufficiently high doses of a recombinant CHV composition of the present invention may be infectious in other animals, particularly other mammals. Mink and other mink-like mammals (e.g., those of the family Mustelidae, such as ermines, ferrets, fishers, martens, otters, and weasels), in particular, may be susceptible to CHV infection, as suggested by the ability of CHV to infect mink lung cells. The host range of recombinant CHV of the present invention can also be altered, as disclosed herein, to infect other animal cells. It is also to be noted that CHV genomes of the present invention can be administered as naked DNA vaccines or in association with other carriers (e.g., liposomes). In accordance with these embodiments, any animal, including, but not limited to, mammals, birds, amphibians, and arthropods (including arachnids and insects) can be administered a therapeutic composition of the present invention. Preferred animals to treat include dogs, cats, humans, ferrets, prairie dogs, other rodents, horses, cattle, sheep, pigs, and poultry, as well as other pets, work animals, economic food animals and zoo animals.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the vaccine can also include an adjuvant and/or a carrier. One advantage of live virus-based vaccines, such as the recombinant CHVs of the present invention, is that adjuvants and carriers are not required to produce an efficacious vaccine, and in some cases, the advantages of recombinant CHV vaccines of the present invention would be precluded by the use of some adjuvants. However, it should be noted that use of adjuvants or carriers is not precluded by the present invention. Adjuvants are typically substances that generally enhance the immune response of an animal to a specific antigen. Suitable adjuvants include, but are not limited to, other bacterial cell wall components; aluminum-based salts; calcium-based salts; silica; polynucleotides; toxoids; serum proteins; other viral coat proteins; other bacterial-derived preparations; block copolymer adjuvants, such as Hunter's Titermax adjuvant (Vaxcell™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

In one embodiment, a therapeutic composition of the present invention is administered to an animal in an effective manner to enable the animal to produce sufficient protective compound(s) and/or to directly mount a sufficient immune response to protect the animal from disease. Acceptable protocols to administer therapeutic compositions in an effective manner include enumeration of individual dose size, number of doses, frequency of dose administration, and mode of administration. Determination of such protocols can be accomplished by those skilled in the art. A suitable single dose is a dose that is capable of protecting an animal from disease when administered one or more times over a suitable time period.

A preferred single dose of a recombinant CHV of the present invention is from about $1 \times 10^4$ to about $1 \times 10^7$ virus plaque forming units (pfu) per kilogram body weight of the animal. Booster vaccinations can be administered from about 2 weeks to several years after the original vaccination. Booster vaccinations preferably are administered when the immune response of the animal becomes insufficient to protect the animal from disease. A preferred administration schedule is one in which from about $1\times10^4$ to about $1\times10^7$ virus plaque forming units per kilogram (kg) body weight of the animal are administered from about 1 to about 2 times over a time period of from about 12 to about 18 months. Modes of administration can include, but are not limited to, subcutaneous, intradermal, intravenous, intranasal, oral, transdermal and intramuscular routes.

A recombinant CHV genome can be administered in a variety of ways, with intramuscular, subcutaneous, intradermal, transdermal, intranasal and oral routes of administration being preferred. A preferred single dose of a recombinant CHV genome ranges from about 1 nanogram (ng) to about 100 micrograms ($\mu$g), depending on the route of administration and/or method of delivery, as can be determined by those skilled in the art; see, for example, Wolff et al., 1990, *Science* 247, 1465–1468. Suitable delivery methods include, for example, injection, as drops, aerosolized and/or topical administration. Suitable excipients include, for example, physiologically acceptable aqueous solutions (e.g., phosphate buffered saline as well as others disclosed above), liposomes (including neutral or cationic liposomes), and other lipid membrane-based vehicles (e.g., micelles or cellular membranes).

In one embodiment, a therapeutic composition of the present invention is administered to a dam to protect her offspring from disease. In this method, the dam is administered the therapeutic composition at such a time as to be able to develop an immune response such that she can passively transfer antibodies produced against a protective compound of the present invention to her offspring. Such a method can also be used to protect offspring from CHV infection and is particularly useful since neonates are most affected by CHV infection.

The efficacy of a therapeutic composition of the present invention to protect an animal from disease can be tested in a variety of ways including, but not limited to, detection of protective protein or RNA within the treated animal, detection of protective antibodies within the treated animal, detection of cellular immunity within the treated animal, or challenge of the treated animal with an appropriate infectious agent, or other disease component, to determine whether the animal is now protected from the disease caused by such an agent or other component. Such techniques are known to those skilled in the art. In one embodiment, anti-CHV antibodies of the present invention are used to monitor recombinant CHV infection and can be used to distinguish wild type infections from infections using recombinant CHV of the present invention (i.e., by using antibodies that specifically recognize either recombinant CHV of the present invention or wild type virus).

In one embodiment, the efficacy of a therapeutic composition of the present invention may be improved by co-administering (a) a recombinant CHV or recombinant CHV genome and (b) a protective compound (e.g., subunit vaccine) encoded by a CHV nucleic acid molecule or heterologous nucleic acid molecule present in the CHV genome. While not being bound by theory, it is believed that administration of a protective compound in conjunction with the recombinant CHV or CHV genome can boost the immune response, particularly the antibody titer. The protective compound can be administered prior to, concomitant with, and/or following administration of the recombinant CHV or CHV genome. The protective compound can be either produced naturally, recombinantly, or synthetically. The protective compound should be sufficiently pure to allow for effective use of the compound as a vaccine; i.e., it should not cause substantial side effects. The protective compound can be joined (i.e., conjugated) to a carrier or other material that enhances the immunogenicity of the compound.

The present invention also includes the use of CHV nucleic acid molecules, CHV proteins, and anti-CHV antibodies as therapeutic compositions to protect animals from CHV infection. Methods to administer such compositions to canids are known to those skilled in the art. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes. A CHV nucleic acid molecule, including recombinant molecules, can be administered as described herein for administration of CHV genomes or CHV of the present invention. Recombinant molecules including heterologous nucleic acid molecules can also be used as therapeutic compositions to protect an animal from disease, using methods as disclosed herein.

It is also within the scope of the present invention to use isolated CHV proteins, mimetopes, CHV nucleic acid molecules and anti-CHV antibodies of the present invention as diagnostic reagents to detect CHV infection. Methods to use such diagnostic reagents to diagnose infection are well known to those skilled in the art.

The following examples are provided for the purposes of illustration and are not intended to limit the scope of the present invention.

EXAMPLES

It is to be noted that the Examples include a number of molecular biology, virology, microbiology, immunology and biochemistry techniques considered to be known to those skilled in the art. Disclosure of such techniques can be found, for example, in Sambrook et al., ibid.; Ausubel et al, 1993, *Current Protocols in Molecular Biology*, Greene/Wiley Interscience, New York, N.Y.; Graham et al, ibid.; and related references. Ausubel et al, ibid. is incorporated by reference herein in its entirety. Nucleic acid and amino acid sequences of the present invention were compared to known sequences using BLAST (NCBI) and DNAsis (Hitachi Software, San Bruno, Calif.).

Example 1

This Example demonstrates the isolation of certain CHV nucleic acid molecules of the present invention.

The disclosed CHV nucleic acid molecules were amplified from a CHV genome by PCR amplification using a variety of primers designed in view of published herpesvirus sequences. The following PCR conditions were used: 0.2 millimolar (mM) dNTPs, 1 µM of each primer, 1× PCR buffer (available from Perkin Elmer Cetus, Emeryville, Calif.), 50 ng of CHV DNA (isolated from CHV strain D 004 as described in Example 2) and 0.5 µl of a thermostable DNA polymerase, all in an about 100 µl total volume. The PCR reactions included an initial denaturation for 3 minutes at 95° C., five cycles of 1 minute each at 95° C., 35° C. for 1 minute, 72° C. for 1 minute, 35 cycles of 1 minute each at 95° C., 37° C. for 1 minute, 72° C. for 1 minute, and finally 10 minutes at 72° C. The resultant PCR products were directly cloned into the PCRII TA cloning vector (available from Invitrogen Corp., San Diego, Calif.) according to the manufacturer's specifications. Primers which were successful in amplifying fragments from a CHV genome, which was determined to be very AT-rich compared to other herpesvirus genomes, are described below.

A. Isolation of a nucleic acid molecule including a partial CHV dUTPase gene and a partial CHV UL51 gene The following primers were designed using dUTPase protein sequence derived from HSV-1 (McGeoch et al, 1988, *J. Gen. Virol.* 69, 1531–1574), EHV-4 (Riggio et al, 1993, *Arch. Virol.* 133, 171–178), BHV-1 (Liang et al, 1993, *Virology* 195, 42–50), and EBV (Lees et al, 1993, *Virology* 195, 578–586: Primer 212S (dUTPase forward) having nucleic acid sequence 5' GG CGA ATT CCI AAR MGI GAI GAR GAY G 3', denoted herein as SEQ ID NO:39; and Primer 365A (dUTPase reverse) having nucleic acid sequence 5' C GCG GAT CCI GTI SWI CCY AAI CC 3', denoted herein as SEQ ID NO:40. These primers led to the amplification of an about 743 nucleotide fragment, which was significantly larger than expected. Nucleic acid sequence analysis, described in Example 3, indicated that the 743 nucleotide fragment contained part of the CUL51 gene as well as part of the CdUTPase gene; as such, the fragment was denoted nCdUTP/CUL51$_{743}$. Nucleic acid sequence analysis also indicated that the dUTPase reverse primer actually hybridized to a region of the CHV DNA genome within the CUL51 gene rather than within the CdUTPase gene. It is believed that the mispriming was due to nucleotide position 19 of SEQ ID NO:40 being a Y instead of an R; the latter sequence would have matched more closely to the targeted priming region, about 290 nucleotides upstream from the 3' end of nucleic acid molecule nCdUTP/CUL51$_{743}$. This result demonstrates the sensitivity of PCR amplification to primer design.

B. Isolation of a CHV gE nucleic acid molecule

The following primers were designed using gE protein sequence derived from FHV-1 (Spatz et al, 1994, *J Gen. Virol.* 75, 1235–1244 ), EHV-1 (Elton et al, 1991, *Gene* 101, 203–208), and BHV-1 (Leung-Tack et al, 1994, *Virology* 199, 409–421): Primer 197S (gE forward) having nucleic acid sequence 5' GGC GAA TTC TAY CAY WSI CAY GTI TA 3', denoted herein as SEQ ID NO:41; and Primer 441A (gE reverse) having nucleic acid sequence 5' CGC GGA TCC RTC RTT ISW IGG DAI ISW IGT 3', denoted herein as SEQ ID NO:42. These primers led to the amplification of an about 750 nucleotide fragment, referred to herein as nCgE$_{750}$ C. Isolation of a CHV TK nucleic acid molecule The following primers were designed using TK protein sequence derived from HSV-1 (McGeoch et al., 1988, ibid.), HSV-2 (Kit et al, 1987, *Antimicrob. Agents Chemother.* 31, 1483–1490, BHV-1 (Kit et al, U.S. Pat. No. 4703011, issued Oct. 27, 1987), FHV-1 (Nunberg et al, 1989, *J. Virol.* 63, 3240–3249), EHV-1 (Robertson et al, 1988, *Nuc. Acids Res.* 16, 11303–11317), and PRV (Prieto et al, 1991, *J. Gen. Virol.* 72, 1435–1439): Primer EJH 002 (TK forward) having nucleic acid sequence 5' GGC GAA TTC GGI AAR WSI ACI RC 3', denoted herein as SEQ ID NO:43; and Primer EJH004 (TK reverse) having nucleic acid sequence 5' GGC GGA TCC GGT TGI CKR TC 3', denoted herein as SEQ ID NO:44. These primers led to the amplification of an about 280 nucleotide fragment, referred to herein as nCTK$_{280}$ D. Isolation of a nucleic acid molecule including CHV gC and CHV UL45 genes The following primers were designed using gC and UL45 sequences derived from Limbach et al., ibid.: Primer gC sense, having nucleic acid sequence 5' CGCGGATCCAAG-GTAATAAGTCAAAATGAG 3', denoted herein as SEQ ID NO:45; and Primer gC ant, having nucleic acid sequence 5' CGCGGATCCGACAAAAACAAAAAGTAATG 3', denoted herein as SEQ ID NO:46. These primers led to the amplification of an about 2100 nucleotide fragment, referred to herein as nCgC/CUL45$_{2100}$.

E. Attempt to isolate a CHV ribonucleotide reductase gene

The following primers were designed using ribonucleotide subunit small subunit protein sequence derived from HSV-1 (McGeoch et al, 1988, ibid.), PRV (Dewind et al, 1993, *J. Gen. Virol.* 74, 351–359), EHV-1 (Telford et al, 1992, *Virology* 189, 04–316) and BHV-1 (Simard et al, 1992, *Virology* 190, 689–701): Primer EJH 021 (RR forward) having nucleic acid sequence 5' CCG AAT TCY TIA TGA THY TIA THG ARG G 3', denoted herein as SEQ ID NO:47; and Primer EJH022 (RR reverse) having nucleic acid sequence 5' CCG GAT CCY TCR AAR AAR TTI GTR TGY TT 3', denoted herein as SEQ ID NO:48. These primers did not lead to the amplification of a fragment under a variety of magnesium and amplification conditions, suggesting the lack of a coding region for a ribonucleotide reductase small subunit in CHV. As a control, these primers were shown to be able to easily amplify a ribonucleotide reductase small subunit fragment from an FHV genome.

Example 2

This Example describes the production of CHV genomic libraries.

Canine herpesvirus strain D 004 (Binn, et al., 1967, *Proc. Soc. Exp. Biol. Med.* 126, 140) was obtained from ATCC. virus were propagated on Madin-Darby Canine Kidney (MDCK) cells according to standard virological procedures. Viral DNA was prepare from CHV-infected MDCK cells by previously described methods; see, for example, Walboomers et al, ibid. The viral DNA was digested with restriction endonucleases HindIII, PstI, EcoRI or XbaI, and the resultant digests were cloned into either vector pSP72 (available from Promega Corp., Madison, Wis.), or pLitmus 28 or 38 (available from New England Biolabs, Beverly, Mass.). DNA was prepared from the resultant recombinant plasmids and the inserts were sorted according to size.

Example 3

This Example describes the isolation of genomic HindIII restriction fragment nucleic acid molecules containing CdUTPase nucleic acid sequences and the nucleic acid sequencing of at least regions of these nucleic acid molecules.

Nucleic acid molecule nCdUTP/CUL51$_{743}$ produced as described in Example 1, was labelled with either $^{32}$P or digoxigenin (available from Boehringer Mannheim Biochemicals (BMB), Indianapolis, Ind.) and used to screen the CHV HindIII fragment-containing library, either by colony hybridization or Southern blotting. Two clones hybridized with nCdUTP/CUL51$_{743}$, one containing a HindIII fragment of about 3000 nucleotides, referred to herein as nCHin$_{3000}$, and another containing a HindIII fragment of about 1,900 nucleotides, referred to herein as nCHin$_{1900}$. The HindIII fragments were further characterized by restriction mapping, as shown in FIG. 1. Also shown is the relative location of nCdUTP/CUL51$_{743}$ (referred to therein as nCdUTP$_{743}$) with respect to the HindIII fragments.

Nucleic acid molecules nCdUTP/CUL51$_{743}$, nCHin$_{3000}$, and nCHin$_{1900}$ were submitted to DNA sequence analysis, using a sequencing strategy as depicted in FIG. 1. Among sequences obtained were SEQ ID NO:13 and SEQ ID NO:14, which include SEQ ID NO:15 and SEQ ID NO:33, as well as SEQ ID NO:21, SEQ ID NO:23, SEQ ID NO:25 and SEQ ID NO:27. The relative locations of genes included in these sequences (i.e., the CUL52, CUL51, CdUTPase and CUL48 genes) are shown in FIG. 1. Also shown is the apparent location of the CUL49 gene.

SEQ ID NO:13 and SEQ ID NO:14 represent the deduced nucleic acid sequences of the two complementary strands of nCdUTP/CUL51$_{743}$. SEQ ID NO:13 includes a partial coding region for a CdUTPase protein of about 152 amino acids, denoted herein as nCdUTP$_{459}$ and represented by SEQ ID NO:15, assuming a first in-frame codon spanning about nucleotides 3–5, and a stop codon spanning about nucleotides 459–461 of SEQ ID NO:13. The amino acid sequence of the encoded protein PCdUTP$_{152}$ is represented by SEQ ID NO:16. SEQ ID NO:14 includes a partial coding region for a CUL51 protein of about 86 amino acids, denoted herein as nCUL51$_{261}$ and represented by SEQ ID NO:33, assuming a first in-frame codon spanning about nucleotides 1–3, and a stop codon spanning about nucleotides 259–261 of SEQ ID NO:14. The amino acid sequence of the encoded protein PCUL51$_{86}$ is represented by SEQ ID NO:34.

SEQ ID NO:21 and SEQ ID NO:23 represent the deduced nucleic acid sequences of the two complementary strands of nCUL48$_{294}$. SEQ ID NO:21 includes a partial coding region for a CUL48 protein of about 97 amino acids, denoted herein as nCUL48$_{291}$ and represented by SEQ ID NO:24, assuming a first in-frame codon spanning about nucleotides 3–5 of SEQ ID NO:21. The amino acid sequence of the encoded protein PCUL48$_{97}$ is represented by SEQ ID NO:22.

SEQ ID NO:25 and SEQ ID NO:27 represent the deduced nucleic acid sequences of the two complementary strands of nCUL52$_{146}$. SEQ ID NO:25 includes a partial coding region for a CUL52 protein of about 48 amino acids, denoted herein as nCUL52$_{144}$ and represented by SEQ ID NO:28, assuming a first in-frame codon spanning about nucleotides 1–3 of SEQ ID NO:25. The amino acid sequence of the encoded protein PCUL52$_{48}$ is represented by SEQ ID NO:26.

Example 4

This Example describes a method to identify restriction enzymes that effect limited cleavage of the CHV genome. Also described is the isolation and sequencing of an AscI fragment containing the entire U.S. region of CHV.

Figure 2:
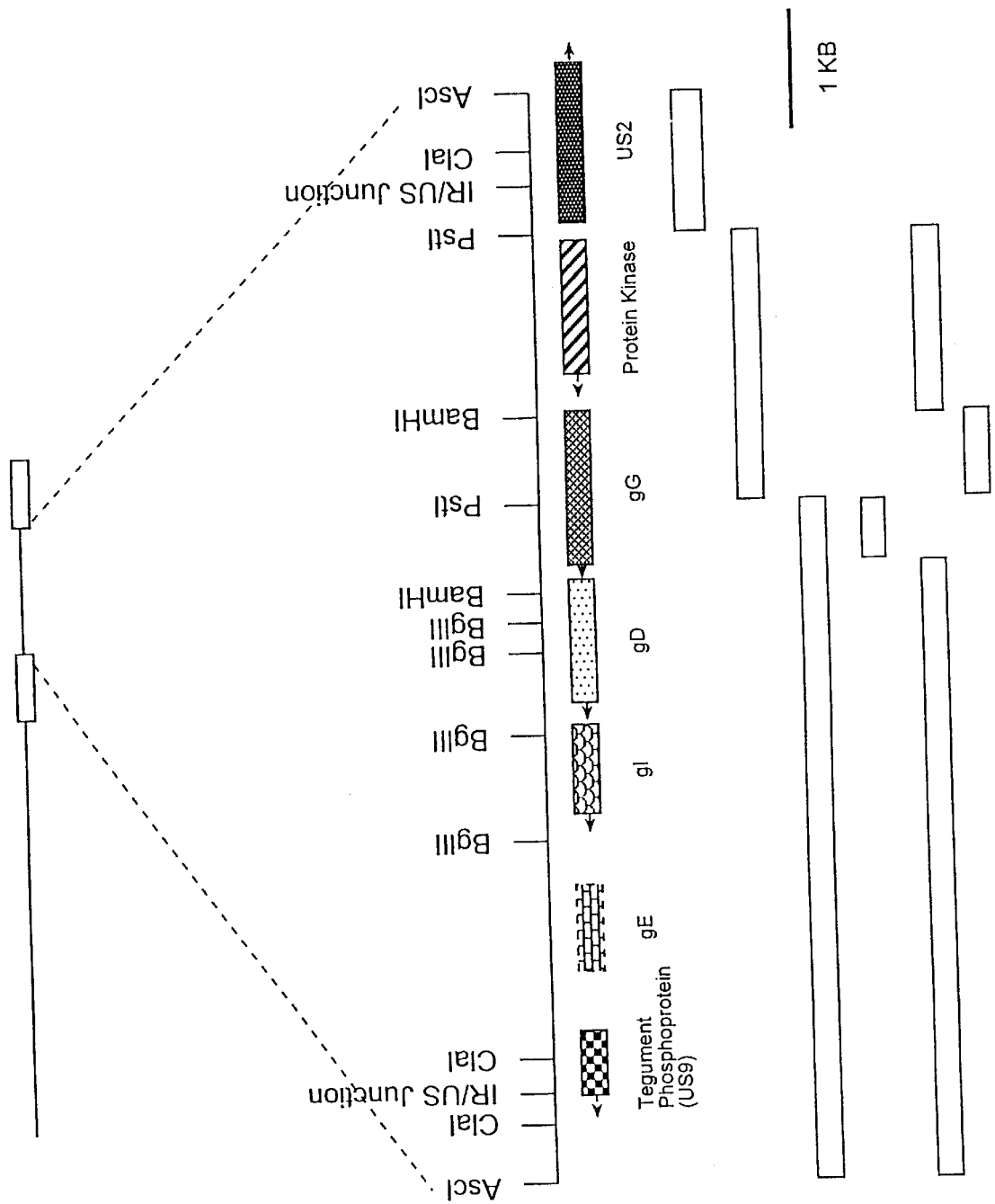
Figure 3:
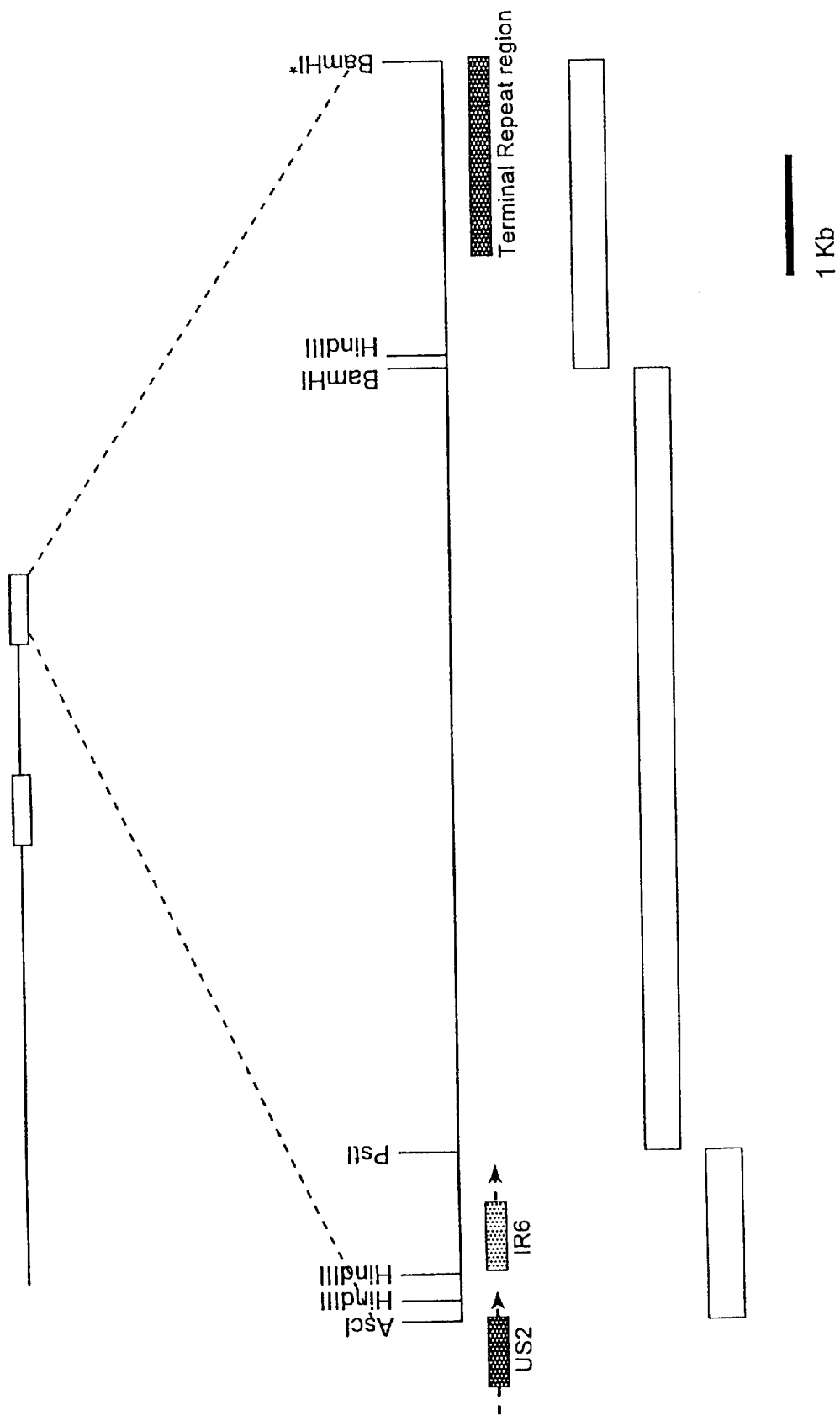

CHV DNA was evaluated for recognition sites for several restriction enzymes with 8-base, or larger, recognition sites. No sites were found for enzymes Sse8387I, I-Sce-I, or NotI. Two AscI sites were found, which were mapped to sites within the inverted repeats surrounding the US region, specifically within CHV gene US2 (see FIG. 2). The AscI fragments, of 9.3, 10.0 and approximately 100–120 kilobases (kb), were cloned into pLitmus 38 and submitted to restriction enzyme mapping analysis. The restriction map of the 9.3-kb AscI fragment, denoted herein as nCAsc9300 is shown in FIG. 2; this fragment apparently contains the entire CUS region, as well as small portions of the internal and terminal IR regions. The 10.0-kb AscI-blunt fragment, denoted herein as nCAsc1000, contains most of the terminal IR region and is shown in FIG. 3. The about 100–120-kb AscI-blunt fragment contains the remainder of the CHV genome. Both AscI sites are located just 5' of the diploid copies of the CHV homolog of the EHV-1 IR6 gene (Breeden et al, 1992, *Virology* 191, 649–660), and the orf1 of BHV-1 (Leung-Tack et al, ibid.). The AscI sites appear to be located within an open reading frame that is the homolog of the EHV US1 gene (Breeden et al ibid.) and the HSV-1 US2 gene (McGeoch et al, 1985, *J. Mol. Biol* 181, 1–13), although the size is somewhat different from these other genes. No function has been ascribed to the HSV-1 US2 gene product, but it has been shown to be dispensable for growth in tissue culture and to attenuate the virus (Meignier et al, 1988, *Virology* 162, 251–254).

Nucleic acid molecules nCAsc$_{9300}$ and nCAsc$_{10000}$ were submitted to DNA sequence analysis using a strategy as depicted in FIG. 2 and FIG. 3. Among sequences obtained were SEQ ID NO:1, SEQ ID NO:2, SEQ ID NO:17, SEQ ID NO:19, SEQ ID NO:29, and SEQ ID NO:31 The relative locations of genes included in these sequences (i.e., the CUS9, CgI, CgD, CgG, CPK, CUS2, and CIR6 genes) are shown in FIG. 2 and FIG. 3. Also shown is the putative location of the CgE gene.

SEQ ID NO:1 and SEQ ID NO:2 represent the deduced nucleic acid sequences of the two complementary strands of nCUS$_{5495}$. Translation of SEQ ID NO:1 and SEQ ID NO:2 indicates that nucleic acid molecule nCUS$_{5495}$ encodes CIR6, CUS2, CPK and CgG proteins as well as a portion of a CgD protein. Specifically, SEQ ID NO:2 includes: a coding region for a CIR6 protein of about 183 amino acids, denoted herein as nCIR6$_{552}$ and represented by SEQ ID NO:3, assuming a start codon spanning about nucleotides 4566–4568 and a stop codon spanning about nucleotides 5115–5117 of SEQ ID NO:2; and a coding region for a CUS2 protein of about 391 amino acids, denoted herein as nCUS2$_{1176}$ and represented by SEQ ID NO:5, assuming a start codon spanning about nucleotides 3232–3234 and a stop codon spanning about nucleotides 4405–4407 of SEQ ID NO:2. The amino acid sequences of the respective encoded proteins PCIR6$_{183}$ and PCUS2$_{391}$ are represented by SEQ ID NO:4 and SEQ ID NO:6. SEQ ID NO:1 includes: a coding region for a CPK protein of about 400 amino acids, denoted herein as nCPK$_{1203}$ and represented by SEQ ID NO:7, assuming a start codon spanning about nucleotides 2384–2386 and a stop codon spanning about nucleotides 3584–3586 of SEQ ID NO:1; a coding region for a CgG protein of about 415 amino acids, denoted herein as $nCgG_{1248}$ and represented by SEQ ID NO:9, assuming a start codon spanning about nucleotides 3698–3700 and a stop codon spanning about nucleotides 4943–4945 of SEQ ID NO:1; and a partial coding region for a CgD protein of about 119 amino acids, denoted herein as $nCgD_{357}$ and represented by SEQ ID NO:11, assuming a start codon spanning about nucleotides 5137–5139. The amino acid sequences of the respective encoded proteins $PCPK_{400}$, $PCgG_{415}$, and $PCgD_{119}$ are represented by SEQ ID NO:8, SEQ ID NO:10 and SEQ ID NO:12.

SEQ ID NO:17 and SEQ ID NO:19 represent the deduced nucleic acid sequences of the two complementary strands of $nCUS9_{579}$. SEQ ID NO:17 includes a coding region for a CUS9 protein of about 149 amino acids, denoted herein as $nCUS9_{450}$ and represented by SEQ ID NO:20, assuming a start codon spanning about nucleotides 54–56 and a stop codon spanning about nucleotides 501–503 of SEQ ID NO:17. The amino acid sequence of the encoded protein $PCUS9_{149}$ is represented by SEQ ID NO:18.

SEQ ID NO:29 and SEQ ID NO:31 represent the deduced nucleic acid sequences of the two complementary strands of $nCgI_{161}$, SEQ ID NO:29 includes a partial coding region for a CgI protein of about 53 amino acids, denoted herein as $nCgI_{159}$ and represented by SEQ ID NO:32, assuming a first in-frame codon spanning about nucleotides 3–5 of SEQ ID NO:29. The amino acid sequence of the encoded protein $PCgI_{53}$ is represented by SEQ ID NO:30.

Example 5

This Example describes the nucleic acid sequencing of additional nucleic acid molecules of the present invention.

Nucleic acid molecule $nCTK_{280}$, produced as described in Example 1, was submitted to DNA sequence analysis to obtain the following sequences. SEQ ID NO:35 and SEQ ID NO:37 represent the deduced nucleic acid sequences of the two complementary strands of $nCTK_{280}$. SEQ ID NO:35 includes a partial coding region for a CTK protein of about 93 amino acids, denoted herein as $nCTK_{279}$ and represented by SEQ ID NO:38, assuming a first in-frame codon spanning about nucleotides 2–4 of SEQ ID NO:35. The amino acid sequence of the encoded protein $PCTK_{93}$ is represented by SEQ ID NO:36.

Example 6

This Example discloses the production of a recombinant CHV genome and recombinant CHV of the present invention.

A cassette including the human CMV immediate early promoter and the poly-adenylation signal from bovine growth hormone separated by a polylinker was PCR amplified from plasmid pcDNA3 (available from Invitrogen) using forward primer EJH058 having nucleic acid sequence 5' TCCCCCGGGGGCGCGCCTTGACATTGAT-TATTGAC 3', denoted SEQ ID NO:49, and reverse primer EJH059 having nucleic acid sequence 5' GCCCT-TAAGGGGCGCGCCAATGCGATGCAATTTCC 3', denoted SEQ ID NO:50. EJH058 has SmaI and AscI sites attached to the 5' end of pcDNA3 homologous sequences, and EJH059 has AflII and AscI sites attached to the 5' end of pcDNA3 homologous sequences. The resultant PCR amplified fragment of about 930 nucleotides was digested with SmaI and AflII and ligated into the SnaBI and AflII sites of plasmid pLitmus 38. This cloning procedure eliminated the entire polylinker region of pLitmus38. The resulting recombinant plasmid, denoted herein as pAscCMV/BGH, contains the CMV promoter - BGH polyadenylation signal cassette, with its original polylinker, in a plasmid such that the entire cassette can be excised with enzyme AscI. This cassette plasmid can also be prepared with other rare-cutting enzyme sites flanking the cassette.

Plasmid pAscCMV/BGH allows for the insertion of heterologous nucleic acid molecules between the CMV promoter and the BGH polyadenylation signal. The resulting heterologous nucleic acid molecule-containing cassette was excised from the plasmid for insertion into a CHV genome. For example, a heterologous nucleic acid molecule containing a lacZ gene was inserted into the polylinker region of pAscCMV/BGH such that the lacZ gene is expressed by the CMV promoter in a eukaryotic system. The cassette containing the lacZ gene, referred to herein as AscCMV/lacZ/BGH is then excised from the plasmid by AscI digestion and gel purified by standard methods.

About 5–10 μg of CHV DNA is digested with AscI, resulting in three fragments as disclosed herein. The DNA fragments are dephosphorylated with calf intestine alkaline phosphatase (available from BMB) for 10 minutes at 37° C.; the enzyme is then inactivated for by incubation for 10 minutes at 65° C. The phosphatase-treated digested CHV DNA is then subjected to extraction with phenol and phenol/chloroform and precipitated with ethanol.

The phosphatase-treated digested CHV genomic DNA is mixed with the gel-purified AscCMV/lacZ/BGH cassette at a molar ratio of approximately 1:2 under standard ligation conditions. Since the viral DNA is dephosphorylated, it should not be able to self ligate; thus all resultant ligated viral molecules should contain two copies of the inserted cassette. The ligated DNA is then subjected to phenol extraction and ethanol precipitated.

The precipitated ligated DNA is resuspended in hepes-buffered saline and submitted to standard viral transfection conditions, such as that described by Graham et al., ibid., along with appropriate controls (e.g., undigested viral DNA, digested and dephosphorylated viral DNA that was self-ligated, and no DNA). Resultant viral plaques are screened under an X-gal overlay for expression of β-galactosidase.

Example 7

This Example discloses the production of another recombinant CHV genome and recombinant CHV of the present invention.

A recombinant, or transfer, vector to be used in the production of a recombinant CHV having a heterologous nucleic acid molecule in a TK gene of the CHV genome is constructed as follows. A CHV TK nucleic acid molecule of the present invention (e.g., $nCTK_{280}$) is ligated into a pLitmus plasmid to produce a pCTK-Litmus plasmid. An expression cassette including a heterologous nucleic acid molecule (e.g., a lacZ gene or a nucleic acid molecule encoding an antigen isolated from a pathogenic organism) ligated to a CMV immediate early promoter and a BHV polyadenylation site in such a manner that the heterologous nucleic acid molecule is expressed in a eukaryotic cell is inserted into the CTK nucleic acid molecule within pCTK-Litmus such that there are CTK flanking sequences on either side of the expression cassette (e.g., into a restriction site internal to $nCTK_{280}$).

A recombinant CHV is produced by co-transfecting the recombinant vector and CHV DNA into canine MDCK cells using previously described methods; see, for example, Graham et al, ibid. Recombinant TK negative CHV are selected for by passage in bromodeoxyuridine; see, for example, Kit et al., 1983, *Virology* 130, 381–389. If the heterologous nucleic acid molecule is the lacZ gene, such recombinant CHV can also be selected as described in Example 6.

Example 8

This Example discloses the production of another recombinant CHV genome and recombinant CHV of the present invention.

A recombinant, or transfer, vector to be used in the production of a recombinant CHV having a heterologous nucleic acid molecule in a dUTPase gene of the CHV genome is constructed as follows. A CHV dUTPase nucleic acid molecule of the present invention (e.g., $nCdUTP_{459}$) is ligated into a pLitmus plasmid to produce a pCdUTP-Litmus plasmid. An expression cassette including a heterologous nucleic acid molecule (e.g., a lacZ gene or a nucleic acid molecule encoding an antigen isolated from a pathogenic organism) ligated to a CMV immediate early promoter and a BHV polyadenylation site in such a manner that the heterologous nucleic acid molecule is expressed in a eukaryotic cell is inserted into the CdUTP nucleic acid molecule within pCdUTP-Litmus such that there are CdUTPase flanking sequences on either side of the expression cassette (e.g., into a restriction site internal to $nCdUTP_{459}$).

A recombinant CHV is produced by co-transfecting the recombinant vector and CHV DNA into canine MDCK cells as described in Example 7. Recombinant dUTPase negative CHV are selected for by passage in mercurithio analogs of deoxyuridine; see, for example, Holliday et al, 1991, *Antiviral Research* 16, 197–203. If the heterologous nucleic acid molecule is the lacZ gene, such recombinant CHV can also be selected as described in Example 6. Recombinant virus carrying the foreign DNA of interest can also be selected by either by plaque hybridizations, or by dot-blot hybridizations of infected cell cultures. Verification of the proper insert within the CHV genome is conducted by Southern hybridization analysis.

Example 9

This Example discloses the production of a recombinant CHV by co-transfection of a set of overlapping cosmid clones comprising the entire viral CHV genome.

A library of CHV cosmid clones is created in the cosmid vector SuperCos (available from Stratagene Cloning Systems, La Jolla, Calif.) according to manufacturer's specifications, except that the vector is modified to contain one or more restriction sites not present in CHV genomic DNA (e.g., Sse83871, I-Sce-I, or NotI) so that the cosmid inserts can be excised prior to cotransfection. A heterologous nucleic acid molecule in an expression cassette, such as one of those described in Examples 6–8, is inserted into a cosmid clone using standard procedures. A recombinant CHV is produced by co-transfection of a set of overlapping cosmid clones comprising the entire viral CHV genome, including the cosmid comprising a heterologous nucleic acid molecule, using techniques as described in van Zihl et al., 1988, *J. Virol.* 62, 2191–2195.

Example 10

This Example describes the nucleic acid sequencing of additional nucleic acid molecules of the present invention.

Nucleic acid molecules $nCAsc_{9300}$ and $nCAsc_{10000}$, produced as described in Example 4, were submitted to additional DNA sequence analysis. The resultant nucleic acid sequences were compiled to produce SEQ ID NO:51 and SEQ ID NO:52. SEQ ID NO:51 and SEQ ID NO:52 represent the deduced nucleic acid sequences of the two complementary strands of a nucleic acid molecule referred to herein as $nCUS_{10592}$. Nucleic acid molecule $nCUS_{10592}$ includes the entire US region of CHV plus terminal repeat and internal repeat sequences. Analysis of SEQ ID NO:51 indicates that the US region spans from nucleotides about 2047 through about 9724 of SEQ ID NO:51, whereas the terminal repeat sequences and inverted repeat sequences span from nucleotides about 1 through about 2046 and from nucleotides about 9725 through about 10592, respectively, of SEQ ID NO:51.

Figure 4:
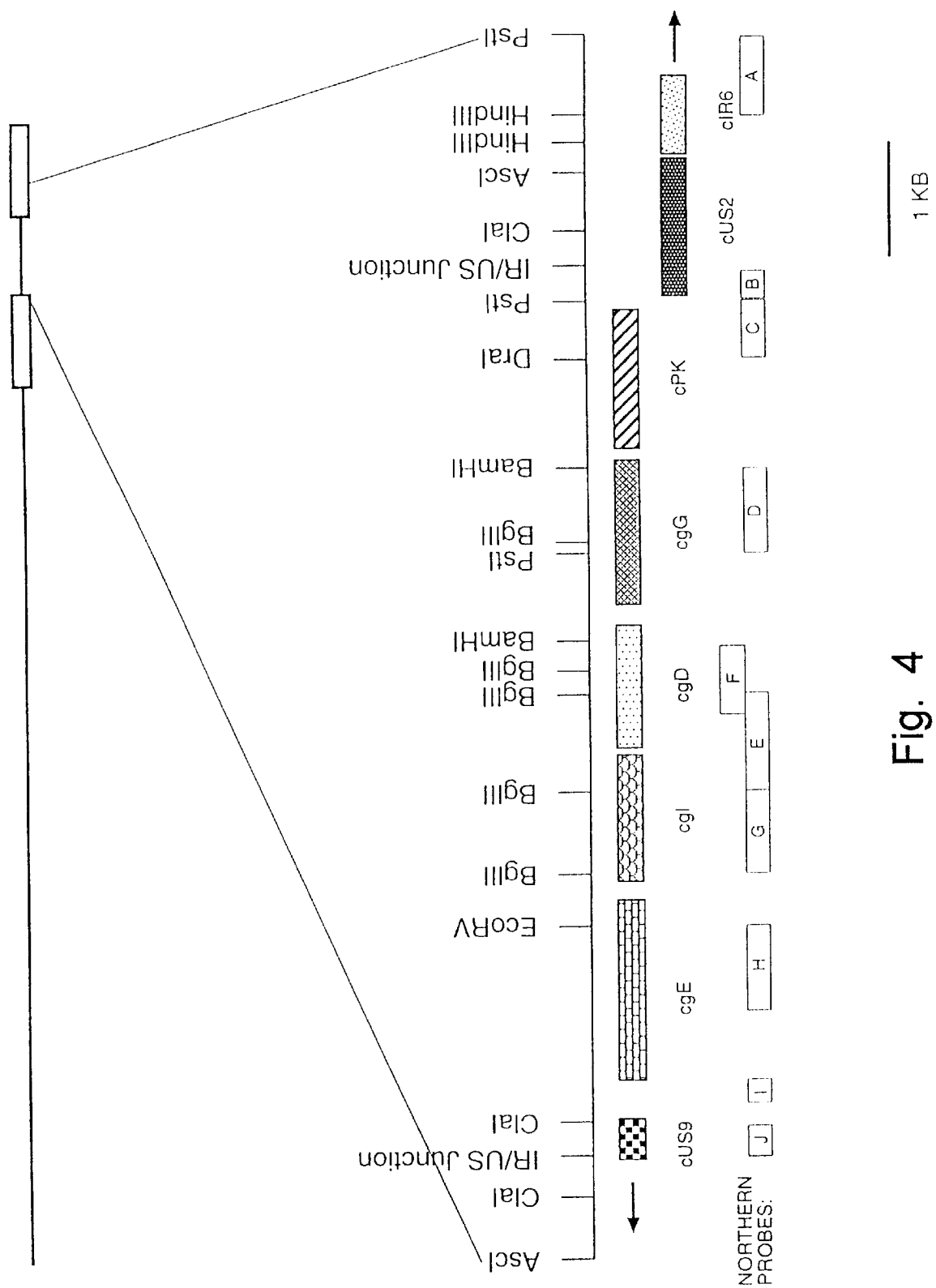

Translation of SEQ ID NO:51 and SEQ ID NO:52 indicates that nucleic acid molecule $nCUS_{10592}$ contains at least the following open reading frames: CIR6, CUS2, CPK, CgG, CgD, CgI, CgE, CUS8.5 and CUS9. The relative locations of these open reading frames is shown in FIG. 4.

Specifically, SEQ ID NO:52 includes: the coding strand of $nCIR6_{552}$ (having SEQ ID NO:3) which encodes a CIR6 protein of about 183 amino acids, assuming a start codon spanning about nucleotides 9672–9674 and a stop codon spanning about nucleotides 10221–10223 of SEQ ID NO:52; and the coding strand of $nCUS2_{1176}$ (having SEQ ID NO:5) which encodes a CUS2 protein of about 391 amino acids, assuming a start codon spanning about nucleotides 8338–8340 and a stop codon spanning about nucleotides 9511–9513 of SEQ ID NO:52. Nucleic acid molecules $nCIR6_{552}$ and $nCUS2_{1176}$ are also described in Example 4 in relation to $nCUS_{5495}$, as are the corresponding nucleic acid sequences and amino acid sequences they encode.

SEQ ID NO:51 includes: the coding strand of $nCPK_{1203}$ (having SEQ ID NO:7) which encodes a CPK protein of about 400 amino acids, assuming a start codon spanning about nucleotides 2375–2377 and a stop codon spanning about nucleotides 3575–3577 of SEQ ID NO:51; the coding strand of $nCgG_{1248}$ (having SEQ ID NO:9) which encodes a CgG protein of about 415 amino acids, assuming a start codon spanning about nucleotides 3689–3691 and a stop codon spanning about nucleotides 4934–4936 of SEQ ID NO:51; the coding strand of $nCgD_{1038}$ (having SEQ ID NO:53, and including SEQ ID NO:11) which encodes a CgD protein of about 345 amino acids, assuming a start codon spanning about nucleotides 5128–5130 and a stop codon spanning about nucleotides 6163–6165 of SEQ ID NO:51; the coding strand of $nCgI_{1095}$ (having SEQ ID NO:55, and including SEQ ID NO:29) which encodes a CgI protein of about 364 amino acids, assuming a start codon spanning about nucleotides 6225–6227 and a stop codon spanning about nucleotides 7317–7319 of SEQ ID NO:51; the coding strand of $nCgE_{1569}$ (having SEQ ID NO:57) which encodes a CgE protein of about 522 amino acids, assuming a start codon spanning about nucleotides 7467–7469 and a stop codon spanning about nucleotides 9033–9035 of SEQ ID NO:51; the coding strand of $nCUS8.5_{237}$ (having SEQ ID NO:59) which encodes a CUS8.5 protein of about 78 amino acids, assuming a start codon spanning about nucleotides 9028–9030 and a stop codon spanning about nucleotides 9262–9264 of SEQ ID NO:51; and the coding strand of $nCUS9_{360}$ (having SEQ ID NO:61) which encodes a CUS9 protein of about 119 amino acids, assuming a start codon spanning about nucleotides 9376–9378 and a stop codon spanning about nucleotides 9733–9735 of SEQ ID NO:51. SEQ ID NO:61 differs from the coding region reported for CUS9 in Example 4 (e.g., SEQ ID NO:20), in that additional sequence analysis indicated that SEQ ID NO:17 included a sequencing error resulting in a frameshift, leading to a longer deduced open reading frame. Nucleic acid molecules $nCPK_{1203}$ and $nCgG_{1248}$ are also described in Example 4 in relation to $nCUS_{5495}$, as are the corresponding nucleic acid sequences and amino acid sequences they encode. The amino acid sequences of the respective encoded proteins $PCgD_{345}$, $PCgI_{364}$ $PCgE_{522}$, $PCUS8.5_{78}$, and $PCUS9_{119}$ are represented by SEQ ID NO:54, SEQ ID NO:56, SEQ ID NO:58, SEQ ID NO:60 and SEQ ID NO:62, respectively.

Example 11

This Example describes the nucleic acid sequencing of additional nucleic acid molecules of the present invention.

Figure 5:
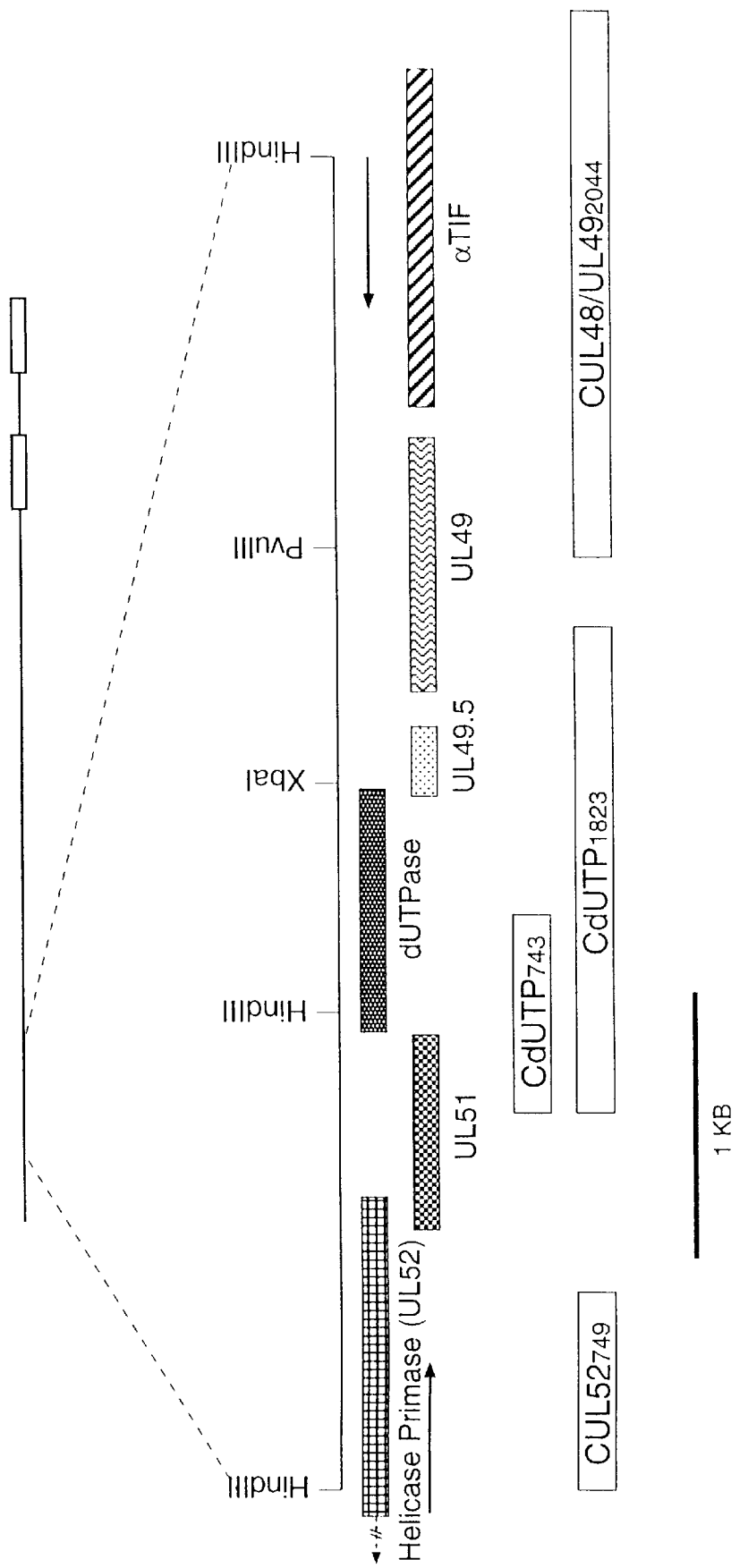

Nucleic acid molecules $nCHin_{3000}$, and $nCHin_{1900}$, produced as described in Example 3, were submitted to additional DNA sequence analysis. Also submitted to additional nucleic acid sequence analysis was nucleic acid molecule $nCHin_{8500}$, a HindIII fragment shown to include the 3' end of CUL48 as well as CgC and CUL45. The resultant nucleic acid sequences were compiled to produce SEQ ID NO:63, SEQ ID NO:64, SEQ ID NO:77, SEQ ID NO:78, SEQ ID NO:85, and SEQ ID NO:86. SEQ ID NO:63 and SEQ ID NO:63 represent the deduced nucleic acid sequences of the two complementary strands of a nucleic acid molecule referred to herein as $nCUL49/CUL48_{2044}$. Translation of SEQ ID NO:63 and SEQ ID NO:64 indicates that nucleic acid molecule $nCUL49/CUL48_{2044}$ contains at least the following open reading frames: CUL48 and the 3' end of CUL49. SEQ ID NO:77 and SEQ ID NO:78 represent the deduced nucleic acid sequences of the two complementary strands of a nucleic acid molecule referred to herein as $nCUL_{1823}$. Translation of SEQ ID NO:77 and SEQ ID NO:78 indicates that nucleic acid molecule $nCUL_{1823}$ contains at least the following open reading frames: CUL51, CdUTPase, CUL49.5, and the 5' end of CUL49. SEQ ID NO:85 and SEQ ID NO:86 represent the deduced nucleic acid sequences of the two complementary strands of a nucleic acid molecule referred to herein as $nCUL52_{749}$. Translation of SEQ ID NO:85 and SEQ ID NO:86 indicates that nucleic acid molecule $nCUL52_{749}$ contains a partial open reading frame for CUL52, the 3' end of which is included in SEQ ID NO:28. The relative location of each of these open reading frames is shown in FIG. 5.

Specifically, SEQ ID NO:63 includes: the coding strand of $nCUL49_{420}$ (having SEQ ID NO:65) which encodes a non-full length CUL49 protein of about 139 amino acids, assuming a stop codon spanning about nucleotides 419–421 of SEQ ID NO:63; and the coding strand of $nCUL48_{1269}$ (having SEQ ID NO:67, and including SEQ ID NO:24) which encodes a CUL48 protein of about 422 amino acids, assuming a start codon spanning about nucleotides 541–543 and a stop codon spanning about nucleotides 1807–1809 of SEQ ID NO:63. The amino acid sequences of the respective encoded proteins $PCUL49_{139}$ and $PCUL48_{422}$ are represented by SEQ ID NO:66 and SEQ ID NO:68, respectively.

SEQ ID NO:77 includes the coding strand of $nCdUTP_{918}$ (having SEQ ID NO:79 and including SEQ ID NO:15) which encodes a CdUTPase protein of about 305 amino acids, assuming a start codon spanning about nucleotides 624–626 and a stop codon spanning about nucleotides 1539–1541 of SEQ ID NO:77. The amino acid sequence of the respective encoded protein $PCdUTP_{305}$ is represented by SEQ ID NO:80.

SEQ ID NO:78 includes: the coding strand of $nCUL51_{261}$ (having SEQ ID NO:33) which encodes a non-full length CUL51 protein of about 86 amino acids, assuming translation begins at about nucleotide 1 and a stop codon spanning about nucleotides 259–261 of SEQ ID NO:78; the coding strand of $nCUL49.5_{261}$ (having SEQ ID NO:81) which encodes a CUL49.5 protein of about 86 amino acids, assuming a start codon spanning about nucleotides 1175–1177 and a stop codon spanning about nucleotides 1433–1435 of SEQ ID NO:78; and the coding strand of $nCUL49_{255}$ (having SEQ ID NO:83) which encodes a non-full length CUL49 protein of about 85 amino acids, assuming a start codon spanning about nucleotides 1586–1588 of SEQ ID NO:78. The amino acid sequence of the respective encoded proteins $PCUL51_{86}$, $PCUL49.5_{86}$, and $PCUL49_{85}$ are represented by SEQ ID NO:34, SEQ ID NO:82 and SEQ ID NO:84, respectively.

SEQ ID NO:85 includes the coding strand of $nCUL52_{747}$ (having SEQ ID NO:87) which encodes a non-full length CUL52 protein of about 249 amino acids, assuming translation begins at about nucleotide 1 of SEQ ID NO:85. The amino acid sequence of the respective encoded protein $PCUL52_{249}$ is represented by SEQ ID NO:88.

Example 12

This Example discloses the production of another recombinant CHV genome and recombinant CHV of the present invention.

A 3.2 kb fragment containing the entire CdUTPase sequence was amplified from CHV genomic DNA using forward primer RSF009 having nucleic acid sequence 5' GCCGGTACCAGGCTTTGGACGAGATTAGG 3', denoted SEQ ID NO:89, and reverse primer RSF008 having nucleic acid sequence 5' GCCGAATTCAATATAATTAATAAACTCTC3', denoted SEQ ID NO:90. RSF009 has an Asp718 site attached to the 5' end of CHV homologous sequences, and RSF008 has an EcoRI site attached to the 5' end of CHV homologous sequences. The resultant PCR-amplified fragment of about 3.2 kb, referred to herein as $nCdUTP_{3200}$, was digested with Asp718 and EcoRI and ligated into plitmus28 (available from New England Biolabs). The resultant recombinant plasmid, denoted herein as $p28CdUTP_{3200}$, was verified by end-sequencing and restriction mapping. Plasmid $p28CdUTP_{3200}$ was then digested with HindIII and XbaI, releasing an 858 base-pair fragment, referred to herein as $nCdUTP_{858}$, containing all of the dUTPase open reading frame except 108 bp at the 3' end. The XbaI site was found to be 49 nucleotides upstream of the start codon of the dUTPase ORF (open reading frame), and is also 70 nucleotides into the UL49.5 ORF on the opposite strand, which overlaps the dUTPase ORF. Previous studies have shown that the UL49.5 ORF in other herpesviruses encodes a membrane protein, and is nonessential for growth in tissue culture (e.g., Liang et al, ibid.).

The cohesive ends on the remaining 2.3 kb fragment of $p28CdUTP_{3200}$, minus the 858 bp HindIII/XbaI fragment, were filled in using Klenow fragment and dNTPs according to standard methods. The resulting blunt-ended fragment was gel purified by standard methods. A heterologous nucleic acid sequence operatively linked to transcription control regions, in this case an AscCMV/lacZ/BGH cassette described in Example 6, was isolated from its plasmid by digestion with AscI, and the cohesive ends were filled in by Klenow fragment and dNTPs. This cassette was ligated to the HindIII and XbaI-digested $p28CdUTP_{3200}$ fragment described above by standard methods resulting in a plasmid containing flanking regions to the CHV dUTPase gene and with the lacZ gene, operatively linked to transcription control regions, inserted into a deletion of the dUTPase gene, herein denoted as pdUTP/lacZ.

A recombinant CHV is produced by co-transfecting the plasmid with the deleted dUTPase gene and the inserted heterologous nucleic acid molecule, in this case pdUTP/lacZ, and CHV DNA into canine cells using previously described methods; see, for example, Graham et al, ibid.). Alternatively, a recombinant CHV is produced by transfecting canine cells with the aforementioned plasmid as described, and then infecting the cells with CHV. Recombinant dUTPase-negative CHV are selected for by passage in mercurithio analogs of deoxyuridine as described in Example 8. If the heterologous nucleic acid molecule is the lacZ gene, such a recombinant CHV can be selected as described in Example 6.

Example 13

This example discloses a method for obtaining higher plaque forming efficiencies to facilitate the production of recombinant CHV genomes and recombinant CHV of the present invention. The method involves the expression of the CHV alpha-tif gene in the presence of CHV genomes introduced into canine cells during CHV production.

The alpha-tif gene of CHV (denoted herein as $nCUL48_{1269}$) was identified to lie on two CHV clones described herein: namely, $nCHin_{3000}$ and $nCHin_{8500}$ Nucleotide sequencing from the ends of these two fragments using universal primers and internal primers designed based on previous sequences was used to determine the entire sequence. A single fragment including the complete alpha-tif gene was PCR amplified from CHV viral DNA using forward primer RSF014 having nucleic acid sequence 5' CCGGAATTCGCTTAGTGAGAGTATAAAC 3', denoted SEQ ID NO:91, and reverse primer RSF016 having nucleic acid sequence 5' CCGGAATTCCCTCATATTATATAC-TAAC 3', denoted SEQ ID NO:92. Both primers have EcoRI sites attached to the 5' end of the CHV homologous sequences. The resultant PCR amplified fragment of about 1351 base pairs was digested with EcoRI and ligated into EcoRI-digested pCDNA3 (available from Invitrogen, described in Example 6). This plasmid contains a neomycin-resistance gene for selection of stably transformed cell lines by techniques well known to those skilled in the art. Resulting plasmids were checked for the proper orientation by digestion with HindIII. A plasmid consisting of pcDNA3 with the alpha-tif gene inserted in the proper orientation for expression was found, and is designated herein as $pATIF_{1351}$ Expression of CHV alpha-tif from $pATIF_{1351}$ was verified by cell-free transcription/translation using T7 RNA polymerase and a rabbit reticulocyte lysate system. These techniques are readily apparent to those skilled in the art, and are available in kit form, for example, from Amersham. Improved CHV DNA infectivity is then achieved by cotransfection of $pATIF_{1351}$ with from about 1 to about 5 $\mu$g of CHV DNA by methods such as described in Examples 6–9 and Example 12.

Alternatively, cell lines that stably express CHV alpha-tif are derived. Three canine cell lines, A72, D17 and CF2Th (all available from ATCC) were transfected with $pATIF_{1351}$ by standard methods, see, for example, Graham et al, ibid. The cells are then subjected to selection using varying amounts of the antibiotic G418 (available from BMB), determined empirically for each cell line. Cloned G418-resistant cell lines are then derived by standard dilution methods. Cell lines stably expressing CHV alpha-tif are then used for standard CHV DNA transfections or co-transfections such as those described in Examples 6–9 and Example 12.

Example 14

This Example describes the identification and sequencing of additional CHV nucleic acid molecules of the present invention.

CHV nucleic acid molecule $nCHin_{5500}$, a CHV HindIII fragment derived as described in Example 2, was submitted to nucleic acid sequence analysis. Sequences derived from the sequence analysis include SEQ ID NO:69, SEQ ID NO:70, SEQ ID NO:73 and SEQ ID NO:74. Translation of these sequences indicated that $nCHin_{5500}$ includes at least a portion of the CgL and CICP4 coding regions. The nucleic acid molecule also apparently contains the CICP0 coding region.

SEQ ID NO:69 and SEQ ID NO:70 represent the deduced nucleic acid sequences of the two complementary strands of a CHV ICP4 nucleic acid molecule referred to herein as $nCICP4_{626}$. Translation of SEQ ID NO:69 indicates that $nCICP4_{626}$ encodes a non-full length CICP4 protein of about 208 amino acids, denoted herein as $PCICP4_{208}$, having an amino acid sequence represented by SEQ ID NO:72. The coding region for $PCICP4_{208}$ is denoted herein as $nCICP4_{624}$, having nucleic acid sequence SEQ D NO:71.

SEQ ID NO:73 and SEQ ID NO:74 represent the deduced nucleic acid sequences of the two complementary strands of a CHV gL nucleic acid molecule referred to herein as $nCgL_{655}$. Translation of SEQ ID NO:74 indicates that $nCgL_{655}$ encodes a non-full length CgL protein of about 171 amino acids, denoted herein as $PCgL_{171}$, having an amino acid sequence represented by SEQ ID NO:76. The coding region for $PCgL_{,171}$ is denoted herein as $nCgL_{516}$, having nucleic acid sequence SEQ ID NO:75, assuming that the open reading frame spans about nucleotides 1 through 516 of SEQ ID NO:74, with a stop codon spanning about nucleotides 514–516.

Example 15

This example describes the mapping of messenger RNA molecules transcribed from nucleic acid molecules of the present invention. These transcripts are useful for verifying expression (or lack of expression) of various genes.

Total RNA was prepared from CHV-infected cells using a phenol/guanidine extraction method familiar to those skilled in the art. See, for example, Chomczynski et al, 1987, *Anal. Biochem.* 162, 156–159. Multiple samples of RNA were separated on formaldehyde/agarose gels and transferred to nitrocellulose by standard methods. Based on the sequences of $nCUS_{10592}$, designated SEQ ID NO:51 and SEQ ID NO:52, nucleic acid fragments were isolated for use as probes, such that they would hybridize to sequences homologous to the open reading frames $nCPK_{1203}$ (SEQ ID NO:7), $nCgG_{1248}$ (SEQ ID NO:9), $nCgD_{1038}$ (SEQ ID NO:53), $nCgI_{,1095}$ (SEQ ID NO:55), $nCgE_{1569}$ (SEQ ID NO:57), nCUS8.5237 (SEQ ID NO:59), $nCUS9_{360}$ (SEQ ID NO:61), $nCIR6_{552}$ (SEQ ID NO:3), and $nCUS2_{1176}$ (SEQ ID NO:5). The probes were as follows: to hybridize with an $nCIR6_{552}$ (SEQ ID NO:3) transcript, a PstI-HindIII restriction fragment extending from about nucleotide 1 to about nucleotide 685 in $nCUS_{10592}$ herein denoted as probe A; to hybridize with an $nCUS2_{1176}$ (SEQ ID NO:5) transcript, a PCR-amplified fragment extending from about nucleotide 2056 to about nucleotide 2273 in $nCUS_{10592}$ herein denoted as probe B; to hybridize with an $nCPK_{1203}$ (SEQ ID NO:7) transcript, a PstI-DraI restriction fragment extending from about nucleotide 2326 to about nucleotide 2788 in nCUS$_{10592}$ herein denoted as probe C; to hybridize with an nCgG$_{1248}$ (SEQ ID NO:9) transcript, a BamHI-PstI restriction fragment extending from about nucleotide 3766 to about nucleotide 4494 in nCUS$_{10592}$ herein denoted as probe D; to hybridize with an nCgD$_{1038}$ (SEQ ID NO:53) transcript, either a BglII-BglII restriction fragment extending from about nucleotide 5728 to about nucleotide 6561 in nCUS$_{10592}$ (this piece slightly overlaps nCgI$_{1095}$) herein denoted as probe E, or a PCR-amplified fragment that will extend from about nucleotide 5295 to about nucleotide 5885 in nCUS$_{10592}$ herein denoted as probe F; to hybridize with an nCgI$_{1095}$ (SEQ ID NO:55) transcript, a BglII-BglII restriction fragment extending from about nucleotide 6561 to about nucleotide 7263 in nCUS$_{10592}$ herein denoted as probe G; to hybridize with an nCgE$_{1569}$ (SEQ ID NO:57) transcript, a deletion subclone extending from about nucleotide 7667 to about nucleotide 8425 in nCUS$_{10592}$ herein denoted as probe H; to hybridize with a putative ncus85237 (SEQ ID NO:59) transcript, a PCR-amplified fragment extending from about nucleotide 9023 to about nucleotide 9242 in nCUS$_{10592}$ herein denoted as probe I; to hybridize to an nCUS9$_{360}$ (SEQ ID NO:61) transcript, a PCR-amplified fragment extending from about nucleotide 9447 to about nucleotide 9715 in nCUS$_{10592}$ herein denoted as probe J. These probes are shown graphically in FIG. 4. The probes were labelled with $^{32}$P DATP using random priming, a technique well known to those skilled in the art. Hybridization of the probes to the RNA samples on nitrocellulose and washing at stringent temperatures were done according to well known methods.

The main transcript sizes that hybridized to the various probes were as follows: probe A hybridized strongly to a transcript of about 0.7 kb, but also hybridized weakly to transcripts of about 1.7, 2.2 and 2.6 kb; probe B hybridized with a transcript of about 2.2 kb; probe C hybridized to a transcript of about 2.6 kb; probe D hybridized to two transcripts of about 1.9 kb and 2.6 kb; probe E hybridized to two transcripts of about 4.2 kb and 3.2 kb; probe G hybridized to two transcripts of about 4.2 kb and 3.2 kb; probe H hybridized to three transcripts of about 1.9 kb, 3.2 kb, and 4.2 kb; probe I hybridized to the same three transcripts as probe H; probe J hybridized to a transcript of about 2.1 kb. These data suggest that the transcripts of US2, US9, and IR6, although starting at different points, terminated in a common general area in the inverted repeats, since probe A hybridized to transcripts that were generally the same size as the US2 and US9 transcripts. Furthermore, these data suggest that the PK and gG transcripts overlapped, probably terminating at a common 3' terminus, since probe C hybridized to only a 2.6 kb transcript but probe D hybridized with both the 2.6 kb transcript and the 1.4 kb transcript. This result was even more likely because only one polyadenylation consensus sequence (AATAAA) was found downstream of the gG ORF, but before the gD ORF. This polyadenylation signal was found from nucleotide 4935–4940 of nCUS$_{10592}$. Similarly, these data indicate the gI and gE transcripts overlapped, probably terminating at a common 3' terminus since probe G hybridized to a transcript of 2.6 kb, while probe H hybridized both to the 2.6 kb transcript and the 1.9 kb transcript. Probes E, G, and H also all hybridized to a 4.2 kb transcript, suggesting that the gD transcript also overlapped the gI and gE transcripts, probably terminating at a common 3' terminus. Verification of this result is if probe F hybridizes only to the 4.2 kb transcript. Probe I hybridized to only the 4.2, 2.6 and 2.9 kb transcripts suggesting two things; first, that these three transcripts probably terminated at polyadenylation signals at about 9186–9181, 9256–9261 or 9260–9265 of nCUS$_{10592}$, also that the putative US8.5 open reading frame is not transcribed to levels detectable by Northern analysis.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:92 submitted herewith are the same.

What is claimed is:

1. An isolated canine herpesvirus (CHV) nucleic acid molecule that hybridizes under stringent hybridization conditions with a CHV nucleic acid region selected from the group consisting of a CdUTPase gene, a CgE gene, a CgG gene, a CgI gene, a CPK gene, a CTK gene, a CIR6 gene, a CUS2 gene, a CUS9 gene, a CUL49 gene, a CUL51 gene, a CUL48 gene, a CULS52 gene, a CgL gene, a CUL49.5 gene, a CICP4 gene, a CUS8.5 open reading frame, and a region of the CHV genomre spanning from the 3' end of the coding region of the CUL41 gene through the 3' end of the coding region of the CUL38 gene.

2. The CHV nucleic acid molecule of claim 1, wherein said CdUTPase gene comprises $nCdUTP_{918}$, wherein said CgE gene comprises $nCgE_{1569}$, wherein said CgG gene comprises $nCgG_{12481}$, wherein said CgI gene comprises $nCgI_{1095}$, wherein said CPK gene comprises $nCPK_{1203}$, wherein said CTK gene comprises $nCTK_{280}$, wherein said CIR6 gene comprises $nCIR6_{552}$, wherein said CUS2 gene comprises $nCUS2_{1176}$, wherein said CUS9 gene comprises $nCUS9_{360}$, wherein said CUL49 gene comprises $nCUL49_{420}$, wherein said CUL51 gene comprises $nCUL51_{261}$, wherein said CUL48 gene comprises $nCUL48_{1269}$, wherein said CUL52 gene comprises $nCUL52_{749}$, wherein said CgL gene comprises $nCgL_{655}$, wherein said CUS8.5 open reading frame comprises $nCUS8.5_{237}$, wherein said CICP4 gene comprises $nCICP4_{626}$, wherein said CUL49.5 gene comprises $nCUL49.5_{261}$, and wherein said CUL49 gene comprises $nCUL49_{255}$.

3. The CHV nucleic acid molecule of claim 1, wherein said CHV nucleic acid molecule comprises a nucleic acid sequence that is at least 80% identical to a nucleic acid sequence selected from the group consisting of SEQ ID NO:1, SEQ ID ND:2, SEQ ID NO:3, SEQ ID NO05, SEQ ID NO:7, SEQ ID NO:9, SEQ ID No:13, SEQ ID NO:14, SEQ ID NO:15, SEQ ID ND:17, SEQ ID NO:19, SEQ ID NO:20, SEQ ID NO:21, SEQ ID NO:23, SEQ ID NO:24, SEQ ID ND:25, SEQ ID NO:27, SEQ ID NO:28, SEQ ID NO:29, SEQ ID NO:31, SEQ ID NO:32, SEQ ID NO:33, SEQ ID NO.35, SEQ ID NO:37, and SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, SEQ ID NO:87, and complements of said sequences.

4. The CHV nucleic acid molecule of claim 1, wherein said nucleic acid molecule hybridizes under stringent hybridization conditions with a nucleic acid molecule selected from the group consisting of $nCIR6_{552}$, $nCUS2_{1176}$, $nCPK_{1203}$, $nCgG_{1248}$, $nCgI_{161}$, $nCgE_{750}$, $nCUS9_{579}$, nCdUTP/CUL51743, $nCTK_{280}$, $nCUL48_{294}$, $nCUL52_{146}$, $nCgI_{1095}$, $nCgE_{1569}$, $nCUS8.5_{237}$, $nCUS9_{360}$, nCUL49/$CUL48_{2044}$, $nCUL49_{420}$, $nCUL48_{1269}$, $nCICP4_{626}$, $nCgL_{655}$, $nCUL_{1823}$, $nCdUTP_{918}$, $nCUL49.5_{261}$, $nCUL49_{255}$, and $nCUL52_{749}$.

5. The CHV nucleic acid molecule of claim 1, wherein said CHV nucleic acid molecule comprises a CHV nucleic acid molecule selected from the group consisting of $nCAsc_{9300}$, $nCAsc_{10000}$, $nCHin_{3000}$, $nCHin_{1900}$, $nCHin_{5500}$, $nCHin_{85001}$, $nCUS_{5495}$, $nCIR6_{552}$, $nCUS2_{1176}$, $nCPK_{1203}$, $nCgG_{1248}$, $nCdUTP/CUL51_{743}$, $nCdUTP_{459}$, $nCUS9_{579}$, $nCUS9_{450}$, $nCUL48_{294}$, $nCUL48_{291}$, $nCUL52_{146}$, $nCUL52_{144}$, $nCg161$, $nCgI_{159}$, $nCgE_{750}$, $nCTK_{280}$, $nCTK_{279}$, $nCUL51_{261}$, $nCUS_{10592}$, $nCgI_{1095}$, $nCgE_{1569}$, $nCUS8.5_{237}$, $nCUS9_{360}$, $nCUL49/CUL48_{2044}$, $nCUL49_{420}$, $nCUL48_{1269}$, $nCICP4_{626}$, $nCICP4_{624}$, $nCgL_{655}$, $nCgL_{516}$, $nCUL_{1823}$, $nCdUTP_{918}$, $nCUL49.5_{261}$, $nCUL49_{255}$, $nCUL52_{749}$, $nCUL52_{747}$, $nCdUTP_{858}$, $nCdUTP_{3200}$, and naturally occuring allelic variants of said CHV nucleic acid molecules.

6. The CHV nucleic acid molecule of claim 1, wherein said CHV nucleic acid molecule is selected from the group consisting of: a CHV nucleic acid molecule comprising a nucleic acid sequence selected from the group consisting of SEQ ID No:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO;333, SEQ ID NO:35, SEQ ID NO:37, SEQ ID NO:38, SEQ ID NO:51, SEQ ID NO:52, SEQ ID NO:55, SEQ ID NO: 57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, SEQ ID NO:87, and complements of said sequences; and a nucleic acid molecule comprising a naturally occurring allelic variant of any of said CHV nucleic acid molecules.

7. The CHV nucleic acid molecule of claim 1, wherein said CHV nucleic acid molecule encodes a protein comprising an amino acid sequence selected from the group consisting of SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and SEQ ID NO:88.

8. A recombinant molecule comprising a CHV nucleic acid molecule as set forth in claim 1 operatively linked to a transcription control sequence.

9. A recombinant cell comprising a CHV nucleic acid molecule as set forth in claim 1.

10. The nucleic acid molecule of claim 1, wherein said nucleic acid molecule comprises a transcript.

11. A recombinant virus comprising an isolated CHV nucleic acid region selected from the group consisting of a CdUTPase gene, a CgE gene, a CgG gene, a CgI gene, a CPK gene, a CTK gene, a CIR6 gene, a CUS2 gene, a CUS9 gene, a CUL49 gene, CUL51 , a CUL48 gene, a CUL52 gene, a CgL gene, a CUL49.5 gene, a CICP4 gene, a CUS8.5 open reading frame, a region of the CHV genome spanning from the 3' end of the coding region of the CUL41 gene through the 3' end of the coding region of the CUL38 gene and portions thereof, wherein the portion encodes an epitope that elicits an immune response.

12. A recombinant vector comprising an isolated CHV nucleic acid region selected from the group consisting of a CdUTPase gene, a CgE gene, a CgG gene, a CgI gene, a CPK gene, a CTK gene, a CIR6 gene, a CUS2 gene, a CUS9 gene, a CUL49 gene, a CUL51 gene, a CUL48 gene, a CUL52 gene, a CgL gene, a CUL49.5 gene, a CICP4 gene, a CUS8.5 open reading frame, a region of the CHV genome spanning from the 3' end of the coding region of the CUL41 gene through the 3' end of the coding region of the CUL38 gene and portions thereof, wherein the portion forms a stable hybrid with the complementary sequence of one of said regions.

13. A recombinant vector, as claimed in claim 12, said CHV nucleic acid region having a heterologous nucleic acid molecule in said CHV nucleic acid region.

14. The recombinant vector of claim 13, wherein said heterologous nucleic acid molecule is operatively linked to a transcription control sequence.

15. A cell comprising said recombinant vector of claim 12.

16. A recombinant CHV comprising a recombinant CR genome, said CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, said CHV being reproduction competent, wherein said CHV is selected from the group consisting of a CdUPase negative CHV, a CgC negative CHV, a CgE negative CHV, a CgG negative CHV, a CgI negative CHV, a CPK negative CHV, a CTK negative CHV, a CIR6 negative CHV, a CUS2 negative CHV, a CUS9 negative CHV, a CUL49 negative CHV, a CUL45 negative CHV, a CUL49.5 negative CHV, and a CUS8.5 negative CHV.

17. The CHV of claim 16, wherein said CHV comprises an inactive gene comprising an alteration selected from the group consisting of a deletion of one or more nucleotides, an insertion of one or more nucleotides, an inversion of one or more nucleotides, and a substitution of one or more nucleotides.

18. The CHV of claim 16, wherein said CHV comprises an inactive gene comprising said heterologous nucleic acid molecule.

19. A recombinant CHV comprising a recombinant CHV genome, said CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, said CHV being competent, wherein said heterologous nucleic acid molecule is in a CHV gene of said genome, wherein said CHV gene is selected from the group consisting of a CdUTPase gene, a CgC gene, a CgE gene, a CgC gene, a CgI gene, a CPK gene, a CTK gene, a CIR6 gene, a CUS2 gene, a CUS9 gene, a CUL49 gene, a CUL45 gene, a COL49.5 gene, and a CTS8.5 open reading frame.

20. A recombinant CHV comprising a recombinant CHV genome, said CHV genome comprising a heterologous nucleic acid molecule operatively linked to a transcription control region, said heterologous nucleic acid molecule being in a region of said CHV genome selected from the group consisting of a nonessential gene of said CHV genome and a intergenic region of said CHV genome, said CHV being reproduction competent, wherein said CHV comprises a recombinant CHV genome having a heterologous nucleic acid molecule in the US region of said CHV genome at a position selected from the group consisting of a nonessential gene in said US region and an intergenic site in said US region.

21. A recombinant CHV, wherein said CHV comprises a recombinant CHV genome having a heterologous nucleic acid molecule operatively linked to a transcription control region, said heterologous nucleic acid molecule being in a region of said genome selected from the group consisting of a non-essential region of an internal inverted repeat region and a non-essential region of a terminal inverted repeat region, said CHV being reproduction competent.

22. A recombinant CHV comprising a recombinant CHV genome, said CHV genome comprising a heterologous nucleic acid molecule operatively linked to a transcription controls region, said heterologous nucleic acid molecule being in a region of said CHV genome selected from the group consisting of a nonessential gene of said CHV genome and an intergenic region of said CHV genome, said CHV being reproduction competent, wherein said region of the CHV genome is selected from the group consisting of nCAsc$_{9300}$, nCAsc$_{10000}$ nCHin$_{3000}$, nCHin$_{1900}$, nCHin$_{5500}$, nCHin$_{8500}$, and naturally occurring allelic variants of said regions, wherein said heterologous nucleic acid molecule does not abrogate growth of said CHV in tissue culture.

23. A recombinant CHV comprising a recombinant, CHV genome, said CHV genome comprising a heterologous nucleic acid molecule operatively linked to transcription control region, said heterologous nucleic acid molecule being in a region of said CHV genome selected from the group consisting of a nonessential gene of said CHV genome and an intergenic region of said CHV genome, said CHV being reproduction competent, wherein said region of the CHV genome is selected from the group consisting of a CHV region comprising nCUS$_{10592}$, a CHV UL region comprising nCUL$_{1823}$, a CHV UL region comprising nCUL49/CUL48$_{2044}$, a CHV UL region comprising nCdUPT$_{3200}$, and naturally occurring allelic variant of said regions, wherein said heterologous nucleic acid molecule does not abrogate growth of said CHV in tissue culture.

24. A recombinant CHV comprising a recombinant CHV genome, said CHV genome comprising a heterologous nucleic acid molecule operatively linked to transcription control region, said heterologous nucleic acid molecule being in a region of said CHV genome selected from the group consisting of a nonessential gene of said CHV genome and an intergenic region of said CHV genome, said CHV being reproduction competent, wherein said region of the CHV genome is selected from the group consisting of nCUS$_{5495}$, nCgC/CUL45$_{2100}$, nCgE$_{750}$, nCgI$_{161}$, nCUS9$_{579}$, nCdUTP/CUL51$_{743}$, nCTK$_{280}$, nCUS$_{10592}$, nCgD$_{1038}$, nCgI$_{1095}$, nCgE$_{1569}$, nCUSS8.5$_{237}$, nCUS9$_{360}$, nCUL49/CUL48$_{2044}$, nCUL49$_{420}$, nCUL$_{1823}$, nCdUTP$_{918}$, nCUL49.5$_{261}$, nCUL49$_{255}$, nCdUTP$_{3200}$, and naturally occurring allelic variants of said regions, wherein said heterologous nucleic acid molecule does not abrogate growth of said CHV in tissue culture.

25. A recombinant CHV comprising a recombinant CHV genome, said CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, said CHV being reproduction competent, wherein said region of the CHV genome comprises a nucleic acid sequence selected from the group consisting of SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:29, SEQ ID NO:31, SEQ ID NO:32, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:77, SEQ ID NO:78, SEQ ID NO:79, SEQ ID NO:81, SEQ ID NO:83, complements of said regions, and naturally occurring allelic variants of said regions, wherein said heterologous nucleic acid molecule does not abrogate growth of said CHV in tissue culture.

26. A recombinant CHV genome comprising a heterologous nucleic acid molecule operatively linked to a transcription control region, said heterologous nucleic acid molecule being in a region of said heterologous nucleic acid molecule being in a region of said CHV genome selected from the group consisting of a nonessential gene of said CHV genome and an intergenic region of said CHV genome, wherein a recombinant CHV comprising said CHV genome is reproduction competent, and wherein said CHV genome is reproduction competent, and wherein said CHV genome is selected from the group consisting of a CdUTPase negative CHV, a CgC negative, a CgE negative CHV, a CgG negative CHV, a CgI negative, a CPK negative CHV, a CTK negative CHV, a CIR6 negative CHV, a CUS2 negative CHV, a CUS9 negative CHV, a CUL49 negative CHV, a CUL45 negative CHV, a CUL49.5 negative CHV, and a CUS8.5 negative CHV.

27. A recombinant CHV genome comprising a heterologous nucleic acid molecule operatively linked to a transcription control region, said heterologous nucleic acid molecule being in a region of said CHV genome selected from the group consisting of nonessential gene of said CHV genome and an intergenic region of said CHV genome, wherein a recombinant CHV comprising said CHV genome is reproduction competent, and wherein said heterologous nucleic acid molecule is in a CHV gene selected from the group consisting of a CdUTPase gene, a CgC gene, a CgE gene, a CgG gene, a CgI gene, a CPK gene, a CTX gene, a CIR6 gene, a CUS2 gene, a CUS9 gene, a CUL49 gene, a CUL45 gene, a CUL49–5 gene, and a CUJS8.5 open reading frame.

28. A recombinant CHV genome comprising a heterologous nucleic acid molecule operatively linked to transcription control region, said heterologous nucleic acid molecules being in a region of said CHV genome selected from the group consisting of a nonessential gene of said CHV genome and an intergenic region of saud CHV genome, wherein a recombinant CHV comprising said CHV genome is reproduction competent, wherein said CHV genome comprises a heterologous nucleic acid molecule in the US region of said CHV genome at a position selected from the group consisting of a non-essential gene in said US region.

29. A recombinant CHV genome comprising a heterologous nucleic acid molecule operatively linked to a transcription control region, said heterologous nucleic acid molecule being in a region of said CHV genome selected from the group consisting of a non-essential region of an internal inverted repeat region and a non-essential region of a terminal inverted repeat region, wherein, a recombinant CHV comprising said CHV genome is reproduction competent.

30. A recombinant CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, wherein a recombinant CHV comprising said CHV genome is reproduction competent, and wherein said CHV genome comprises a heterologous nucleic acid molecule in a region of said CHV genome selected from the group consisting of nCAsc$_{9300}$, nCAsc$_{10000}$, nCHIN$_{3000}$, nCHIN$_{1900}$, nCHIN$_{5500}$, nCHIN$_{8500}$, and naturally occurring allelic variants of said regions, wherein said heterologous nucleic acid molecule does not abrogate growth of said CHV in tissue culture.

31. A recombinant CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, wherein a recombinant CHV comprising said CHV genome is reproduction competent, wherein said region of said CHV genome is selected from the group consisting of a CHV region comprising $nCUS_{10592}$, region comprising $nCUL_{1823}$, a CHV UL region comprising $nCUL49/CUL48_{2044}$, region comprising $nCdUTP_{3200}$, and naturally occurring allelic variants of said regions, wherein said heterologous nucleic acid molecule does not abrogate growth of said CHV in tissue culture.

32. A recombinant CHV genome comprising a heterologous nucleic acid molecule operatively linked to a transcription control region, said heterologous nucleic acid molecule being in a region of said CHV genome selected from the group consisting of a nonessential gene of said CHV genome and an intergenic region of said CHV genome, wherein a recombinant CHV comprising said CHV genome is reproduction competent, and wherein said region of said CHV genome is selected from the group consisting of $nCUS_{5495}$, $nCgC/CUL45_{2200}$, $nCgE_{750}$, $nCgI_{161}$, $nCUS9_{579}$, $nCdUTP/CUL51_{743}$, $nCTK_{280}$, $nCUS_{10592}$, $nCgD_{1039}$, $nCgI_{1045}$, $nCgE_{1569}$ $nCUS8.5_{237}$, $nCUS9_{360}$ $nCUL49/CUL48$, $nCUL49$, $nCUL_{420}$, $nCdUTP_{918}$, $nCUL49.5_{261}$, $nCUL49_{255}$, $nCdUTP_{3200}$, and naturally occurring allelic variants of said regions, wherein said heterologous nucleic acid molecule does not abrogate growth of said CHV in tissue culture.

33. A recombinant CHV genome comprising a heterologous nucleic acid molecule operatively linked to a transcription control region, said heterologous nucleic acid molecule being in a region of said CHV genome selected from the group consisting of a non-essential gene of said CHV genome and an intergenic region of said CHV genome, wherein a recombinant CHV comprising said CHV genome is reproduction competent, wherein said region of said CHV genome is represented by a nucleic acid sequence comprising a nucleic acid sequence selected from the group consisting of SEQ ID NO:1, SEQ ID NO2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:29, SEQ ID NO:31, SEQ ID NO:32, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:77, SEQ ID NO:78, SEQ ID NO:79, SEQ ID NO:81, SEQ ID NO: 83, complements of said regions, and naturally occurring allelic variants of said regions, wherein said heterologous nucleic acid molecule does not abrogate growth of said CHV in tissue culture.

34. The CHV of claim 19, 21, 22, 23, 24, or 25, wherein said CHV comprises a recombinant CHV genome having an inactive gene.

35. The CHV of claim 16, 19, 21, 22, 22, 24 or 25, wherein said CHV is attenuated.

36. The CHV of claim 16, 19, 21, 22, 23, 24 or 25, wherein said CHV comprises a recombinant CHV genome having a heterologous nucleic acid molecule in a region of said CHV genome spanning from the 3' end of the coding region of the CUL41 gene through the 3' end of the coding region of the CUL38a gene.

37. The CHV of claim 16, 19, 21, 22, 23, 24 or 25, wherein said CHV comprises a recombinant CHV genome having a heterologous nucleic acid molecule in a naturally-occurring AscI restriction endonuclease site within said CHV genome.

38. The CHV of claims 16, 19, 21, 22, 23, 24 or 25 wherein said heterologous nucleic acid molecule encodes a compound selected from the group consisting of proteins and RNA species.

39. The CHV of claim 38, wherein said compound is derived from an infectious agent selected from the group consisting of protozoan parasites, helminth parasites, ectoparasites, fungi, bacteria, and viruses.

40. The CHV of claims 16, 19, 21, 22, 23, 24 or 25, wherein said heterologous nucleic acid molecule comprises a gene encoding an immunomodulator.

41. The CHV of claims 16, 19, 21, 22, 23, 24 or 25, wherein said CHV infects dogs.

42. The CHV genome of claim 27, 29, 30, 31, 32 or 33, wherein said CHV genome comprises an inactive gene.

43. The CHV genome of claim 42, wherein said inactive gene comprises an alteration selected from the group consisting of a deletion of one or more nucleotides, an insertion of one or more nucleotides, an inversion of one or more nucleotides, and a substitution of one or more nucleotides.

44. The CHV genome of claim 42, wherein said inactive gene comprises said heterologous nucleic acid molecule.

45. The CHV genome of claim 26, 27, 29, 30, 31, 32 or 33, wherein said heterologous nucleic acid molecule is in a region of said CHV genome spanning from the 3' end of the coding region of the CUL41 gene through the 3' end of the coding region of the CUL38 gene.

46. The CHV genome of claim 26, 27, 29, 30, 31, 32 or 33, wherein said CHV genome comprises a heterologous nucleic acid molecule in a naturally-occurring AscI restriction endonuclease site in said CHV genome.

47. The CHV genome of claims 26, 27, 29, 30, 31, 32 or 33, wherein said heterologous nucleic acid molecule encodes a compound selected from the group consisting of proteins and RNA species.

48. The CHV genome of claim 47, wherein said compound is derived from an infectious agent selected from the group consisting of protozoan parasites, helminth parasites, ectoparasites, fungi, bacteria, and viruses.

49. The CHV genome of claims 26, 27, 29, 30, 31, 32 or 33, wherein said heterologous nucleic acid molecule comprises a gene encoding an immunomodulator.

50. A transfected cell comprising a CHV genome as set forth in claim 26, 27, 29, 30, 31, 32 or 33.

51. The CHV genome of claim 26, 27, 29, 30, 31, 32 or 33, wherein said CHV genome comprises a recombinant dog herpesvirus genome.

* * * * *

UNITED STATES PATENT AND TRADEMARK OFFICE
CERTIFICATE OF CORRECTION

PATENT NO. : 5,804,197
DATED : September 8, 1998
INVENTOR(S) : Haanes et al.

It is certified that error appears in the above-identified patent and that said Letters Patent is hereby corrected as shown below:

Claim 1,
Line 45, delete "genomre" and insert –genome–therefor

Claim 2,
Line 51, delete "nCgG$_{12481}$" and insert –nCgG$_{1248}$–therefor

Claim 3,
Line 38, delete "NO05" and insert –NO:5–therefor
Line 40, delete "ND:17" and insert –NO:17–therefor
Line 42, delete "ND:25" and insert –NO:25– therefor Claim 4,
Line 58, delete "nCdUTP/CUL51743" and insert –nCdUTP/CUL51$_{743}$– therefor Claim 5,
Line 67, delete "nCHin$_{85001}$" and insert –nCHin$_{8500}$–therefor Claim 6,
Line 21, delete "NO:333" and insert –NO:33–therefor Claim 11,
Line 53, delete "CUL51," and insert –a CUL51, –therefor Claim 16,
Line 13, delete "CR" and insert –CHV– therefor Claim 19,
Line 44, after "being", insert –reproduction–
Line 47, delete the second occurrence of "CgC" and insert –CgC–therefor
Line 49, delete "COL49.5" and insert –CUL49.5– therefor
Line 50, delete "CTS8.5" and insert –CUS8.5–therefor

UNITED STATES PATENT AND TRADEMARK OFFICE
CERTIFICATE OF CORRECTION

PATENT NO.  : 5,804,197
DATED       : September 8, 1998
INVENTOR(S) : Haanes et al.

It is certified that error appears in the above-identified patent and that said Letters Patent is hereby corrected as shown below:

Claim 20,
Line 57, delete "a" and insert –an– therefor

Claim 22,
Line 8, delete "controls" and insert –control– therefor

Claim 23,
Line 18, delete the comma after "recombinant"
Line 30, delete "variant" and insert –variants– therefor Claim 24,
Line 44, delete "nCUSS8.5$_{237}$" and insert nCUS8.5$_{237}$-therefor Claim 26,
Lines 12-13, delete the phrase "and wherein said CHV genome is reproduction competent,"
Line 15, add –CHV– after "CgC negative"
Line 16, add –CHV– after "CgI negative"

Claim 27,
Line 30, delete "CTX" and insert –CTK– therefor
Line 32, delete "CUL49-5" and insert –CUL49.5– therefor
Line 32, delete "CUJS8.5" and insert –CUS8.5– therefor Claim 28,
Line 34, add –a– after "to"
Line 35, delete "molecules" and insert –molecule– therefor
Line 38, delete "saud" and insert –said– therefor
Line 43, after "region" and before ".", add the phrase –and an intergenic site in said US region–

UNITED STATES PATENT AND TRADEMARK OFFICE
CERTIFICATE OF CORRECTION

PATENT NO. : 5,804,197
DATED : September 8, 1998
INVENTOR(S) : Haanes et al.

It is certified that error appears in the above-identified patent and that said Letters Patent is hereby corrected as shown below:

Claim 29,
Line 50, delete "," after wherein"

Claim 30,
Lines 63-64, delete "nCHIN$_{3000}$, nCHIN$_{1900}$, nCHIN$_{5500}$, nCHIN$_{8500}$" and insert –nCHin$_{3000}$, nCHin$_{1900}$, nCHin$_{5500}$, nCHin$_{8500}$– therefor Claim 31,
Line 10, after "nCUS$_{10592}$," add –a CHV UL–
Line 12, after "CUL48$_{2044}$," add –a CHV UL–

Claim 32,
Line 25, delete "nCgC/CUL45$_{2200}$" and insert –nCgC/CUL45$_{2100}$-therefor
Line 26, delete "nCgD$_{1039}$" and insert –nCgD$_{1038}$-therefor
Line 26, "nCgI$_{1045}$" and insert –nCgI$_{1095}$-therefor
Line 27, add -,- after "NCUS9$_{360}$"
Line 27, delete "nCUL49/CUL48" and insert –nCUL49/CUL48$_{2044}$-therefor
Line 28, delete "nCUL 49" and insert –nCUL49$_{420}$– therefore

UNITED STATES PATENT AND TRADEMARK OFFICE
CERTIFICATE OF CORRECTION

PATENT NO. : 5,804,197
DATED : September 8, 1998
INVENTOR(S) : Haanes et al.

It is certified that error appears in the above-identified patent and that said Letters Patent is hereby corrected as shown below:

Claim 32, cont'd
Line 28, delete "nCUL420" and insert –nCUL$_{1823}$-therefor

Claim 33,
Line 43, delete "NO2" and insert –NO:2-therefor

Claim 36,
Line 6, delete "CUL38a" and insert –CUL38– therefor

Signed and Sealed this

Nineteenth Day of June, 2001

*Attest:*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 92

( 2 ) INFORMATION FOR SEQ ID NO:1:

( i ) SEQUENCE CHARACTERISTICS:
        ( A ) LENGTH: 5495 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CTGCAGTGTA   TTTAAAAAAT   AAAATCTATG   AATGAAATCT   ATGAATGAAA   TCTATGAATG        60

AAATCTATGA   ATGAAATCTA   TGAATGAAAT   CTATGAATGA   AATCTATGAA   TGAAATCTAT       120

GAATGAAATC   TATGAATGAA   ATCTATGAAT   GAAATCTATG   AATGAAATCT   ATGAATGAAA       180
```

-continued

```
TCTATGAATG  AAATCTATGA  ATGAAATCTA  TGAATGAAAT  CTATGAATGA  AATCTATGAA   240
TGAAATCTAT  GAATGAAATC  TATGAATGAA  ATCTATGAAT  GAAATCTATG  AATGAAATCT   300
ATGAGACAAG  TATTTTAAAA  ATATTTTAAA  TTTATAAGGT  TAAGTACAGT  AGGCGGTTGG   360
GTAAACATTT  TTAGTTTTTC  AAGTTTTTAG  TTTTTCTGGT  ATCCTACCCA  ACACAAATGC   420
ATCTTCGGAT  ACATTTATTT  TAAGAGAGTA  ATCACTTTTT  AGAATATATC  TTATTGGTGG   480
TACATTTATA  AATTTTGGAC  CATCCCAATA  ACACTTCGAT  TCCACAAGCG  AAGAAGGTAC   540
TTCCATAAGC  TGAGAAGCGT  TTACTTGATT  GTAGGGAGAA  CTTGGCGTTT  CAAAATCCTT   600
TAGAACGTAT  AGTCTGCAAT  ACATAGGTTC  AATATCATCT  TCATACCTCT  CATCAGGATA   660
TGAAAATGGA  AGTTTCACAA  AGGTTCCATC  ACGAAGCTTT  TTGAAGAATC  GTACATCCGT   720
AGGTGGTGTA  GGAACAATAG  TGAAGGCGTG  CGGTTCACCC  TGGTTTTTCA  CACGTGCAAG   780
CGCTGGTGTG  GTTTTAGGGC  GAACTGGAAA  ATAACCAGGC  GGAACTTGTG  CGTAGAATCC   840
TTCATTAAGT  TCTCCACGAC  AGCGTCTGAA  GTATGATGGC  ATATTAGCTT  GATCGGAGTT   900
GTTATCAAAT  AGAGCAAATG  AAGCACTCAT  TTTAAAACTT  TTTAGTTAAG  CTTTAAAAAC   960
AAGTGAAGAT  TTAAAAATGT  AGGATAAAAT  GCCAGTTTAT  ATACAGTAAG  AATATGGGAG  1020
TGGTTCACAT  AAAAAACCAG  AATTTCAGGT  TTACATCTAC  TGTTTATTCA  CAACAAATAT  1080
AAACAAACTT  AGTTTCCACA  TAAACATGAA  CTAAATAGAG  ATGAACGTTG  AGCGTTGGTA  1140
GGTTGTGTAG  AAGACATACC  ATCGTTTTCA  TTTTTGGTTA  TTGTTTTGGC  GCGCCTTGAA  1200
AATAATCGTT  TAAAAATATT  TGGTTTGGAT  AGCCTTTTCA  TAGGTTTCAC  CCCATGCAAG  1260
TCATCCTCTT  CTGGTTCAGG  AATTTCTTCA  TAACCATTAT  GGGATATTAT  TGCACACATA  1320
AATGATTCGA  TTACCGGGGG  GGCAGAACGT  GTCTCATTTA  TATAAAGAGA  ATCACATACA  1380
TCGCTTATAG  AACATGTAGA  ACTGTCAGAA  TCCTCTTTAA  AACTATTTTT  AATTTCACAA  1440
TTAGTTTCTT  CTAGTTCATT  ATCCACCATC  GCATTAGCGT  ATTTCCAAAT  ATCATTCTCT  1500
GAGGAATAAT  GAGATGCAGA  GCATGAAGAA  GAGGATGAGG  AGGAGGAGGA  TGAAGATGAG  1560
GATATAGAGG  GACATCTTGG  AGAGCTTTCA  AAGTTGAATG  GAGTATTAAA  TGTTGTACCA  1620
TAAAAAATGT  CACTTAACAT  AGGGGGTACT  TTAAAGGAGG  ACAGAAAGGT  GTCTAATACA  1680
GGTACCCATA  TAAACGAGGG  GCAATAAACA  CTCCCAGAAT  CATCGATATG  TTTTACATTA  1740
TTTTTGGAAA  TCTCAAGACA  CTCAGGTTTC  CAGGATGGTT  CCGGCCATTC  ACATGATACA  1800
TATGCATAAA  TTAGTCGCTT  TGGTCCTGGG  ATATTAGAAA  TGACTGGCTC  ACATAAATCC  1860
GCTGCACCGA  AAACCCATAG  ATTAAGAGGA  TAGTTTCCAA  ATATACCAGA  GTTTAGATAG  1920
TTATACCCCG  AAACAGCCGA  TTTCCATTCG  ATGCTAGCCC  CAGGTTTATC  CTCATAAAAT  1980
AAAAAGTCCT  CCTCCTCCCC  CTCCGTTGGT  TTTAAAAATT  TACTATTAGA  GGTTGATGTT  2040
CTTACTATAG  GCCTTGAAAC  TCTAGGTAGA  TGTTTTATAG  AGTCCATAAA  ATAACATAAG  2100
TTTGCAGATC  GTAATATTAT  AGGCATAGCC  AATCGTGTGA  GAGAAAGGAT  ATAGCATTGT  2160
CTAGCCATAA  AACACCAAAG  ATCAGGATGA  ACATCTTGGG  AGTTCCTGG   TAACGCCCCA  2220
TTTTTGTCAA  TAAACGTAAC  AATATTAACT  TCAACCACAC  CCATAATTAA  ATTTTATGTA  2280
TGAATCCAAT  AAAGGTTAAT  ACACACCTAA  TTTATGTTAT  AATTTTAGAA  GAAGCTGCAG  2340
TTGATGAGTT  GATATTAACA  TAACAATTTC  ACAATTACCT  GATATGGCAA  AGTGTACCAC  2400
CGAAAAGTTT  TGTTGTATCA  GCGTGAATAG  AGAATCTTCT  GTCGATCCAG  AAGACTTCTA  2460
TAAACCGGTT  CCTCTAACTT  CAGATTTGAT  TGAAGAGGAT  AACCTACATC  AAGACAAAAT  2520
AATGGATGAG  GATTTATACT  CGGATTTTAG  TGATGATGAC  TTTATGGATT  ATACAAAAAA  2580
```

| | | | | | | |
|---|---|---|---|---|---|---|
| TCCAACTGAA | AGTGAAAATG | AAAGAGAAAG | TGACGAAGAA | GTTGAAGAAA | GTTATGAAAG | 2640 |
| TGATGAAGAT | AAAAAAAGTT | TATCTCCTAC | TAAAAGCGAA | GGAATTGAAG | CGGCTGAAGC | 2700 |
| GCTAAAGTTT | TCTGTTGTTA | AATCGTTAAC | GCCTGGGTCA | GAAGGAAGAG | TTTTTATTGC | 2760 |
| TCTTAAAAAA | GATAAAGATA | CAAGCTATAA | GGTAATTTTA | AAAATTGGAC | AAAGGGGAAA | 2820 |
| CACGCTTGTG | GAATCGTTAA | TTTTGAGAAA | TATTAGTCAC | CAATCTATAA | TTAAACTTCA | 2880 |
| AGACACTCTT | TTTTATAAAG | AGTTAACATG | TTTGGTGTTA | CCGTATTATA | AATATGATCT | 2940 |
| ATATAATTTT | TTAATGGATC | ATGGGAAATC | TCTGTCTTTT | GAATCTGTAA | TTAAAATTGA | 3000 |
| AAAACAAATA | TTAACTGGAC | TTCAATATAT | TCATGGAAAA | AAAATTATTC | ATCGAGATAT | 3060 |
| AAAAACTGAA | AATATTTTCT | TGGATAATGA | CTCTAATGTT | TGTATAGGTG | ATTTTGGGGC | 3120 |
| TTCTCAATTT | CCTGTTTCCT | CACCAGATTA | TTTGGGAATT | GCGGGGACTA | TTGAAACTAA | 3180 |
| TGCTCCTGAA | GTTCTATCAA | AGGATGCGTA | CAACTGTAAA | GCTGATATTT | GGAGTGCTGG | 3240 |
| TATAATTTTA | TTTGAAATGC | TTGCATATCC | TAATGTTTTG | TTTGAGGAGG | AAGAAAGAGA | 3300 |
| TAGTAGCGAT | TTAATAAACA | ATTGTAATCT | TCATCTTATA | AAAATTATAT | CAACTCTGAA | 3360 |
| GATTAACCCA | AATGAATTTC | CATCTGATTT | GGAATCTAAT | CTAGTAAAAC | ATTTTATAAA | 3420 |
| ATATGCTAAT | AATGATAGAC | CTCCATTTAC | ACGATATAAT | CGTCTAAATA | ACCTTAAATT | 3480 |
| ACATCTCGAT | GGTGAATTTT | TAATTCATAA | AATGCTAACA | TTTGATGCAT | CTCTACGACC | 3540 |
| AAGTGCGGAA | GAACTATTAT | CCTATCAGAT | TTTTAGTAAA | CAATAAATTT | CATAAAAATG | 3600 |
| GGCGTGGAAT | TTTTTATTGT | TTTATATAAA | ACGGGTGTTT | GAAAGCTCTT | TTTTATTAAT | 3660 |
| TTTATTTTTA | CATCCTAGCT | ACAATATTAT | AGTTATCATG | TTGTATACGC | TGTTTTTTGT | 3720 |
| TTTTTATTTT | AAGGTAGTTT | TATCTCGCAT | AGCTCCGCTA | GAGTTGTGTT | ATGCGGATCC | 3780 |
| TAAAGAAAAT | ACAACTGAAC | CTACACAACT | TCCTACAGGG | GAACAATCTA | AGACTCTTAT | 3840 |
| TCCCGTGGTA | ACAAACGGAT | ATGTTGAATA | CTCTAAAGGA | TGTGAACTAC | GATTACTAGA | 3900 |
| TACATATGTA | AATGTATCTT | CACGACCAGA | AAAAAAGGTT | AATGCTACAA | TTGGATGGTC | 3960 |
| ATTTGATCTT | GGTTGTCAAA | TTCCTTTAAT | TTATAGAGAA | TATTATAATT | GTACTGGTAA | 4020 |
| TATAATACCA | TCACCAGAAA | CTTGTGATGG | TTATTCTTTA | ACTTGGTAA | AATCTGAAAG | 4080 |
| TATATCATCT | TATGCACTTG | TTAATGTTAG | TTTGCTTATT | CAACCAGGAA | TTTTTGATTC | 4140 |
| TGGTAGATAT | TTATACTCAC | TTGTTTTTGG | AAACGATAGT | TATAACGGAA | GAATTGAAGT | 4200 |
| TCGAGTGGAT | AATGAGACAG | ACTATCCATG | TTTTATGATG | CATGGATTGA | CTGTAAAAAA | 4260 |
| GGGTGATAAA | CTTCATATTC | CTTATAAACC | ATCCACAAAT | CCTAATCATA | AACGATATAG | 4320 |
| AGGTTGTTTT | CCAATATCAA | ATACTGAGCT | ATGGAATAAT | ATTAGTGATG | AAAGTGTTGG | 4380 |
| TAGATATTCA | TATGATGAAG | AATATGAAGA | ATATGAAGAA | GAAAACGAAG | ATTTTGAAGA | 4440 |
| TCTACAATCA | AAAGATTGCC | GCAAATCCAA | TCTTTTTGAT | ATGAAGAAGA | CTTTTAATTT | 4500 |
| GGCTGCAGGT | TCTCAAAGTT | TATTGATTGC | TAGTTTGGGT | AAATCAATTT | CAGAACAACC | 4560 |
| GTGGTCATTT | AAAATTAATG | AAAGTTATGA | ACTTTTTAAT | AATTTGTCTA | TCACCCTTCA | 4620 |
| ATCGGAAGAA | GATTCTAATA | TACTGAATCC | TGAAATTGTA | ACGTTACCA | CACCACCACC | 4680 |
| TACTGAAAAT | ACACATATGT | TTATGTCAAA | TAATGAAACT | ATGTATGAAG | AAGAAAGTGT | 4740 |
| TTTAAGCATT | ATTCAATTGT | TTAACAATGG | TTATAATAAT | TGTAATACCC | ATATAAAGGT | 4800 |
| AATTGGATTT | GGAACAATTA | TCTTTATTAT | TTTATTTTTT | GTTGCTGTGT | TTTTTTGTGG | 4860 |
| ATATACTTGT | GTATTAAACT | CTCGTATTAA | AATGATTAAC | CATGCTTATA | TACAACCCCA | 4920 |
| GAAATTAAAT | TTTTATGATA | TTTAATAAAA | CTATTATGAA | ACTTCTTATA | ACTTATTTGT | 4980 |

| | | | | | | |
|---|---|---|---|---|---|---|
| TTTTATTAAA | TGGGTTGGGT | TGGTTTTAAA | ATTACATACG | TGTATTAAGA | ATTAACATCA | 5040 |
| TAAAGGACAC | ACCCATGAAA | AACATTTAAA | TTCTATTAAT | TTGAACGGAT | TAAACATTTT | 5100 |
| CTCATTTTAA | GAGTTGCTAC | GACTTTTGAT | AGTAAAATGA | TTAAACTTCT | ATTTATCTTA | 5160 |
| TTTTATTTTA | ACCCAATAAC | TGGATATAAA | TGGGTAGACC | CTCCTCGTAG | GTATAATTAC | 5220 |
| ACCGTTTTAA | GAATGATTCC | AGATATTCCA | AATCCAATGG | ATCCTTCTAA | AAACGCTGAA | 5280 |
| GTTCGGTATG | TAACTTCTAC | TGACCCATGT | GATATGGTTG | CTTTGATTTC | TAATCCAAAT | 5340 |
| ATAGAATCTA | CAATTAAAAC | GATTCAATTT | GTGCAAAAGA | AAAAATTTTA | CAATGCATCT | 5400 |
| CTTAGTTGGT | TTAAAGTTGG | AGATGATTGT | ACATATCCAA | TATATTTAAT | TCAATATTTT | 5460 |
| GATTGTGATC | CTCAAAGAGA | ATTTGGCATA | TGTTT | | | 5495 |

( 2 ) INFORMATION FOR SEQ ID NO:2:

( i ) SEQUENCE CHARACTERISTICS:
        ( A ) LENGTH: 5495 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| AAACATATGC | CAAATTCTCT | TGAGGATCA | CAATCAAAAT | ATTGAATTAA | ATATATTGGA | 60 |
| TATGTACAAT | CATCTCCAAC | TTTAAACCAA | CTAAGAGATG | CATTGTAAAA | TTTTTTCTTT | 120 |
| TGCACAAATT | GAATCGTTTT | AATTGTAGAT | TCTATATTTG | GATTAGAAAT | CAAAGCAACC | 180 |
| ATATCACATG | GGTCAGTAGA | AGTTACATAC | CGAACTTCAG | CGTTTTTAGA | AGGATCCATT | 240 |
| GGATTTGGAA | TATCTGGAAT | CATTCTTAAA | ACGGTGTAAT | TATACCTACG | AGGAGGGTCT | 300 |
| ACCCATTTAT | ATCCAGTTAT | TGGGTAAAAA | TAAATAAGA | TAAATAGAAG | TTTAATCATT | 360 |
| TTACTATCAA | AAGTCGTAGC | AACTCTTAAA | ATGAGAAAAT | GTTTAATCCG | TTCAAATTAA | 420 |
| TAGAATTTAA | ATGTTTTTCA | TGGGTGTGTC | CTTTATGATG | TTAATTCTTA | ATACACGTAT | 480 |
| GTAATTTTAA | AACCAACCCA | ACCCATTTAA | TAAAAACAAA | TAAGTTATAA | GAAGTTTCAT | 540 |
| AATAGTTTTA | TTAAATATCA | TAAAAATTTA | ATTTCTGGGG | TTGTATATAA | GCATGGTTAA | 600 |
| TCATTTTAAT | ACGAGAGTTT | AATACACAAG | TATATCCACA | AAAAACACA | GCAACAAAAA | 660 |
| ATAAAATAAT | AAAGATAATT | GTTCCAAATC | CAATTACCTT | TATATGGGTA | TTACAATTAT | 720 |
| TATAACCATT | GTTAAACAAT | TGAATAATGC | TTAAAACACT | TTCTTCTTCA | TACATAGTTT | 780 |
| CATTATTTGA | CATAAACATA | TGTGTATTTT | CAGTAGGTGG | TGGTGTGGTA | AACGTTACAA | 840 |
| TTTCAGGATT | CAGTATATTA | GAATCTTCTT | CCGATTGAAG | GGTGATAGAC | AAATTATTAA | 900 |
| AAAGTTCATA | ACTTTCATTA | ATTTTAAATG | ACCACGGTTG | TTCTGAAATT | GATTTACCCA | 960 |
| AACTAGCAAT | CAATAAACTT | TGAGAACCTG | CAGCCAAATT | AAAAGTCTTC | TTCATATCAA | 1020 |
| AAAGATTGGA | TTTGCGGCAA | TCTTTTGATT | GTAGATCTTC | AAAATCTTCG | TTTTCTTCTT | 1080 |
| CATATTCTTC | ATATTCTTCA | TCATATGAAT | ATCTACCAAC | ACTTTCATCA | CTAATATTAT | 1140 |
| TCCATAGCTC | AGTATTTGAT | ATTGGAAAAC | AACCTCTATA | TCGTTTATGA | TTAGGATTTG | 1200 |
| TGGATGGTTT | ATAAGGAATA | TGAAGTTTAT | CACCCTTTTT | TACAGTCAAT | CCATGCATCA | 1260 |
| TAAAACATGG | ATAGTCTGTC | TCATTATCCA | CTCGAACTTC | AATTCTTCCG | TTATAACTAT | 1320 |
| CGTTTCCAAA | AACAAGTGAG | TATAAATATC | TACCAGAATC | AAAAATTCCT | GGTTGAATAA | 1380 |
| GCAAACTAAC | ATTAACAAGT | GCATAAGATG | ATATACTTTC | AGATTTTACC | AAAGTTAAAG | 1440 |
| AATAACCATC | ACAAGTTTCT | GGTGATGGTA | TTATATTACC | AGTACAATTA | TAATATTCTC | 1500 |

```
TATAAATTAA AGGAATTTGA CAACCAAGAT CAAATGACCA TCCAATTGTA GCATTAACCT   1560
TTTTTTCTGG TCGTGAAGAT ACATTTACAT ATGTATCTAG TAATCGTAGT TCACATCCTT   1620
TAGAGTATTC AACATATCCG TTTGTTACCA CGGGAATAAG AGTCTTAGAT TGTTCCCCTG   1680
TAGGAAGTTG TGTAGGTTCA GTTGTATTTT CTTTAGGATC CGCATAACAC AACTCTAGCG   1740
GAGCTATGCG AGATAAAACT ACCTTAAAAT AAAAAACAAA AACAGCGTA  TACAACATGA   1800
TAACTATAAT ATTGTAGCTA GGATGTAAAA ATAAAATTAA TAAAAAGAG  CTTTCAAACA   1860
CCCGTTTTAT ATAAAACAAT AAAAAATTCC ACGCCCATTT TTATGAAATT TATTGTTTAC   1920
TAAAAATCTG ATAGGATAAT AGTTCTTCCG CACTTGGTCG TAGAGATGCA TCAAATGTTA   1980
GCATTTTATG AATTAAAAAT TCACCATCGA GATGTAATTT AAGGTTATTT AGACGATTAT   2040
ATCGTGTAAA TGGAGGTCTA TCATTATTAG CATATTTTAT AAAATGTTTT ACTAGATTAG   2100
ATTCCAAATC AGATGGAAAT TCATTGGGT  TAATCTTCAG AGTTGATATA ATTTTTATAA   2160
GATGAAGATT ACAATTGTTT ATTAAATCGC TACTATCTCT TTCTTCCTCC TCAAACAAAA   2220
CATTAGGATA TGCAAGCATT TCAAATAAAA TTATACCAGC ACTCCAAATA TCAGCTTTAC   2280
AGTTGTACGC ATCCTTTGAT AGAACTTCAG GAGCATTAGT TTCAATAGTC CCCGCAATTC   2340
CCAAATAATC TGGTGAGGAA ACAGGAAATT GAGAAGCCCC AAAATCACCT ATACAAACAT   2400
TAGAGTCATT ATCCAAGAAA ATATTTTCAG TTTTTATATC TCGATGAATA ATTTTTTTC   2460
CATGAATATA TTGAAGTCCA GTTAATATTT GTTTTTCAAT TTAATTACA  GATTCAAAAG   2520
ACAGAGATTT CCCATGATCC ATTAAAAAAT TATATAGATC ATATTTATAA TACGGTAACA   2580
CCAAACATGT TAACTCTTTA TAAAAAGAG  TGTCTTGAAG TTTAATTATA GATTGGTGAC   2640
TAATATTTCT CAAAATTAAC GATTCCACAA GCGTGTTTCC CCTTTGTCCA ATTTTTAAAA   2700
TTACCTTATA GCTTGTATCT TTATCTTTTT TAAGAGCAAT AAAAACTCTT CCTTCTGACC   2760
CAGGCGTTAA CGATTTAACA ACAGAAAACT TTAGCGCTTC AGCCGCTTCA ATTCCTTCGC   2820
TTTTAGTAGG AGATAAACTT TTTTTATCTT CATCACTTTC ATAACTTTCT TCAACTTCTT   2880
CGTCACTTTC TCTTTCATTT TCACTTTCAG TTGGATTTTT TGTATAATCC ATAAAGTCAT   2940
CATCACTAAA ATCCGAGTAT AAATCCTCAT CCATTATTTT GTCTTGATGT AGGTTATCCT   3000
CTTCAATCAA ATCTGAAGTT AGAGGAACCG GTTATAGAA  GTCTTCTGGA TCGACAGAAG   3060
ATTCTCTATT CACGCTGATA CAACAAAACT TTTCGGTGGT ACACTTTGCC ATATCAGGTA   3120
ATTGTGAAAT TGTTATGTTA ATATCAACTC ATCAACTGCA GCTTCTTCTA AAATTATAAC   3180
ATAAATTAGG TGTGTATTAA CCTTTATTGG ATTCATACAT AAAATTTAAT TATGGGTGTG   3240
GTTGAAGTTA ATATTGTTAC GTTTATTGAC AAAAATGGGG CGTTACCAGG AAACTCCCAA   3300
GATGTTCATC CTGATCTTTG GTGTTTTATG GCTAGACAAT GCTATATCCT TTCTCTCACA   3360
CGATTGGCTA TGCCTATAAT ATTACGATCT GCAAACTTAT GTTATTTAT  GGACTCTATA   3420
AAACATCTAC CTAGAGTTTC AAGGCCTATA GTAAGAACAT CAACCTCTAA TAGTAAATTT   3480
TTAAAACCAA CGGAGGGGGA GGAGGAGGAC TTTTTATTTT ATGAGGATAA ACCTGGGGCT   3540
AGCATCGAAT GGAAATCGGC TGTTTCGGGG TATAACTATC TAAACTCTGG TATATTTGGA   3600
AACTATCCTC TTAATCTATG GGTTTTCGGT GCAGCGGATT TATGTGAGCC AGTCATTTCT   3660
AATATCCCAG GACCAAAGCG ACTAATTTAT GCATATGTAT CATGTGAATG GCCGGAACCA   3720
TCCTGGAAAC CTGAGTGTCT TGAGATTCC  AAAAATAATG TAAAACATAT CGATGATTCT   3780
GGGAGTGTTT ATTGCCCCTC GTTTATATGG GTACCTGTAT TAGACACCTT TCTGTCCTCC   3840
TTTAAAGTAC CCCCTATGTT AAGTGACATT TTTTATGGTA CAACATTTAA TACTCCATTC   3900
```

-continued

```
AACTTTGAAA GCTCTCCAAG ATGTCCCTCT ATATCCTCAT CTTCATCCTC CTCCTCCTCA    3960
TCCTCTTCTT CATGCTCTGC ATCTCATTAT TCCTCAGAGA ATGATATTTG GAAATACGCT    4020
AATGCGATGG TGGATAATGA ACTAGAAGAA ACTAATTGTG AAATTAAAAA TAGTTTTAAA    4080
GAGGATTCTG ACAGTTCTAC ATGTTCTATA AGCGATGTAT GTGATTCTCT TTATATAAAT    4140
GAGACACGTT CTGCCCCCCC GGTAATCGAA TCATTTATGT GTGCAATAAT ATCCCATAAT    4200
GGTTATGAAG AAATTCCTGA ACCAGAAGAG GATGACTTGC ATGGGGTGAA ACCTATGAAA    4260
AGGCTATCCA AACCAAATAT TTTTAAACGA TTATTTTCAA GGCGCGCCAA AACAATAACC    4320
AAAAATGAAA ACGATGGTAT GTCTTCTACA CAACCTACCA ACGCTCAACG TTCATCTCTA    4380
TTTAGTTCAT GTTTATGTGG AAACTAAGTT TGTTTATATT TGTTGTGAAT AAACAGTAGA    4440
TGTAAACCTG AAATTCTGGT TTTTTATGTG AACCACTCCC ATATTCTTAC TGTATATAAA    4500
CTGGCATTTT ATCCTACATT TTTAAATCTT CACTTGTTTT TAAAGCTTAA CTAAAAGTT    4560
TTAAAATGAG TGCTTCATTT GCTCTATTTG ATAACAACTC CGATCAAGCT AATATGCCAT    4620
CATACTTCAG ACGCTGTCGT GGAGAACTTA ATGAAGGATT CTACGCACAA GTTCCGCCTG    4680
GTTATTTTCC AGTTCGCCCT AAAACCACAC CAGCGCTTGC ACGTGTGAAA AACCAGGGTG    4740
AACCGCACGC CTTCACTATT GTTCCTACAC CACCTACGGA TGTACGATTC TTCAAAAAGC    4800
TTCGTGATGG AACCTTTGTG AAACTTCCAT TTTCATATCC TGATGAGAGG TATGAAGATG    4860
ATATTGAACC TATGTATTGC AGACTATACG TTCTAAAGGA TTTTGAAACG CCAAGTTCTC    4920
CCTACAATCA AGTAAACGCT TCTCAGCTTA TGGAAGTACC TTCTTCGCTT GTGGAATCGA    4980
AGTGTTATTG GGATGGTCCA AAATTTATAA ATGTACCACC AATAAGATAT ATTCTAAAAA    5040
GTGATTACTC TCTTAAAATA AATGTATCCG AAGATGCATT TGTGTTGGGT AGGATACCAG    5100
AAAAACTAAA AACTTGAAAA ACTAAAAATG TTTACCCAAC CGCCTACTGT ACTTAACCTT    5160
ATAAATTTAA AATATTTTTA AAATACTTGT CTCATAGATT TCATTCATAG ATTTCATTCA    5220
TAGATTTCAT TCATAGATTT CATTCATAGA TTTCATTCAT AGATTTCATT CATAGATTTC    5280
ATTCATAGAT TTCATTCATA GATTTCATTC ATAGATTTCA TTCATAGATT TCATTCATAG    5340
ATTTCATTCA TAGATTTCAT TCATAGATTT CATTCATAGA TTTCATTCAT AGATTTCATT    5400
CATAGATTTC ATTCATAGAT TTCATTCATA GATTTCATTC ATAGATTTCA TTCATAGATT    5460
TCATTCATAG ATTTTATTTT TTAAATACAC TGCAG                               5495
```

( 2 ) INFORMATION FOR SEQ ID NO:3:

( i ) SEQUENCE CHARACTERISTICS:
        ( A ) LENGTH: 552 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..552

( x i ) SEQUENCE DESCRIPTION: SEQ ID NO:3:

```
ATG AGT GCT TCA TTT GCT CTA TTT GAT AAC AAC TCC GAT CAA GCT AAT    48
Met Ser Ala Ser Phe Ala Leu Phe Asp Asn Asn Ser Asp Gln Ala Asn
 1               5                  10                  15

ATG CCA TCA TAC TTC AGA CGC TGT CGT GGA GAA CTT AAT GAA GGA TTC    96
Met Pro Ser Tyr Phe Arg Arg Cys Arg Gly Glu Leu Asn Glu Gly Phe
            20                  25                  30
```

| | | | | | | | | | | | | | | | | |
|---|---|---|---|---|---|---|---|---|---|---|---|---|---|---|---|---|
| TAC | GCA | CAA | GTT | CCG | CCT | GGT | TAT | TTT | CCA | GTT | CGC | CCT | AAA | ACC | ACA | 144 |
| Tyr | Ala | Gln | Val | Pro | Pro | Gly | Tyr | Phe | Pro | Val | Arg | Pro | Lys | Thr | Thr | |
| | | 35 | | | | | 40 | | | | | 45 | | | | |
| CCA | GCG | CTT | GCA | CGT | GTG | AAA | AAC | CAG | GGT | GAA | CCG | CAC | GCC | TTC | ACT | 192 |
| Pro | Ala | Leu | Ala | Arg | Val | Lys | Asn | Gln | Gly | Glu | Pro | His | Ala | Phe | Thr | |
| | 50 | | | | | 55 | | | | | 60 | | | | | |
| ATT | GTT | CCT | ACA | CCA | CCT | ACG | GAT | GTA | CGA | TTC | TTC | AAA | AAG | CTT | CGT | 240 |
| Ile | Val | Pro | Thr | Pro | Pro | Thr | Asp | Val | Arg | Phe | Phe | Lys | Lys | Leu | Arg | |
| 65 | | | | | 70 | | | | | 75 | | | | | 80 | |
| GAT | GGA | ACC | TTT | GTG | AAA | CTT | CCA | TTT | TCA | TAT | CCT | GAT | GAG | AGG | TAT | 288 |
| Asp | Gly | Thr | Phe | Val | Lys | Leu | Pro | Phe | Ser | Tyr | Pro | Asp | Glu | Arg | Tyr | |
| | | | | 85 | | | | | 90 | | | | | 95 | | |
| GAA | GAT | GAT | ATT | GAA | CCT | ATG | TAT | TGC | AGA | CTA | TAC | GTT | CTA | AAG | GAT | 336 |
| Glu | Asp | Asp | Ile | Glu | Pro | Met | Tyr | Cys | Arg | Leu | Tyr | Val | Leu | Lys | Asp | |
| | | | 100 | | | | | 105 | | | | | 110 | | | |
| TTT | GAA | ACG | CCA | AGT | TCT | CCC | TAC | AAT | CAA | GTA | AAC | GCT | TCT | CAG | CTT | 384 |
| Phe | Glu | Thr | Pro | Ser | Ser | Pro | Tyr | Asn | Gln | Val | Asn | Ala | Ser | Gln | Leu | |
| | | 115 | | | | | 120 | | | | | 125 | | | | |
| ATG | GAA | GTA | CCT | TCT | TCG | CTT | GTG | GAA | TCG | AAG | TGT | TAT | TGG | GAT | GGT | 432 |
| Met | Glu | Val | Pro | Ser | Ser | Leu | Val | Glu | Ser | Lys | Cys | Tyr | Trp | Asp | Gly | |
| | 130 | | | | | 135 | | | | | 140 | | | | | |
| CCA | AAA | TTT | ATA | AAT | GTA | CCA | CCA | ATA | AGA | TAT | ATT | CTA | AAA | AGT | GAT | 480 |
| Pro | Lys | Phe | Ile | Asn | Val | Pro | Pro | Ile | Arg | Tyr | Ile | Leu | Lys | Ser | Asp | |
| 145 | | | | | 150 | | | | | 155 | | | | | 160 | |
| TAC | TCT | CTT | AAA | ATA | AAT | GTA | TCC | GAA | GAT | GCA | TTT | GTG | TTG | GGT | AGG | 528 |
| Tyr | Ser | Leu | Lys | Ile | Asn | Val | Ser | Glu | Asp | Ala | Phe | Val | Leu | Gly | Arg | |
| | | | | 165 | | | | | 170 | | | | | 175 | | |
| ATA | CCA | GAA | AAA | CTA | AAA | ACT | TGA | | | | | | | | | 552 |
| Ile | Pro | Glu | Lys | Leu | Lys | Thr | * | | | | | | | | | |
| | | | 180 | | | | | | | | | | | | | |

(2) INFORMATION FOR SEQ ID NO:4:

(i) SEQUENCE CHARACTERISTICS:
        (A) LENGTH: 183 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met | Ser | Ala | Ser | Phe | Ala | Leu | Phe | Asp | Asn | Asn | Ser | Asp | Gln | Ala | Asn |
| 1 | | | | 5 | | | | | 10 | | | | | 15 | |
| Met | Pro | Ser | Tyr | Phe | Arg | Arg | Cys | Arg | Gly | Glu | Leu | Asn | Glu | Gly | Phe |
| | | | 20 | | | | | 25 | | | | | 30 | | |
| Tyr | Ala | Gln | Val | Pro | Pro | Gly | Tyr | Phe | Pro | Val | Arg | Pro | Lys | Thr | Thr |
| | | | 35 | | | | | 40 | | | | | 45 | | |
| Pro | Ala | Leu | Ala | Arg | Val | Lys | Asn | Gln | Gly | Glu | Pro | His | Ala | Phe | Thr |
| | 50 | | | | | 55 | | | | | 60 | | | | |
| Ile | Val | Pro | Thr | Pro | Pro | Thr | Asp | Val | Arg | Phe | Phe | Lys | Lys | Leu | Arg |
| 65 | | | | | 70 | | | | | 75 | | | | | 80 |
| Asp | Gly | Thr | Phe | Val | Lys | Leu | Pro | Phe | Ser | Tyr | Pro | Asp | Glu | Arg | Tyr |
| | | | | 85 | | | | | 90 | | | | | 95 | |
| Glu | Asp | Asp | Ile | Glu | Pro | Met | Tyr | Cys | Arg | Leu | Tyr | Val | Leu | Lys | Asp |
| | | | 100 | | | | | 105 | | | | | 110 | | |
| Phe | Glu | Thr | Pro | Ser | Ser | Pro | Tyr | Asn | Gln | Val | Asn | Ala | Ser | Gln | Leu |
| | | 115 | | | | | 120 | | | | | 125 | | | |
| Met | Glu | Val | Pro | Ser | Ser | Leu | Val | Glu | Ser | Lys | Cys | Tyr | Trp | Asp | Gly |
| | 130 | | | | | 135 | | | | | 140 | | | | |
| Pro | Lys | Phe | Ile | Asn | Val | Pro | Pro | Ile | Arg | Tyr | Ile | Leu | Lys | Ser | Asp |

```
1 4 5                           1 5 0                           1 5 5                           1 6 0
Tyr  Ser  Leu  Lys  Ile  Asn  Val  Ser  Glu  Asp  Ala  Phe  Val  Leu  Gly  Arg
                    1 6 5                          1 7 0                     1 7 5

Ile  Pro  Glu  Lys  Leu  Lys  Thr
                    1 8 0
```

( 2 ) INFORMATION FOR SEQ ID NO:5:

( i ) SEQUENCE CHARACTERISTICS:
        ( A ) LENGTH: 1176 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1176

( x i ) SEQUENCE DESCRIPTION: SEQ ID NO:5:

```
ATG  GGT  GTG  GTT  GAA  GTT  AAT  ATT  GTT  ACG  TTT  ATT  GAC  AAA  AAT  GGG         48
Met  Gly  Val  Val  Glu  Val  Asn  Ile  Val  Thr  Phe  Ile  Asp  Lys  Asn  Gly
 1                   5                        1 0                       1 5

GCG  TTA  CCA  GGA  AAC  TCC  CAA  GAT  GTT  CAT  CCT  GAT  CTT  TGG  TGT  TTT         96
Ala  Leu  Pro  Gly  Asn  Ser  Gln  Asp  Val  His  Pro  Asp  Leu  Trp  Cys  Phe
                    2 0                        2 5                       3 0

ATG  GCT  AGA  CAA  TGC  TAT  ATC  CTT  TCT  CTC  ACA  CGA  TTG  GCT  ATG  CCT        144
Met  Ala  Arg  Gln  Cys  Tyr  Ile  Leu  Ser  Leu  Thr  Arg  Leu  Ala  Met  Pro
               3 5                        4 0                       4 5

ATA  ATA  TTA  CGA  TCT  GCA  AAC  TTA  TGT  TAT  TTT  ATG  GAC  TCT  ATA  AAA        192
Ile  Ile  Leu  Arg  Ser  Ala  Asn  Leu  Cys  Tyr  Phe  Met  Asp  Ser  Ile  Lys
          5 0                        5 5                       6 0

CAT  CTA  CCT  AGA  GTT  TCA  AGG  CCT  ATA  GTA  AGA  ACA  TCA  ACC  TCT  AAT        240
His  Leu  Pro  Arg  Val  Ser  Arg  Pro  Ile  Val  Arg  Thr  Ser  Thr  Ser  Asn
 6 5                     7 0                        7 5                        8 0

AGT  AAA  TTT  TTA  AAA  CCA  ACG  GAG  GGG  GAG  GAG  GAG  GAC  TTT  TTA  TTT        288
Ser  Lys  Phe  Leu  Lys  Pro  Thr  Glu  Gly  Glu  Glu  Glu  Asp  Phe  Leu  Phe
                    8 5                        9 0                       9 5

TAT  GAG  GAT  AAA  CCT  GGG  GCT  AGC  ATC  GAA  TGG  AAA  TCG  GCT  GTT  TCG        336
Tyr  Glu  Asp  Lys  Pro  Gly  Ala  Ser  Ile  Glu  Trp  Lys  Ser  Ala  Val  Ser
               1 0 0                      1 0 5                     1 1 0

GGG  TAT  AAC  TAT  CTA  AAC  TCT  GGT  ATA  TTT  GGA  AAC  TAT  CCT  CTT  AAT        384
Gly  Tyr  Asn  Tyr  Leu  Asn  Ser  Gly  Ile  Phe  Gly  Asn  Tyr  Pro  Leu  Asn
               1 1 5                      1 2 0                     1 2 5

CTA  TGG  GTT  TTC  GGT  GCA  GCG  GAT  TTA  TGT  GAG  CCA  GTC  ATT  TCT  AAT        432
Leu  Trp  Val  Phe  Gly  Ala  Ala  Asp  Leu  Cys  Glu  Pro  Val  Ile  Ser  Asn
     1 3 0                       1 3 5                     1 4 0

ATC  CCA  GGA  CCA  AAG  CGA  CTA  ATT  TAT  GCA  TAT  GTA  TCA  TGT  GAA  TGG        480
Ile  Pro  Gly  Pro  Lys  Arg  Leu  Ile  Tyr  Ala  Tyr  Val  Ser  Cys  Glu  Trp
1 4 5                    1 5 0                      1 5 5                     1 6 0

CCG  GAA  CCA  TCC  TGG  AAA  CCT  GAG  TGT  CTT  GAG  ATT  TCC  AAA  AAT  AAT        528
Pro  Glu  Pro  Ser  Trp  Lys  Pro  Glu  Cys  Leu  Glu  Ile  Ser  Lys  Asn  Asn
                    1 6 5                      1 7 0                     1 7 5

GTA  AAA  CAT  ATC  GAT  GAT  TCT  GGG  AGT  GTT  TAT  TGC  CCC  TCG  TTT  ATA        576
Val  Lys  His  Ile  Asp  Asp  Ser  Gly  Ser  Val  Tyr  Cys  Pro  Ser  Phe  Ile
               1 8 0                      1 8 5                     1 9 0

TGG  GTA  CCT  GTA  TTA  GAC  ACC  TTT  CTG  TCC  TCC  TTT  AAA  GTA  CCC  CCT        624
Trp  Val  Pro  Val  Leu  Asp  Thr  Phe  Leu  Ser  Ser  Phe  Lys  Val  Pro  Pro
          1 9 5                      2 0 0                     2 0 5

ATG  TTA  AGT  GAC  ATT  TTT  TAT  GGT  ACA  ACA  TTT  AAT  ACT  CCA  TTC  AAC        672
Met  Leu  Ser  Asp  Ile  Phe  Tyr  Gly  Thr  Thr  Phe  Asn  Thr  Pro  Phe  Asn
 2 1 0                       2 1 5                     2 2 0
```

| | | | | | | | | | | | | | | | | |
|---|---|---|---|---|---|---|---|---|---|---|---|---|---|---|---|---|
| TTT | GAA | AGC | TCT | CCA | AGA | TGT | CCC | TCT | ATA | TCC | TCA | TCT | TCA | TCC | TCC | 720 |
| Phe | Glu | Ser | Ser | Pro | Arg | Cys | Pro | Ser | Ile | Ser | Ser | Ser | Ser | Ser | Ser | |
| 225 | | | | 230 | | | | 235 | | | | | | | 240 | |
| TCC | TCC | TCA | TCC | TCT | TCT | TCA | TGC | TCT | GCA | TCT | CAT | TAT | TCC | TCA | GAG | 768 |
| Ser | Ser | Ser | Ser | Ser | Ser | Ser | Cys | Ser | Ala | Ser | His | Tyr | Ser | Ser | Glu | |
| | | | | 245 | | | | | 250 | | | | | 255 | | |
| AAT | GAT | ATT | TGG | AAA | TAC | GCT | AAT | GCG | ATG | GTG | GAT | AAT | GAA | CTA | GAA | 816 |
| Asn | Asp | Ile | Trp | Lys | Tyr | Ala | Asn | Ala | Met | Val | Asp | Asn | Glu | Leu | Glu | |
| | | | 260 | | | | | 265 | | | | | 270 | | | |
| GAA | ACT | AAT | TGT | GAA | ATT | AAA | AAT | AGT | TTT | AAA | GAG | GAT | TCT | GAC | AGT | 864 |
| Glu | Thr | Asn | Cys | Glu | Ile | Lys | Asn | Ser | Phe | Lys | Glu | Asp | Ser | Asp | Ser | |
| | | 275 | | | | | 280 | | | | | 285 | | | | |
| TCT | ACA | TGT | TCT | ATA | AGC | GAT | GTA | TGT | GAT | TCT | CTT | TAT | ATA | AAT | GAG | 912 |
| Ser | Thr | Cys | Ser | Ile | Ser | Asp | Val | Cys | Asp | Ser | Leu | Tyr | Ile | Asn | Glu | |
| | | 290 | | | | | 295 | | | | | 300 | | | | |
| ACA | CGT | TCT | GCC | CCC | CCG | GTA | ATC | GAA | TCA | TTT | ATG | TGT | GCA | ATA | ATA | 960 |
| Thr | Arg | Ser | Ala | Pro | Pro | Val | Ile | Glu | Ser | Phe | Met | Cys | Ala | Ile | Ile | |
| 305 | | | | | 310 | | | | | 315 | | | | | 320 | |
| TCC | CAT | AAT | GGT | TAT | GAA | GAA | ATT | CCT | GAA | CCA | GAA | GAG | GAT | GAC | TTG | 1008 |
| Ser | His | Asn | Gly | Tyr | Glu | Glu | Ile | Pro | Glu | Pro | Glu | Glu | Asp | Asp | Leu | |
| | | | | 325 | | | | | 330 | | | | | 335 | | |
| CAT | GGG | GTG | AAA | CCT | ATG | AAA | AGG | CTA | TCC | AAA | CCA | AAT | ATT | TTT | AAA | 1056 |
| His | Gly | Val | Lys | Pro | Met | Lys | Arg | Leu | Ser | Lys | Pro | Asn | Ile | Phe | Lys | |
| | | | 340 | | | | | 345 | | | | | 350 | | | |
| CGA | TTA | TTT | TCA | AGG | CGC | GCC | AAA | ACA | ATA | ACC | AAA | AAT | GAA | AAC | GAT | 1104 |
| Arg | Leu | Phe | Ser | Arg | Arg | Ala | Lys | Thr | Ile | Thr | Lys | Asn | Glu | Asn | Asp | |
| | | 355 | | | | | 360 | | | | | 365 | | | | |
| GGT | ATG | TCT | TCT | ACA | CAA | CCT | ACC | AAC | GCT | CAA | CGT | TCA | TCT | CTA | TTT | 1152 |
| Gly | Met | Ser | Ser | Thr | Gln | Pro | Thr | Asn | Ala | Gln | Arg | Ser | Ser | Leu | Phe | |
| | | 370 | | | | | 375 | | | | | 380 | | | | |
| AGT | TCA | TGT | TTA | TGT | GGA | AAC | TAA | | | | | | | | | 1176 |
| Ser | Ser | Cys | Leu | Cys | Gly | Asn | * | | | | | | | | | |
| 385 | | | | | 390 | | | | | | | | | | | |

(2) INFORMATION FOR SEQ ID NO:6:

(i) SEQUENCE CHARACTERISTICS:
        (A) LENGTH: 391 amino acids
        (B) TYPE: amino acid
        (D) TOPOLOGY: linear (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Met | Gly | Val | Val | Glu | Val | Asn | Ile | Val | Thr | Phe | Ile | Asp | Lys | Asn | Gly |
| 1 | | | | 5 | | | | | 10 | | | | | 15 | |
| Ala | Leu | Pro | Gly | Asn | Ser | Gln | Asp | Val | His | Pro | Asp | Leu | Trp | Cys | Phe |
| | | | 20 | | | | | 25 | | | | | 30 | | |
| Met | Ala | Arg | Gln | Cys | Tyr | Ile | Leu | Ser | Leu | Thr | Arg | Leu | Ala | Met | Pro |
| | | 35 | | | | | 40 | | | | | 45 | | | |
| Ile | Ile | Leu | Arg | Ser | Ala | Asn | Leu | Cys | Tyr | Phe | Met | Asp | Ser | Ile | Lys |
| | 50 | | | | | 55 | | | | | 60 | | | | |
| His | Leu | Pro | Arg | Val | Ser | Arg | Pro | Ile | Val | Arg | Thr | Ser | Thr | Ser | Asn |
| 65 | | | | | 70 | | | | | 75 | | | | | 80 |
| Ser | Lys | Phe | Leu | Lys | Pro | Thr | Glu | Gly | Glu | Glu | Asp | Phe | Leu | Phe | |
| | | | | 85 | | | | | 90 | | | | | 95 | |
| Tyr | Glu | Asp | Lys | Pro | Gly | Ala | Ser | Ile | Glu | Trp | Lys | Ser | Ala | Val | Ser |
| | | | 100 | | | | | 105 | | | | | 110 | | |
| Gly | Tyr | Asn | Tyr | Leu | Asn | Ser | Gly | Ile | Phe | Gly | Asn | Tyr | Pro | Leu | Asn |
| | | 115 | | | | | 120 | | | | | 125 | | | |

| | | | | | | | | | | | | | | |
|---|---|---|---|---|---|---|---|---|---|---|---|---|---|---|
| Leu | Trp 130 | Val | Phe | Gly | Ala | Ala 135 | Asp | Leu | Cys | Glu | Pro 140 | Val | Ile | Ser | Asn |
| Ile 145 | Pro | Gly | Pro | Lys | Arg 150 | Leu | Ile | Tyr | Ala | Tyr 155 | Val | Ser | Cys | Glu | Trp 160 |
| Pro | Glu | Pro | Ser | Trp 165 | Lys | Pro | Glu | Cys | Leu 170 | Glu | Ile | Ser | Lys | Asn 175 | Asn |
| Val | Lys | His | Ile 180 | Asp | Asp | Ser | Gly | Ser 185 | Val | Tyr | Cys | Pro | Ser 190 | Phe | Ile |
| Trp | Val | Pro 195 | Val | Leu | Asp | Thr | Phe 200 | Leu | Ser | Ser | Phe | Lys 205 | Val | Pro | Pro |
| Met | Leu 210 | Ser | Asp | Ile | Phe | Tyr 215 | Gly | Thr | Thr | Phe | Asn 220 | Thr | Pro | Phe | Asn |
| Phe 225 | Glu | Ser | Ser | Pro | Arg 230 | Cys | Pro | Ser | Ile | Ser 235 | Ser | Ser | Ser | Ser | Ser 240 |
| Ser | Ser | Ser | Ser | Ser 245 | Ser | Ser | Cys | Ser | Ala 250 | Ser | His | Tyr | Ser | Ser 255 | Glu |
| Asn | Asp | Ile | Trp 260 | Lys | Tyr | Ala | Asn | Ala 265 | Met | Val | Asp | Asn | Glu 270 | Leu | Glu |
| Glu | Thr | Asn 275 | Cys | Glu | Ile | Lys | Asn 280 | Ser | Phe | Lys | Glu | Asp 285 | Ser | Asp | Ser |
| Ser | Thr 290 | Cys | Ser | Ile | Ser | Asp 295 | Val | Cys | Asp | Ser | Leu 300 | Tyr | Ile | Asn | Glu |
| Thr 305 | Arg | Ser | Ala | Pro | Pro 310 | Val | Ile | Glu | Ser | Phe 315 | Met | Cys | Ala | Ile | Ile 320 |
| Ser | His | Asn | Gly | Tyr 325 | Glu | Glu | Ile | Pro | Glu 330 | Pro | Glu | Glu | Asp | Asp 335 | Leu |
| His | Gly | Val | Lys 340 | Pro | Met | Lys | Arg | Leu 345 | Ser | Lys | Pro | Asn | Ile 350 | Phe | Lys |
| Arg | Leu | Phe 355 | Ser | Arg | Arg | Ala | Lys 360 | Thr | Ile | Thr | Lys | Asn 365 | Glu | Asn | Asp |
| Gly | Met 370 | Ser | Ser | Thr | Gln | Pro 375 | Thr | Asn | Ala | Gln | Arg 380 | Ser | Ser | Leu | Phe |
| Ser 385 | Ser | Cys | Leu | Cys | Gly 390 | Asn | | | | | | | | | |

( 2 ) INFORMATION FOR SEQ ID NO:7:

( i ) SEQUENCE CHARACTERISTICS:
        ( A ) LENGTH: 1203 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1203

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| ATG | GCA | AAG | TGT | ACC | ACC | GAA | AAG | TTT | TGT | TGT | ATC | AGC | GTG | AAT | AGA | 48 |
| Met 1 | Ala | Lys | Cys | Thr 5 | Thr | Glu | Lys | Phe | Cys 10 | Cys | Ile | Ser | Val | Asn 15 | Arg | |
| GAA | TCT | TCT | GTC | GAT | CCA | GAA | GAC | TTC | TAT | AAA | CCG | GTT | CCT | CTA | ACT | 96 |
| Glu | Ser | Ser | Val 20 | Asp | Pro | Glu | Asp | Phe 25 | Tyr | Lys | Pro | Val | Pro 30 | Leu | Thr | |
| TCA | GAT | TTG | ATT | GAA | GAG | GAT | AAC | CTA | CAT | CAA | GAC | AAA | ATA | ATG | GAT | 144 |
| Ser | Asp | Leu 35 | Ile | Glu | Glu | Asp | Asn 40 | Leu | His | Gln | Asp | Lys 45 | Ile | Met | Asp | |

-continued

| | | | | | | | | | | | | | | | | |
|---|---|---|---|---|---|---|---|---|---|---|---|---|---|---|---|---|
| GAG | GAT | TTA | TAC | TCG | GAT | TTT | AGT | GAT | GAT | GAC | TTT | ATG | GAT | TAT | ACA | 192 |
| Glu | Asp | Leu | Tyr | Ser | Asp | Phe | Ser | Asp | Asp | Asp | Phe | Met | Asp | Tyr | Thr | |
| | | 50 | | | | 55 | | | | | 60 | | | | | |
| AAA | AAT | CCA | ACT | GAA | AGT | GAA | AAT | GAA | AGA | GAA | AGT | GAC | GAA | GAA | GTT | 240 |
| Lys | Asn | Pro | Thr | Glu | Ser | Glu | Asn | Glu | Arg | Glu | Ser | Asp | Glu | Glu | Val | |
| 65 | | | | | 70 | | | | | 75 | | | | | 80 | |
| GAA | GAA | AGT | TAT | GAA | AGT | GAT | GAA | GAT | AAA | AAA | AGT | TTA | TCT | CCT | ACT | 288 |
| Glu | Glu | Ser | Tyr | Glu | Ser | Asp | Glu | Asp | Lys | Lys | Ser | Leu | Ser | Pro | Thr | |
| | | | | 85 | | | | | 90 | | | | | 95 | | |
| AAA | AGC | GAA | GGA | ATT | GAA | GCG | GCT | GAA | GCG | CTA | AAG | TTT | TCT | GTT | GTT | 336 |
| Lys | Ser | Glu | Gly | Ile | Glu | Ala | Ala | Glu | Ala | Leu | Lys | Phe | Ser | Val | Val | |
| | | | 100 | | | | | 105 | | | | | 110 | | | |
| AAA | TCG | TTA | ACG | CCT | GGG | TCA | GAA | GGA | AGA | GTT | TTT | ATT | GCT | CTT | AAA | 384 |
| Lys | Ser | Leu | Thr | Pro | Gly | Ser | Glu | Gly | Arg | Val | Phe | Ile | Ala | Leu | Lys | |
| | | 115 | | | | | 120 | | | | | 125 | | | | |
| AAA | GAT | AAA | GAT | ACA | AGC | TAT | AAG | GTA | ATT | TTA | AAA | ATT | GGA | CAA | AGG | 432 |
| Lys | Asp | Lys | Asp | Thr | Ser | Tyr | Lys | Val | Ile | Leu | Lys | Ile | Gly | Gln | Arg | |
| | 130 | | | | | 135 | | | | | 140 | | | | | |
| GGA | AAC | ACG | CTT | GTG | GAA | TCG | TTA | ATT | TTG | AGA | AAT | ATT | AGT | CAC | CAA | 480 |
| Gly | Asn | Thr | Leu | Val | Glu | Ser | Leu | Ile | Leu | Arg | Asn | Ile | Ser | His | Gln | |
| 145 | | | | | 150 | | | | | 155 | | | | | 160 | |
| TCT | ATA | ATT | AAA | CTT | CAA | GAC | ACT | CTT | TTT | TAT | AAA | GAG | TTA | ACA | TGT | 528 |
| Ser | Ile | Ile | Lys | Leu | Gln | Asp | Thr | Leu | Phe | Tyr | Lys | Glu | Leu | Thr | Cys | |
| | | | | 165 | | | | | 170 | | | | | 175 | | |
| TTG | GTG | TTA | CCG | TAT | TAT | AAA | TAT | GAT | CTA | TAT | AAT | TTT | TTA | ATG | GAT | 576 |
| Leu | Val | Leu | Pro | Tyr | Tyr | Lys | Tyr | Asp | Leu | Tyr | Asn | Phe | Leu | Met | Asp | |
| | | | 180 | | | | | 185 | | | | | 190 | | | |
| CAT | GGG | AAA | TCT | CTG | TCT | TTT | GAA | TCT | GTA | ATT | AAA | ATT | GAA | AAA | CAA | 624 |
| His | Gly | Lys | Ser | Leu | Ser | Phe | Glu | Ser | Val | Ile | Lys | Ile | Glu | Lys | Gln | |
| | | 195 | | | | | 200 | | | | | 205 | | | | |
| ATA | TTA | ACT | GGA | CTT | CAA | TAT | ATT | CAT | GGA | AAA | AAA | ATT | ATT | CAT | CGA | 672 |
| Ile | Leu | Thr | Gly | Leu | Gln | Tyr | Ile | His | Gly | Lys | Lys | Ile | Ile | His | Arg | |
| | 210 | | | | | 215 | | | | | 220 | | | | | |
| GAT | ATA | AAA | ACT | GAA | AAT | ATT | TTC | TTG | GAT | AAT | GAC | TCT | AAT | GTT | TGT | 720 |
| Asp | Ile | Lys | Thr | Glu | Asn | Ile | Phe | Leu | Asp | Asn | Asp | Ser | Asn | Val | Cys | |
| 225 | | | | | 230 | | | | | 235 | | | | | 240 | |
| ATA | GGT | GAT | TTT | GGG | GCT | TCT | CAA | TTT | CCT | GTT | TCC | TCA | CCA | GAT | TAT | 768 |
| Ile | Gly | Asp | Phe | Gly | Ala | Ser | Gln | Phe | Pro | Val | Ser | Ser | Pro | Asp | Tyr | |
| | | | | 245 | | | | | 250 | | | | | 255 | | |
| TTG | GGA | ATT | GCG | GGG | ACT | ATT | GAA | ACT | AAT | GCT | CCT | GAA | GTT | CTA | TCA | 816 |
| Leu | Gly | Ile | Ala | Gly | Thr | Ile | Glu | Thr | Asn | Ala | Pro | Glu | Val | Leu | Ser | |
| | | | 260 | | | | | 265 | | | | | 270 | | | |
| AAG | GAT | GCG | TAC | AAC | TGT | AAA | GCT | GAT | ATT | TGG | AGT | GCT | GGT | ATA | ATT | 864 |
| Lys | Asp | Ala | Tyr | Asn | Cys | Lys | Ala | Asp | Ile | Trp | Ser | Ala | Gly | Ile | Ile | |
| | | 275 | | | | | 280 | | | | | 285 | | | | |
| TTA | TTT | GAA | ATG | CTT | GCA | TAT | CCT | AAT | GTT | TTG | TTT | GAG | GAG | GAA | GAA | 912 |
| Leu | Phe | Glu | Met | Leu | Ala | Tyr | Pro | Asn | Val | Leu | Phe | Glu | Glu | Glu | Glu | |
| | 290 | | | | | 295 | | | | | 300 | | | | | |
| AGA | GAT | AGT | AGC | GAT | TTA | ATA | AAC | AAT | TGT | AAT | CTT | CAT | CTT | ATA | AAA | 960 |
| Arg | Asp | Ser | Ser | Asp | Leu | Ile | Asn | Asn | Cys | Asn | Leu | His | Leu | Ile | Lys | |
| 305 | | | | | 310 | | | | | 315 | | | | | 320 | |
| ATT | ATA | TCA | ACT | CTG | AAG | ATT | AAC | CCA | AAT | GAA | TTT | CCA | TCT | GAT | TTG | 1008 |
| Ile | Ile | Ser | Thr | Leu | Lys | Ile | Asn | Pro | Asn | Glu | Phe | Pro | Ser | Asp | Leu | |
| | | | | 325 | | | | | 330 | | | | | 335 | | |
| GAA | TCT | AAT | CTA | GTA | AAA | CAT | TTT | ATA | AAA | TAT | GCT | AAT | AAT | GAT | AGA | 1056 |
| Glu | Ser | Asn | Leu | Val | Lys | His | Phe | Ile | Lys | Tyr | Ala | Asn | Asn | Asp | Arg | |
| | | | 340 | | | | | 345 | | | | | 350 | | | |
| CCT | CCA | TTT | ACA | CGA | TAT | AAT | CGT | CTA | AAT | AAC | CTT | AAA | TTA | CAT | CTC | 1104 |
| Pro | Pro | Phe | Thr | Arg | Tyr | Asn | Arg | Leu | Asn | Asn | Leu | Lys | Leu | His | Leu | |
| | | 355 | | | | | 360 | | | | | 365 | | | | |

```
GAT  GGT  GAA  TTT  TTA  ATT  CAT  AAA  ATG  CTA  ACA  TTT  GAT  GCA  TCT  CTA    1152
Asp  Gly  Glu  Phe  Leu  Ile  His  Lys  Met  Leu  Thr  Phe  Asp  Ala  Ser  Leu
     370                          375                      380

CGA  CCA  AGT  GCG  GAA  GAA  CTA  TTA  TCC  TAT  CAG  ATT  TTT  AGT  AAA  CAA    1200
Arg  Pro  Ser  Ala  Glu  Glu  Leu  Leu  Ser  Tyr  Gln  Ile  Phe  Ser  Lys  Gln
385                      390                      395                      400

TAA                                                                                1203
 *
```

( 2 ) INFORMATION FOR SEQ ID NO:8:

( i ) SEQUENCE CHARACTERISTICS:
        ( A ) LENGTH: 400 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Ala  Lys  Cys  Thr  Thr  Glu  Lys  Phe  Cys  Cys  Ile  Ser  Val  Asn  Arg
 1                        5                       10                      15

Glu  Ser  Ser  Val  Asp  Pro  Glu  Asp  Phe  Tyr  Lys  Pro  Val  Pro  Leu  Thr
               20                       25                      30

Ser  Asp  Leu  Ile  Glu  Glu  Asp  Asn  Leu  His  Gln  Asp  Lys  Ile  Met  Asp
          35                       40                      45

Glu  Asp  Leu  Tyr  Ser  Asp  Phe  Ser  Asp  Asp  Phe  Met  Asp  Tyr  Thr
     50                       55                      60

Lys  Asn  Pro  Thr  Glu  Ser  Glu  Asn  Glu  Arg  Glu  Ser  Asp  Glu  Glu  Val
65                       70                      75                           80

Glu  Glu  Ser  Tyr  Glu  Ser  Asp  Glu  Asp  Lys  Lys  Ser  Leu  Ser  Pro  Thr
                    85                       90                      95

Lys  Ser  Glu  Gly  Ile  Glu  Ala  Ala  Glu  Ala  Leu  Lys  Phe  Ser  Val  Val
               100                      105                     110

Lys  Ser  Leu  Thr  Pro  Gly  Ser  Glu  Gly  Arg  Val  Phe  Ile  Ala  Leu  Lys
          115                      120                     125

Lys  Asp  Lys  Asp  Thr  Ser  Tyr  Lys  Val  Ile  Leu  Lys  Ile  Gly  Gln  Arg
     130                      135                     140

Gly  Asn  Thr  Leu  Val  Glu  Ser  Leu  Ile  Leu  Arg  Asn  Ile  Ser  His  Gln
145                      150                     155                          160

Ser  Ile  Ile  Lys  Leu  Gln  Asp  Thr  Leu  Phe  Tyr  Lys  Glu  Leu  Thr  Cys
                    165                      170                     175

Leu  Val  Leu  Pro  Tyr  Tyr  Lys  Tyr  Asp  Leu  Tyr  Asn  Phe  Leu  Met  Asp
               180                      185                     190

His  Gly  Lys  Ser  Leu  Ser  Phe  Glu  Ser  Val  Ile  Lys  Ile  Glu  Lys  Gln
          195                      200                     205

Ile  Leu  Thr  Gly  Leu  Gln  Tyr  Ile  His  Gly  Lys  Lys  Ile  Ile  His  Arg
     210                      215                     220

Asp  Ile  Lys  Thr  Glu  Asn  Ile  Phe  Leu  Asp  Asn  Asp  Ser  Asn  Val  Cys
225                      230                     235                          240

Ile  Gly  Asp  Phe  Gly  Ala  Ser  Gln  Phe  Pro  Val  Ser  Ser  Pro  Asp  Tyr
               245                      250                     255

Leu  Gly  Ile  Ala  Gly  Thr  Ile  Glu  Thr  Asn  Ala  Pro  Glu  Val  Leu  Ser
               260                      265                     270

Lys  Asp  Ala  Tyr  Asn  Cys  Lys  Ala  Asp  Ile  Trp  Ser  Ala  Gly  Ile  Ile
               275                      280                     285

Leu  Phe  Glu  Met  Leu  Ala  Tyr  Pro  Asn  Val  Leu  Phe  Glu  Glu  Glu  Glu
     290                      295                     300
```

| | | | | | | | | | | | | | | | |
|---|---|---|---|---|---|---|---|---|---|---|---|---|---|---|---|
| Arg | Asp | Ser | Ser | Asp | Leu | Ile | Asn | Asn | Cys | Asn | Leu | His | Leu | Ile | Lys |
| 305 | | | | 310 | | | | | 315 | | | | | | 320 |
| Ile | Ile | Ser | Thr | Leu | Lys | Ile | Asn | Pro | Asn | Glu | Phe | Pro | Ser | Asp | Leu |
| | | | | 325 | | | | | 330 | | | | | 335 | |
| Glu | Ser | Asn | Leu | Val | Lys | His | Phe | Ile | Lys | Tyr | Ala | Asn | Asn | Asp | Arg |
| | | | 340 | | | | | 345 | | | | | 350 | | |
| Pro | Pro | Phe | Thr | Arg | Tyr | Asn | Arg | Leu | Asn | Asn | Leu | Lys | Leu | His | Leu |
| | | 355 | | | | | 360 | | | | | 365 | | | |
| Asp | Gly | Glu | Phe | Leu | Ile | His | Lys | Met | Leu | Thr | Phe | Asp | Ala | Ser | Leu |
| | 370 | | | | | 375 | | | | | 380 | | | | |
| Arg | Pro | Ser | Ala | Glu | Glu | Leu | Leu | Ser | Tyr | Gln | Ile | Phe | Ser | Lys | Gln |
| 385 | | | | | 390 | | | | | 395 | | | | | 400 |

(2) INFORMATION FOR SEQ ID NO:9:

(i) SEQUENCE CHARACTERISTICS:
        (A) LENGTH: 1248 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1248

(xi) SEQUENCE DESCRIPTION: SEQ ID NO:9:

| | | | | | | | | | | | | | | | | |
|---|---|---|---|---|---|---|---|---|---|---|---|---|---|---|---|---|
| ATG | TTG | TAT | ACG | CTG | TTT | TTT | GTT | TTT | TAT | TTT | AAG | GTA | GTT | TTA | TCT | 48 |
| Met | Leu | Tyr | Thr | Leu | Phe | Phe | Val | Phe | Tyr | Phe | Lys | Val | Val | Leu | Ser | |
| 1 | | | | 5 | | | | | 10 | | | | | 15 | | |
| CGC | ATA | GCT | CCG | CTA | GAG | TTG | TGT | TAT | GCG | GAT | CCT | AAA | GAA | AAT | ACA | 96 |
| Arg | Ile | Ala | Pro | Leu | Glu | Leu | Cys | Tyr | Ala | Asp | Pro | Lys | Glu | Asn | Thr | |
| | | | 20 | | | | | 25 | | | | | 30 | | | |
| ACT | GAA | CCT | ACA | CAA | CTT | CCT | ACA | GGG | GAA | CAA | TCT | AAG | ACT | CTT | ATT | 144 |
| Thr | Glu | Pro | Thr | Gln | Leu | Pro | Thr | Gly | Glu | Gln | Ser | Lys | Thr | Leu | Ile | |
| | | 35 | | | | | 40 | | | | | 45 | | | | |
| CCC | GTG | GTA | ACA | AAC | GGA | TAT | GTT | GAA | TAC | TCT | AAA | GGA | TGT | GAA | CTA | 192 |
| Pro | Val | Val | Thr | Asn | Gly | Tyr | Val | Glu | Tyr | Ser | Lys | Gly | Cys | Glu | Leu | |
| | 50 | | | | | 55 | | | | | 60 | | | | | |
| CGA | TTA | CTA | GAT | ACA | TAT | GTA | AAT | GTA | TCT | TCA | CGA | CCA | GAA | AAA | AAG | 240 |
| Arg | Leu | Leu | Asp | Thr | Tyr | Val | Asn | Val | Ser | Ser | Arg | Pro | Glu | Lys | Lys | |
| 65 | | | | | 70 | | | | | 75 | | | | | 80 | |
| GTT | AAT | GCT | ACA | ATT | GGA | TGG | TCA | TTT | GAT | CTT | GGT | TGT | CAA | ATT | CCT | 288 |
| Val | Asn | Ala | Thr | Ile | Gly | Trp | Ser | Phe | Asp | Leu | Gly | Cys | Gln | Ile | Pro | |
| | | | | 85 | | | | | 90 | | | | | 95 | | |
| TTA | ATT | TAT | AGA | GAA | TAT | TAT | AAT | TGT | ACT | GGT | AAT | ATA | ATA | CCA | TCA | 336 |
| Leu | Ile | Tyr | Arg | Glu | Tyr | Tyr | Asn | Cys | Thr | Gly | Asn | Ile | Ile | Pro | Ser | |
| | | | 100 | | | | | 105 | | | | | 110 | | | |
| CCA | GAA | ACT | TGT | GAT | GGT | TAT | TCT | TTA | ACT | TTG | GTA | AAA | TCT | GAA | AGT | 384 |
| Pro | Glu | Thr | Cys | Asp | Gly | Tyr | Ser | Leu | Thr | Leu | Val | Lys | Ser | Glu | Ser | |
| | | 115 | | | | | 120 | | | | | 125 | | | | |
| ATA | TCA | TCT | TAT | GCA | CTT | GTT | AAT | GTT | AGT | TTG | CTT | ATT | CAA | CCA | GGA | 432 |
| Ile | Ser | Ser | Tyr | Ala | Leu | Val | Asn | Val | Ser | Leu | Leu | Ile | Gln | Pro | Gly | |
| | | 130 | | | | | 135 | | | | | 140 | | | | |
| ATT | TTT | GAT | TCT | GGT | AGA | TAT | TTA | TAC | TCA | CTT | GTT | TTT | GGA | AAC | GAT | 480 |
| Ile | Phe | Asp | Ser | Gly | Arg | Tyr | Leu | Tyr | Ser | Leu | Val | Phe | Gly | Asn | Asp | |
| 145 | | | | 150 | | | | | 155 | | | | | 160 | | |
| AGT | TAT | AAC | GGA | AGA | ATT | GAA | GTT | CGA | GTG | GAT | AAT | GAG | ACA | GAC | TAT | 528 |
| Ser | Tyr | Asn | Gly | Arg | Ile | Glu | Val | Arg | Val | Asp | Asn | Glu | Thr | Asp | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| CCA | TGT | TTT | ATG | ATG | CAT | GGA | TTG | ACT | GTA | AAA | AAG | GGT | GAT | AAA | CTT | 576 |
| Pro | Cys | Phe | Met | Met | His | Gly | Leu | Thr | Val | Lys | Lys | Gly | Asp | Lys | Leu | |
| | 180 | | | | | | 185 | | | | | 190 | | | | |
| CAT | ATT | CCT | TAT | AAA | CCA | TCC | ACA | AAT | CCT | AAT | CAT | AAA | CGA | TAT | AGA | 624 |
| His | Ile | Pro | Tyr | Lys | Pro | Ser | Thr | Asn | Pro | Asn | His | Lys | Arg | Tyr | Arg | |
| | | 195 | | | | | 200 | | | | | 205 | | | | |
| GGT | TGT | TTT | CCA | ATA | TCA | AAT | ACT | GAG | CTA | TGG | AAT | AAT | ATT | AGT | GAT | 672 |
| Gly | Cys | Phe | Pro | Ile | Ser | Asn | Thr | Glu | Leu | Trp | Asn | Asn | Ile | Ser | Asp | |
| | 210 | | | | | 215 | | | | | 220 | | | | | |
| GAA | AGT | GTT | GGT | AGA | TAT | TCA | TAT | GAT | GAA | GAA | TAT | GAA | GAA | TAT | GAA | 720 |
| Glu | Ser | Val | Gly | Arg | Tyr | Ser | Tyr | Asp | Glu | Glu | Tyr | Glu | Glu | Tyr | Glu | |
| 225 | | | | | 230 | | | | | 235 | | | | | 240 | |
| GAA | GAA | AAC | GAA | GAT | TTT | GAA | GAT | CTA | CAA | TCA | AAA | GAT | TGC | CGC | AAA | 768 |
| Glu | Glu | Asn | Glu | Asp | Phe | Glu | Asp | Leu | Gln | Ser | Lys | Asp | Cys | Arg | Lys | |
| | | | | 245 | | | | | 250 | | | | | 255 | | |
| TCC | AAT | CTT | TTT | GAT | ATG | AAG | AAG | ACT | TTT | AAT | TTG | GCT | GCA | GGT | TCT | 816 |
| Ser | Asn | Leu | Phe | Asp | Met | Lys | Lys | Thr | Phe | Asn | Leu | Ala | Ala | Gly | Ser | |
| | | | 260 | | | | | 265 | | | | | 270 | | | |
| CAA | AGT | TTA | TTG | ATT | GCT | AGT | TTG | GGT | AAA | TCA | ATT | TCA | GAA | CAA | CCG | 864 |
| Gln | Ser | Leu | Leu | Ile | Ala | Ser | Leu | Gly | Lys | Ser | Ile | Ser | Glu | Gln | Pro | |
| | | 275 | | | | | 280 | | | | | 285 | | | | |
| TGG | TCA | TTT | AAA | ATT | AAT | GAA | AGT | TAT | GAA | CTT | TTT | AAT | AAT | TTG | TCT | 912 |
| Trp | Ser | Phe | Lys | Ile | Asn | Glu | Ser | Tyr | Glu | Leu | Phe | Asn | Asn | Leu | Ser | |
| | 290 | | | | | 295 | | | | | 300 | | | | | |
| ATC | ACC | CTT | CAA | TCG | GAA | GAA | GAT | TCT | AAT | ATA | CTG | AAT | CCT | GAA | ATT | 960 |
| Ile | Thr | Leu | Gln | Ser | Glu | Glu | Asp | Ser | Asn | Ile | Leu | Asn | Pro | Glu | Ile | |
| 305 | | | | | 310 | | | | | 315 | | | | | 320 | |
| GTA | ACG | TTT | ACC | ACA | CCA | CCA | CCT | ACT | GAA | AAT | ACA | CAT | ATG | TTT | ATG | 1008 |
| Val | Thr | Phe | Thr | Thr | Pro | Pro | Pro | Thr | Glu | Asn | Thr | His | Met | Phe | Met | |
| | | | | 325 | | | | | 330 | | | | | 335 | | |
| TCA | AAT | AAT | GAA | ACT | ATG | TAT | GAA | GAA | GAA | AGT | GTT | TTA | AGC | ATT | ATT | 1056 |
| Ser | Asn | Asn | Glu | Thr | Met | Tyr | Glu | Glu | Glu | Ser | Val | Leu | Ser | Ile | Ile | |
| | | | 340 | | | | | 345 | | | | | 350 | | | |
| CAA | TTG | TTT | AAC | AAT | GGT | TAT | AAT | AAT | TGT | AAT | ACC | CAT | ATA | AAG | GTA | 1104 |
| Gln | Leu | Phe | Asn | Asn | Gly | Tyr | Asn | Asn | Cys | Asn | Thr | His | Ile | Lys | Val | |
| | | 355 | | | | | 360 | | | | | 365 | | | | |
| ATT | GGA | TTT | GGA | ACA | ATT | ATC | TTT | ATT | ATT | TTA | TTT | TTT | GTT | GCT | GTG | 1152 |
| Ile | Gly | Phe | Gly | Thr | Ile | Ile | Phe | Ile | Ile | Leu | Phe | Phe | Val | Ala | Val | |
| | 370 | | | | | 375 | | | | | 380 | | | | | |
| TTT | TTT | TGT | GGA | TAT | ACT | TGT | GTA | TTA | AAC | TCT | CGT | ATT | AAA | ATG | ATT | 1200 |
| Phe | Phe | Cys | Gly | Tyr | Thr | Cys | Val | Leu | Asn | Ser | Arg | Ile | Lys | Met | Ile | |
| 385 | | | | | 390 | | | | | 395 | | | | | 400 | |
| AAC | CAT | GCT | TAT | ATA | CAA | CCC | CAG | AAA | TTA | AAT | TTT | TAT | GAT | ATT | TAA | 1248 |
| Asn | His | Ala | Tyr | Ile | Gln | Pro | Gln | Lys | Leu | Asn | Phe | Tyr | Asp | Ile | * | |
| | | | | 405 | | | | | 410 | | | | | 415 | | |

( 2 ) INFORMATION FOR SEQ ID NO:10:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Met | Leu | Tyr | Thr | Leu | Phe | Phe | Val | Phe | Tyr | Phe | Lys | Val | Val | Leu | Ser |
| 1 | | | | 5 | | | | | 10 | | | | | 15 | |
| Arg | Ile | Ala | Pro | Leu | Glu | Leu | Cys | Tyr | Ala | Asp | Pro | Lys | Glu | Asn | Thr |
| | | | 20 | | | | | 25 | | | | | 30 | | |
| Thr | Glu | Pro | Thr | Gln | Leu | Pro | Thr | Gly | Glu | Gln | Ser | Lys | Thr | Leu | Ile |
| | | | 35 | | | | | 40 | | | | | 45 | | |

```
Pro  Val  Val  Thr  Asn  Gly  Tyr  Val  Glu  Tyr  Ser  Lys  Gly  Cys  Glu  Leu
     50                  55                      60

Arg  Leu  Leu  Asp  Thr  Tyr  Val  Asn  Val  Ser  Ser  Arg  Pro  Glu  Lys  Lys
65                       70                  75                           80

Val  Asn  Ala  Thr  Ile  Gly  Trp  Ser  Phe  Asp  Leu  Gly  Cys  Gln  Ile  Pro
                    85                  90                            95

Leu  Ile  Tyr  Arg  Glu  Tyr  Tyr  Asn  Cys  Thr  Gly  Asn  Ile  Ile  Pro  Ser
               100                 105                      110

Pro  Glu  Thr  Cys  Asp  Gly  Tyr  Ser  Leu  Thr  Leu  Val  Lys  Ser  Glu  Ser
          115                      120                 125

Ile  Ser  Ser  Tyr  Ala  Leu  Val  Asn  Val  Ser  Leu  Leu  Ile  Gln  Pro  Gly
     130                      135                 140

Ile  Phe  Asp  Ser  Gly  Arg  Tyr  Leu  Tyr  Ser  Leu  Val  Phe  Gly  Asn  Asp
145                      150                      155                      160

Ser  Tyr  Asn  Gly  Arg  Ile  Glu  Val  Arg  Val  Asp  Asn  Glu  Thr  Asp  Tyr
               165                      170                      175

Pro  Cys  Phe  Met  Met  His  Gly  Leu  Thr  Val  Lys  Lys  Gly  Asp  Lys  Leu
               180                 185                      190

His  Ile  Pro  Tyr  Lys  Pro  Ser  Thr  Asn  Pro  Asn  His  Lys  Arg  Tyr  Arg
          195                      200                      205

Gly  Cys  Phe  Pro  Ile  Ser  Asn  Thr  Glu  Leu  Trp  Asn  Asn  Ile  Ser  Asp
     210                      215                      220

Glu  Ser  Val  Gly  Arg  Tyr  Ser  Tyr  Asp  Glu  Glu  Tyr  Glu  Glu  Tyr  Glu
225                      230                 235                           240

Glu  Glu  Asn  Glu  Asp  Phe  Glu  Asp  Leu  Gln  Ser  Lys  Asp  Cys  Arg  Lys
                    245                      250                      255

Ser  Asn  Leu  Phe  Asp  Met  Lys  Lys  Thr  Phe  Asn  Leu  Ala  Ala  Gly  Ser
               260                      265                      270

Gln  Ser  Leu  Leu  Ile  Ala  Ser  Leu  Gly  Lys  Ser  Ile  Ser  Glu  Gln  Pro
          275                      280                 285

Trp  Ser  Phe  Lys  Ile  Asn  Glu  Ser  Tyr  Glu  Leu  Phe  Asn  Asn  Leu  Ser
     290                      295                 300

Ile  Thr  Leu  Gln  Ser  Glu  Glu  Asp  Ser  Asn  Ile  Leu  Asn  Pro  Glu  Ile
305                      310                 315                           320

Val  Thr  Phe  Thr  Thr  Pro  Pro  Pro  Thr  Glu  Asn  Thr  His  Met  Phe  Met
                    325                      330                      335

Ser  Asn  Asn  Glu  Thr  Met  Tyr  Glu  Glu  Glu  Ser  Val  Leu  Ser  Ile  Ile
                    340                      345                      350

Gln  Leu  Phe  Asn  Asn  Gly  Tyr  Asn  Asn  Cys  Asn  Thr  His  Ile  Lys  Val
          355                      360                      365

Ile  Gly  Phe  Gly  Thr  Ile  Ile  Phe  Ile  Ile  Leu  Phe  Phe  Val  Ala  Val
     370                      375                 380

Phe  Phe  Cys  Gly  Tyr  Thr  Cys  Val  Leu  Asn  Ser  Arg  Ile  Lys  Met  Ile
385                      390                      395                      400

Asn  His  Ala  Tyr  Ile  Gln  Pro  Gln  Lys  Leu  Asn  Phe  Tyr  Asp  Ile
               405                      410                      415
```

( 2 ) INFORMATION FOR SEQ ID NO:11:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 1..357

( x i ) SEQUENCE DESCRIPTION: SEQ ID NO:11:

```
ATG ATT AAA CTT CTA TTT ATC TTA TTT TAT TTT AAC CCA ATA ACT GGA     48
Met Ile Lys Leu Leu Phe Ile Leu Phe Tyr Phe Asn Pro Ile Thr Gly
 1               5                  10                  15

TAT AAA TGG GTA GAC CCT CCT CGT AGG TAT AAT TAC ACC GTT TTA AGA     96
Tyr Lys Trp Val Asp Pro Pro Arg Arg Tyr Asn Tyr Thr Val Leu Arg
             20                  25                  30

ATG ATT CCA GAT ATT CCA AAT CCA ATG GAT CCT TCT AAA AAC GCT GAA    144
Met Ile Pro Asp Ile Pro Asn Pro Met Asp Pro Ser Lys Asn Ala Glu
             35                  40                  45

GTT CGG TAT GTA ACT TCT ACT GAC CCA TGT GAT ATG GTT GCT TTG ATT    192
Val Arg Tyr Val Thr Ser Thr Asp Pro Cys Asp Met Val Ala Leu Ile
         50                  55                  60

TCT AAT CCA AAT ATA GAA TCT ACA ATT AAA ACG ATT CAA TTT GTG CAA    240
Ser Asn Pro Asn Ile Glu Ser Thr Ile Lys Thr Ile Gln Phe Val Gln
 65                  70                  75                  80

AAG AAA AAA TTT TAC AAT GCA TCT CTT AGT TGG TTT AAA GTT GGA GAT    288
Lys Lys Lys Phe Tyr Asn Ala Ser Leu Ser Trp Phe Lys Val Gly Asp
                 85                  90                  95

GAT TGT ACA TAT CCA ATA TAT TTA ATT CAA TAT TTT GAT TGT GAT CCT    336
Asp Cys Thr Tyr Pro Ile Tyr Leu Ile Gln Tyr Phe Asp Cys Asp Pro
             100                 105                 110

CAA AGA GAA TTT GGC ATA TGT                                        357
Gln Arg Glu Phe Gly Ile Cys
             115
```

( 2 ) INFORMATION FOR SEQ ID NO:12:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Ile Lys Leu Leu Phe Ile Leu Phe Tyr Phe Asn Pro Ile Thr Gly
 1               5                  10                  15

Tyr Lys Trp Val Asp Pro Pro Arg Arg Tyr Asn Tyr Thr Val Leu Arg
             20                  25                  30

Met Ile Pro Asp Ile Pro Asn Pro Met Asp Pro Ser Lys Asn Ala Glu
             35                  40                  45

Val Arg Tyr Val Thr Ser Thr Asp Pro Cys Asp Met Val Ala Leu Ile
         50                  55                  60

Ser Asn Pro Asn Ile Glu Ser Thr Ile Lys Thr Ile Gln Phe Val Gln
 65                  70                  75                  80

Lys Lys Lys Phe Tyr Asn Ala Ser Leu Ser Trp Phe Lys Val Gly Asp
                 85                  90                  95

Asp Cys Thr Tyr Pro Ile Tyr Leu Ile Gln Tyr Phe Asp Cys Asp Pro
             100                 105                 110

Gln Arg Glu Phe Gly Ile Cys
             115
```

( 2 ) INFORMATION FOR SEQ ID NO:13:

( i ) SEQUENCE CHARACTERISTICS:
        ( A ) LENGTH: 743 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

| | | | | | | |
|---|---|---|---|---|---|---|
| CGAAGCGGGA | GGAGGATGCT | GGTTATGATA | TACCATCTCC | AAATTTAGTT | CAAATAAAAC | 60 |
| CGGGATATAG | TTACCTTTTT | TGTCTTCCTA | TTTTTCAATT | AGAAATGAAA | AACCCACCAA | 120 |
| TCGCTTGTAT | TTTTGGTAGA | TCATCCTTAA | ATTCAAGCGG | AATAATTGTT | CTTCCAACTA | 180 |
| TATGGAAACC | AAAAACAATT | TGTCAATTTT | TTATTAAAAA | TATATCCTCT | AAAACTGTAA | 240 |
| CTATAGAAAA | AGGTCAGAGA | ATAGCTCAGT | TAGTTCTTTT | AAAAAACAAT | CAACCACTAT | 300 |
| GGTTACAACC | ACAAATTAAT | TGTCATTCTT | TATTTCCAAA | GTCAAACTAT | TTAAGCTTAT | 360 |
| CAAATCGAGA | ATGTGATATG | TGGAAGTTTA | CAGAAGATCT | GAATTTTGAA | GCACCGAAAA | 420 |
| GTTTACGAGG | AATAAATGGA | TTTGGATCCA | CGGGATTGTA | AAATTCGTTA | ATAAAGTTAT | 480 |
| ATTTAAAGTG | CCAAACTTTC | ACGTGTCATT | TTTTGGGAC | CGTTCTTTT | TTGTTTAGTC | 540 |
| GATAAAATAT | TTTCAGTTTC | CATAGAACTT | ATTAGAGGTT | CTGTATCTAG | TATATCTGTA | 600 |
| GAATTATTTT | CATCATATTT | AACGGTTTGA | AGAGATAAGG | GTTTTGTTGT | ATTAGAATCT | 660 |
| ATACCAAGGG | TTTTTTCTAA | AACCGCTACA | TCTGCCATAA | CAATATTATT | TTCTGAAGTC | 720 |
| ATTTTTATGG | CTTGGGCACC | ACC | | | | 743 |

( 2 ) INFORMATION FOR SEQ ID NO:14:

( i ) SEQUENCE CHARACTERISTICS:
( A ) LENGTH: 743 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

| | | | | | | |
|---|---|---|---|---|---|---|
| GGTGGTGCCC | AAGCCATAAA | AATGACTTCA | GAAAATAATA | TTGTTATGGC | AGATGTAGCG | 60 |
| GTTTTAGAAA | AAACCCTTGG | TATAGATTCT | AATACAACAA | AACCCTTATC | TCTTCAAACC | 120 |
| GTTAAATATG | ATGAAAATAA | TTCTACAGAT | ATACTAGATA | CAGAACCTCT | AATAAGTTCT | 180 |
| ATGGAAACTG | AAAATATTTT | ATCGACTAAA | CAAAAAAGAA | ACGGTCCCAA | AAAAATGACA | 240 |
| CGTGAAAGTT | TGGCACTTTA | AATATAACTT | TATTAACGAA | TTTTACAATC | CCGTGGATCC | 300 |
| AAATCCATTT | ATTCCTCGTA | AACTTTTCGG | TGCTTCAAAA | TTCAGATCTT | CTGTAAACTT | 360 |
| CCACATATCA | CATTCTCGAT | TTGATAAGCT | TAAATAGTTT | GACTTTGGAA | ATAAAGAATG | 420 |
| ACAATTAATT | TGTGGTTGTA | ACCATAGTGG | TTGATTGTTT | TTTAAAAGAA | CTAACTGAGC | 480 |
| TATTCTCTGA | CCTTTTCTA | TAGTTACAGT | TTTAGAGGAT | ATATTTTAA | TAAAAAATTG | 540 |
| ACAAATTGTT | TTTGGTTTCC | ATATAGTTGG | AAGAACAATT | ATTCCGCTTG | AATTTAAGGA | 600 |
| TGATCTACCA | AAAATACAAG | CGATTGGTGG | GTTTTCATT | TCTAATTGAA | AAATAGGAAG | 660 |
| ACAAAAAAGG | TAACTATATC | CCGGTTTTAT | TTGAACTAAA | TTTGGAGATG | GTATATCATA | 720 |
| ACCAGCATCC | TCCTCCCGCT | TCG | | | | 743 |

( 2 ) INFORMATION FOR SEQ ID NO:15:

( i ) SEQUENCE CHARACTERISTICS:
( A ) LENGTH: 459 base pairs
( B ) TYPE: nucleic acid
( C ) STRANDEDNESS: single (D) TOPOLOGY: linear (ii) MOLECULE TYPE: cDNA (ix) FEATURE:
    (A) NAME/KEY: CDS
    (B) LOCATION: 1..459

(xi) SEQUENCE DESCRIPTION: SEQ ID NO:15:

```
AAG CGG GAG GAG GAT GCT GGT TAT GAT ATA CCA TCT CCA AAT TTA GTT      48
Lys Arg Glu Glu Asp Ala Gly Tyr Asp Ile Pro Ser Pro Asn Leu Val
 1               5                  10                  15

CAA ATA AAA CCG GGA TAT AGT TAC CTT TTT TGT CTT CCT ATT TTT CAA      96
Gln Ile Lys Pro Gly Tyr Ser Tyr Leu Phe Cys Leu Pro Ile Phe Gln
                20                  25                  30

TTA GAA ATG AAA AAC CCA CCA ATC GCT TGT ATT TTT GGT AGA TCA TCC     144
Leu Glu Met Lys Asn Pro Pro Ile Ala Cys Ile Phe Gly Arg Ser Ser
            35                  40                  45

TTA AAT TCA AGC GGA ATA ATT GTT CTT CCA ACT ATA TGG AAA CCA AAA     192
Leu Asn Ser Ser Gly Ile Ile Val Leu Pro Thr Ile Trp Lys Pro Lys
        50                  55                  60

ACA ATT TGT CAA TTT TTT ATT AAA AAT ATA TCC TCT AAA ACT GTA ACT     240
Thr Ile Cys Gln Phe Phe Ile Lys Asn Ile Ser Ser Lys Thr Val Thr
65                  70                  75                  80

ATA GAA AAA GGT CAG AGA ATA GCT CAG TTA GTT CTT TTA AAA AAC AAT     288
Ile Glu Lys Gly Gln Arg Ile Ala Gln Leu Val Leu Leu Lys Asn Asn
                85                  90                  95

CAA CCA CTA TGG TTA CAA CCA CAA ATT AAT TGT CAT TCT TTA TTT CCA     336
Gln Pro Leu Trp Leu Gln Pro Gln Ile Asn Cys His Ser Leu Phe Pro
                100                 105                 110

AAG TCA AAC TAT TTA AGC TTA TCA AAT CGA GAA TGT GAT ATG TGG AAG     384
Lys Ser Asn Tyr Leu Ser Leu Ser Asn Arg Glu Cys Asp Met Trp Lys
            115                 120                 125

TTT ACA GAA GAT CTG AAT TTT GAA GCA CCG AAA AGT TTA CGA GGA ATA     432
Phe Thr Glu Asp Leu Asn Phe Glu Ala Pro Lys Ser Leu Arg Gly Ile
        130                 135                 140

AAT GGA TTT GGA TCC ACG GGA TTG TAA                                 459
Asn Gly Phe Gly Ser Thr Gly Leu *
145                 150
```

(2) INFORMATION FOR SEQ ID NO:16:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO:16:

```
Lys Arg Glu Glu Asp Ala Gly Tyr Asp Ile Pro Ser Pro Asn Leu Val
 1               5                  10                  15

Gln Ile Lys Pro Gly Tyr Ser Tyr Leu Phe Cys Leu Pro Ile Phe Gln
                20                  25                  30

Leu Glu Met Lys Asn Pro Pro Ile Ala Cys Ile Phe Gly Arg Ser Ser
            35                  40                  45

Leu Asn Ser Ser Gly Ile Ile Val Leu Pro Thr Ile Trp Lys Pro Lys
        50                  55                  60

Thr Ile Cys Gln Phe Phe Ile Lys Asn Ile Ser Ser Lys Thr Val Thr
65                  70                  75                  80

Ile Glu Lys Gly Gln Arg Ile Ala Gln Leu Val Leu Leu Lys Asn Asn
                85                  90                  95
```

| | | | | | | | | | | | | | | |
|---|---|---|---|---|---|---|---|---|---|---|---|---|---|---|
| Gln | Pro | Leu | Trp | Leu | Gln | Pro | Gln | Ile | Asn | Cys | His | Ser | Leu | Phe | Pro |
| | | | 100 | | | | | 105 | | | | | 110 | | |
| Lys | Ser | Asn | Tyr | Leu | Ser | Leu | Ser | Asn | Arg | Glu | Cys | Asp | Met | Trp | Lys |
| | | 115 | | | | | 120 | | | | | 125 | | | |
| Phe | Thr | Glu | Asp | Leu | Asn | Phe | Glu | Ala | Pro | Lys | Ser | Leu | Arg | Gly | Ile |
| | 130 | | | | | 135 | | | | | 140 | | | | |
| Asn | Gly | Phe | Gly | Ser | Thr | Gly | Leu | | | | | | | | |
| 145 | | | | | 150 | | | | | | | | | | |

( 2 ) INFORMATION FOR SEQ ID NO:17:

( i ) SEQUENCE CHARACTERISTICS:
        ( A ) LENGTH: 579 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 54..503

( x i ) SEQUENCE DESCRIPTION: SEQ ID NO:17:

```
AATTATTACT CTAAATCTCA CTTCATTATA CTTATATAAT AATATAAAAC CTT ATG        56
                                                          Met
                                                            1
```

| | | | | | | | | | | | | | | | |
|---|---|---|---|---|---|---|---|---|---|---|---|---|---|---|---|
| TTT | GTC | ATT | ATT | AAC | TTA | ACA | CTA | GAT | GGT | ACT | ATA | AAG | CTA | ACT | TAC | 104 |
| Phe | Val | Ile | Ile | Asn | Leu | Thr | Leu | Asp | Gly | Thr | Ile | Lys | Leu | Thr | Tyr | |
| | | | 5 | | | | | 10 | | | | | 15 | | | |
| AAT | ATA | AAT | AGT | AAG | ATT | AGT | TTA | TAT | AAA | TTA | CAT | TTA | ATG | GCT | TTA | 152 |
| Asn | Ile | Asn | Ser | Lys | Ile | Ser | Leu | Tyr | Lys | Leu | His | Leu | Met | Ala | Leu | |
| | | 20 | | | | | 25 | | | | | 30 | | | | |
| CCA | GAT | AAC | GTT | TTT | AGT | ATT | ATT | AAT | GAA | AAT | TAT | ATC | GAT | GGA | ATT | 200 |
| Pro | Asp | Asn | Val | Phe | Ser | Ile | Ile | Asn | Glu | Asn | Tyr | Ile | Asp | Gly | Ile | |
| | 35 | | | | | 40 | | | | | 45 | | | | | |
| TTA | ACT | ATG | AAA | ATG | GGT | GAA | GAA | ATA | GAA | AGC | TCA | TCA | CCA | TTA | AAT | 248 |
| Leu | Thr | Met | Lys | Met | Gly | Glu | Glu | Ile | Glu | Ser | Ser | Ser | Pro | Leu | Asn | |
| 50 | | | | | 55 | | | | | 60 | | | | | 65 | |
| GAA | ACA | AAT | GTT | AAT | ATA | GAT | CAA | CAT | ACA | ATA | GAT | ATT | TTT | GAT | TAC | 296 |
| Glu | Thr | Asn | Val | Asn | Ile | Asp | Gln | His | Thr | Ile | Asp | Ile | Phe | Asp | Tyr | |
| | | | | 70 | | | | | 75 | | | | | 80 | | |
| GAT | TCA | GAT | AAT | GGA | TGT | TAT | TAT | AGT | GAA | AGA | GAT | AAT | GAA | ACC | GCA | 344 |
| Asp | Ser | Asp | Asn | Gly | Cys | Tyr | Tyr | Ser | Glu | Arg | Asp | Asn | Glu | Thr | Ala | |
| | | | 85 | | | | | 90 | | | | | 95 | | | |
| ACT | CTT | TTT | TTA | AAA | CGT | GTT | GGT | TAT | AGA | GAA | ACC | TCA | AAA | AAG | CGT | 392 |
| Thr | Leu | Phe | Leu | Lys | Arg | Val | Gly | Tyr | Arg | Glu | Thr | Ser | Lys | Lys | Arg | |
| | | 100 | | | | | 105 | | | | | 110 | | | | |
| AAA | CGG | ATT | TGT | GGA | TTT | ATT | GTT | TTA | GCA | ATT | TTT | ATG | GTT | ATT | ATA | 440 |
| Lys | Arg | Ile | Cys | Gly | Phe | Ile | Val | Leu | Ala | Ile | Phe | Met | Val | Ile | Ile | |
| | 115 | | | | | 120 | | | | | 125 | | | | | |
| TTA | TGT | TTT | TTA | TCA | ATA | ATT | TTG | GGA | GTT | TTT | ATA | GCG | CCT | CAT | ATT | 488 |
| Leu | Cys | Phe | Leu | Ser | Ile | Ile | Leu | Gly | Val | Phe | Ile | Ala | Pro | His | Ile | |
| 130 | | | | | 135 | | | | | 140 | | | | | 145 | |

| | | | | | | | |
|---|---|---|---|---|---|---|---|
| TAT | AAA | GGC | CTA | TAG | TAAGAACATC | AACCTCTAAT | AGGTAAATTT | TTAAAACCAA | 543 |
| Tyr | Lys | Gly | Leu | * | | | |
| | | | | 150 | | | |

```
CGGAGGGGGA GGAGGAGGAC TTTTTATTTT ATGAGA                              579
```

( 2 ) INFORMATION FOR SEQ ID NO:18:

( i ) SEQUENCE CHARACTERISTICS:
        ( A ) LENGTH: 149 amino acids (B) TYPE: amino acid
(D) TOPOLOGY: linear (i i) MOLECULE TYPE: protein (x i) SEQUENCE DESCRIPTION: SEQ ID NO:18:

| Met | Phe | Val | Ile | Ile | Asn | Leu | Thr | Leu | Asp | Gly | Thr | Ile | Lys | Leu | Thr |
|---|---|---|---|---|---|---|---|---|---|---|---|---|---|---|---|
| 1 | | | | 5 | | | | | 10 | | | | | 15 | |
| Tyr | Asn | Ile | Asn | Ser | Lys | Ile | Ser | Leu | Tyr | Lys | Leu | His | Leu | Met | Ala |
| | | | 20 | | | | | 25 | | | | | 30 | | |
| Leu | Pro | Asp | Asn | Val | Phe | Ser | Ile | Ile | Asn | Glu | Asn | Tyr | Ile | Asp | Gly |
| | | | 35 | | | | | 40 | | | | | 45 | | |
| Ile | Leu | Thr | Met | Lys | Met | Gly | Glu | Glu | Ile | Glu | Ser | Ser | Pro | Leu | |
| | | 50 | | | | | 55 | | | | | 60 | | | |
| Asn | Glu | Thr | Asn | Val | Asn | Ile | Asp | Gln | His | Thr | Ile | Asp | Ile | Phe | Asp |
| 65 | | | | | 70 | | | | | 75 | | | | | 80 |
| Tyr | Asp | Ser | Asp | Asn | Gly | Cys | Tyr | Tyr | Ser | Glu | Arg | Asp | Asn | Glu | Thr |
| | | | | 85 | | | | | 90 | | | | | 95 | |
| Ala | Thr | Leu | Phe | Leu | Lys | Arg | Val | Gly | Tyr | Arg | Glu | Thr | Ser | Lys | Lys |
| | | | | 100 | | | | | 105 | | | | | 110 | |
| Arg | Lys | Arg | Ile | Cys | Gly | Phe | Ile | Val | Leu | Ala | Ile | Phe | Met | Val | Ile |
| | | | 115 | | | | | 120 | | | | | 125 | | |
| Ile | Leu | Cys | Phe | Leu | Ser | Ile | Ile | Leu | Gly | Val | Phe | Ile | Ala | Pro | His |
| | | | 130 | | | | | 135 | | | | | 140 | | |
| Ile | Tyr | Lys | Gly | Leu | | | | | | | | | | | |
| 145 | | | | | 150 | | | | | | | | | | |

(2) INFORMATION FOR SEQ ID NO:19:

(i) SEQUENCE CHARACTERISTICS:
(A) LENGTH: 579 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:19:

| TCTCATAAAA | TAAAAAGTCC | TCCTCCTCCC | CCTCCGTTGG | TTTTAAAAAT | TTACCTATTA | 60 |
| GAGGTTGATG | TTCTTACTAT | AGGCCTTTAT | AAATATGAGG | CGCTATAAAA | ACTCCCAAAA | 120 |
| TTATTGATAA | AAAACATAAT | ATAATAACCA | TAAAAATTGC | TAAAACAATA | AATCCACAAA | 180 |
| TCCGTTTACG | CTTTTTTGAG | GTTTCTCTAT | AACCAACACG | TTTTAAAAAA | AGAGTTGCGG | 240 |
| TTTCATTATC | TCTTTCACTA | TAATAACATC | CATTATCTGA | ATCGTAATCA | AAAATATCTA | 300 |
| TTGTATGTTG | ATCTATATTA | ACATTTGTTT | CATTTAATGG | TGATGAGCTT | TCTATTTCTT | 360 |
| CACCCATTTT | CATAGTTAAA | ATTCCATCGA | TATAATTTTC | ATTAATAATA | CTAAAAACGT | 420 |
| TATCTGGTAA | AGCCATTAAA | TGTAATTTAT | ATAAACTAAT | CTTACTATTT | ATATTGTAAG | 480 |
| TTAGCTTTAT | AGTACCATCT | AGTGTTAAGT | TAATAATGAC | AAACATAAGG | TTTTATATTA | 540 |
| TTATATAAGT | ATAATGAAGT | GAGATTTAGA | GTAATAATT | | | 579 |

(2) INFORMATION FOR SEQ ID NO:20:

(i) SEQUENCE CHARACTERISTICS:
(A) LENGTH: 450 base pairs
(B) TYPE: nucleic acid
(C) STRANDEDNESS: single
(D) TOPOLOGY: linear (i i) MOLECULE TYPE: DNA (genomic)

( x i ) SEQUENCE DESCRIPTION: SEQ ID NO:20:

| | | | | | |
|---|---|---|---|---|---|
| ATGTTTGTCA | TTATTAACTT | AACACTAGAT | GGTACTATAA | AGCTAACTTA | CAATATAAAT | 60
| AGTAAGATTA | GTTTATATAA | ATTACATTTA | ATGGCTTTAC | CAGATAACGT | TTTTAGTATT | 120
| ATTAATGAAA | ATTATATCGA | TGGAATTTTA | ACTATGAAAA | TGGGTGAAGA | AATAGAAAGC | 180
| TCATCACCAT | TAAATGAAAC | AAATGTTAAT | ATAGATCAAC | ATACAATAGA | TATTTTTGAT | 240
| TACGATTCAG | ATAATGGATG | TTATTATAGT | GAAAGAGATA | ATGAAACCGC | AACTCTTTTT | 300
| TTAAAACGTG | TTGGTTATAG | AGAAACCTCA | AAAAAGCGTA | AACGGATTTG | TGGATTTATT | 360
| GTTTTAGCAA | TTTTTATGGT | TATTATATTA | TGTTTTTTAT | CAATAATTTT | GGGAGTTTTT | 420
| ATAGCGCCTC | ATATTTATAA | AGGCCTATAG | | | | 450

( 2 ) INFORMATION FOR SEQ ID NO:21:

( i ) SEQUENCE CHARACTERISTICS:
( A ) LENGTH: 294 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 3..293

( i x ) FEATURE:
( A ) NAME/KEY: R = A or G
( B ) LOCATION: 49

( x i ) SEQUENCE DESCRIPTION: SEQ ID NO:21:

```
TC  CAA  AGT  GTT  TTT  GTT  TCA  TTG  TCT  TAT  TCT  TGG  AGC  CAC  CGA  CGA       47
    Gln  Ser  Val  Phe  Val  Ser  Leu  Ser  Tyr  Ser  Trp  Ser  His  Arg  Arg
    1              5                        10                       15

CRG  TTT  GAG  TGT  ATA  TTT  CAT  CCA  ATT  TTA  TTT  AAT  CAT  GGT  ATT  GTG       95
Xaa  Phe  Glu  Cys  Ile  Phe  His  Pro  Ile  Leu  Phe  Asn  His  Gly  Ile  Val
               20                       25                       30

AAT  TTG  GAA  AAT  AAC  CCT  TTG  ACA  TTT  AAG  GAA  CTA  CAA  AAA  ATA  AAT      143
Asn  Leu  Glu  Asn  Asn  Pro  Leu  Thr  Phe  Lys  Glu  Leu  Gln  Lys  Ile  Asn
               35                       40                       45

TAT  AGA  CGT  CAT  ATT  CTT  GGT  TTA  CCA  TTG  ATT  AGA  GCT  GGA  TTG  GTA      191
Tyr  Arg  Arg  His  Ile  Leu  Gly  Leu  Pro  Leu  Ile  Arg  Ala  Gly  Leu  Val
          50                        55                       60

GAA  GAA  GAT  AAT  CAA  CCT  TTA  ATG  ATA  CCT  CCA  GAG  TTT  TCC  AGT  AAA      239
Glu  Glu  Asp  Asn  Gln  Pro  Leu  Met  Ile  Pro  Pro  Glu  Phe  Ser  Ser  Lys
     65                        70                       75

CTA  CCT  CGA  ACA  ATA  GGA  TTT  TTA  ACT  CAA  CAA  ATT  AGA  GCC  AAA  ATG      287
Leu  Pro  Arg  Thr  Ile  Gly  Phe  Leu  Thr  Gln  Gln  Ile  Arg  Ala  Lys  Met
80                        85                       90                       95

GAA  GCT  T                                                                         294
Glu  Ala
```

( 2 ) INFORMATION FOR SEQ ID NO:22:

( i ) SEQUENCE CHARACTERISTICS:
( A ) LENGTH: 97 amino acids
( B ) TYPE: amino acid
( D ) TOPOLOGY: linear ( i i ) MOLECULE TYPE: protein ( i x ) FEATURE:
( A ) NAME/KEY: Xaa = Arg or Gln
( B ) LOCATION: 16

( x i ) SEQUENCE DESCRIPTION: SEQ ID NO:22:

| Gln | Ser | Val | Phe | Val | Ser | Leu | Ser | Tyr | Ser | Trp | Ser | His | Arg | Arg | Xaa |
|---|---|---|---|---|---|---|---|---|---|---|---|---|---|---|---|
| 1 | | | | 5 | | | | | 10 | | | | | 15 | |

| Phe | Glu | Cys | Ile | Phe | His | Pro | Ile | Leu | Phe | Asn | His | Gly | Ile | Val | Asn |
|---|---|---|---|---|---|---|---|---|---|---|---|---|---|---|---|
| | | | 20 | | | | | 25 | | | | | 30 | | |

| Leu | Glu | Asn | Asn | Pro | Leu | Thr | Phe | Lys | Glu | Leu | Gln | Lys | Ile | Asn | Tyr |
|---|---|---|---|---|---|---|---|---|---|---|---|---|---|---|---|
| | | | 35 | | | | 40 | | | | | 45 | | | |

| Arg | Arg | His | Ile | Leu | Gly | Leu | Pro | Leu | Ile | Arg | Ala | Gly | Leu | Val | Glu |
|---|---|---|---|---|---|---|---|---|---|---|---|---|---|---|---|
| | 50 | | | | | 55 | | | | | 60 | | | | |

| Glu | Asp | Asn | Gln | Pro | Leu | Met | Ile | Pro | Pro | Glu | Phe | Ser | Ser | Lys | Leu |
|---|---|---|---|---|---|---|---|---|---|---|---|---|---|---|---|
| 65 | | | | | 70 | | | | | 75 | | | | | 80 |

| Pro | Arg | Thr | Ile | Gly | Phe | Leu | Thr | Gln | Gln | Ile | Arg | Ala | Lys | Met | Glu |
|---|---|---|---|---|---|---|---|---|---|---|---|---|---|---|---|
| | | | | 85 | | | | | 90 | | | | | 95 | |

Ala ( 2 ) INFORMATION FOR SEQ ID NO:23:

( i ) SEQUENCE CHARACTERISTICS:
        ( A ) LENGTH: 294 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
AAGCTTCCAT   TTTGGCTCTA   ATTTGTTGAG   TTAAAAATCC   TATTGTTCGA   GGTAGTTTAC        60
TGGAAAACTC   TGGAGGTATC   ATTAAAGGTT   GATTATCTTC   TTCTACCAAT   CCAGCTCTAA       120
TCAATGGTAA   ACCAAGAATA   TGACGTCTAT   AATTTATTTT   TTGTAGTTCC   TTAAATGTCA       180
AAGGGTTATT   TTCCAAATTC   ACAATACCAT   GATTAAATAA   AATTGGATGA   AATATACACT       240
CAAACYGTCG   TCGGTGGCTC   CAAGAATAAG   ACAATGAAAC   AAAAACACTT   TGGA             294
```

( 2 ) INFORMATION FOR SEQ ID NO:24:

( i ) SEQUENCE CHARACTERISTICS:
        ( A ) LENGTH: 291 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
CAAAGTGTTT   TTGTTTCATT   GTCTTATTCT   TGGAGCCACC   GACGACRGTT   TGAGTGTATA        60
TTTCATCCAA   TTTTATTTAA   TCATGGTATT   GTGAATTTGG   AAAATAACCC   TTTGACATTT       120
AAGGAACTAC   AAAAAATAAA   TTATAGACGT   CATATTCTTG   GTTACCATT    GATTAGAGCT       180
GGATTGGTAG   AAGAAGATAA   TCAACCTTTA   ATGATACCTC   CAGAGTTTTC   CAGTAAACTA       240
CCTCGAACAA   TAGGATTTTT   AACTCAACAA   ATTAGAGCCA   AAATGGAAGC   T                291
```

( 2 ) INFORMATION FOR SEQ ID NO:25:

( i ) SEQUENCE CHARACTERISTICS:
        ( A ) LENGTH: 146 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 1..146

( x i ) SEQUENCE DESCRIPTION: SEQ ID NO:25:

```
CTA GAA GAT TAT ATA ACA CAT CGA ATT AAT GCC GAT ATT TCA GAG GTT        48
Leu Glu Asp Tyr Ile Thr His Arg Ile Asn Ala Asp Ile Ser Glu Val
 1               5                  10                  15

GGT GTA TTG AGA AAT TAT ATT TCT GCT GAT AGA CAG AGT TTA AAA GTT        96
Gly Val Leu Arg Asn Tyr Ile Ser Ala Asp Arg Gln Ser Leu Lys Val
                20                  25                  30

TCT GAT AGA GAG TTT ATT AAT TAT ATT TAC TTG GCA CAT TTT GAA AGC TT    146
Ser Asp Arg Glu Phe Ile Asn Tyr Ile Tyr Leu Ala His Phe Glu Ser
                35                  40                  45
```

( 2 ) INFORMATION FOR SEQ ID NO:26:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Leu Glu Asp Tyr Ile Thr His Arg Ile Asn Ala Asp Ile Ser Glu Val
 1               5                  10                  15

Gly Val Leu Arg Asn Tyr Ile Ser Ala Asp Arg Gln Ser Leu Lys Val
                20                  25                  30

Ser Asp Arg Glu Phe Ile Asn Tyr Ile Tyr Leu Ala His Phe Glu Ser
                35                  40                  45
```

( 2 ) INFORMATION FOR SEQ ID NO:27:

( i ) SEQUENCE CHARACTERISTICS:
        ( A ) LENGTH: 146 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
AAGCTTTCAA AATGTGCCAA GTAAATATAA TTAATAAACT CTCTATCAGA AACTTTTAAA     60
CTCTGTCTAT CAGCAGAAAT ATAATTTCTC AATACACCAA CCTCTGAAAT ATCGGCATTA    120
ATTCGATGTG TTATATAATC TTCTAG                                         146
```

( 2 ) INFORMATION FOR SEQ ID NO:28:

( i ) SEQUENCE CHARACTERISTICS:
        ( A ) LENGTH: 144 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
CTAGAAGATT ATATAACACA TCGAATTAAT GCCGATATTT CAGAGGTTGG TGTATTGAGA     60
AATTATATTT CTGCTGATAG ACAGAGTTTA AAAGTTTCTG ATAGAGAGTT TATTAATTAT    120
ATTTACTTGG CACATTTTGA AAGC                                           144
```

( 2 ) INFORMATION FOR SEQ ID NO:29:

( i ) SEQUENCE CHARACTERISTICS:
  ( A ) LENGTH: 161 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 3..161

( x i ) SEQUENCE DESCRIPTION: SEQ ID NO:29:

| TT | ATG | TCA | GTG | GAC | GTT | ATA | TTT | CTC | GAT | GAC | CAA | CAT | CTG | TCA | GTA | 47 |
|    | Met | Ser | Val | Asp | Val | Ile | Phe | Leu | Asp | Asp | Gln | His | Leu | Ser | Val |    |
|    | 1   |     |     |     | 5   |     |     |     |     | 10  |     |     |     |     | 15  |    |

| AAT | AAT | TAT | AGC | GGA | ACT | ATT | GAG | TTT | ATT | CAT | TTT | AAT | AAC | TCT | TGT | 95 |
| Asn | Asn | Tyr | Ser | Gly | Thr | Ile | Glu | Phe | Ile | His | Phe | Asn | Asn | Ser | Cys |    |
|     |     |     |     | 20  |     |     |     |     | 25  |     |     |     |     | 30  |     |    |

| TAT | ACC | GTT | TAT | CAA | ACT | ATT | GAA | TAT | TTT | TCT | TGT | CCT | CGC | ATT | TTT | 143 |
| Tyr | Thr | Val | Tyr | Gln | Thr | Ile | Glu | Tyr | Phe | Ser | Cys | Pro | Arg | Ile | Phe |     |
|     |     |     | 35  |     |     |     |     | 40  |     |     |     |     | 45  |     |     |     |

| AAT | AAT | GCT | TTT | AGA | TCT | 161 |
| Asn | Asn | Ala | Phe | Arg | Ser |     |
|     | 50  |     |     |     |     |     |

( 2 ) INFORMATION FOR SEQ ID NO:30:

( i ) SEQUENCE CHARACTERISTICS:
  ( A ) LENGTH: 53 amino acids
  ( B ) TYPE: amino acid
  ( D ) TOPOLOGY: linear ( i i ) MOLECULE TYPE: protein ( x i ) SEQUENCE DESCRIPTION: SEQ ID NO:30:

| Met | Ser | Val | Asp | Val | Ile | Phe | Leu | Asp | Asp | Gln | His | Leu | Ser | Val | Asn |
| 1   |     |     |     | 5   |     |     |     |     | 10  |     |     |     |     | 15  |     |

| Asn | Tyr | Ser | Gly | Thr | Ile | Glu | Phe | Ile | His | Phe | Asn | Asn | Ser | Cys | Tyr |
|     |     |     | 20  |     |     |     |     | 25  |     |     |     |     | 30  |     |     |

| Thr | Val | Tyr | Gln | Thr | Ile | Glu | Tyr | Phe | Ser | Cys | Pro | Arg | Ile | Phe | Asn |
|     |     |     | 35  |     |     |     |     | 40  |     |     |     |     | 45  |     |     |

| Asn | Ala | Phe | Arg | Ser |
|     | 50  |     |     |     |

( 2 ) INFORMATION FOR SEQ ID NO:31:

( i ) SEQUENCE CHARACTERISTICS:
  ( A ) LENGTH: 161 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:31:

| AGATCTAAAA | GCATTATTAA | AAATGCGAGG | ACAAGAAAAA | TATTCAATAG | TTTGATAAAC | 60 |
| GGTATAACAA | GAGTTATTAA | AATGAATAAA | CTCAATAGTT | CCGCTATAAT | TATTTACTGA | 120 |
| CAGATGTTGG | TCATCGAGAA | ATATAACGTC | CACTGACATA | A | | 161 |

( 2 ) INFORMATION FOR SEQ ID NO:32:

( i ) SEQUENCE CHARACTERISTICS:
  ( A ) LENGTH: 159 base pairs
  ( B ) TYPE: nucleic acid
  ( C ) STRANDEDNESS: single (D) TOPOLOGY: linear (ii) MOLECULE TYPE: DNA (genomic)

(xi) SEQUENCE DESCRIPTION: SEQ ID NO:32:

```
ATGTCAGTGG ACGTTATATT TCTCGATGAC CAACATCTGT CAGTAAATAA TTATAGCGGA      60
ACTATTGAGT TTATTCATTT TAATAACTCT TGTTATACCG TTTATCAAAC TATTGAATAT     120
TTTTCTTGTC CTCGCATTTT TAATAATGCT TTTAGATCT                            159
```

(2) INFORMATION FOR SEQ ID NO:33:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..261

(xi) SEQUENCE DESCRIPTION: SEQ ID NO:33:

```
GGT GGT GCC CAA GCC ATA AAA ATG ACT TCA GAA AAT AAT ATT GTT ATG       48
Gly Gly Ala Gln Ala Ile Lys Met Thr Ser Glu Asn Asn Ile Val Met
 1               5                  10                  15

GCA GAT GTA GCG GTT TTA GAA AAA ACC CTT GGT ATA GAT TCT AAT ACA       96
Ala Asp Val Ala Val Leu Glu Lys Thr Leu Gly Ile Asp Ser Asn Thr
             20                  25                  30

ACA AAA CCC TTA TCT CTT CAA ACC GTT AAA TAT GAT GAA AAT AAT TCT      144
Thr Lys Pro Leu Ser Leu Gln Thr Val Lys Tyr Asp Glu Asn Asn Ser
         35                  40                  45

ACA GAT ATA CTA GAT ACA GAA CCT CTA ATA AGT TCT ATG GAA ACT GAA      192
Thr Asp Ile Leu Asp Thr Glu Pro Leu Ile Ser Ser Met Glu Thr Glu
     50                  55                  60

AAT ATT TTA TCG ACT AAA CAA AAA AGA AAC GGT CCC AAA AAA ATG ACA      240
Asn Ile Leu Ser Thr Lys Gln Lys Arg Asn Gly Pro Lys Lys Met Thr
 65                  70                  75                  80

CGT GAA AGT TTG GCA CTT TAA                                          261
Arg Glu Ser Leu Ala Leu  *
                 85
```

(2) INFORMATION FOR SEQ ID NO:34:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO:34:

```
Gly Gly Ala Gln Ala Ile Lys Met Thr Ser Glu Asn Asn Ile Val Met
 1               5                  10                  15

Ala Asp Val Ala Val Leu Glu Lys Thr Leu Gly Ile Asp Ser Asn Thr
             20                  25                  30

Thr Lys Pro Leu Ser Leu Gln Thr Val Lys Tyr Asp Glu Asn Asn Ser
         35                  40                  45

Thr Asp Ile Leu Asp Thr Glu Pro Leu Ile Ser Ser Met Glu Thr Glu
     50                  55                  60

Asn Ile Leu Ser Thr Lys Gln Lys Arg Asn Gly Pro Lys Lys Met Thr
 65                  70                  75                  80
```

Arg Glu Ser Leu Ala Leu
                85

( 2 ) INFORMATION FOR SEQ ID NO:35:

( i ) SEQUENCE CHARACTERISTICS:
        ( A ) LENGTH: 280 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..280

( x i ) SEQUENCE DESCRIPTION: SEQ ID NO:35:

```
T  GCA  TTA  AAT  TTT  ATT  AAA  TTA  GAA  AAA  AAT  AAT  CCA  GTA  TAT  TAT           46
   Ala  Leu  Asn  Phe  Ile  Lys  Leu  Glu  Lys  Asn  Asn  Pro  Val  Tyr  Tyr
   1              5                        10                       15

TTT  CCG  GAA  CCT  ATG  GCA  TTC  TGG  CGT  ATC  ATC  CTA  GAA  ACA  GAT  ATT          94
Phe  Pro  Glu  Pro  Met  Ala  Phe  Trp  Arg  Ile  Ile  Leu  Glu  Thr  Asp  Ile
                    20                       25                       30

GTG  CAA  GGT  ATA  TAC  TCA  GTA  CAA  GAC  CGG  AAG  CTG  CGT  GGT  GAA  TTA         142
Val  Gln  Gly  Ile  Tyr  Ser  Val  Gln  Asp  Arg  Lys  Leu  Arg  Gly  Glu  Leu
               35                       40                       45

AGC  CTA  AAT  GAT  GCG  TCA  TTA  ATT  ACA  GCT  CAA  CTT  CAA  ACT  AAA  TTT         190
Ser  Leu  Asn  Asp  Ala  Ser  Leu  Ile  Thr  Ala  Gln  Leu  Gln  Thr  Lys  Phe
               50                       55                       60

TCT  ACG  CCA  TAT  ATT  TTA  CTT  CAT  TCC  AAT  GTA  TCC  AAA  TTT  TTT  GGA         238
Ser  Thr  Pro  Tyr  Ile  Leu  Leu  His  Ser  Asn  Val  Ser  Lys  Phe  Phe  Gly
          65                       70                       75

GAA  AAT  GTA  ACA  TTT  GGA  ATT  CCG  GAA  GTA  ATA  TTT  ATT  TTT                    280
Glu  Asn  Val  Thr  Phe  Gly  Ile  Pro  Glu  Val  Ile  Phe  Ile  Phe
80                  85                       90
```

( 2 ) INFORMATION FOR SEQ ID NO:36:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Ala  Leu  Asn  Phe  Ile  Lys  Leu  Glu  Lys  Asn  Asn  Pro  Val  Tyr  Tyr  Phe
1                   5                        10                       15

Pro  Glu  Pro  Met  Ala  Phe  Trp  Arg  Ile  Ile  Leu  Glu  Thr  Asp  Ile  Val
                    20                       25                       30

Gln  Gly  Ile  Tyr  Ser  Val  Gln  Asp  Arg  Lys  Leu  Arg  Gly  Glu  Leu  Ser
               35                       40                       45

Leu  Asn  Asp  Ala  Ser  Leu  Ile  Thr  Ala  Gln  Leu  Gln  Thr  Lys  Phe  Ser
               50                       55                       60

Thr  Pro  Tyr  Ile  Leu  Leu  His  Ser  Asn  Val  Ser  Lys  Phe  Phe  Gly  Glu
65                       70                       75                       80

Asn  Val  Thr  Phe  Gly  Ile  Pro  Glu  Val  Ile  Phe  Ile  Phe
                    85                       90
```

( 2 ) INFORMATION FOR SEQ ID NO:37:

( i ) SEQUENCE CHARACTERISTICS:
        ( A ) LENGTH: 280 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:37:

| | | | | | |
|---|---|---|---|---|---|
| AAAAATAAAT | ATTACTTCCG | GAATTCCAAA | TGTTACATTT | TCTCCAAAAA | ATTTGGATAC | 60 |
| ATTGGAATGA | AGTAAAATAT | ATGGCGTAGA | AAATTTAGTT | TGAAGTTGAG | CTGTAATTAA | 120 |
| TGACGCATCA | TTTAGGCTTA | ATTCACCACG | CAGCTTCCGG | TCTTGTACTG | AGTATATACC | 180 |
| TTGCACAATA | TCTGTTTCTA | GGATGATACG | CCAGAATGCC | ATAGGTTCCG | GAAAATAATA | 240 |
| TACTGGATTA | TTTTTTTCTA | ATTAATAAA | ATTAATGCA | | | 280 |

(2) INFORMATION FOR SEQ ID NO:38:

(i) SEQUENCE CHARACTERISTICS:
    (A) LENGTH: 279 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:38:

| | | | | | |
|---|---|---|---|---|---|
| GCATTAAATT | TTATTAAATT | AGAAAAAAAT | AATCCAGTAT | ATTATTTTCC | GGAACCTATG | 60 |
| GCATTCTGGC | GTATCATCCT | AGAAACAGAT | ATTGTGCAAG | GTATATACTC | AGTACAAGAC | 120 |
| CGGAAGCTGC | GTGGTGAATT | AAGCCTAAAT | GATGCGTCAT | TAATTACAGC | TCAACTTCAA | 180 |
| ACTAAATTTT | CTACGCCATA | TATTTACTT | CATTCCAATG | TATCCAAATT | TTTTGGAGAA | 240 |
| AATGTAACAT | TTGGAATTCC | GGAAGTAATA | TTTATTTTT | | | 279 |

(2) INFORMATION FOR SEQ ID NO:39:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: misc_feature
    (B) LOCATION: 1..27
    (D) OTHER INFORMATION: /label=primer (i x) FEATURE:
    (A) NAME/KEY: N = Inosine
    (B) LOCATION: 11

(i x) FEATURE:
    (A) NAME/KEY: N = Inosine
    (B) LOCATION: 17

(i x) FEATURE:
    (A) NAME/KEY: N = Inosine
    (B) LOCATION: 20

(x i) SEQUENCE DESCRIPTION: SEQ ID NO:39:

GGCGAATTCC NAARMGNGAN GARGAYG    27

(2) INFORMATION FOR SEQ ID NO:40:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (i i) MOLECULE TYPE: DNA (genomic)

(i x) FEATURE:
        (A) NAME/KEY: misc_feature
        (B) LOCATION: 1..24
        (D) OTHER INFORMATION: /label=primer (i x) FEATURE:
        (A) NAME/KEY: N = Inosine
        (B) LOCATION: 11

(i x) FEATURE:
        (A) NAME/KEY: N = Inosine
        (B) LOCATION: 16

(i x) FEATURE:
        (A) NAME/KEY: N = Inosine
        (B) LOCATION: 22

(x i) SEQUENCE DESCRIPTION: SEQ ID NO:40:

CGCGGATCCG NTNSWNCCYA ANCC         24

(2) INFORMATION FOR SEQ ID NO:41:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: misc_feature
        (B) LOCATION: 1..26
        (D) OTHER INFORMATION: /label=primer (i x) FEATURE:
        (A) NAME/KEY: N = Inosine
        (B) LOCATION: 18

(i x) FEATURE:
        (A) NAME/KEY: N = Inosine
        (B) LOCATION: 24

(x i) SEQUENCE DESCRIPTION: SEQ ID NO:41:

GGCGAATTCT AYCAYWSNCA YGTNTA         26

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: misc_feature
        (B) LOCATION: 1..30
        (D) OTHER INFORMATION: /label=primer (i x) FEATURE:
        (A) NAME/KEY: N = Inosine
        (B) LOCATION: 16

(i x) FEATURE:
        (A) NAME/KEY: N = Inosine
        (B) LOCATION: 19

(i x) FEATURE:
        (A) NAME/KEY: N = Inosine
        (B) LOCATION: 24

( i x ) FEATURE:
  ( A ) NAME/KEY: N = Inosine
  ( B ) LOCATION: 25

( i x ) FEATURE:
  ( A ) NAME/KEY: N = Inosine
  ( B ) LOCATION: 28

( x i ) SEQUENCE DESCRIPTION: SEQ ID NO:42:

CGCGGATCCR TCRTTNSWNG GDANNSWNGT                             30

( 2 ) INFORMATION FOR SEQ ID NO:43:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..20
    ( D ) OTHER INFORMATION: /label=primer ( i x ) FEATURE:
    ( A ) NAME/KEY: N = Inosine
    ( B ) LOCATION: 12

( i x ) FEATURE:
    ( A ) NAME/KEY: N = Inosine
    ( B ) LOCATION: 18

( i x ) FEATURE:
    ( A ) NAME/KEY: N = Inosine
    ( B ) LOCATION: 21

( x i ) SEQUENCE DESCRIPTION: SEQ ID NO:43:

GGCGAATTCG GNAARWSNAC NRC                                    23

( 2 ) INFORMATION FOR SEQ ID NO:44:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..20
    ( D ) OTHER INFORMATION: /label=primer ( i x ) FEATURE:
    ( A ) NAME/KEY: N = Inosine
    ( B ) LOCATION: 15

( x i ) SEQUENCE DESCRIPTION: SEQ ID NO:44:

GGCGGATCCG GTTGNCKRTC                                        20

( 2 ) INFORMATION FOR SEQ ID NO:45:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:

(A) NAME/KEY: misc_feature
(B) LOCATION: 1..30
(D) OTHER INFORMATION: /label=label (xi) SEQUENCE DESCRIPTION: SEQ ID NO:45:

CGCGGATCCA AGGTAATAAG TCAAAATGAG 30

(2) INFORMATION FOR SEQ ID NO:46:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..29
(D) OTHER INFORMATION: /label=primer (xi) SEQUENCE DESCRIPTION: SEQ ID NO:46:

CGCGGATCCG ACAAAAACAA AAAGTAATG 29

(2) INFORMATION FOR SEQ ID NO:47:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..26
(D) OTHER INFORMATION: /label=primer (ix) FEATURE:
(A) NAME/KEY: N = Inosine
(B) LOCATION: 11

(ix) FEATURE:
(A) NAME/KEY: N = Inosine
(B) LOCATION: 20

(xi) SEQUENCE DESCRIPTION: SEQ ID NO:47:

CCGAATTCYT NATGATHYTN ATHGARGG 28

(2) INFORMATION FOR SEQ ID NO:48:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..29
(D) OTHER INFORMATION: /label=primer (ix) FEATURE:
(A) NAME/KEY: N = Inosine
(B) LOCATION: 21

(xi) SEQUENCE DESCRIPTION: SEQ ID NO:48:

CCGGATCCYT CRAARAARTT NGTRTGYTT 29

( 2 ) INFORMATION FOR SEQ ID NO:49:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..35
        ( D ) OTHER INFORMATION: /label=primer ( x i ) SEQUENCE DESCRIPTION: SEQ ID NO:49:

| | | | | |
|---|---|---|---|---|
| TCCCCCGGGG | GCGCGCCTTG | ACATTGATTA | TTGAC | 3 5 |

( 2 ) INFORMATION FOR SEQ ID NO:50:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..35
        ( D ) OTHER INFORMATION: /label=primer ( x i ) SEQUENCE DESCRIPTION: SEQ ID NO:50:

| | | | | |
|---|---|---|---|---|
| GCCCTTAAGG | GGCGCGCCAA | TGCGATGCAA | TTTCC | 3 5 |

( 2 ) INFORMATION FOR SEQ ID NO:51:

( i ) SEQUENCE CHARACTERISTICS:
        ( A ) LENGTH: 10592 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

| | | | | | | |
|---|---|---|---|---|---|---|
| CTGCAGTGTA | TTTAAAAAAT | AAAAATCTAT | GAATGAAATC | TATGAATGAA | ATCTATGAAT | 6 0 |
| GAAATCTATG | AATGAAATCT | ATGAATGAAA | TCTATGAATG | AAATCTATGA | ATGAAATCTA | 1 2 0 |
| TGAATGAAAT | CTATGAATGA | AATCTATGAA | TGAAATCTAT | GAATGAAATC | TATGAATGAA | 1 8 0 |
| ATCTATGAAT | GAAATCTATG | AATGAAATCT | ATGAATGAAA | TCTATGAATG | AAATCTATGA | 2 4 0 |
| ATGAAATCTA | TGAATGAAAT | CTATGAATGA | AATCTATGAA | TGAAATCTAT | GAGACAAAGT | 3 0 0 |
| AATTTTTAAA | AATATTTTAA | ATTTTATTAA | GAGTATAGGT | TACAAGGTTT | AATGCGTTGG | 3 6 0 |
| GTAAACATTT | TAGTTTTCAA | GTTTTAGTTT | TCTGGTATCT | ACCAACACAA | ATGCATCTTC | 4 2 0 |
| GGATACATTA | TTTAGAGAGT | AATCACTTTT | TAGAATATAT | CTTATTGGTG | GTACATTTAT | 4 8 0 |
| AAATTTTGGA | CCATCCCAAT | AACACTTCGA | TTCCACAAGC | GAAGAAGGTA | CTTCCATAAG | 5 4 0 |
| CTGAGAAGCG | TTTACTTGAT | TGTAGGGAGA | ACTTGGCGTT | TCAAAATCCT | TTAGAACGTA | 6 0 0 |
| TAGTCTGCAA | TACATAGGTT | CAATATCATC | TTCATACCTC | TCATCAGGAT | ATGAAAATGG | 6 6 0 |
| AAGTTTCACA | AAGGTTCCAT | CACGAAGCTT | TTTGAAGAAT | CGTACATCCG | TAGGTGGTGT | 7 2 0 |
| AGGAACAATA | GTGAAGGCGT | GCGGTTCACC | CTGGTTTTTC | ACACGTGCAA | GCGCTGGTGT | 7 8 0 |
| GGTTTTAGGG | CGAACTGGAA | AATAACCAGG | CGGAACTTGT | GCGTAGAATC | CTTCATTAAG | 8 4 0 |

```
TTCTCCACGA  CAGCGTCTGA  AGTATGATGG  CATATTAGCT  TGATCGGAGT  TGTTATCAAA   900
TAGAGCAAAT  GAAGCACTCA  TTTTAAAACT  TTTTAGTTAA  GCTTTAAAAA  CAAGTGAAGA   960
TTTAAAAATG  TAGGATAAAA  TGCCAGTTTA  TATACAGTAA  GAATATGGGA  GTGGTTCACA  1020
TAAAAAACCA  GAATTTCAGG  TTTACATCTA  CTGTTTATTC  ACAACAAATA  TAAACAAACT  1080
TAGTTTCCAC  ATAAACATGA  ACTAAATAGA  GATGAACGTT  GAGCGTTGGT  AGGTTGTGTA  1140
GAAGACATAC  CATCGTTTTC  ATTTTTGGTT  ATTGTTTTGG  CGCGCCTTGA  AAATAATCGT  1200
TTAAAAATAT  TTGGTTTGGA  TAGCCTTTTC  ATAGGTTTCA  CCCCATGCAA  GTCATCCTCT  1260
TCTGGTTCAG  GAATTTCTTC  ATAACCATTA  TGGGATATTA  TTGCACACAT  AAATGATTCG  1320
ATTACCGGGG  GGGCAGAACG  TGTCTCATTT  ATATAAAGAG  AATCACATAC  ATCGCTTATA  1380
GAACATGTAG  AACTGTCAGA  ATCCTCTTTA  AAACTATTTT  TAATTTCACA  ATTAGTTTCT  1440
TCTAGTTCAT  TATCCACCAT  CGCATTAGCG  TATTTCCAAA  TATCATTCTC  TGAGGAATAA  1500
TGAGATGCAG  AGCATGAAGA  AGAGGATGAG  GAGGAGGAGG  ATGAAGATGA  GGATATAGAG  1560
GGACATCTTG  GAGAGCTTTC  AAAGTTGAAT  GGAGTATTAA  ATGTTGTACC  ATAAAAAATG  1620
TCACTTAACA  TAGGGGGTAC  TTTAAGGAG   GACAGAAAGG  TGTCTAATAC  AGGTACCCAT  1680
ATAAACGAGG  GGCAATAAAC  ACTCCAGAA   TCATCGATAT  GTTTACATT   ATTTTGGAA   1740
ATCTCAAGAC  ACTCAGGTTT  CCAGGATGGT  TCCGGCCATT  CACATGATAC  ATATGCATAA  1800
ATTAGTCGCT  TTGGTCCTGG  GATATTAGAA  ATGACTGGCT  CACATAAATC  CGCTGCACCG  1860
AAAACCCATA  GATTAAGAGG  ATAGTTTCCA  AATATACCAG  AGTTTAGATA  GTTATACCCC  1920
GAAACAGCCG  ATTTCCATTC  GATGCTAGCC  CCAGGTTTAT  CCTCATAAAA  TAAAAAGTCC  1980
TCCTCCTCCC  CCTCCGTTGG  TTTTAAAAAT  TTACTATTAG  AGGTTGATGT  TCTTACTATA  2040
GGCCTTGAAA  CTCTAGGTAG  ATGTTTTATA  GAGTCCATAA  AATAACATAA  GTTTGCAGAT  2100
CGTAATATTA  TAGGCATAGC  CAATCGTGTG  AGAGAAAGGA  TATAGCATTG  TCTAGCCATA  2160
AAACACCAAA  GATCAGGATG  AACATCTTGG  GAGTTTCCTG  GTAACGCCCC  ATTTTGTCA   2220
ATAAACGTAA  CAATATTAAC  TTCAACCACA  CCCATAATTA  AATTTTATGT  ATGAATCCAA  2280
TAAAGGTTAA  TACACACCTA  ATTTATGTTA  TAATTTTAGA  AGAAGCTGCA  GTTGATGAGT  2340
TGATATTAAC  ATAACAATTT  CACAATTACC  TGATATGGCA  AAGTGTACCA  CCGAAAAGTT  2400
TTGTTGTATC  AGCGTGAATA  GAGAATCTTC  TGTCGATCCA  GAAGACTTCT  ATAAACCGGT  2460
TCCTCTAACT  TCAGATTTGA  TTGAAGAGGA  TAACCTACAT  CAAGACAAAA  TAATGGATGA  2520
GGATTTATAC  TCGGATTTTA  GTGATGATGA  CTTTATGGAT  TATACAAAAA  ATCCAACTGA  2580
AAGTGAAAAT  GAAAGAGAAA  GTGACGAAGA  AGTTGAAGAA  AGTTATGAAA  GTGATGAAGA  2640
TAAAAAAGT   TTATCTCCTA  CTAAAAGCGA  AGGAATTGAA  GCGGCTGAAG  CGCTAAAGTT  2700
TTCTGTTGTT  AAATCGTTAA  CGCCTGGGTC  AGAAGGAAGA  GTTTTTATTG  CTCTTAAAAA  2760
AGATAAAGAT  ACAAGCTATA  AGGTAATTTT  AAAAATTGGA  CAAAGGGGAA  ACACGCTTGT  2820
GGAATCGTTA  ATTTTGAGAA  ATATTAGTCA  CCAATCTATA  ATTAAACTTC  AAGACACTCT  2880
TTTTTATAAA  GAGTTAACAT  GTTTGGTGTT  ACCGTATTAT  AAATATGATC  TATATAATTT  2940
TTTAATGGAT  CATGGGAAAT  CTCTGTCTTT  TGAATCTGTA  ATTAAAATTG  AAAAACAAAT  3000
ATTAACTGGA  CTTCAATATA  TTCATGGAAA  AAAAATTATT  CATCGAGATA  TAAAAACTGA  3060
AAATATTTTC  TTGGATAATG  ACTCTAATGT  TTGTATAGGT  GATTTTGGGG  CTTCTCAATT  3120
TCCTGTTTCC  TCACCAGATT  ATTTGGGAAT  TGCGGGGACT  ATTGAAACTA  ATGCTCCTGA  3180
AGTTCTATCA  AAGGATGCGT  ACAACTGTAA  AGCTGATATT  TGGAGTGCTG  GTATAATTTT  3240
```

```
ATTTGAAATG CTTGCATATC CTAATGTTTT GTTGAGGAG  GAAGAAAGAG ATAGTAGCGA  3300
TTTAATAAAC AATTGTAATC TTCATCTTAT AAAAATTATA TCAACTCTGA AGATTAACCC  3360
AAATGAATTT CCATCTGATT TGGAATCTAA TCTAGTAAAA CATTTTATAA AATATGCTAA  3420
TAATGATAGA CCTCCATTTA CACGATATAA TCGTCTAAAT AACCTTAAAT TACATCTCGA  3480
TGGTGAATTT TTAATTCATA AAATGCTAAC ATTTGATGCA TCTCTACGAC CAAGTGCGGA  3540
AGAACTATTA TCCTATCAGA TTTTTAGTAA ACAATAAATT TCATAAAAAT GGGCGTGGAA  3600
TTTTTTATTG TTTTATATAA AACGGGTGTT TGAAAGCTCT TTTTTATTAA TTTTATTTTT  3660
ACATCCTAGC TACAATATTA TAGTTATCAT GTTGTATACG CTGTTTTTG  TTTTTTATTT  3720
TAAGGTAGTT TTATCTCGCA TAGCTCCGCT AGAGTTGTGT TATGCGGATC CTAAAGAAAA  3780
TACAACTGAA CCTACACAAC TTCCTACAGG GGAACAATCT AAGACTCTTA TTCCCGTGGT  3840
AACAAACGGA TATGTTGAAT ACTCTAAAGG ATGTGAACTA CGATTACTAG ATACATATGT  3900
AAATGTATCT TCACGACCAG AAAAAAAGGT TAATGCTACA ATTGGATGGT CATTTGATCT  3960
TGGTTGTCAA ATTCCTTTAA TTATAGAGA  ATATTATAAT TGTACTGGTA ATATAATACC  4020
ATCACCAGAA ACTTGTGATG GTTATTCTTT AACTTTGGTA AAATCTGAAA GTATATCATC  4080
TTATGCACTT GTTAATGTTA GTTTGCTTAT TCAACCAGGA ATTTTTGATT CTGGTAGATA  4140
TTTATACTCA CTTGTTTTTG GAAACGATAG TTATAACGGA AGAATTGAAG TTCGAGTGGA  4200
TAATGAGACA GACTATCCAT GTTTTATGAT GCATGGATTG ACTGTAAAAA AGGGTGATAA  4260
ACTTCATATT CCTTATAAAC CATCCACAAA TCCTAATCAT AAACGATATA GAGGTTGTTT  4320
TCCAATATCA AATACTGAGC TATGGAATAA TATTAGTGAT GAAAGTGTTG GTAGATATTC  4380
ATATGATGAA GAATATGAAG AATATGAAGA AGAAAACGAA GATTTTGAAG ATCTACAATC  4440
AAAAGATTGC CGCAAATCCA ATCTTTTGA  TATGAAGAAG ACTTTTAATT TGGCTGCAGG  4500
TTCTCAAAGT TTATTGATTG CTAGTTTGGG TAAATCAATT TCAGAACAAC CGTGGTCATT  4560
TAAAATTAAT GAAAGTTATG AACTTTTTAA TAATTTGTCT ATCACCCTTC AATCGGAAGA  4620
AGATTCTAAT ATACTGAATC CTGAAATTGT AACGTTTACC ACACCACCAC CTACTGAAAA  4680
TACACATATG TTTATGTCAA ATAATGAAAC TATGTATGAA GAAGAAAGTG TTTTAAGCAT  4740
TATTCAATTG TTTAACAATG GTTATAATAA TTGTAATACC CATATAAAGG TAATTGGATT  4800
TGGAACAATT ATCTTTATTA TTTTATTTTT TGTTGCTGTG TTTTTTTGTG GATATACTTG  4860
TGTATTAAAC TCTCGTATTA AAATGATTAA CCATGCTTAT ATACAACCCC AGAAATTAAA  4920
TTTTTATGAT ATTTAATAAA ACTATTATGA AACTTCTTAT AACTTATTTG TTTTTATTAA  4980
ATGGGTTGGG TTGGTTTTAA AATTACATAC GTGTATTAAG AATTAACATC ATAAAGGACA  5040
CACCCATGAA AAACATTTAA ATTCTATTAA TTTGAACGGA TTAAACATTT TCTCATTTTA  5100
AGAGTTGCTA CGACTTTTGA TAGTAAAATG ATTAAACTTC TATTTATCTT ATTTTATTTT  5160
AACCCAATAA CTGGATATAA ATGGGTAGAC CCTCCTCGTA GGTATAATTA CACCGTTTTA  5220
AGAATGATTC CAGATATTCC AAATCCAATG GATCCTTCTA AAAACGCTGA AGTTCGGTAT  5280
GTAACTTCTA CTGACCCATG TGATATGGTT GCTTTGATTT CTAATCCAAA TATAGAATCT  5340
ACAATTAAAA CGATTCAATT TGTGCAAAAG AAAAAATTTT ACAATGCATC TCTTAGTTGG  5400
TTTAAAGTTG GAGATGATTG TACATATCCA ATATATTTAA TTCAATATTT TGATTGTGAT  5460
CCTCAAAGAG AATTTGGCAT ATGTTAAAAA AGATCTCCAG ATTTTTGGAA ACCATCGTTA  5520
GTTGGTTACA CATTTTTAAC TGATGATGAA TTGGGATTAG TTTTAGCTGC CCCCGCTCCA  5580
TTTAATCAAG GTCAATATAG ACGGGTTATT CAAATTGAAA ATGAAGTTTT TTATACTGAT  5640
```

```
TTTATGGTTC  AATTACCACG  AGAAACTTGT  TATTTTTCTA  AAGAAGATAA  ATTTGAACCA   5700
ACTTTTATGG  AATGGTGTAA  GGAATCTAGA  TCTGTAGGAG  CATCAAAAGT  TGACGATGAA   5760
CTTTTTTATC  TAAATAGAGC  TGGTCCCCAA  ACCCTGCTTA  AATATTATGT  TATTAAAGAT   5820
TTTTATAGAC  TTAACGGTAG  AGAACCTCCA  ATAAATTTA   AAGAAGCTCT  TAGATACGAT   5880
ATACCATATA  AAGTGAATGA  TAAATTTGAT  GATGAATTAC  CATCGAGGCC  ACATATTAGT   5940
AATACTATTA  ATAAAACTAT  TAAAGAAATT  GTAAATCTTG  AAGATTATTT  TAAAAATACA   6000
AATGTTATAG  ATACTACTAC  CCCAACACCA  ATAAATAATA  CCCCAAAAAA  TATAACCGTG   6060
GGAATTGTTA  TAATTATATT  AATAATACTA  TTTATAATTG  GATTTTTTGT  TTATAAAAGA   6120
CAAAAAATAT  ATAATAATTA  TAAAAAATTA  ACAACAAATG  TTTAGCCTTT  ATAAATTAAT   6180
TTACAGAATA  AACAACTGGG  CGGTCTTTTG  TTTAATAAAA  ATTCATGTAC  CTACAACTTT   6240
TATTCACTTG  CAAGAGGGTT  GAGACCAGAT  TACTTATAAC  TATGTTTCTA  CCTATTTTAT   6300
TTCTTTTTTT  ATATGGTGTA  AATGGATTTG  TTTACAAAGG  TACGTATATA  AGTATGTTTT   6360
TAAATACTAG  TTCTGGCTTT  TCTATTTTTC  CCGATGATAA  ATTTATTGTC  AGTGGACGTT   6420
TATTATTTCT  CGATGACCAA  CATCTGTCAG  TAAATAATTA  TAGCGGAACT  ATTGAGTTTA   6480
TTCATTTTAA  TAACTCTTGT  TATACCGTTT  ATCAAACTAT  TGAATATTTT  TCTTGTCCTC   6540
GCATTTTTAA  TAATGCTTTT  AGATCTTGTT  TAAAAAGGT   ATCAAAACAT  CATGAAAGTC   6600
AACTTCGGAT  AAATTCATCT  ATAGAAAACG  GTGTTTTGTT  GGAAATTACA  AATCCTAAAC   6660
CAAATGATTC  AGGTGTTTAT  TTTATACGAG  TTCAATTGGA  AAATAATAAA  ACAGATGTGT   6720
TTGGAATACC  TGCATTTATT  TATTCCTTTA  ATATGTCAAA  CGAAGTAAAT  AAATCAAACT   6780
TCGATGATGT  TACTACATCT  TTATATACCT  CATCACACCC  TTCTTCCCAA  ACTATTACAC   6840
CTATCTATTT  AAATGAAAAA  CACGAACCGA  TATGTCATAC  TGTAAAAAAG  GATGAAAATG   6900
TGTATGAACT  TTTACTAGGT  TTGCATGGAA  ATATAACTGA  TGATATTTTT  CTCGATGAGG   6960
ATTCTGAATT  GCTTAAAAGA  GTAAATATAC  CTACAACGAC  AAATAATTAT  ATATTTAAGC   7020
CTTACCTAGA  CCAACGTAAT  AGAAAATTTT  TAATTATTGT  AATTTCGATT  TCGATAATTT   7080
TACTTATTCT  TTTGGTATTA  ATTGGATCAA  TTATTAACAA  TATTATTCGT  AGACACTTTT   7140
CTTCTTCTAG  GCGTATTTAT  CGTCCTAAAG  GTAACTCGGA  ATCTGAAAAT  ATAGAACTGA   7200
CATGTGGGGA  AAACTCAGTA  AACAAAAATA  ATCCATTACC  AAAAAAACCT  AACCGCCAAA   7260
AAAGATCTTC  AACTATTCAA  AGGGAGACAT  CTCTTGAAAC  TATTAAGGAA  GAAGTATAAT   7320
TTTAAAAATA  TTTACCTACG  TAGGTTGATG  ACGACTTGTA  TGACTAAAAA  TTAGAATTTA   7380
AATGATGAAA  ATTTTTAAA   AATAATATAG  TATTCCAAAG  AGCCTTTTAG  GAAAATCATC   7440
AAGTCTCCAT  TTCTCCAATC  TTTACGATGT  TTCGTTTATT  TTTTTAATC   GCGTCTACAT   7500
TATGTTCGGT  AAGATTTGGT  TTTTCAACAA  TTCGTAATGT  TATTGTTTCT  GAAAAATCTG   7560
GATTTGTAAT  TGATGGTTAT  AGTACTAACC  CACCATTTAA  TGAGACTAAA  AAATTTACTA   7620
GAGGATGGGT  ATTTTTACAA  ACCCCCCCTT  CTTATTGTAA  AGATGGGATA  TCAATATCTA   7680
ATATATGCAT  TGAACGTAAT  ATTTGTGAAG  AAGATATTTT  TTTGAATAAA  CGATGTACAA   7740
TTAAAACTAT  TAATTATCCC  TTAGCTGTAG  CAGATTTTGA  GATTAGTAAT  AATACTATTA   7800
AAAAAATAAA  TGATGTTTAT  TTTGTTAATG  ATAGTGTTTT  TCCAATAATA  ACTACAAATA   7860
AAGTGGTAT   CCATATCACA  AATGTGACTA  TAAATAATTC  TGGAATTTAT  ACATTGTATG   7920
AAAATAATGA  TAAGTGGAGT  CATCAATCAA  AAATCTTGGT  AACTATAAAG  AAAAAGAAA    7980
CAGTAATTAC  TAAACCTAAA  GTATATATAA  AAAAACATGG  TGGATTTTTT  CATGTAAAAA   8040
```

```
ATTATCACTC  TCATGTATTT  GTACCAAATG  ATTCATTTAA  AATTGAACTT  AATCTTGAAT   8100
CGGAAATTTA  TGATTCTGAA  TTTTCAGCAA  GTATTGATTG  GTATTATATG  AAAACTAGCT   8160
CGGAATGTTC  AGTGTTTCAT  ATATATGAAA  CTTGTATATT  TCACCCTCAT  GCAAACTCTT   8220
GTTTGAATCC  AATAAACCCA  TTGTGTAGTT  TTACTTCCCC  TTTGAGGGCA  ACATCACTAA   8280
TTAATAGATT  TTATTTTAGA  TGTAAACCTG  AAGGTAAAAA  CTGGACAACT  GATTGTATAA   8340
ACACCTTTTC  TATTAATGCA  GATAAACATA  TTAAACAGCA  TTCAAATAAT  GTAGATTTGA   8400
TTTTTTTAAA  TACTCCAACT  AATGCATCTG  GTTTGTATGT  TTTTATTCTT  AAGTATAATG   8460
GTCATCCAGA  GGCTTGGACA  TATACTTTGG  TTTCAACGGT  TAAAAATTTT  ATGAATGTAA   8520
TTAAGGATAT  GACACGCCCC  CTTTTGTCAA  ATAATAAAT   GAAAAACCT   GAGCATTCTA   8580
CTCAACCACC  AACCATAACC  AACATAACAC  CTGGCTTTAA  ATCTAAAAAT  TGGGTAGATA   8640
AATATATAAT  TTCAGTAGCG  GTGGTTTCTT  GTATTACTAT  TGTTATATTG  ATTGTGGTAA   8700
TAACCTTTTG  TGTTCATCAA  TGTATCGGTT  TAAATCGTAA  ACCATATGAA  ATTATAAACC   8760
CATTTAATAC  AGCTTATAAA  AGTATACCTA  CAAATGAAAA  AAATATTCTT  CATTTTGCTG   8820
AAGTAACAGA  ATCTGATTAT  TCCTCCGACG  AATCCTTCGA  CAGTGACTCA  GAAGAGCTAA   8880
ATCAACGAGG  TGAAACAATA  CAACAAGGGA  AAAAGGAACA  ATCTGGATAT  ACTATTTGGT   8940
TTAATGAAGA  TTTAGAAGAA  TCCGTCTCCA  AAAAACTTAA  CCAACCAAAC  TATTCAAAAA   9000
TAATTAATAG  CTTAAAATCA  ATCCAGAATG  AATAAATCTA  AACTCTCATT  TAAAGAAAAA   9060
AACGCTATAT  ATGAATTTAA  AAATATTTTA  TCAAACACTT  CATTGTCAAC  TTTTCCTGTA   9120
TTATCGTTTA  ATGAGGAGCC  AAAATCCAGA  TTTTTTAAAA  TGTTAAAAAA  TATTTTACTG   9180
GAAAAAATAA  AAAAAACTTC  AATGGATTAT  TTAATTTATT  GTACTCTAAA  AATCTCACTT   9240
TCATTTATAC  TTTATAATAA  ATAAAATTAT  TAAAAAAACT  TTATTGTTTT  GTCATTATTA   9300
ACTTTAACAC  TAGATGGTAC  TATAAAGCTA  ACTTACAATA  TAAATAGTAA  GATTAGTTTA   9360
TATAAATTAC  ATTTAATGGC  TTACCAGAT   AACGTTTTTA  GTATTATTAA  TGAAAATTAT   9420
ATCGATGGAA  TTTTAACTAT  GAAAATGGGT  GAAGAAATAG  AAAGCTCATC  ACCATTAAAT   9480
GAAACAAATG  TTAATATAGA  TCAACATACA  ATAGATATTT  TTGATTACGA  TTCAGATAAT   9540
GGATGTTATT  ATAGTGAAAG  AGATAATGAA  ACCGCAACTC  TTTTTTTAAA  ACGTGTTGGT   9600
TATAGAGAAA  CCTCAAAAAA  GCGTAAACGG  ATTTGTGGAT  TTATTGTTTT  AGCAATTTTT   9660
ATGGTTATTA  TATTATGTTT  TTTATCAATA  ATTTTGGGAG  TTTTTATAGC  GCCTCATATT   9720
TATAAAGGCC  TATAGTAAGA  ACATCAACCT  CTAATAGTAA  ATTTTAAAA   CCAACGGAGG   9780
GGGAGGAGGA  GGACTTTTTA  TTTTATGAGG  ATAAACCTGG  GGCTAGCATC  GAATGGAAAT   9840
CGGCTGTTTC  GGGGTATAAC  TATCTAAACT  CTGGTATATT  TGGAAACTAT  CCTCTTAATC   9900
TATGGGTTTT  CGGTGCAGCG  GATTTATGTG  AGCCAGTCAT  TTCTAATATC  CCAGGACCAA   9960
AGCGACTAAT  TTATGCATAT  GTATCATGTG  AATGGCCGGA  ACCATCCTGG  AAACCTGAGT  10020
GTCTTGAGAT  TTCCAAAAAT  AATGTAAAAC  ATATCGATGA  TTCTGGGAGT  GTTTATTGCC  10080
CCTCGTTTAT  ATGGGTACCT  GTATTAGACA  CCTTTCTGTC  CTCCTTTAAA  GTACCCCTA   10140
TGTTAAGTGA  CATTTTTTAT  GGTACAACAT  TTAATACTCC  ATTCAACTTT  GAAAGCTCTC  10200
CAAGATGTCC  CTCTATATCC  TCATCTTCAT  CCTCCTCCTC  CTCATCCTCT  TCTTCATGCT  10260
CTGCATCTCA  TTATTCCTCA  GAGAATGATA  TTTGGAAATA  CGCTAATGCG  ATGGTGGATA  10320
ATGAACTAGA  AGAAACTAAT  TGTGAAATTA  AAAATAGTTT  TAAAGAGGAT  TCTGACAGTT  10380
CTACATGTTC  TATAAGCGAT  GTATGTGATT  CTCTTTATAT  AAATGAGACA  CGTTCTGCCC  10440
```

| | | | | | |
|---|---|---|---|---|---|
| CCCCGGTAAT | CGAATCATTT | ATGTGTGCAA | TAATATCCCA | TAATGGTTAT | GAAGAAATTC | 10500
| CTGAACCAGA | AGAGGATGAC | TTGCATGGGG | TGAAACCTAT | GAAAAGGCTA | TCCAAACCAA | 10560
| ATATTTTTAA | ACGATTATTT | TCAAGGCGCG | CC | | | 10592

( 2 ) INFORMATION FOR SEQ ID NO:52:

( i ) SEQUENCE CHARACTERISTICS:
        ( A ) LENGTH: 10592 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

| | | | | | |
|---|---|---|---|---|---|
| GGCGCGCCTT | GAAAATAATC | GTTAAAAAT | ATTTGGTTTG | GATAGCCTTT | TCATAGGTTT | 60
| CACCCCATGC | AAGTCATCCT | CTTCTGGTTC | AGGAATTTCT | TCATAACCAT | TATGGGATAT | 120
| TATTGCACAC | ATAAATGATT | CGATTACCGG | GGGGGCAGAA | CGTGTCTCAT | TTATATAAAG | 180
| AGAATCACAT | ACATCGCTTA | TAGAACATGT | AGAACTGTCA | GAATCCTCTT | TAAAACTATT | 240
| TTTAATTTCA | CAATTAGTTT | CTTCTAGTTC | ATTATCCACC | ATCGCATTAG | CGTATTTCCA | 300
| AATATCATTC | TCTGAGGAAT | AATGAGATGC | AGAGCATGAA | GAAGAGGATG | AGGAGGAGGA | 360
| GGATGAAGAT | GAGGATATAG | AGGGACATCT | TGGAGAGCTT | TCAAAGTTGA | ATGGAGTATT | 420
| AAATGTTGTA | CCATAAAAAA | TGTCACTTAA | CATAGGGGT | ACTTTAAAGG | AGGACAGAAA | 480
| GGTGTCTAAT | ACAGGTACCC | ATATAAACGA | GGGGCAATAA | ACACTCCCAG | AATCATCGAT | 540
| ATGTTTTACA | TTATTTTTGG | AAATCTCAAG | ACACTCAGGT | TTCCAGGATG | GTTCCGGCCA | 600
| TTCACATGAT | ACATATGCAT | AAATTAGTCG | CTTTGGTCCT | GGGATATTAG | AAATGACTGG | 660
| CTCACATAAA | TCCGCTGCAC | CGAAAACCCA | TAGATTAAGA | GGATAGTTTC | CAAATATACC | 720
| AGAGTTTAGA | TAGTTATACC | CCGAAACAGC | CGATTTCCAT | TCGATGCTAG | CCCCAGGTTT | 780
| ATCCTCATAA | AATAAAAAGT | CCTCCTCCTC | CCCCTCCGTT | GGTTTTAAAA | ATTTACTATT | 840
| AGAGGTTGAT | GTTCTTACTA | TAGGCCTTTA | TAAATATGAG | GCGCTATAAA | AACTCCCAAA | 900
| ATTATTGATA | AAAAACATAA | TATAATAACC | ATAAAAATTG | CTAAACAAT | AAATCCACAA | 960
| ATCCGTTTAC | GCTTTTTTGA | GGTTTCTCTA | TAACCAACAC | GTTTAAAAA | AAGAGTTGCG | 1020
| GTTTCATTAT | CTCTTTCACT | ATAATAACAT | CCATTATCTG | AATCGTAATC | AAAAATATCT | 1080
| ATTGTATGTT | GATCTATATT | AACATTGTT | TCATTAATG | GTGATGAGCT | TTCTATTTCT | 1140
| TCACCCATTT | TCATAGTTAA | AATTCCATCG | ATATAATTTT | CATTAATAAT | ACTAAAAACG | 1200
| TTATCTGGTA | AAGCCATTAA | ATGTAATTTA | TATAAACTAA | TCTTACTATT | TATATTGTAA | 1260
| GTTAGCTTTA | TAGTACCATC | TAGTGTTAAA | GTTAATAATG | ACAAAACAAT | AAAGTTTTT | 1320
| TAATAATTTT | ATTTATTATA | AAGTATAAAT | GAAAGTGAGA | TTTTAGAGT | ACAATAAATT | 1380
| AAATAATCCA | TTGAAGTTTT | TTTTATTTTT | TCCAGTAAAA | TATTTTAAA | CATTTTAAAA | 1440
| AATCTGGATT | TTGGCTCCTC | ATTAAACGAT | AATACAGGAA | AAGTTGACAA | TGAAGTGTTT | 1500
| GATAAAATAT | TTTTAAATTC | ATATATAGCG | TTTTTTCTT | TAAATGAGAG | TTTAGATTTA | 1560
| TTCATTCTGG | ATTGATTTTA | AGCTATTAAT | TATTTTTGAA | TAGTTGGTT | GGTTAAGTTT | 1620
| TTTGGAGACG | GATTCTTCTA | AATCTTCATT | AAACCAAATA | GTATATCCAG | ATTGTTCCTT | 1680
| TTTCCCTTGT | TGTATTGTTT | CACCTCGTTG | ATTTAGCTCT | TCTGAGTCAC | TGTCGAAGGA | 1740
| TTCGTCGGAG | GAATAATCAG | ATTCTGTTAC | TTCAGCAAAA | TGAAGAATAT | TTTTTTCATT | 1800

-continued

| | | | | | | |
|---|---|---|---|---|---|---|
| TGTAGGTATA | CTTTTATAAG | CTGTATTAAA | TGGGTTTATA | ATTTCATATG | GTTTACGATT | 1860 |
| TAAACCGATA | CATTGATGAA | CACAAAAGGT | TATTACCACA | ATCAATATAA | CAATAGTAAT | 1920 |
| ACAAGAAACC | ACCGCTACTG | AAATTATATA | TTTATCTACC | CAATTTTTAG | ATTTAAAGCC | 1980 |
| AGGTGTTATG | TTGGTTATGG | TTGGTGGTTG | AGTAGAATGC | TCAGGTTTTT | TCATTTTATT | 2040 |
| ATTTGACAAA | AGGGGCGTG | TCATATCCTT | AATTACATTC | ATAAAATTTT | TAACCGTTGA | 2100 |
| AACCAAAGTA | TATGTCCAAG | CCTCTGGATG | ACCATTATAC | TTAAGAATAA | AAACATACAA | 2160 |
| ACCAGATGCA | TTAGTTGGAG | TATTTAAAAA | AATCAAATCT | ACATTATTTG | AATGCTGTTT | 2220 |
| AATATGTTTA | TCTGCATTAA | TAGAAAAGGT | GTTTATACAA | TCAGTTGTCC | AGTTTTTACC | 2280 |
| TTCAGGTTTA | CATCTAAAAT | AAAATCTATT | AATTAGTGAT | GTTGCCCTCA | AGGGGAAGT | 2340 |
| AAAACTACAC | AATGGGTTTA | TTGGATTCAA | ACAAGAGTTT | GCATGAGGGT | GAAATATACA | 2400 |
| AGTTTCATAT | ATATGAAACA | CTGAACATTC | CGAGCTAGTT | TTCATATAAT | ACCAATCAAT | 2460 |
| ACTTGCTGAA | AATTCAGAAT | CATAAATTTC | CGATTCAAGA | TTAAGTTCAA | TTTTAAATGA | 2520 |
| ATCATTTGGT | ACAAATACAT | GAGAGTGATA | ATTTTTTACA | TGAAAAAATC | CACCATGTTT | 2580 |
| TTTTATATAT | ACTTTAGGTT | TAGTAATTAC | TGTTTCTTTT | TTCTTTATAG | TTACCAAGAT | 2640 |
| TTTTGATTGA | TGACTCCACT | TATCATTATT | TTCATACAAT | GTATAAATTC | CAGAATTATT | 2700 |
| TATAGTCACA | TTTGTGATAT | GGATACCACT | TTTATTTGTA | GTTATTATTG | GAAAAACACT | 2760 |
| ATCATTAACA | AAATAAACAT | CATTTATTTT | TTAATAGTA | TTATTACTAA | TCTCAAAATC | 2820 |
| TGCTACAGCT | AAGGGATAAT | TAATAGTTTT | AATTGTACAT | CGTTATTCA | AAAAAATATC | 2880 |
| TTCTTCACAA | ATATTACGTT | CAATGCATAT | ATTAGATATT | GATATCCCAT | CTTTACAATA | 2940 |
| AGAAGGGGGG | GTTTGTAAAA | ATACCCATCC | TCTAGTAAAT | TTTTAGTCT | CATTAAATGG | 3000 |
| TGGGTTAGTA | CTATAACCAT | CAATTACAAA | TCCAGATTTT | TCAGAAACAA | TAACATTACG | 3060 |
| AATTGTTGAA | AAACCAAATC | TTACCGAACA | TAATGTAGAC | GCGATTAAAA | AAAATAAACG | 3120 |
| AAACATCGTA | AAGATTGGAG | AAATGGAGAC | TTGATGATTT | TCCTAAAAGG | CTCTTTGGAA | 3180 |
| TACTATATTA | TTTTTAAAAA | ATTTTCATCA | TTTAAATTCT | AATTTTAGT | CATACAAGTC | 3240 |
| GTCATCAACC | TACGTAGGTA | AATATTTTTA | AAATTATACT | TCTTCCTTAA | TAGTTTCAAG | 3300 |
| AGATGTCTCC | CTTTGAATAG | TTGAAGATCT | TTTTTGGCGG | TTAGGTTTTT | TTGGTAATGG | 3360 |
| ATTATTTTTG | TTTACTGAGT | TTTCCCCACA | TGTCAGTTCT | ATATTTTCAG | ATTCCGAGTT | 3420 |
| ACCTTTAGGA | CGATAAATAC | GCCTAGAAGA | AGAAAAGTGT | CTACGAATAA | TATTGTTAAT | 3480 |
| AATTGATCCA | ATTAATACCA | AAAGAATAAG | TAAAATTATC | GAAATCGAAA | TTACAATAAT | 3540 |
| TAAAAATTTT | CTATTACGTT | GGTCTAGGTA | AGGCTTAAAT | ATATAATTAT | TTGTCGTTGT | 3600 |
| AGGTATATTT | ACTCTTTTAA | GCAATTCAGA | ATCCTCATCG | AGAAAAATAT | CATCAGTTAT | 3660 |
| ATTTCCATGC | AAACCTAGTA | AAAGTTCATA | CACATTTTCA | TCCTTTTTTA | CAGTATGACA | 3720 |
| TATCGGTTCG | TGTTTTTCAT | TTAAATAGAT | AGGTGTAATA | GTTGGGAAG | AAGGGTGTGA | 3780 |
| TGAGGTATAT | AAAGATGTAG | TAACATCATC | GAAGTTTGAT | TTATTTACTT | CGTTTGACAT | 3840 |
| ATTAAAGGAA | TAAATAAATG | CAGGTATTCC | AAACACATCT | GTTTTATTAT | TTTCCAATTG | 3900 |
| AACTCGTATA | AAATAAACAC | CTGAATCATT | TGGTTTAGGA | TTTGTAATTT | CCAACAAAAC | 3960 |
| ACCGTTTTCT | ATAGATGAAT | TTATCCGAAG | TTGACTTTCA | TGATGTTTTG | ATACCTTTTT | 4020 |
| TAAACAAGAT | CTAAAAGCAT | TATTAAAAAT | GCGAGGACAA | GAAAAATATT | CAATAGTTTG | 4080 |
| ATAAACGGTA | TAACAAGAGT | TATTAAAATG | AATAAACTCA | ATAGTTCCGC | TATAATTATT | 4140 |
| TACTGACAGA | TGTTGGTCAT | CGAGAAATAA | TAAACGTCCA | CTGACAATAA | ATTTATCATC | 4200 |

-continued

| | | | | | | |
|---|---|---|---|---|---|---|
| GGGAAAAATA | GAAAAGCCAG | AACTAGTATT | TAAAAACATA | CTTATATACG | TACCTTTGTA | 4260 |
| AACAAATCCA | TTTACACCAT | ATAAAAAAG | AAATAAAATA | GGTAGAAACA | TAGTTATAAG | 4320 |
| TAATCTGGTC | TCAACCCTCT | TGCAAGTGAA | TAAAAGTTGT | AGGTACATGA | ATTTTTATTA | 4380 |
| AACAAAAGAC | CGCCCAGTTG | TTTATTCTGT | AAATTAATTT | ATAAAGGCTA | AACATTTGTT | 4440 |
| GTTAATTTTT | TATAATTATT | ATATATTTTT | TGTCTTTTAT | AAACAAAAAA | TCCAATTATA | 4500 |
| AATAGTATTA | TTAATATAAT | TATAACAATT | CCCACGGTTA | TATTTTTTGG | GGTATTATTT | 4560 |
| ATTGGTGTTG | GGGTAGTAGT | ATCTATAACA | TTTGTATTTT | TAAAATAATC | TTCAAGATTT | 4620 |
| ACAATTTCTT | TAATAGTTTT | ATTAATAGTA | TTACTAATAT | GTGGCCTCGA | TGGTAATTCA | 4680 |
| TCATCAAATT | TATCATTCAC | TTTATATGGT | ATATCGTATC | TAAGAGCTTC | TTTAAATTTT | 4740 |
| ATTGGAGGTT | CTCTACCGTT | AAGTCTATAA | AAATCTTTAA | TAACATAATA | TTTAAGCAGG | 4800 |
| GTTTGGGGAC | CAGCTCTATT | TAGATAAAAA | AGTTCATCGT | CAACTTTTGA | TGCTCCTACA | 4860 |
| GATCTAGATT | CCTTACACCA | TTCCATAAAA | GTTGGTTCAA | ATTTATCTTC | TTTAGAAAAA | 4920 |
| TAACAAGTTT | CTCGTGGTAA | TTGAACCATA | AAATCAGTAT | AAAAACTTC | ATTTTCAATT | 4980 |
| TGAATAACCC | GTCTATATTG | ACCTTGATTA | AATGGAGCGG | GGGCAGCTAA | AACTAATCCC | 5040 |
| AATTCATCAT | CAGTTAAAAA | TGTGTAACCA | ACTAACGATG | GTTTCCAAAA | ATCTGGAGAT | 5100 |
| CTTTTTAAAC | ATATGCCAAA | TTCTCTTTGA | GGATCACAAT | CAAAATATTG | AATTAAATAT | 5160 |
| ATTGGATATG | TACAATCATC | TCCAACTTTA | AACCAACTAA | GAGATGCATT | GTAAAATTTT | 5220 |
| TTCTTTTGCA | CAAATTGAAT | CGTTTTAATT | GTAGATTCTA | TATTTGGATT | AGAAATCAAA | 5280 |
| GCAACCATAT | CACATGGGTC | AGTAGAAGTT | ACATACCGAA | CTTCAGCGTT | TTTAGAAGGA | 5340 |
| TCCATTGGAT | TTGGAATATC | TGGAATCATT | CTTAAAACGG | TGTAATTATA | CCTACGAGGA | 5400 |
| GGGTCTACCC | ATTTATATCC | AGTTATTGGG | TTAAAATAAA | ATAAGATAAA | TAGAAGTTTA | 5460 |
| ATCATTTTAC | TATCAAAAGT | CGTAGCAACT | CTTAAAATGA | GAAAATGTTT | AATCCGTTCA | 5520 |
| AATTAATAGA | ATTTAAATGT | TTTTCATGGG | TGTGTCCTTT | ATGATGTTAA | TTCTTAATAC | 5580 |
| ACGTATGTAA | TTTTAAAACC | AACCCAACCC | ATTTAATAAA | AACAAATAAG | TTATAAGAAG | 5640 |
| TTTCATAATA | GTTTTATTAA | ATATCATAAA | AATTTAATTT | CTGGGGTTGT | ATATAAGCAT | 5700 |
| GGTTAATCAT | TTTAATACGA | GAGTTTAATA | CACAAGTATA | TCCACAAAAA | AACACAGCAA | 5760 |
| CAAAAAATAA | AATAATAAAG | ATAATTGTTC | CAAATCCAAT | TACCTTTATA | TGGGTATTAC | 5820 |
| AATTATTATA | ACCATTGTTA | AACAATTGAA | TAATGCTTAA | AACACTTTCT | TCTTCATACA | 5880 |
| TAGTTTCATT | ATTTGACATA | AACATATGTG | TATTTCAGT | AGGTGGTGGT | GTGGTAAACG | 5940 |
| TTACAATTTC | AGGATTCAGT | ATATTAGAAT | CTTCTTCCGA | TTGAAGGGTG | ATAGACAAAT | 6000 |
| TATTAAAAAG | TTCATAACTT | TCATTAATTT | TAAATGACCA | CGGTTGTTCT | GAAATTGATT | 6060 |
| TACCCAAACT | AGCAATCAAT | AAACTTTGAG | AACCTGCAGC | CAAATTAAAA | GTCTTCTTCA | 6120 |
| TATCAAAAAG | ATTGGATTTG | CGGCAATCTT | TTGATTGTAG | ATCTTCAAAA | TCTTCGTTTT | 6180 |
| CTTCTTCATA | TTCTTCATAT | TCTTCATCAT | ATGAATATCT | ACCAACACTT | TCATCACTAA | 6240 |
| TATTATTCCA | TAGCTCAGTA | TTTGATATTG | GAAAACAACC | TCTATATCGT | TTATGATTAG | 6300 |
| GATTGTGGA | TGGTTTATAA | GGAATATGAA | GTTATCACC | CTTTTTTACA | GTCAATCCAT | 6360 |
| GCATCATAAA | ACATGGATAG | TCTGTCTCAT | TATCCACTCG | AACTTCAATT | CTTCCGTTAT | 6420 |
| AACTATCGTT | TCCAAAAACA | AGTGAGTATA | AATATCTACC | AGAATCAAAA | ATTCCTGGTT | 6480 |
| GAATAAGCAA | ACTAACATTA | ACAAGTGCAT | AAGATGATAT | ACTTTCAGAT | TTTACCAAAG | 6540 |
| TTAAAGAATA | ACCATCACAA | GTTTCTGGTG | ATGGTATTAT | ATTACCAGTA | CAATTATAAT | 6600 |

| | | | | | | |
|---|---|---|---|---|---|---|
| ATTCTCTATA | AATTAAAGGA | ATTTGACAAC | CAAGATCAAA | TGACCATCCA | ATTGTAGCAT | 6660 |
| TAACCTTTTT | TTCTGGTCGT | GAAGATACAT | TTACATATGT | ATCTAGTAAT | CGTAGTTCAC | 6720 |
| ATCCTTTAGA | GTATTCAACA | TATCCGTTTG | TTACCACGGG | AATAAGAGTC | TTAGATTGTT | 6780 |
| CCCCTGTAGG | AAGTTGTGTA | GGTTCAGTTG | TATTTTCTTT | AGGATCCGCA | TAACACAACT | 6840 |
| CTAGCGGAGC | TATGCGAGAT | AAAACTACCT | TAAAATAAAA | AACAAAAAAC | AGCGTATACA | 6900 |
| ACATGATAAC | TATAATATTG | TAGCTAGGAT | GTAAAAATAA | AATTAATAAA | AAAGAGCTTT | 6960 |
| CAAACACCCG | TTTTATATAA | AACAATAAAA | AATTCCACGC | CCATTTTTAT | GAAATTTATT | 7020 |
| GTTACTAAA | AATCTGATAG | GATAATAGTT | CTTCCGCACT | TGGTCGTAGA | GATGCATCAA | 7080 |
| ATGTTAGCAT | TTTATGAATT | AAAAATTCAC | CATCGAGATG | TAATTTAAGG | TTATTTAGAC | 7140 |
| GATTATATCG | TGTAAATGGA | GGTCTATCAT | TATTAGCATA | TTTTATAAAA | TGTTTTACTA | 7200 |
| GATTAGATTC | CAAATCAGAT | GGAAATTCAT | TTGGGTTAAT | CTTCAGAGTT | GATATAATTT | 7260 |
| TTATAAGATG | AAGATTACAA | TTGTTTATTA | AATCGCTACT | ATCTCTTTCT | TCCTCCTCAA | 7320 |
| ACAAACATT | AGGATATGCA | AGCATTTCAA | ATAAAATTAT | ACCAGCACTC | CAAATATCAG | 7380 |
| CTTTACAGTT | GTACGCATCC | TTTGATAGAA | CTTCAGGAGC | ATTAGTTTCA | ATAGTCCCCG | 7440 |
| CAATTCCCAA | ATAATCTGGT | GAGGAAACAG | GAAATTGAGA | AGCCCCAAAA | TCACCTATAC | 7500 |
| AAACATTAGA | GTCATTATCC | AAGAAAATAT | TTTCAGTTTT | TATATCTCGA | TGAATAATTT | 7560 |
| TTTTTCCATG | AATATATTGA | AGTCCAGTTA | ATATTTGTTT | TTCAATTTTA | ATTACAGATT | 7620 |
| CAAAGACAG | AGATTTCCCA | TGATCCATTA | AAAAATTATA | TAGATCATAT | TTATAATACG | 7680 |
| GTAACACCAA | ACATGTTAAC | TCTTTATAAA | AAAGAGTGTC | TTGAAGTTTA | ATTATAGATT | 7740 |
| GGTGACTAAT | ATTTCTCAAA | ATTAACGATT | CCACAAGCGT | GTTTCCCTT | TGTCCAATTT | 7800 |
| TTAAAATTAC | CTTATAGCTT | GTATCTTTAT | CTTTTTAAG | AGCAATAAAA | ACTCTTCCTT | 7860 |
| CTGACCCAGG | CGTTAACGAT | TTAACAACAG | AAAACTTTAG | CGCTTCAGCC | GCTTCAATTC | 7920 |
| CTTCGCTTTT | AGTAGGAGAT | AAACTTTTTT | TATCTTCATC | ACTTTCATAA | CTTTCTTCAA | 7980 |
| CTTCTTCGTC | ACTTTCTCTT | TCATTTTCAC | TTTCAGTTGG | ATTTTTTGTA | TAATCCATAA | 8040 |
| AGTCATCATC | ACTAAAATCC | GAGTATAAAT | CCTCATCCAT | TATTTTGTCT | TGATGTAGGT | 8100 |
| TATCCTCTTC | AATCAAATCT | GAAGTTAGAG | GAACCGGTTT | ATAGAAGTCT | TCTGGATCGA | 8160 |
| CAGAAGATTC | TCTATTCACG | CTGATACAAC | AAAACTTTTC | GGTGGTACAC | TTTGCCATAT | 8220 |
| CAGGTAATTG | TGAAATTGTT | ATGTTAATAT | CAACTCATCA | ACTGCAGCTT | CTTCTAAAAT | 8280 |
| TATAACATAA | ATTAGGTGTG | TATTAACCTT | TATTGGATTC | ATACATAAAA | TTTAATTATG | 8340 |
| GGTGTGGTTG | AAGTTAATAT | TGTTACGTTT | ATTGACAAAA | ATGGGGCGTT | ACCAGGAAAC | 8400 |
| TCCCAAGATG | TTCATCCTGA | TCTTTGGTGT | TTTATGGCTA | GACAATGCTA | TATCCTTTCT | 8460 |
| CTCACACGAT | TGGCTATGCC | TATAATATTA | CGATCTGCAA | ACTTATGTTA | TTTTATGGAC | 8520 |
| TCTATAAAAC | ATCTACCTAG | AGTTTCAAGG | CCTATAGTAA | GAACATCAAC | CTCTAATAGT | 8580 |
| AAATTTTTAA | AACCAACGGA | GGGGGAGGAG | GAGGACTTTT | TATTTTATGA | GGATAAACCT | 8640 |
| GGGGCTAGCA | TCGAATGGAA | ATCGGCTGTT | TCGGGTATA | ACTATCTAAA | CTCTGGTATA | 8700 |
| TTTGGAAACT | ATCCTCTTAA | TCTATGGGTT | TTCGGTGCAG | CGGATTTATG | TGAGCCAGTC | 8760 |
| ATTTCTAATA | TCCCAGGACC | AAAGCGACTA | ATTTATGCAT | ATGTATCATG | TGAATGGCCG | 8820 |
| GAACCATCCT | GGAAACCTGA | GTGTCTTGAG | ATTTCCAAAA | ATAATGTAAA | ACATATCGAT | 8880 |
| GATTCTGGGA | GTGTTTATTG | CCCCTCGTTT | ATATGGGTAC | CTGTATTAGA | CACCTTTCTG | 8940 |
| TCCTCCTTTA | AAGTACCCCC | TATGTTAAGT | GACATTTTTT | ATGGTACAAC | ATTTAATACT | 9000 |

| | | | | | |
|---|---|---|---|---|---|
| CCATTCAACT | TTGAAAGCTC | TCCAAGATGT | CCCTCTATAT | CCTCATCTTC | ATCCTCCTCC | 9060 |
| TCCTCATCCT | CTTCTTCATG | CTCTGCATCT | CATTATTCCT | CAGAGAATGA | TATTTGGAAA | 9120 |
| TACGCTAATG | CGATGGTGGA | TAATGAACTA | GAAGAAACTA | ATTGTGAAAT | TAAAAATAGT | 9180 |
| TTTAAAGAGG | ATTCTGACAG | TTCTACATGT | TCTATAAGCG | ATGTATGTGA | TTCTCTTTAT | 9240 |
| ATAAATGAGA | CACGTTCTGC | CCCCCCGGTA | ATCGAATCAT | TTATGTGTGC | AATAATATCC | 9300 |
| CATAATGGTT | ATGAAGAAAT | TCCTGAACCA | GAAGAGGATG | ACTTGCATGG | GGTGAAACCT | 9360 |
| ATGAAAGGC | TATCCAAACC | AAATATTTTT | AAACGATTAT | TTTCAAGGCG | CGCCAAAACA | 9420 |
| ATAACCAAAA | ATGAAAACGA | TGGTATGTCT | TCTACACAAC | CTACCAACGC | TCAACGTTCA | 9480 |
| TCTCTATTTA | GTTCATGTTT | ATGTGGAAAC | TAAGTTTGTT | TATATTTGTT | GTGAATAAAC | 9540 |
| AGTAGATGTA | AACCTGAAAT | TCTGGTTTTT | TATGTGAACC | ACTCCCATAT | TCTTACTGTA | 9600 |
| TATAAACTGG | CATTTTATCC | TACATTTTA | AATCTTCACT | TGTTTTAAA | GCTTAACTAA | 9660 |
| AAAGTTTTAA | AATGAGTGCT | TCATTTGCTC | TATTTGATAA | CAACTCCGAT | CAAGCTAATA | 9720 |
| TGCCATCATA | CTTCAGACGC | TGTCGTGGAG | AACTTAATGA | AGGATTCTAC | GCACAAGTTC | 9780 |
| CGCCTGGTTA | TTTTCCAGTT | CGCCCTAAAA | CCACACCAGC | GCTTGCACGT | GTGAAAAACC | 9840 |
| AGGGTGAACC | GCACGCCTTC | ACTATTGTTC | CTACACCACC | TACGGATGTA | CGATTCTTCA | 9900 |
| AAAAGCTTCG | TGATGGAACC | TTTGTGAAAC | TTCCATTTTC | ATATCCTGAT | GAGAGGTATG | 9960 |
| AAGATGATAT | TGAACCTATG | TATTGCAGAC | TATACGTTCT | AAAGGATTTT | GAAACGCCAA | 10020 |
| GTTCTCCCTA | CAATCAAGTA | AACGCTTCTC | AGCTTATGGA | AGTACCTTCT | TCGCTTGTGG | 10080 |
| AATCGAAGTG | TTATTGGGAT | GGTCCAAAAT | TTATAAATGT | ACCACCAATA | AGATATATTC | 10140 |
| TAAAAGTGA | TTACTCTCTA | AATAATGTAT | CCGAAGATGC | ATTTGTGTTG | GTAGATACCA | 10200 |
| GAAAACTAAA | ACTTGAAAAC | TAAAATGTTT | ACCCAACGCA | TTAAACCTTG | TAACCTATAC | 10260 |
| TCTTAATAAA | ATTTAAAATA | TTTTTAAAAA | TTACTTTGTC | TCATAGATTT | CATTCATAGA | 10320 |
| TTTCATTCAT | AGATTTCATT | CATAGATTTC | ATTCATAGAT | TTCATTCATA | GATTTCATTC | 10380 |
| ATAGATTTCA | TTCATAGATT | TCATTCATAG | ATTTCATTCA | TAGATTTCAT | TCATAGATTT | 10440 |
| CATTCATAGA | TTTCATTCAT | AGATTTCATT | CATAGATTTC | ATTCATAGAT | TTCATTCATA | 10500 |
| GATTTCATTC | ATAGATTTCA | TTCATAGATT | TCATTCATAG | ATTTCATTCA | TAGATTTCAT | 10560 |
| TCATAGATTT | TTATTTTTTA | AATACACTGC | AG | | | 10592 |

( 2 ) INFORMATION FOR SEQ ID NO:53:

( i ) SEQUENCE CHARACTERISTICS:
        ( A ) LENGTH: 1038 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1035

( x i ) SEQUENCE DESCRIPTION: SEQ ID NO:53:

```
ATG  ATT  AAA  CTT  CTA  TTT  ATC  TTA  TTT  TAT  TTT  AAC  CCA  ATA  ACT  GGA       48
Met  Ile  Lys  Leu  Leu  Phe  Ile  Leu  Phe  Tyr  Phe  Asn  Pro  Ile  Thr  Gly
 1                    5                        10                       15

TAT  AAA  TGG  GTA  GAC  CCT  CCT  CGT  AGG  TAT  AAT  TAC  ACC  GTT  TTA  AGA       96
Tyr  Lys  Trp  Val  Asp  Pro  Pro  Arg  Arg  Tyr  Asn  Tyr  Thr  Val  Leu  Arg
                    20                       25                       30

ATG  ATT  CCA  GAT  ATT  CCA  AAT  CCA  ATG  GAT  CCT  TCT  AAA  AAC  GCT  GAA      144
```

```
Met Ile Pro Asp Ile Pro Asn Pro Met Asp Pro Ser Lys Asn Ala Glu
        35              40                  45

GTT CGG TAT GTA ACT TCT ACT GAC CCA TGT GAT ATG GTT GCT TTG ATT    192
Val Arg Tyr Val Thr Ser Thr Asp Pro Cys Asp Met Val Ala Leu Ile
    50              55                  60

TCT AAT CCA AAT ATA GAA TCT ACA ATT AAA ACG ATT CAA TTT GTG CAA    240
Ser Asn Pro Asn Ile Glu Ser Thr Ile Lys Thr Ile Gln Phe Val Gln
65              70                  75                       80

AAG AAA AAA TTT TAC AAT GCA TCT CTT AGT TGG TTT AAA GTT GGA GAT    288
Lys Lys Lys Phe Tyr Asn Ala Ser Leu Ser Trp Phe Lys Val Gly Asp
                85                  90                       95

GAT TGT ACA TAT CCA ATA TAT TTA ATT CAA TAT TTT GAT TGT GAT CCT    336
Asp Cys Thr Tyr Pro Ile Tyr Leu Ile Gln Tyr Phe Asp Cys Asp Pro
            100                 105                 110

CAA AGA GAA TTT GGC ATA TGT TTA AAA AGA TCT CCA GAT TTT TGG AAA    384
Gln Arg Glu Phe Gly Ile Cys Leu Lys Arg Ser Pro Asp Phe Trp Lys
        115                 120                 125

CCA TCG TTA GTT GGT TAC ACA TTT TTA ACT GAT GAT GAA TTG GGA TTA    432
Pro Ser Leu Val Gly Tyr Thr Phe Leu Thr Asp Asp Glu Leu Gly Leu
    130                 135                 140

GTT TTA GCT GCC CCC GCT CCA TTT AAT CAA GGT CAA TAT AGA CGG GTT    480
Val Leu Ala Ala Pro Ala Pro Phe Asn Gln Gly Gln Tyr Arg Arg Val
145                 150                 155                 160

ATT CAA ATT GAA AAT GAA GTT TTT TAT ACT GAT TTT ATG GTT CAA TTA    528
Ile Gln Ile Glu Asn Glu Val Phe Tyr Thr Asp Phe Met Val Gln Leu
                165                 170                 175

CCA CGA GAA ACT TGT TAT TTT TCT AAA GAA GAT AAA TTT GAA CCA ACT    576
Pro Arg Glu Thr Cys Tyr Phe Ser Lys Glu Asp Lys Phe Glu Pro Thr
            180                 185                 190

TTT ATG GAA TGG TGT AAG GAA TCT AGA TCT GTA GGA GCA TCA AAA GTT    624
Phe Met Glu Trp Cys Lys Glu Ser Arg Ser Val Gly Ala Ser Lys Val
        195                 200                 205

GAC GAT GAA CTT TTT TAT CTA AAT AGA GCT GGT CCC CAA ACC CTG CTT    672
Asp Asp Glu Leu Phe Tyr Leu Asn Arg Ala Gly Pro Gln Thr Leu Leu
    210                 215                 220

AAA TAT TAT GTT ATT AAA GAT TTT TAT AGA CTT AAC GGT AGA GAA CCT    720
Lys Tyr Tyr Val Ile Lys Asp Phe Tyr Arg Leu Asn Gly Arg Glu Pro
225                 230                 235                 240

CCA ATA AAA TTT AAA GAA GCT CTT AGA TAC GAT ATA CCA TAT AAA GTG    768
Pro Ile Lys Phe Lys Glu Ala Leu Arg Tyr Asp Ile Pro Tyr Lys Val
                245                 250                 255

AAT GAT AAA TTT GAT GAT GAA TTA CCA TCG AGG CCA CAT ATT AGT AAT    816
Asn Asp Lys Phe Asp Asp Glu Leu Pro Ser Arg Pro His Ile Ser Asn
            260                 265                 270

ACT ATT AAT AAA ACT ATT AAA GAA ATT GTA AAT CTT GAA GAT TAT TTT    864
Thr Ile Asn Lys Thr Ile Lys Glu Ile Val Asn Leu Glu Asp Tyr Phe
        275                 280                 285

AAA AAT ACA AAT GTT ATA GAT ACT ACT ACC CCA ACA CCA ATA AAT AAT    912
Lys Asn Thr Asn Val Ile Asp Thr Thr Thr Pro Thr Pro Ile Asn Asn
    290                 295                 300

ACC CCA AAA AAT ATA ACC GTG GGA ATT GTA ATT ATA TTA ATA ATA        960
Thr Pro Lys Asn Ile Thr Val Gly Ile Val Ile Ile Leu Ile Ile
305                 310                 315                 320

CTA TTT ATA ATT GGA TTT TTT GTT TAT AAA AGA CAA AAA ATA TAT AAT    1008
Leu Phe Ile Ile Gly Phe Phe Val Tyr Lys Arg Gln Lys Ile Tyr Asn
                325                 330                 335

AAT TAT AAA AAA TTA ACA ACA AAT GTT TAG                            1038
Asn Tyr Lys Lys Leu Thr Thr Asn Val
        340                 345
```

( 2 ) INFORMATION FOR SEQ ID NO:54:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:54:

```
Met Ile Lys Leu Leu Phe Ile Leu Phe Tyr Phe Asn Pro Ile Thr Gly
 1               5                  10                  15
Tyr Lys Trp Val Asp Pro Pro Arg Arg Tyr Asn Tyr Thr Val Leu Arg
                20                  25                  30
Met Ile Pro Asp Ile Pro Asn Pro Met Asp Pro Ser Lys Asn Ala Glu
                35                  40                  45
Val Arg Tyr Val Thr Ser Thr Asp Pro Cys Asp Met Val Ala Leu Ile
        50                  55                  60
Ser Asn Pro Asn Ile Glu Ser Thr Ile Lys Thr Ile Gln Phe Val Gln
65                  70                  75                      80
Lys Lys Lys Phe Tyr Asn Ala Ser Leu Ser Trp Phe Lys Val Gly Asp
                85                  90                  95
Asp Cys Thr Tyr Pro Ile Tyr Leu Ile Gln Tyr Phe Asp Cys Asp Pro
                100                 105                 110
Gln Arg Glu Phe Gly Ile Cys Leu Lys Arg Ser Pro Asp Phe Trp Lys
                115                 120                 125
Pro Ser Leu Val Gly Tyr Thr Phe Leu Thr Asp Asp Glu Leu Gly Leu
        130                 135                 140
Val Leu Ala Ala Pro Ala Pro Phe Asn Gln Gly Gln Tyr Arg Arg Val
145                 150                 155                 160
Ile Gln Ile Glu Asn Glu Val Phe Tyr Thr Asp Phe Met Val Gln Leu
                165                 170                 175
Pro Arg Glu Thr Cys Tyr Phe Ser Lys Glu Asp Lys Phe Glu Pro Thr
                180                 185                 190
Phe Met Glu Trp Cys Lys Glu Ser Arg Ser Val Gly Ala Ser Lys Val
            195                 200                 205
Asp Asp Glu Leu Phe Tyr Leu Asn Arg Ala Gly Pro Gln Thr Leu Leu
        210                 215                 220
Lys Tyr Tyr Val Ile Lys Asp Phe Tyr Arg Leu Asn Gly Arg Glu Pro
225                 230                 235                 240
Pro Ile Lys Phe Lys Glu Ala Leu Arg Tyr Asp Ile Pro Tyr Lys Val
                245                 250                 255
Asn Asp Lys Phe Asp Asp Glu Leu Pro Ser Arg Pro His Ile Ser Asn
                260                 265                 270
Thr Ile Asn Lys Thr Ile Lys Glu Ile Val Asn Leu Glu Asp Tyr Phe
            275                 280                 285
Lys Asn Thr Asn Val Ile Asp Thr Thr Thr Pro Thr Pro Ile Asn Asn
        290                 295                 300
Thr Pro Lys Asn Ile Thr Val Gly Ile Val Ile Ile Ile Leu Ile Ile
305                 310                 315                 320
Leu Phe Ile Ile Gly Phe Phe Val Tyr Lys Arg Gln Lys Ile Tyr Asn
                325                 330                 335
Asn Tyr Lys Lys Leu Thr Thr Asn Val
                340                 345
```

( 2 ) INFORMATION FOR SEQ ID NO:55:

( i ) SEQUENCE CHARACTERISTICS:
  ( A ) LENGTH: 1095 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 1..1092

( x i ) SEQUENCE DESCRIPTION: SEQ ID NO:55:

```
ATG TAC CTA CAA CTT TTA TTC ACT TGC AAG AGG GTT GAG ACC AGA TTA    48
Met Tyr Leu Gln Leu Leu Phe Thr Cys Lys Arg Val Glu Thr Arg Leu
 1               5                  10                  15

CTT ATA ACT ATG TTT CTA CCT ATT TTA TTT CTT TTT TTA TAT GGT GTA    96
Leu Ile Thr Met Phe Leu Pro Ile Leu Phe Leu Phe Leu Tyr Gly Val
             20                  25                  30

AAT GGA TTT GTT TAC AAA GGT ACG TAT ATA AGT ATG TTT TTA AAT ACT   144
Asn Gly Phe Val Tyr Lys Gly Thr Tyr Ile Ser Met Phe Leu Asn Thr
         35                  40                  45

AGT TCT GGC TTT TCT ATT TTT CCC GAT GAT AAA TTT ATT GTC AGT GGA   192
Ser Ser Gly Phe Ser Ile Phe Pro Asp Asp Lys Phe Ile Val Ser Gly
     50                  55                  60

CGT TTA TTA TTT CTC GAT GAC CAA CAT CTG TCA GTA AAT AAT TAT AGC   240
Arg Leu Leu Phe Leu Asp Asp Gln His Leu Ser Val Asn Asn Tyr Ser
 65                  70                  75                  80

GGA ACT ATT GAG TTT ATT CAT TTT AAT AAC TCT TGT TAT ACC GTT TAT   288
Gly Thr Ile Glu Phe Ile His Phe Asn Asn Ser Cys Tyr Thr Val Tyr
                 85                  90                  95

CAA ACT ATT GAA TAT TTT TCT TGT CCT CGC ATT TTT AAT AAT GCT TTT   336
Gln Thr Ile Glu Tyr Phe Ser Cys Pro Arg Ile Phe Asn Asn Ala Phe
             100                 105                 110

AGA TCT TGT TTA AAA AAG GTA TCA AAA CAT CAT GAA AGT CAA CTT CGG   384
Arg Ser Cys Leu Lys Lys Val Ser Lys His His Glu Ser Gln Leu Arg
         115                 120                 125

ATA AAT TCA TCT ATA GAA AAC GGT GTT TTG TTG GAA ATT ACA AAT CCT   432
Ile Asn Ser Ser Ile Glu Asn Gly Val Leu Leu Glu Ile Thr Asn Pro
     130                 135                 140

AAA CCA AAT GAT TCA GGT GTT TAT TTT ATA CGA GTT CAA TTG GAA AAT   480
Lys Pro Asn Asp Ser Gly Val Tyr Phe Ile Arg Val Gln Leu Glu Asn
145                 150                 155                 160

AAT AAA ACA GAT GTG TTT GGA ATA CCT GCA TTT ATT TAT TCC TTT AAT   528
Asn Lys Thr Asp Val Phe Gly Ile Pro Ala Phe Ile Tyr Ser Phe Asn
                 165                 170                 175

ATG TCA AAC GAA GTA AAT AAA TCA AAC TTC GAT GAT GTT ACT ACA TCT   576
Met Ser Asn Glu Val Asn Lys Ser Asn Phe Asp Asp Val Thr Thr Ser
             180                 185                 190

TTA TAT ACC TCA TCA CAC CCT TCT TCC CAA ACT ATT ACA CCT ATC TAT   624
Leu Tyr Thr Ser Ser His Pro Ser Ser Gln Thr Ile Thr Pro Ile Tyr
         195                 200                 205

TTA AAT GAA AAA CAC GAA CCG ATA TGT CAT ACT GTA AAA AAG GAT GAA   672
Leu Asn Glu Lys His Glu Pro Ile Cys His Thr Val Lys Lys Asp Glu
     210                 215                 220

AAT GTG TAT GAA CTT TTA CTA GGT TTG CAT GGA AAT ATA ACT GAT GAT   720
Asn Val Tyr Glu Leu Leu Leu Gly Leu His Gly Asn Ile Thr Asp Asp
225                 230                 235                 240

ATT TTT CTC GAT GAG GAT TCT GAA TTG CTT AAA AGA GTA AAT ATA CCT   768
Ile Phe Leu Asp Glu Asp Ser Glu Leu Leu Lys Arg Val Asn Ile Pro
                 245                 250                 255

ACA ACG ACA AAT AAT TAT ATA TTT AAG CCT TAC CTA GAC CAA CGT AAT   816
Thr Thr Thr Asn Asn Tyr Ile Phe Lys Pro Tyr Leu Asp Gln Arg Asn
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 260 |     |     |     | 265 |     |     |     | 270 |     |     |     |      |
| AGA | AAA | TTT | TTA | ATT | ATT | GTA | ATT | TCG | ATT | TCG | ATA | ATT | TTA | CTT | ATT | 864  |
| Arg | Lys | Phe | Leu | Ile | Ile | Val | Ile | Ser | Ile | Ser | Ile | Ile | Leu | Leu | Ile |      |
|     |     | 275 |     |     |     |     | 280 |     |     |     |     | 285 |     |     |     |      |
| CTT | TTG | GTA | TTA | ATT | GGA | TCA | ATT | ATT | AAC | AAT | ATT | ATT | CGT | AGA | CAC | 912  |
| Leu | Leu | Val | Leu | Ile | Gly | Ser | Ile | Ile | Asn | Asn | Ile | Ile | Arg | Arg | His |      |
|     | 290 |     |     |     |     | 295 |     |     |     |     |     | 300 |     |     |     |      |
| TTT | TCT | TCT | TCT | AGG | CGT | ATT | TAT | CGT | CCT | AAA | GGT | AAC | TCG | GAA | TCT | 960  |
| Phe | Ser | Ser | Ser | Arg | Arg | Ile | Tyr | Arg | Pro | Lys | Gly | Asn | Ser | Glu | Ser |      |
| 305 |     |     |     |     | 310 |     |     |     |     | 315 |     |     |     |     | 320 |      |
| GAA | AAT | ATA | GAA | CTG | ACA | TGT | GGG | GAA | AAC | TCA | GTA | AAC | AAA | AAT | AAT | 1008 |
| Glu | Asn | Ile | Glu | Leu | Thr | Cys | Gly | Glu | Asn | Ser | Val | Asn | Lys | Asn | Asn |      |
|     |     |     |     | 325 |     |     |     |     | 330 |     |     |     |     | 335 |     |      |
| CCA | TTA | CCA | AAA | AAA | CCT | AAC | CGC | CAA | AAA | AGA | TCT | TCA | ACT | ATT | CAA | 1056 |
| Pro | Leu | Pro | Lys | Lys | Pro | Asn | Arg | Gln | Lys | Arg | Ser | Ser | Thr | Ile | Gln |      |
|     |     |     | 340 |     |     |     |     |     | 345 |     |     |     | 350 |     |     |      |
| AGG | GAG | ACA | TCT | CTT | GAA | ACT | ATT | AAG | GAA | GAA | GTA | TAA |     |     |     | 1095 |
| Arg | Glu | Thr | Ser | Leu | Glu | Thr | Ile | Lys | Glu | Glu | Val |     |     |     |     |      |
|     |     | 355 |     |     |     |     | 360 |     |     |     |     |     |     |     |     |      |

( 2 ) INFORMATION FOR SEQ ID NO:56:

( i ) SEQUENCE CHARACTERISTICS:
        ( A ) LENGTH: 364 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

|     |     |     |     |     |     |     |     |     |     |     |     |     |     |     |
| --- | --- | --- | --- | --- | --- | --- | --- | --- | --- | --- | --- | --- | --- | --- |
| Met | Tyr | Leu | Gln | Leu | Leu | Phe | Thr | Cys | Lys | Arg | Val | Glu | Thr | Arg | Leu |
| 1   |     |     |     | 5   |     |     |     |     | 10  |     |     |     |     | 15  |     |
| Leu | Ile | Thr | Met | Phe | Leu | Pro | Ile | Leu | Phe | Leu | Phe | Leu | Tyr | Gly | Val |
|     |     |     | 20  |     |     |     |     | 25  |     |     |     |     | 30  |     |     |
| Asn | Gly | Phe | Val | Tyr | Lys | Gly | Thr | Tyr | Ile | Ser | Met | Phe | Leu | Asn | Thr |
|     |     | 35  |     |     |     |     | 40  |     |     |     |     | 45  |     |     |     |
| Ser | Ser | Gly | Phe | Ser | Ile | Phe | Pro | Asp | Asp | Lys | Phe | Ile | Val | Ser | Gly |
|     | 50  |     |     |     |     | 55  |     |     |     |     | 60  |     |     |     |     |
| Arg | Leu | Leu | Phe | Leu | Asp | Asp | Gln | His | Leu | Ser | Val | Asn | Asn | Tyr | Ser |
| 65  |     |     |     |     | 70  |     |     |     |     | 75  |     |     |     |     | 80  |
| Gly | Thr | Ile | Glu | Phe | Ile | His | Phe | Asn | Asn | Ser | Cys | Tyr | Thr | Val | Tyr |
|     |     |     |     | 85  |     |     |     |     | 90  |     |     |     |     | 95  |     |
| Gln | Thr | Ile | Glu | Tyr | Phe | Ser | Cys | Pro | Arg | Ile | Phe | Asn | Asn | Ala | Phe |
|     |     |     | 100 |     |     |     |     | 105 |     |     |     |     | 110 |     |     |
| Arg | Ser | Cys | Leu | Lys | Lys | Val | Ser | Lys | His | His | Glu | Ser | Gln | Leu | Arg |
|     |     | 115 |     |     |     |     | 120 |     |     |     |     | 125 |     |     |     |
| Ile | Asn | Ser | Ser | Ile | Glu | Asn | Gly | Val | Leu | Leu | Glu | Ile | Thr | Asn | Pro |
|     | 130 |     |     |     |     | 135 |     |     |     |     | 140 |     |     |     |     |
| Lys | Pro | Asn | Asp | Ser | Gly | Val | Tyr | Phe | Ile | Arg | Val | Gln | Leu | Glu | Asn |
| 145 |     |     |     |     | 150 |     |     |     |     | 155 |     |     |     |     | 160 |
| Asn | Lys | Thr | Asp | Val | Phe | Gly | Ile | Pro | Ala | Phe | Ile | Tyr | Ser | Phe | Asn |
|     |     |     |     | 165 |     |     |     |     | 170 |     |     |     |     | 175 |     |
| Met | Ser | Asn | Glu | Val | Asn | Lys | Ser | Asn | Phe | Asp | Asp | Val | Thr | Thr | Ser |
|     |     |     | 180 |     |     |     |     | 185 |     |     |     |     | 190 |     |     |
| Leu | Tyr | Thr | Ser | Ser | His | Pro | Ser | Ser | Gln | Thr | Ile | Thr | Pro | Ile | Tyr |
|     |     | 195 |     |     |     |     | 200 |     |     |     |     | 205 |     |     |     |
| Leu | Asn | Glu | Lys | His | Glu | Pro | Ile | Cys | His | Thr | Val | Lys | Lys | Asp | Glu |
|     | 210 |     |     |     |     | 215 |     |     |     |     | 220 |     |     |     |     |

```
Asn  Val  Tyr  Glu  Leu  Leu  Leu  Gly  Leu  His  Gly  Asn  Ile  Thr  Asp  Asp
225                      230                 235                          240

Ile  Phe  Leu  Asp  Glu  Asp  Ser  Glu  Leu  Leu  Lys  Arg  Val  Asn  Ile  Pro
                    245                      250                     255

Thr  Thr  Thr  Asn  Asn  Tyr  Ile  Phe  Lys  Pro  Tyr  Leu  Asp  Gln  Arg  Asn
               260                 265                          270

Arg  Lys  Phe  Leu  Ile  Ile  Val  Ile  Ser  Ile  Ser  Ile  Ile  Leu  Leu  Ile
          275                      280                     285

Leu  Leu  Val  Leu  Ile  Gly  Ser  Ile  Ile  Asn  Asn  Ile  Ile  Arg  Arg  His
     290                      295                     300

Phe  Ser  Ser  Ser  Arg  Arg  Ile  Tyr  Arg  Pro  Lys  Gly  Asn  Ser  Glu  Ser
305                 310                      315                          320

Glu  Asn  Ile  Glu  Leu  Thr  Cys  Gly  Glu  Asn  Ser  Val  Asn  Lys  Asn  Asn
               325                      330                     335

Pro  Leu  Pro  Lys  Lys  Pro  Asn  Arg  Gln  Lys  Arg  Ser  Ser  Thr  Ile  Gln
               340                      345                     350

Arg  Glu  Thr  Ser  Leu  Glu  Thr  Ile  Lys  Glu  Glu  Val
          355                      360
```

( 2 ) INFORMATION FOR SEQ ID NO:57:

( i ) SEQUENCE CHARACTERISTICS:
        ( A ) LENGTH: 1569 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1566

( x i ) SEQUENCE DESCRIPTION: SEQ ID NO:57:

```
ATG  TTT  CGT  TTA  TTT  TTT  TTA  ATC  GCG  TCT  ACA  TTA  TGT  TCG  GTA  AGA       48
Met  Phe  Arg  Leu  Phe  Phe  Leu  Ile  Ala  Ser  Thr  Leu  Cys  Ser  Val  Arg
  1                      5                      10                     15

TTT  GGT  TTT  TCA  ACA  ATT  CGT  AAT  GTT  ATT  GTT  TCT  GAA  AAA  TCT  GGA       96
Phe  Gly  Phe  Ser  Thr  Ile  Arg  Asn  Val  Ile  Val  Ser  Glu  Lys  Ser  Gly
                    20                     25                     30

TTT  GTA  ATT  GAT  GGT  TAT  AGT  ACT  AAC  CCA  CCA  TTT  AAT  GAG  ACT  AAA      144
Phe  Val  Ile  Asp  Gly  Tyr  Ser  Thr  Asn  Pro  Pro  Phe  Asn  Glu  Thr  Lys
               35                      40                     45

AAA  TTT  ACT  AGA  GGA  TGG  GTA  TTT  TTA  CAA  ACC  CCC  CCT  TCT  TAT  TGT      192
Lys  Phe  Thr  Arg  Gly  Trp  Val  Phe  Leu  Gln  Thr  Pro  Pro  Ser  Tyr  Cys
     50                      55                     60

AAA  GAT  GGG  ATA  TCA  ATA  TCT  AAT  ATA  TGC  ATT  GAA  CGT  AAT  ATT  TGT      240
Lys  Asp  Gly  Ile  Ser  Ile  Ser  Asn  Ile  Cys  Ile  Glu  Arg  Asn  Ile  Cys
 65                      70                     75                     80

GAA  GAA  GAT  ATT  TTT  TTG  AAT  AAA  CGA  TGT  ACA  ATT  AAA  ACT  ATT  AAT      288
Glu  Glu  Asp  Ile  Phe  Leu  Asn  Lys  Arg  Cys  Thr  Ile  Lys  Thr  Ile  Asn
                    85                     90                     95

TAT  CCC  TTA  GCT  GTA  GCA  GAT  TTT  GAG  ATT  AGT  AAT  AAT  ACT  ATT  AAA      336
Tyr  Pro  Leu  Ala  Val  Ala  Asp  Phe  Glu  Ile  Ser  Asn  Asn  Thr  Ile  Lys
               100                     105                    110

AAA  ATA  AAT  GAT  GTT  TAT  TTT  GTT  AAT  GAT  AGT  GTT  TTT  CCA  ATA  ATA      384
Lys  Ile  Asn  Asp  Val  Tyr  Phe  Val  Asn  Asp  Ser  Val  Phe  Pro  Ile  Ile
          115                     120                    125

ACT  ACA  AAT  AAA  AGT  GGT  ATC  CAT  ATC  ACA  AAT  GTG  ACT  ATA  AAT  AAT      432
Thr  Thr  Asn  Lys  Ser  Gly  Ile  His  Ile  Thr  Asn  Val  Thr  Ile  Asn  Asn
     130                     135                    140
```

-continued

| | | | | | | | | | | | | | | | | |
|---|---|---|---|---|---|---|---|---|---|---|---|---|---|---|---|---|
| TCT | GGA | ATT | TAT | ACA | TTG | TAT | GAA | AAT | AAT | GAT | AAG | TGG | AGT | CAT | CAA | 480 |
| Ser | Gly | Ile | Tyr | Thr | Leu | Tyr | Glu | Asn | Asn | Asp | Lys | Trp | Ser | His | Gln | |
| 145 | | | | 150 | | | | | 155 | | | | | | 160 | |
| TCA | AAA | ATC | TTG | GTA | ACT | ATA | AAG | AAA | AAA | GAA | ACA | GTA | ATT | ACT | AAA | 528 |
| Ser | Lys | Ile | Leu | Val | Thr | Ile | Lys | Lys | Lys | Glu | Thr | Val | Ile | Thr | Lys | |
| | | | | 165 | | | | | 170 | | | | | 175 | | |
| CCT | AAA | GTA | TAT | ATA | AAA | AAA | CAT | GGT | GGA | TTT | TTT | CAT | GTA | AAA | AAT | 576 |
| Pro | Lys | Val | Tyr | Ile | Lys | Lys | His | Gly | Gly | Phe | Phe | His | Val | Lys | Asn | |
| | | | 180 | | | | | 185 | | | | | 190 | | | |
| TAT | CAC | TCT | CAT | GTA | TTT | GTA | CCA | AAT | GAT | TCA | TTT | AAA | ATT | GAA | CTT | 624 |
| Tyr | His | Ser | His | Val | Phe | Val | Pro | Asn | Asp | Ser | Phe | Lys | Ile | Glu | Leu | |
| | | 195 | | | | | 200 | | | | | 205 | | | | |
| AAT | CTT | GAA | TCG | GAA | ATT | TAT | GAT | TCT | GAA | TTT | TCA | GCA | AGT | ATT | GAT | 672 |
| Asn | Leu | Glu | Ser | Glu | Ile | Tyr | Asp | Ser | Glu | Phe | Ser | Ala | Ser | Ile | Asp | |
| | 210 | | | | | 215 | | | | | 220 | | | | | |
| TGG | TAT | TAT | ATG | AAA | ACT | AGC | TCG | GAA | TGT | TCA | GTG | TTT | CAT | ATA | TAT | 720 |
| Trp | Tyr | Tyr | Met | Lys | Thr | Ser | Ser | Glu | Cys | Ser | Val | Phe | His | Ile | Tyr | |
| 225 | | | | 230 | | | | | 235 | | | | | | 240 | |
| GAA | ACT | TGT | ATA | TTT | CAC | CCT | CAT | GCA | AAC | TCT | TGT | TTG | AAT | CCA | ATA | 768 |
| Glu | Thr | Cys | Ile | Phe | His | Pro | His | Ala | Asn | Ser | Cys | Leu | Asn | Pro | Ile | |
| | | | | 245 | | | | | 250 | | | | | 255 | | |
| AAC | CCA | TTG | TGT | AGT | TTT | ACT | TCC | CCT | TTG | AGG | GCA | ACA | TCA | CTA | ATT | 816 |
| Asn | Pro | Leu | Cys | Ser | Phe | Thr | Ser | Pro | Leu | Arg | Ala | Thr | Ser | Leu | Ile | |
| | | | 260 | | | | | 265 | | | | | 270 | | | |
| AAT | AGA | TTT | TAT | TTT | AGA | TGT | AAA | CCT | GAA | GGT | AAA | AAC | TGG | ACA | ACT | 864 |
| Asn | Arg | Phe | Tyr | Phe | Arg | Cys | Lys | Pro | Glu | Gly | Lys | Asn | Trp | Thr | Thr | |
| | | 275 | | | | | 280 | | | | | 285 | | | | |
| GAT | TGT | ATA | AAC | ACC | TTT | TCT | ATT | AAT | GCA | GAT | AAA | CAT | ATT | AAA | CAG | 912 |
| Asp | Cys | Ile | Asn | Thr | Phe | Ser | Ile | Asn | Ala | Asp | Lys | His | Ile | Lys | Gln | |
| | 290 | | | | | 295 | | | | | 300 | | | | | |
| CAT | TCA | AAT | AAT | GTA | GAT | TTG | ATT | TTT | TTA | AAT | ACT | CCA | ACT | AAT | GCA | 960 |
| His | Ser | Asn | Asn | Val | Asp | Leu | Ile | Phe | Leu | Asn | Thr | Pro | Thr | Asn | Ala | |
| 305 | | | | 310 | | | | | 315 | | | | | | 320 | |
| TCT | GGT | TTG | TAT | GTT | TTT | ATT | CTT | AAG | TAT | AAT | GGT | CAT | CCA | GAG | GCT | 1008 |
| Ser | Gly | Leu | Tyr | Val | Phe | Ile | Leu | Lys | Tyr | Asn | Gly | His | Pro | Glu | Ala | |
| | | | | 325 | | | | | 330 | | | | | 335 | | |
| TGG | ACA | TAT | ACT | TTG | GTT | TCA | ACG | GTT | AAA | AAT | TTT | ATG | AAT | GTA | ATT | 1056 |
| Trp | Thr | Tyr | Thr | Leu | Val | Ser | Thr | Val | Lys | Asn | Phe | Met | Asn | Val | Ile | |
| | | | 340 | | | | | 345 | | | | | 350 | | | |
| AAG | GAT | ATG | ACA | CGC | CCC | CTT | TTG | TCA | AAT | AAT | AAA | ATG | AAA | AAA | CCT | 1104 |
| Lys | Asp | Met | Thr | Arg | Pro | Leu | Leu | Ser | Asn | Asn | Lys | Met | Lys | Lys | Pro | |
| | | 355 | | | | | 360 | | | | | 365 | | | | |
| GAG | CAT | TCT | ACT | CAA | CCA | CCA | ACC | ATA | ACC | AAC | ATA | ACA | CCT | GGC | TTT | 1152 |
| Glu | His | Ser | Thr | Gln | Pro | Pro | Thr | Ile | Thr | Asn | Ile | Thr | Pro | Gly | Phe | |
| | 370 | | | | | 375 | | | | | 380 | | | | | |
| AAA | TCT | AAA | AAT | TGG | GTA | GAT | AAA | TAT | ATA | ATT | TCA | GTA | GCG | GTG | GTT | 1200 |
| Lys | Ser | Lys | Asn | Trp | Val | Asp | Lys | Tyr | Ile | Ile | Ser | Val | Ala | Val | Val | |
| 385 | | | | 390 | | | | | 395 | | | | | | 400 | |
| TCT | TGT | ATT | ACT | ATT | GTT | ATA | TTG | ATT | GTG | GTA | ATA | ACC | TTT | TGT | GTT | 1248 |
| Ser | Cys | Ile | Thr | Ile | Val | Ile | Leu | Ile | Val | Val | Ile | Thr | Phe | Cys | Val | |
| | | | | 405 | | | | | 410 | | | | | 415 | | |
| CAT | CAA | TGT | ATC | GGT | TTA | AAT | CGT | AAA | CCA | TAT | GAA | ATT | ATA | AAC | CCA | 1296 |
| His | Gln | Cys | Ile | Gly | Leu | Asn | Arg | Lys | Pro | Tyr | Glu | Ile | Ile | Asn | Pro | |
| | | | 420 | | | | | 425 | | | | | 430 | | | |
| TTT | AAT | ACA | GCT | TAT | AAA | AGT | ATA | CCT | ACA | AAT | GAA | AAA | AAT | ATT | CTT | 1344 |
| Phe | Asn | Thr | Ala | Tyr | Lys | Ser | Ile | Pro | Thr | Asn | Glu | Lys | Asn | Ile | Leu | |
| | | 435 | | | | | 440 | | | | | 445 | | | | |
| CAT | TTT | GCT | GAA | GTA | ACA | GAA | TCT | GAT | TAT | TCC | TCC | GAC | GAA | TCC | TTC | 1392 |
| His | Phe | Ala | Glu | Val | Thr | Glu | Ser | Asp | Tyr | Ser | Ser | Asp | Glu | Ser | Phe | |
| | 450 | | | | | 455 | | | | | 460 | | | | | |

```
GAC  AGT  GAC  TCA  GAA  GAG  CTA  AAT  CAA  CGA  GGT  GAA  ACA  ATA  CAA  CAA    1440
Asp  Ser  Asp  Ser  Glu  Glu  Leu  Asn  Gln  Arg  Gly  Glu  Thr  Ile  Gln  Gln
465            	     470                 475                      480

GGG  AAA  AAG  GAA  CAA  TCT  GGA  TAT  ACT  ATT  TGG  TTT  AAT  GAA  GAT  TTA    1488
Gly  Lys  Lys  Glu  Gln  Ser  Gly  Tyr  Thr  Ile  Trp  Phe  Asn  Glu  Asp  Leu
                    485                 490                      495

GAA  GAA  TCC  GTC  TCC  AAA  AAA  CTT  AAC  CAA  CCA  AAC  TAT  TCA  AAA  ATA    1536
Glu  Glu  Ser  Val  Ser  Lys  Lys  Leu  Asn  Gln  Pro  Asn  Tyr  Ser  Lys  Ile
               500                 505                      510

ATT  AAT  AGC  TTA  AAA  TCA  ATC  CAG  AAT  GAA  TAA                              1569
Ile  Asn  Ser  Leu  Lys  Ser  Ile  Gln  Asn  Glu
          515                      520
```

(2) INFORMATION FOR SEQ ID NO:58:

(i) SEQUENCE CHARACTERISTICS:
        (A) LENGTH: 522 amino acids
        (B) TYPE: amino acid
        (D) TOPOLOGY: linear (ii) MOLECULE TYPE: protein (xi) SEQUENCE DESCRIPTION: SEQ ID NO:58:

```
Met  Phe  Arg  Leu  Phe  Phe  Leu  Ile  Ala  Ser  Thr  Leu  Cys  Ser  Val  Arg
1              	     5                   10                      15

Phe  Gly  Phe  Ser  Thr  Ile  Arg  Asn  Val  Ile  Val  Ser  Glu  Lys  Ser  Gly
                    20                  25                       30

Phe  Val  Ile  Asp  Gly  Tyr  Ser  Thr  Asn  Pro  Pro  Phe  Asn  Glu  Thr  Lys
               35                  40                       45

Lys  Phe  Thr  Arg  Gly  Trp  Val  Phe  Leu  Gln  Thr  Pro  Pro  Ser  Tyr  Cys
     50                  55                       60

Lys  Asp  Gly  Ile  Ser  Ile  Ser  Asn  Ile  Cys  Ile  Glu  Arg  Asn  Ile  Cys
65                       70                       75                       80

Glu  Glu  Asp  Ile  Phe  Leu  Asn  Lys  Arg  Cys  Thr  Ile  Lys  Thr  Ile  Asn
                    85                  90                       95

Tyr  Pro  Leu  Ala  Val  Ala  Asp  Phe  Glu  Ile  Ser  Asn  Asn  Thr  Ile  Lys
               100                 105                      110

Lys  Ile  Asn  Asp  Val  Tyr  Phe  Val  Asn  Asp  Ser  Val  Phe  Pro  Ile  Ile
          115                 120                      125

Thr  Thr  Asn  Lys  Ser  Gly  Ile  His  Ile  Thr  Asn  Val  Thr  Ile  Asn  Asn
     130                 135                      140

Ser  Gly  Ile  Tyr  Thr  Leu  Tyr  Glu  Asn  Asn  Asp  Lys  Trp  Ser  His  Gln
145                 150                      155                      160

Ser  Lys  Ile  Leu  Val  Thr  Ile  Lys  Lys  Lys  Glu  Thr  Val  Ile  Thr  Lys
                    165                 170                      175

Pro  Lys  Val  Tyr  Ile  Lys  Lys  His  Gly  Gly  Phe  Phe  His  Val  Lys  Asn
               180                 185                      190

Tyr  His  Ser  His  Val  Phe  Val  Pro  Asn  Asp  Ser  Phe  Lys  Ile  Glu  Leu
          195                 200                      205

Asn  Leu  Glu  Ser  Glu  Ile  Tyr  Asp  Ser  Glu  Phe  Ser  Ala  Ser  Ile  Asp
     210                 215                      220

Trp  Tyr  Tyr  Met  Lys  Thr  Ser  Ser  Glu  Cys  Ser  Val  Phe  His  Ile  Tyr
225                 230                      235                      240

Glu  Thr  Cys  Ile  Phe  His  Pro  His  Ala  Asn  Ser  Cys  Leu  Asn  Pro  Ile
                    245                 250                      255

Asn  Pro  Leu  Cys  Ser  Phe  Thr  Ser  Pro  Leu  Arg  Ala  Thr  Ser  Leu  Ile
               260                 265                      270

Asn  Arg  Phe  Tyr  Phe  Arg  Cys  Lys  Pro  Glu  Gly  Lys  Asn  Trp  Thr  Thr
```

|   |   |   |   |   | 275 |   |   |   |   | 280 |   |   |   |   | 285 |
|---|---|---|---|---|---|---|---|---|---|---|---|---|---|---|---|

Asp Cys Ile Asn Thr Phe Ser Ile Asn Ala Asp Lys His Ile Lys Gln
    290                      295                      300

His Ser Asn Asn Val Asp Leu Ile Phe Leu Asn Thr Pro Thr Asn Ala
305                  310                  315                  320

Ser Gly Leu Tyr Val Phe Ile Leu Lys Tyr Asn Gly His Pro Glu Ala
                325                  330                  335

Trp Thr Tyr Thr Leu Val Ser Thr Val Lys Asn Phe Met Asn Val Ile
            340                  345                350

Lys Asp Met Thr Arg Pro Leu Leu Ser Asn Asn Lys Met Lys Lys Pro
        355                  360            365

Glu His Ser Thr Gln Pro Pro Thr Ile Thr Asn Ile Thr Pro Gly Phe
370                  375                380

Lys Ser Lys Asn Trp Val Asp Lys Tyr Ile Ile Ser Val Ala Val Val
385                  390                  395                400

Ser Cys Ile Thr Ile Val Ile Leu Ile Val Ile Thr Phe Cys Val
                405                410                415

His Gln Cys Ile Gly Leu Asn Arg Lys Pro Tyr Glu Ile Ile Asn Pro
            420                425                430

Phe Asn Thr Ala Tyr Lys Ser Ile Pro Thr Asn Glu Lys Asn Ile Leu
        435                  440            445

His Phe Ala Glu Val Thr Glu Ser Asp Tyr Ser Ser Asp Glu Ser Phe
    450                  455                460

Asp Ser Asp Ser Glu Glu Leu Asn Gln Arg Gly Glu Thr Ile Gln Gln
465                  470                  475                480

Gly Lys Lys Glu Gln Ser Gly Tyr Thr Ile Trp Phe Asn Glu Asp Leu
                  485                490                495

Glu Glu Ser Val Ser Lys Lys Leu Asn Gln Pro Asn Tyr Ser Lys Ile
            500                505              510

Ile Asn Ser Leu Lys Ser Ile Gln Asn Glu
        515                520

( 2 ) INFORMATION FOR SEQ ID NO:59:

( i ) SEQUENCE CHARACTERISTICS:
        ( A ) LENGTH: 237 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..234

( x i ) SEQUENCE DESCRIPTION: SEQ ID NO:59:

ATG AAT AAA TCT AAA CTC TCA TTT AAA GAA AAA AAC GCT ATA TAT GAA    48
Met Asn Lys Ser Lys Leu Ser Phe Lys Glu Lys Asn Ala Ile Tyr Glu
 1              5                  10                15

TTT AAA AAT ATT TTA TCA AAC ACT TCA TTG TCA ACT TTT CCT GTA TTA    96
Phe Lys Asn Ile Leu Ser Asn Thr Ser Leu Ser Thr Phe Pro Val Leu
            20                  25                30

TCG TTT AAT GAG GAG CCA AAA TCC AGA TTT TTT AAA ATG TTT AAA AAT  144
Ser Phe Asn Glu Glu Pro Lys Ser Arg Phe Phe Lys Met Phe Lys Asn
        35                  40                45

ATT TTA CTG GAA AAA ATA AAA AAA ACT TCA ATG GAT TAT TTA ATT TAT  192
Ile Leu Leu Glu Lys Ile Lys Lys Thr Ser Met Asp Tyr Leu Ile Tyr
    50                  55                60

```
TGT  ACT  CTA  AAA  ATC  TCA  CTT  TCA  TTT  ATA  CTT  TAT  AAT  AAA            234
Cys  Thr  Leu  Lys  Ile  Ser  Leu  Ser  Phe  Ile  Leu  Tyr  Asn  Lys
 65                  70                       75

TAA                                                                              237
```

( 2 ) INFORMATION FOR SEQ ID NO:60:

( i ) SEQUENCE CHARACTERISTICS:
        ( A ) LENGTH: 78 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

```
Met  Asn  Lys  Ser  Lys  Leu  Ser  Phe  Lys  Glu  Lys  Asn  Ala  Ile  Tyr  Glu
 1                   5                       10                       15

Phe  Lys  Asn  Ile  Leu  Ser  Asn  Thr  Ser  Leu  Ser  Thr  Phe  Pro  Val  Leu
                20                       25                       30

Ser  Phe  Asn  Glu  Glu  Pro  Lys  Ser  Arg  Phe  Phe  Lys  Met  Phe  Lys  Asn
           35                       40                       45

Ile  Leu  Leu  Glu  Lys  Ile  Lys  Lys  Thr  Ser  Met  Asp  Tyr  Leu  Ile  Tyr
      50                       55                       60

Cys  Thr  Leu  Lys  Ile  Ser  Leu  Ser  Phe  Ile  Leu  Tyr  Asn  Lys
 65                       70                       75
```

( 2 ) INFORMATION FOR SEQ ID NO:61:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..357

( x i ) SEQUENCE DESCRIPTION: SEQ ID NO:61:

```
ATG  GCT  TTA  CCA  GAT  AAC  GTT  TTT  AGT  ATT  ATT  AAT  GAA  AAT  TAT  ATC   48
Met  Ala  Leu  Pro  Asp  Asn  Val  Phe  Ser  Ile  Ile  Asn  Glu  Asn  Tyr  Ile
 1                   5                       10                       15

GAT  GGA  ATT  TTA  ACT  ATG  AAA  ATG  GGT  GAA  GAA  ATA  GAA  AGC  TCA  TCA   96
Asp  Gly  Ile  Leu  Thr  Met  Lys  Met  Gly  Glu  Glu  Ile  Glu  Ser  Ser  Ser
                20                       25                       30

CCA  TTA  AAT  GAA  ACA  AAT  GTT  AAT  ATA  GAT  CAA  CAT  ACA  ATA  GAT  ATT  144
Pro  Leu  Asn  Glu  Thr  Asn  Val  Asn  Ile  Asp  Gln  His  Thr  Ile  Asp  Ile
           35                       40                       45

TTT  GAT  TAC  GAT  TCA  GAT  AAT  GGA  TGT  TAT  TAT  AGT  GAA  AGA  GAT  AAT  192
Phe  Asp  Tyr  Asp  Ser  Asp  Asn  Gly  Cys  Tyr  Tyr  Ser  Glu  Arg  Asp  Asn
      50                       55                       60

GAA  ACC  GCA  ACT  CTT  TTT  TTA  AAA  CGT  GTT  GGT  TAT  AGA  GAA  ACC  TCA  240
Glu  Thr  Ala  Thr  Leu  Phe  Leu  Lys  Arg  Val  Gly  Tyr  Arg  Glu  Thr  Ser
 65                       70                       75                       80

AAA  AAG  CGT  AAA  CGG  ATT  TGT  GGA  TTT  ATT  GTT  TTA  GCA  ATT  TTT  ATG  288
Lys  Lys  Arg  Lys  Arg  Ile  Cys  Gly  Phe  Ile  Val  Leu  Ala  Ile  Phe  Met
                     85                       90                       95

GTT  ATT  ATA  TTA  TGT  TTT  TTA  TCA  ATA  ATT  TTG  GGA  GTT  TTT  ATA  GCG  336
Val  Ile  Ile  Leu  Cys  Phe  Leu  Ser  Ile  Ile  Leu  Gly  Val  Phe  Ile  Ala
                    100                      105                      110

CCT  CAT  ATT  TAT  AAA  GGC  CTA  TAG                                           360
Pro  His  Ile  Tyr  Lys  Gly  Leu
```

115

(2) INFORMATION FOR SEQ ID NO:62:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:62:

```
Met Ala Leu Pro Asp Asn Val Phe Ser Ile Ile Asn Glu Asn Tyr Ile
 1               5                  10                  15
Asp Gly Ile Leu Thr Met Lys Met Gly Glu Ile Glu Ser Ser Ser
                20                  25                  30
Pro Leu Asn Glu Thr Asn Val Asn Ile Asp Gln His Thr Ile Asp Ile
            35                  40                  45
Phe Asp Tyr Asp Ser Asp Asn Gly Cys Tyr Tyr Ser Glu Arg Asp Asn
        50                  55                  60
Glu Thr Ala Thr Leu Phe Leu Lys Arg Val Gly Tyr Arg Glu Thr Ser
 65                 70                  75                  80
Lys Lys Arg Lys Arg Ile Cys Gly Phe Ile Val Leu Ala Ile Phe Met
                85                  90                  95
Val Ile Ile Leu Cys Phe Leu Ser Ile Ile Leu Gly Val Phe Ile Ala
            100                 105                 110
Pro His Ile Tyr Lys Gly Leu
            115
```

(2) INFORMATION FOR SEQ ID NO:63:

(i) SEQUENCE CHARACTERISTICS:
        (A) LENGTH: 2044 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

```
AAATTTACTA GAACAGAACC TGGATCTGGT GTTATTTTTT CCAGTAAGCC TATATCCCTT      60
CAGTAATACC CCAAAAACAC CAAAATTTCC ATGGTATGGA GCCACTCATT TGTATAACAA     120
AAATGTTTTT TGTGAAGCTG TACGTCGATG TGCTTCTAAA CATGCTATAG AAGCCGCATC     180
ATCTATTTGG GATTTAAATC CACCACAGTC AAATGAAGAA TTGGAAAAGT TTCTAACTAA     240
AGCGGTTATT CGCATAACCA TATCTGAGGG ACTAGGTATT TTAAAAACTG CAAATACCCC     300
ATTTAGCTGT GGTCAAAAAA CTGCTGATGA TGTTAAATTT AAGTCTCACT CCTCACGTAG     360
GAGTAAGAGT CAGTCAAGAA GTAGACACAG TCGGGGTGAT TTCGACGACA GTAGTGATTA     420
AAGTTTGTTA CACCCACTAA TTTAAATAAA TAAAAAATTT ATATTTAAAG CTATTTGTCT     480
GTCTTTTTTT GTTATATATA TTCTTGCTTA GTGAGAGTAT AAACTATTTT GTTTTTAAAA     540
ATGGAATTTA ACATAGAAGA CTTTGATGAA TCGTTGCTAG GGGCTGTTGG ATACTCTAAT     600
AATTTTAAAG GTAAGCAAAG CCTTCCGATT AAGGCTTCTA GTCCATCATC GTTAATTAAA     660
AATCTTTTAG ATGAATTAAA TTTTCCGGAA GGTCCTAGTT TATTATCTTC TATGGAAAAA     720
TGGAATGAGG ATTTATTTTC CTGCATCCCA AGATTTTTGG AAATCTACAT TGAAAATTCT     780
ATTTTATCAA CATCTGTCGA TGAGGTTATT AAAAATTTGG ATAATTCTTT AAATTATGAT     840
GATGTAATCG ATTTTCAGGT CCATGGACCT GAAACATTTC CAAAAACCCC ATTATTGGAA     900
```

```
GAGGAATTGG  AAAATTATGT  AACATCTGTT  CAAAGTATT   TTTTATCTGA  ACTTAAAGCT    960
AGAGAAGTTA  CATATTCATT  TCTACTCACT  AAATATTGTA  AAGCGCTTTT  GTTATATCTT   1020
CGCTATAATA  CAAAATCATC  GATTAAGGGT  AATAAGGACA  TAAATGCATT  TCACCAAAAA   1080
TTTAAACAAA  ATGTGCGGGA  ACGTTATTAT  AGAGAGGTTG  CAAATATAGC  ACGATTGTTA   1140
TATTTACATC  TGTATTTATC  AGTAACTAGG  GAAGTGTCTT  GGAAACTACA  TGCCGATCAA   1200
GTATTACTCC  AAAGTGTTTT  TGTTTCATTG  TCTTATTCTT  GGAGCCACCG  ACGACAGTTT   1260
GAGTGTATAT  TTCATCCAAT  TTTATTTAAT  CATGGTATTG  TGAATTTGGA  AAATAACCCT   1320
TTGACATTTA  AGGAACTACA  AAAAATAAAT  TATAGACGTC  ATATTCTTGG  TTTACCATTG   1380
ATTAGAGCTG  GATTGGTAGA  AGAAGATAAT  CAACCTTTAA  TGATACCTCC  AGAGTTTTCC   1440
AGTAAACTAC  CTCGAACAAT  AGGATTTTTA  ACTCAACAAA  TTAGAGCCAA  AATGGAAGCT   1500
TATTCAGACA  ACCATCCTGT  AACACCAAAA  TTTCCTCGTA  TTGAACATTC  ATATGCTAAA   1560
CCTATAGATC  CTATTAACTA  TGGAACTACA  ATAGAAGCTA  TGATGGACCC  ACCATCACCA   1620
AGCGCTATTT  TACCAGGAGA  TCCAAATCCT  GAAATTAATG  TTAAGGTTAA  AAGCACTGTT   1680
TCATCCTTTC  AAATTCCACC  TAATATTACC  TTGGAAGAAC  TGGAGTCAGG  TGAATATAAT   1740
TTATTTACAG  ATGGTGTTAC  CTACAATGAT  ATACCTGAAA  ATGAGTTAAA  TAAAATGTTT   1800
CAATTATAAT  TTTTTTTTAA  TTTTTTCCAT  TTAAAACGTT  AGTATATAAT  ATGAGGTTAT   1860
ATTAATCAAT  AACACCAATA  TATTGGGGAA  TTGCCACTAA  GATACACGTG  AGTGGTACTT   1920
TTGTAGTTAG  TGGGTATAAA  TAAGGTGGGG  TAAGGTGGGG  TTCAAATCAT  TTTTTATTAC   1980
TCAGTGTTTG  CTTAAGAAAT  TATATATTTA  ATATATTTAC  TATGGAAAGA  GACCATGGTT   2040
TTGC                                                                    2044
```

( 2 ) INFORMATION FOR SEQ ID NO:64:

( i ) SEQUENCE CHARACTERISTICS:
        ( A ) LENGTH: 2044 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

```
GCAAAACCAT  GGTCTCTTTC  CATAGTAAAT  ATATTAAATA  TATAATTTCT  TAAGCAAACA     60
CTGAGTAATA  AAAAATGATT  TGAACCCCAC  CTTACCCCAC  CTTATTTATA  CCCACTAACT    120
ACAAAGTAC   CACTCACGTG  TATCTTAGTG  GCAATTCCCC  AATATATTGG  TGTTATTGAT    180
TAATATAACC  TCATATTATA  TACTAACGTT  TTAAATGGAA  AAAATTAAAA  AAAAATTATA    240
ATTGAAACAT  TTTATTTAAC  TCATTTTCAG  GTATATCATT  GTAGGTAACA  CCATCTGTAA    300
ATAAATTATA  TTCACCTGAC  TCCAGTTCTT  CCAAGGTAAT  ATTAGGTGGA  ATTTGAAAGG    360
ATGAAACAGT  GCTTTTAACC  TTAACATTAA  TTTCAGGATT  TGGATCTCCT  GGTAAAATAG    420
CGCTTGGTGA  TGGTGGGTCC  ATCATAGCTT  CTATTGTAGT  TCCATAGTTA  ATAGGATCTA    480
TAGGTTTAGC  ATATGAATGT  TCAATACGAG  GAAATTTTGG  TGTTACAGGA  TGGTTGTCTG    540
AATAAGCTTC  CATTTTGGCT  CTAATTTGTT  GAGTTAAAAA  TCCTATTGTT  CGAGGTAGTT    600
TACTGGAAAA  CTCTGGAGGT  ATCATTAAAG  GTTGATTATC  TTCTTCTACC  AATCCAGCTC    660
TAATCAATGG  TAAACCAAGA  ATATGACGTC  TATAATTTAT  TTTTGTAGT   TCCTTAAATG    720
TCAAAGGGTT  ATTTTCCAAA  TTCACAATAC  CATGATTAAA  TAAAATTGGA  TGAAATATAC    780
```

| | | | | | |
|---|---|---|---|---|---|
| ACTCAAACTG | TCGTCGGTGG | CTCCAAGAAT | AAGACAATGA | AACAAAAACA | CTTTGGAGTA | 840 |
| ATACTTGATC | GGCATGTAGT | TTCCAAGACA | CTTCCCTAGT | TACTGATAAA | TACAGATGTA | 900 |
| AATATAACAA | TCGTGCTATA | TTTGCAACCT | CTCTATAATA | ACGTCCCGC | ACATTTTGTT | 960 |
| TAAATTTTTG | GTGAAATGCA | TTTATGTCCT | TATTACCCTT | AATCGATGAT | TTTGTATTAT | 1020 |
| AGCGAAGATA | TAACAAAAGC | GCTTTACAAT | ATTTAGTGAG | TAGAAATGAA | TATGTAACTT | 1080 |
| CTCTAGCTTT | AAGTTCAGAT | AAAAAATACT | TTTGAACAGA | TGTTACATAA | TTTTCCAATT | 1140 |
| CCTCTTCCAA | TAATGGGGTT | TTTGGAAATG | TTTCAGGTCC | ATGGACCTGA | AAATCGATTA | 1200 |
| CATCATCATA | ATTTAAAGAA | TTATCCAAAT | TTTTAATAAC | CTCATCGACA | GATGTTGATA | 1260 |
| AAATAGAATT | TTCAATGTAG | ATTTCCAAAA | ATCTTGGGAT | GCAGGAAAAT | AAATCCTCAT | 1320 |
| TCCATTTTTC | CATAGAAGAT | AATAAACTAG | GACCTTCCGG | AAAATTTAAT | TCATCTAAAA | 1380 |
| GATTTTTAAT | TAACGATGAT | GGACTAGAAG | CCTTAATCGG | AAGGCTTTGC | TTACCTTTAA | 1440 |
| AATTATTAGA | GTATCCAACA | GCCCCTAGCA | ACGATTCATC | AAAGTCTTCT | ATGTAAATT | 1500 |
| CCATTTTTAA | AAACAAAATA | GTTATACTC | TCACTAAGCA | AGAATATATA | TAACAAAAAA | 1560 |
| AGACAGACAA | ATAGCTTTAA | ATATAAATTT | TTTATTTATT | TAAATTAGTG | GGTGTAACAA | 1620 |
| ACTTTAATCA | CTACTGTCGT | CGAAATCACC | CCGACTGTGT | CTACTTCTTG | ACTGACTCTT | 1680 |
| ACTCCTACGT | GAGGAGTGAG | ACTTAAATTT | AACATCATCA | GCAGTTTTTT | GACCACAGCT | 1740 |
| AAATGGGGTA | TTTGCAGTTT | TTAAAATACC | TAGTCCCTCA | GATATGGTTA | TGCGAATAAC | 1800 |
| CGCTTTAGTT | AGAAACTTTT | CCAATTCTTC | ATTTGACTGT | GGTGGATTTA | AATCCCAAAT | 1860 |
| AGATGATGCG | GCTTCTATAG | CATGTTTAGA | AGCACATCGA | CGTACAGCTT | CACAAAAAAC | 1920 |
| ATTTTTGTTA | TACAAATGAG | TGGCTCCATA | CCATGGAAAT | TTTGGTGTTT | TTGGGGTATT | 1980 |
| ACTGAAGGGA | TATAGGCTTA | CTGGAAAAAA | TAACACCAGA | TCCAGGTTCT | GTTCTAGTAA | 2040 |
| ATTT | | | | | | 2044 |

( 2 ) INFORMATION FOR SEQ ID NO:65:

( i ) SEQUENCE CHARACTERISTICS:
        ( A ) LENGTH: 420 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..417

( x i ) SEQUENCE DESCRIPTION: SEQ ID NO:65:

| | | | | | | | | | | | | | | | | |
|---|---|---|---|---|---|---|---|---|---|---|---|---|---|---|---|---|
| AAT | TTA | CTA | GAA | CAG | AAC | CTG | GAT | CTG | GTG | TTA | TTT | TTT | CCA | GTA | AGC | 48 |
| Asn | Leu | Leu | Glu | Gln | Asn | Leu | Asp | Leu | Val | Leu | Phe | Phe | Pro | Val | Ser | |
| 1 | | | | 5 | | | | | 10 | | | | | 15 | | |
| CTA | TAT | CCC | TTC | AGT | AAT | ACC | CCA | AAA | ACA | CCA | AAA | TTT | CCA | TGG | TAT | 96 |
| Leu | Tyr | Pro | Phe | Ser | Asn | Thr | Pro | Lys | Thr | Pro | Lys | Phe | Pro | Trp | Tyr | |
| | | | 20 | | | | | 25 | | | | | 30 | | | |
| GGA | GCC | ACT | CAT | TTG | TAT | AAC | AAA | AAT | GTT | TTT | TGT | GAA | GCT | GTA | CGT | 144 |
| Gly | Ala | Thr | His | Leu | Tyr | Asn | Lys | Asn | Val | Phe | Cys | Glu | Ala | Val | Arg | |
| | | | 35 | | | | | 40 | | | | | 45 | | | |
| CGA | TGT | GCT | TCT | AAA | CAT | GCT | ATA | GAA | GCC | GCA | TCA | TCT | ATT | TGG | GAT | 192 |
| Arg | Cys | Ala | Ser | Lys | His | Ala | Ile | Glu | Ala | Ala | Ser | Ser | Ile | Trp | Asp | |
| | | | | 50 | | | | | 55 | | | | | 60 | | |
| TTA | AAT | CCA | CCA | CAG | TCA | AAT | GAA | GAA | TTG | GAA | AAG | TTT | CTA | ACT | AAA | 240 |
| Leu | Asn | Pro | Pro | Gln | Ser | Asn | Glu | Glu | Leu | Glu | Lys | Phe | Leu | Thr | Lys | |
| 65 | | | | | 70 | | | | | 75 | | | | | 80 | |

```
GCG GTT ATT CGC ATA ACC ATA TCT GAG GGA CTA GGT ATT TTA AAA ACT      288
Ala Val Ile Arg Ile Thr Ile Ser Glu Gly Leu Gly Ile Leu Lys Thr
             85                  90                  95

GCA AAT ACC CCA TTT AGC TGT GGT CAA AAA ACT GCT GAT GAT GTT AAA      336
Ala Asn Thr Pro Phe Ser Cys Gly Gln Lys Thr Ala Asp Asp Val Lys
            100                 105                 110

TTT AAG TCT CAC TCC TCA CGT AGG AGT AAG AGT CAG TCA AGA AGT AGA      384
Phe Lys Ser His Ser Ser Arg Arg Ser Lys Ser Gln Ser Arg Ser Arg
            115                 120                 125

CAC AGT CGG GGT GAT TTC GAC GAC AGT AGT GAT TAA                      420
His Ser Arg Gly Asp Phe Asp Asp Ser Ser Asp
            130                 135
```

( 2 ) INFORMATION FOR SEQ ID NO:66:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:66:

```
Asn Leu Leu Glu Gln Asn Leu Asp Leu Val Leu Phe Phe Pro Val Ser
 1               5                  10                  15

Leu Tyr Pro Phe Ser Asn Thr Pro Lys Thr Pro Lys Phe Pro Trp Tyr
             20                  25                  30

Gly Ala Thr His Leu Tyr Asn Lys Asn Val Phe Cys Glu Ala Val Arg
             35                  40                  45

Arg Cys Ala Ser Lys His Ala Ile Glu Ala Ala Ser Ser Ile Trp Asp
         50                  55                  60

Leu Asn Pro Pro Gln Ser Asn Glu Glu Leu Glu Lys Phe Leu Thr Lys
 65                  70                  75                  80

Ala Val Ile Arg Ile Thr Ile Ser Glu Gly Leu Gly Ile Leu Lys Thr
             85                  90                  95

Ala Asn Thr Pro Phe Ser Cys Gly Gln Lys Thr Ala Asp Asp Val Lys
            100                 105                 110

Phe Lys Ser His Ser Ser Arg Arg Ser Lys Ser Gln Ser Arg Ser Arg
            115                 120                 125

His Ser Arg Gly Asp Phe Asp Asp Ser Ser Asp
            130                 135
```

( 2 ) INFORMATION FOR SEQ ID NO:67:

( i ) SEQUENCE CHARACTERISTICS:
        ( A ) LENGTH: 1269 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1266

( x i ) SEQUENCE DESCRIPTION: SEQ ID NO:67:

```
ATG GAA TTT AAC ATA GAA GAC TTT GAT GAA TCG TTG CTA GGG GCT GTT       48
Met Glu Phe Asn Ile Glu Asp Phe Asp Glu Ser Leu Leu Gly Ala Val
 1               5                  10                  15

GGA TAC TCT AAT AAT TTT AAA GGT AAG CAA AGC CTT CCG ATT AAG GCT       96
Gly Tyr Ser Asn Asn Phe Lys Gly Lys Gln Ser Leu Pro Ile Lys Ala
             20                  25                  30
```

| | | | | | | | | | | | | | | | | |
|---|---|---|---|---|---|---|---|---|---|---|---|---|---|---|---|---|
| TCT | AGT | CCA | TCA | TCG | TTA | ATT | AAA | AAT | CTT | TTA | GAT | GAA | TTA | AAT | TTT | 144 |
| Ser | Ser | Pro | Ser | Ser | Leu | Ile | Lys | Asn | Leu | Leu | Asp | Glu | Leu | Asn | Phe | |
| | | 35 | | | | | 40 | | | | | 45 | | | | |
| CCG | GAA | GGT | CCT | AGT | TTA | TTA | TCT | TCT | ATG | GAA | AAA | TGG | AAT | GAG | GAT | 192 |
| Pro | Glu | Gly | Pro | Ser | Leu | Leu | Ser | Ser | Met | Glu | Lys | Trp | Asn | Glu | Asp | |
| | | 50 | | | | | 55 | | | | | 60 | | | | |
| TTA | TTT | TCC | TGC | ATC | CCA | AGA | TTT | TTG | GAA | ATC | TAC | ATT | GAA | AAT | TCT | 240 |
| Leu | Phe | Ser | Cys | Ile | Pro | Arg | Phe | Leu | Glu | Ile | Tyr | Ile | Glu | Asn | Ser | |
| 65 | | | | | 70 | | | | | 75 | | | | | 80 | |
| ATT | TTA | TCA | ACA | TCT | GTC | GAT | GAG | GTT | ATT | AAA | AAT | TTG | GAT | AAT | TCT | 288 |
| Ile | Leu | Ser | Thr | Ser | Val | Asp | Glu | Val | Ile | Lys | Asn | Leu | Asp | Asn | Ser | |
| | | | | 85 | | | | | 90 | | | | | 95 | | |
| TTA | AAT | TAT | GAT | GAT | GTA | ATC | GAT | TTT | CAG | GTC | CAT | GGA | CCT | GAA | ACA | 336 |
| Leu | Asn | Tyr | Asp | Asp | Val | Ile | Asp | Phe | Gln | Val | His | Gly | Pro | Glu | Thr | |
| | | | | 100 | | | | | 105 | | | | | 110 | | |
| TTT | CCA | AAA | ACC | CCA | TTA | TTG | GAA | GAG | GAA | TTG | GAA | AAT | TAT | GTA | ACA | 384 |
| Phe | Pro | Lys | Thr | Pro | Leu | Leu | Glu | Glu | Glu | Leu | Glu | Asn | Tyr | Val | Thr | |
| | | | 115 | | | | | 120 | | | | | 125 | | | |
| TCT | GTT | CAA | AAG | TAT | TTT | TTA | TCT | GAA | CTT | AAA | GCT | AGA | GAA | GTT | ACA | 432 |
| Ser | Val | Gln | Lys | Tyr | Phe | Leu | Ser | Glu | Leu | Lys | Ala | Arg | Glu | Val | Thr | |
| | 130 | | | | | 135 | | | | | 140 | | | | | |
| TAT | TCA | TTT | CTA | CTC | ACT | AAA | TAT | TGT | AAA | GCG | CTT | TTG | TTA | TAT | CTT | 480 |
| Tyr | Ser | Phe | Leu | Leu | Thr | Lys | Tyr | Cys | Lys | Ala | Leu | Leu | Leu | Tyr | Leu | |
| 145 | | | | | 150 | | | | | 155 | | | | | 160 | |
| CGC | TAT | AAT | ACA | AAA | TCA | TCG | ATT | AAG | GGT | AAT | AAG | GAC | ATA | AAT | GCA | 528 |
| Arg | Tyr | Asn | Thr | Lys | Ser | Ser | Ile | Lys | Gly | Asn | Lys | Asp | Ile | Asn | Ala | |
| | | | | 165 | | | | | 170 | | | | | 175 | | |
| TTT | CAC | CAA | AAA | TTT | AAA | CAA | AAT | GTG | CGG | GAA | CGT | TAT | TAT | AGA | GAG | 576 |
| Phe | His | Gln | Lys | Phe | Lys | Gln | Asn | Val | Arg | Glu | Arg | Tyr | Tyr | Arg | Glu | |
| | | | 180 | | | | | 185 | | | | | 190 | | | |
| GTT | GCA | AAT | ATA | GCA | CGA | TTG | TTA | TAT | TTA | CAT | CTG | TAT | TTA | TCA | GTA | 624 |
| Val | Ala | Asn | Ile | Ala | Arg | Leu | Leu | Tyr | Leu | His | Leu | Tyr | Leu | Ser | Val | |
| | | 195 | | | | | 200 | | | | | 205 | | | | |
| ACT | AGG | GAA | GTG | TCT | TGG | AAA | CTA | CAT | GCC | GAT | CAA | GTA | TTA | CTC | CAA | 672 |
| Thr | Arg | Glu | Val | Ser | Trp | Lys | Leu | His | Ala | Asp | Gln | Val | Leu | Leu | Gln | |
| | 210 | | | | | 215 | | | | | 220 | | | | | |
| AGT | GTT | TTT | GTT | TCA | TTG | TCT | TAT | TCT | TGG | AGC | CAC | CGA | CGA | CAG | TTT | 720 |
| Ser | Val | Phe | Val | Ser | Leu | Ser | Tyr | Ser | Trp | Ser | His | Arg | Arg | Gln | Phe | |
| 225 | | | | | 230 | | | | | 235 | | | | | 240 | |
| GAG | TGT | ATA | TTT | CAT | CCA | ATT | TTA | TTT | AAT | CAT | GGT | ATT | GTG | AAT | TTG | 768 |
| Glu | Cys | Ile | Phe | His | Pro | Ile | Leu | Phe | Asn | His | Gly | Ile | Val | Asn | Leu | |
| | | | | 245 | | | | | 250 | | | | | 255 | | |
| GAA | AAT | AAC | CCT | TTG | ACA | TTT | AAG | GAA | CTA | CAA | AAA | ATA | AAT | TAT | AGA | 816 |
| Glu | Asn | Asn | Pro | Leu | Thr | Phe | Lys | Glu | Leu | Gln | Lys | Ile | Asn | Tyr | Arg | |
| | | | 260 | | | | | 265 | | | | | 270 | | | |
| CGT | CAT | ATT | CTT | GGT | TTA | CCA | TTG | ATT | AGA | GCT | GGA | TTG | GTA | GAA | GAA | 864 |
| Arg | His | Ile | Leu | Gly | Leu | Pro | Leu | Ile | Arg | Ala | Gly | Leu | Val | Glu | Glu | |
| | | 275 | | | | | 280 | | | | | 285 | | | | |
| GAT | AAT | CAA | CCT | TTA | ATG | ATA | CCT | CCA | GAG | TTT | TCC | AGT | AAA | CTA | CCT | 912 |
| Asp | Asn | Gln | Pro | Leu | Met | Ile | Pro | Pro | Glu | Phe | Ser | Ser | Lys | Leu | Pro | |
| | 290 | | | | | 295 | | | | | 300 | | | | | |
| CGA | ACA | ATA | GGA | TTT | TTA | ACT | CAA | CAA | ATT | AGA | GCC | AAA | ATG | GAA | GCT | 960 |
| Arg | Thr | Ile | Gly | Phe | Leu | Thr | Gln | Gln | Ile | Arg | Ala | Lys | Met | Glu | Ala | |
| 305 | | | | | 310 | | | | | 315 | | | | | 320 | |
| TAT | TCA | GAC | AAC | CAT | CCT | GTA | ACA | CCA | AAA | TTT | CCT | CGT | ATT | GAA | CAT | 1008 |
| Tyr | Ser | Asp | Asn | His | Pro | Val | Thr | Pro | Lys | Phe | Pro | Arg | Ile | Glu | His | |
| | | | | 325 | | | | | 330 | | | | | 335 | | |
| TCA | TAT | GCT | AAA | CCT | ATA | GAT | CCT | ATT | AAC | TAT | GGA | ACT | ACA | ATA | GAA | 1056 |
| Ser | Tyr | Ala | Lys | Pro | Ile | Asp | Pro | Ile | Asn | Tyr | Gly | Thr | Thr | Ile | Glu | |
| | | | 340 | | | | | 345 | | | | | 350 | | | |

```
GCT  ATG  ATG  GAC  CCA  CCA  TCA  CCA  AGC  GCT  ATT  TTA  CCA  GGA  GAT  CCA    1104
Ala  Met  Met  Asp  Pro  Pro  Ser  Pro  Ser  Ala  Ile  Leu  Pro  Gly  Asp  Pro
     355                          360                     365

AAT  CCT  GAA  ATT  AAT  GTT  AAG  GTT  AAA  AGC  ACT  GTT  TCA  TCC  TTT  CAA    1152
Asn  Pro  Glu  Ile  Asn  Val  Lys  Val  Lys  Ser  Thr  Val  Ser  Ser  Phe  Gln
     370                     375                     380

ATT  CCA  CCT  AAT  ATT  ACC  TTG  GAA  GAA  CTG  GAG  TCA  GGT  GAA  TAT  AAT    1200
Ile  Pro  Pro  Asn  Ile  Thr  Leu  Glu  Glu  Leu  Glu  Ser  Gly  Glu  Tyr  Asn
385                     390                     395                          400

TTA  TTT  ACA  GAT  GGT  GTT  ACC  TAC  AAT  GAT  ATA  CCT  GAA  AAT  GAG  TTA    1248
Leu  Phe  Thr  Asp  Gly  Val  Thr  Tyr  Asn  Asp  Ile  Pro  Glu  Asn  Glu  Leu
               405                     410                     415

AAT  AAA  ATG  TTT  CAA  TTA  TAA                                                 1269
Asn  Lys  Met  Phe  Gln  Leu
               420
```

( 2 ) INFORMATION FOR SEQ ID NO:68:

( i ) SEQUENCE CHARACTERISTICS:
    ( A ) LENGTH: 422 amino acids
    ( B ) TYPE: amino acid
    ( D ) TOPOLOGY: linear ( i i ) MOLECULE TYPE: protein ( x i ) SEQUENCE DESCRIPTION: SEQ ID NO:68:

```
Met  Glu  Phe  Asn  Ile  Glu  Asp  Phe  Asp  Glu  Ser  Leu  Leu  Gly  Ala  Val
 1                    5                    10                       15

Gly  Tyr  Ser  Asn  Asn  Phe  Lys  Gly  Lys  Gln  Ser  Leu  Pro  Ile  Lys  Ala
               20                    25                       30

Ser  Ser  Pro  Ser  Ser  Leu  Ile  Lys  Asn  Leu  Leu  Asp  Glu  Leu  Asn  Phe
          35                    40                       45

Pro  Glu  Gly  Pro  Ser  Leu  Leu  Ser  Ser  Met  Glu  Lys  Trp  Asn  Glu  Asp
     50                    55                       60

Leu  Phe  Ser  Cys  Ile  Pro  Arg  Phe  Leu  Glu  Ile  Tyr  Ile  Glu  Asn  Ser
 65                    70                       75                       80

Ile  Leu  Ser  Thr  Ser  Val  Asp  Glu  Val  Ile  Lys  Asn  Leu  Asp  Asn  Ser
               85                    90                       95

Leu  Asn  Tyr  Asp  Asp  Val  Ile  Asp  Phe  Gln  Val  His  Gly  Pro  Glu  Thr
               100                   105                      110

Phe  Pro  Lys  Thr  Pro  Leu  Leu  Glu  Glu  Glu  Leu  Glu  Asn  Tyr  Val  Thr
          115                   120                      125

Ser  Val  Gln  Lys  Tyr  Phe  Leu  Ser  Glu  Leu  Lys  Ala  Arg  Glu  Val  Thr
     130                   135                      140

Tyr  Ser  Phe  Leu  Leu  Thr  Lys  Tyr  Cys  Lys  Ala  Leu  Leu  Leu  Tyr  Leu
145                   150                      155                       160

Arg  Tyr  Asn  Thr  Lys  Ser  Ser  Ile  Lys  Gly  Asn  Lys  Asp  Ile  Asn  Ala
               165                   170                      175

Phe  His  Gln  Lys  Phe  Lys  Gln  Asn  Val  Arg  Glu  Arg  Tyr  Tyr  Arg  Glu
               180                   185                      190

Val  Ala  Asn  Ile  Ala  Arg  Leu  Leu  Tyr  Leu  His  Leu  Tyr  Leu  Ser  Val
          195                   200                      205

Thr  Arg  Glu  Val  Ser  Trp  Lys  Leu  His  Ala  Asp  Gln  Val  Leu  Leu  Gln
     210                   215                      220

Ser  Val  Phe  Val  Ser  Leu  Ser  Tyr  Ser  Trp  Ser  His  Arg  Arg  Gln  Phe
225                   230                      235                       240

Glu  Cys  Ile  Phe  His  Pro  Ile  Leu  Phe  Asn  His  Gly  Ile  Val  Asn  Leu
               245                   250                      255
```

| | | | | | | | | | | | | | | |
|---|---|---|---|---|---|---|---|---|---|---|---|---|---|---|
| Glu | Asn | Asn | Pro<br>260 | Leu | Thr | Phe | Lys | Glu<br>265 | Leu | Gln | Lys | Ile | Asn<br>270 | Tyr | Arg |
| Arg | His | Ile<br>275 | Leu | Gly | Leu | Pro | Leu<br>280 | Ile | Arg | Ala | Gly | Leu<br>285 | Val | Glu | Glu |
| Asp | Asn<br>290 | Gln | Pro | Leu | Met | Ile<br>295 | Pro | Pro | Glu | Phe | Ser<br>300 | Ser | Lys | Leu | Pro |
| Arg<br>305 | Thr | Ile | Gly | Phe | Leu<br>310 | Thr | Gln | Gln | Ile | Arg<br>315 | Ala | Lys | Met | Glu | Ala<br>320 |
| Tyr | Ser | Asp | Asn | His<br>325 | Pro | Val | Thr | Pro | Lys<br>330 | Phe | Pro | Arg | Ile | Glu<br>335 | His |
| Ser | Tyr | Ala | Lys<br>340 | Pro | Ile | Asp | Pro | Ile<br>345 | Asn | Tyr | Gly | Thr | Thr<br>350 | Ile | Glu |
| Ala | Met | Met<br>355 | Asp | Pro | Pro | Ser | Pro<br>360 | Ser | Ala | Ile | Leu | Pro<br>365 | Gly | Asp | Pro |
| Asn | Pro<br>370 | Glu | Ile | Asn | Val | Lys<br>375 | Val | Lys | Ser | Thr | Val<br>380 | Ser | Ser | Phe | Gln |
| Ile<br>385 | Pro | Pro | Asn | Ile | Thr<br>390 | Leu | Glu | Glu | Leu | Glu<br>395 | Ser | Gly | Glu | Tyr | Asn<br>400 |
| Leu | Phe | Thr | Asp | Gly<br>405 | Val | Thr | Tyr | Asn | Asp<br>410 | Ile | Pro | Glu | Asn | Glu<br>415 | Leu |
| Asn | Lys | Met | Phe<br>420 | Gln | Leu | | | | | | | | | | |

( 2 ) INFORMATION FOR SEQ ID NO:69:

( i ) SEQUENCE CHARACTERISTICS:
        ( A ) LENGTH: 626 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

| | | | | | |
|---|---|---|---|---|---|
| AAGCTTATTG | TCCGTGCTTT | GCTGATGGTT | TCTGGAACTG | TCTCCCCTAT | TTTAAGATAC | 60 |
| AATATAGAAG | GAGTAAAATG | TAAACTAAGT | TCATGGAACC | TTACAACCGC | TGCCTTTTCT | 120 |
| ACCCCATCTA | CTGTTAATGA | AAAAATTAAT | GATGTGGTTG | AAACAACTTC | AAACCCTTTG | 180 |
| AGTAAACTAA | AAAGAATTG | TAATAGAGAA | AAGGAACTTT | CAAAATCAAA | AAGTATAGTT | 240 |
| TCAGGAGGTG | TTAGTGTTCA | TGGATTAGAA | CAAAGCTGTA | GCTCTCATAC | CTCCAATTTT | 300 |
| CAGAAATGCC | CAGATAAAAC | CAAGTCATCA | AATAAAATG | ATGCAAACAA | ACGTGAGTCA | 360 |
| AGGGGAAAAA | GAAAGTCTGA | ACCAATAGTA | AATAGTTTTG | GAGTCGCAAA | AGTTTCATCC | 420 |
| AACCCACCGC | CATCAAAAAA | GAGAGCATCA | TCACAATCTA | CCGGACCACT | TGGACCAATG | 480 |
| CCAGAAGAAG | GACCGACCCC | CAAGGGTGGT | TTTAGAAGAA | TACCTTCTGG | GGATTGTCAT | 540 |
| ACCCCAGTTC | CAAGGGACAT | TGTAAAATCT | ATCTACTGTT | CACCAGAGAC | TGTGAAAGAA | 600 |
| TTAACAGATC | ATCCATTGTT | TCCTGA | | | | 626 |

( 2 ) INFORMATION FOR SEQ ID NO:70:

( i ) SEQUENCE CHARACTERISTICS:
        ( A ) LENGTH: 626 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

| | | | | | |
|---|---|---|---|---|---|
| TCAGGAAACA | ATGGATGATC | TGTTAATTCT | TTCACAGTCT | CTGGTGAACA | GTAGATAGAT | 60 |
| TTTACAATGT | CCCTTGGAAC | TGGGGTATGA | CAATCCCCAG | AAGGTATTCT | TCTAAAACCA | 120 |
| CCCTTGGGGG | TCGGTCCTTC | TTCTGGCATT | GGTCCAAGTG | GTCCGGTAGA | TTGTGATGAT | 180 |
| GCTCTCTTTT | TTGATGGCGG | TGGGTTGGAT | GAAACTTTTG | CGACTCCAAA | ACTATTTACT | 240 |
| ATTGGTTCAG | ACTTTCTTTT | TCCCCTTGAC | TCACGTTTGT | TTGCATCATT | TTTATTTGAT | 300 |
| GACTTGGTTT | TATCTGGGCA | TTTCTGAAAA | TTGGAGGTAT | GAGAGCTACA | GCTTTGTTCT | 360 |
| AATCCATGAA | CACTAACACC | TCCTGAAACT | ATACTTTTTG | ATTTTGAAAG | TTCCTTTTCT | 420 |
| CTATTACAAT | TCTTTTTTAG | TTTACTCAAA | GGGTTTGAAG | TTGTTTCAAC | CACATCATTA | 480 |
| ATTTTTTCAT | TAACAGTAGA | TGGGGTAGAA | AAGGCAGCGG | TTGTAAGGTT | CCATGAACTT | 540 |
| AGTTTACATT | TTACTCCTTC | TATATTGTAT | CTTAAAATAG | GGGAGACAGT | TCCAGAAACC | 600 |
| ATCAGCAAAG | CACGGACAAT | AAGCTT | | | | 626 |

( 2 ) INFORMATION FOR SEQ ID NO:71:

( i ) SEQUENCE CHARACTERISTICS:
        ( A ) LENGTH: 624 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..624

( x i ) SEQUENCE DESCRIPTION: SEQ ID NO:71:

```
AAG CTT ATT GTC CGT GCT TTG CTG ATG GTT TCT GGA ACT GTC TCC CCT        48
Lys Leu Ile Val Arg Ala Leu Leu Met Val Ser Gly Thr Val Ser Pro
 1               5                  10                  15

ATT TTA AGA TAC AAT ATA GAA GGA GTA AAA TGT AAA CTA AGT TCA TGG        96
Ile Leu Arg Tyr Asn Ile Glu Gly Val Lys Cys Lys Leu Ser Ser Trp
             20                  25                  30

AAC CTT ACA ACC GCT GCC TTT TCT ACC CCA TCT ACT GTT AAT GAA AAA       144
Asn Leu Thr Thr Ala Ala Phe Ser Thr Pro Ser Thr Val Asn Glu Lys
         35                  40                  45

ATT AAT GAT GTG GTT GAA ACA ACT TCA AAC CCT TTG AGT AAA CTA AAA       192
Ile Asn Asp Val Val Glu Thr Thr Ser Asn Pro Leu Ser Lys Leu Lys
     50                  55                  60

AAG AAT TGT AAT AGA GAA AAG GAA CTT TCA AAA TCA AAA AGT ATA GTT       240
Lys Asn Cys Asn Arg Glu Lys Glu Leu Ser Lys Ser Lys Ser Ile Val
 65                  70                  75                  80

TCA GGA GGT GTT AGT GTT CAT GGA TTA GAA CAA AGC TGT AGC TCT CAT       288
Ser Gly Gly Val Ser Val His Gly Leu Glu Gln Ser Cys Ser Ser His
                 85                  90                  95

ACC TCC AAT TTT CAG AAA TGC CCA GAT AAA ACC AAG TCA TCA AAT AAA       336
Thr Ser Asn Phe Gln Lys Cys Pro Asp Lys Thr Lys Ser Ser Asn Lys
            100                 105                 110

AAT GAT GCA AAC AAA CGT GAG TCA AGG GGA AAA AGA AAG TCT GAA CCA       384
Asn Asp Ala Asn Lys Arg Glu Ser Arg Gly Lys Arg Lys Ser Glu Pro
        115                 120                 125

ATA GTA AAT AGT TTT GGA GTC GCA AAA GTT TCA TCC AAC CCA CCG CCA       432
Ile Val Asn Ser Phe Gly Val Ala Lys Val Ser Ser Asn Pro Pro Pro
    130                 135                 140

TCA AAA AAG AGA GCA TCA TCA CAA TCT ACC GGA CCA CTT GGA CCA ATG       480
Ser Lys Lys Arg Ala Ser Ser Gln Ser Thr Gly Pro Leu Gly Pro Met
145                 150                 155                 160
```

| | | | | | | | | | | | | | | | | |
|---|---|---|---|---|---|---|---|---|---|---|---|---|---|---|---|---|
| CCA | GAA | GAA | GGA | CCG | ACC | CCC | AAG | GGT | GGT | TTT | AGA | AGA | ATA | CCT | TCT | 528 |
| Pro | Glu | Glu | Gly | Pro<br>165 | Thr | Pro | Lys | Gly | Gly<br>170 | Phe | Arg | Arg | Ile | Pro<br>175 | Ser | |
| GGG | GAT | TGT | CAT | ACC | CCA | GTT | CCA | AGG | GAC | ATT | GTA | AAA | TCT | ATC | TAC | 576 |
| Gly | Asp | Cys | His<br>180 | Thr | Pro | Val | Pro | Arg<br>185 | Asp | Ile | Val | Lys | Ser<br>190 | Ile | Tyr | |
| TGT | TCA | CCA | GAG | ACT | GTG | AAA | GAA | TTA | ACA | GAT | CAT | CCA | TTG | TTT | CCT | 624 |
| Cys | Ser | Pro<br>195 | Glu | Thr | Val | Lys | Glu<br>200 | Leu | Thr | Asp | His | Pro<br>205 | Leu | Phe | Pro | |

( 2 ) INFORMATION FOR SEQ ID NO:72:

( i ) SEQUENCE CHARACTERISTICS:
( A ) LENGTH: 208 amino acids
( B ) TYPE: amino acid
( D ) TOPOLOGY: linear ( i i ) MOLECULE TYPE: protein ( x i ) SEQUENCE DESCRIPTION: SEQ ID NO:72:

Lys Leu Ile Val Arg Ala Leu Leu Met Val Ser Gly Thr Val Ser Pro
 1               5                   10                  15

Ile Leu Arg Tyr Asn Ile Glu Gly Val Lys Cys Lys Leu Ser Ser Trp
             20                  25                  30

Asn Leu Thr Thr Ala Ala Phe Ser Thr Pro Ser Thr Val Asn Glu Lys
         35                  40                  45

Ile Asn Asp Val Val Glu Thr Thr Ser Asn Pro Leu Ser Lys Leu Lys
     50                  55                  60

Lys Asn Cys Asn Arg Glu Lys Glu Leu Ser Lys Ser Lys Ser Ile Val
 65                  70                  75                  80

Ser Gly Gly Val Ser Val His Gly Leu Glu Gln Ser Cys Ser Ser His
                 85                  90                  95

Thr Ser Asn Phe Gln Lys Cys Pro Asp Lys Thr Lys Ser Ser Asn Lys
             100                 105                 110

Asn Asp Ala Asn Lys Arg Glu Ser Arg Gly Lys Arg Lys Ser Glu Pro
         115                 120                 125

Ile Val Asn Ser Phe Gly Val Ala Lys Val Ser Ser Asn Pro Pro Pro
     130                 135                 140

Ser Lys Lys Arg Ala Ser Ser Gln Ser Thr Gly Pro Leu Gly Pro Met
145                 150                 155                 160

Pro Glu Glu Gly Pro Thr Pro Lys Gly Gly Phe Arg Arg Ile Pro Ser
                 165                 170                 175

Gly Asp Cys His Thr Pro Val Pro Arg Asp Ile Val Lys Ser Ile Tyr
             180                 185                 190

Cys Ser Pro Glu Thr Val Lys Glu Leu Thr Asp His Pro Leu Phe Pro
         195                 200                 205

( 2 ) INFORMATION FOR SEQ ID NO:73:

( i ) SEQUENCE CHARACTERISTICS:
( A ) LENGTH: 655 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:73:

AAGCTTGACT TGTTGATTAA AGTTAAAGAA TTGTTTAACA AATTAACATT CTTAGGTCTT    60

CCTCTAGGTC GTTTAATAAC AGGCTCATTT TTGTTGTCTG TAGAGTCATA CCTGTTTTCG   120

5,804,197

163                                                                                                          164
-continued

| | | | | | |
|---|---|---|---|---|---|
| AGTTTGTGTT | TAGAAGTCAT | CATAAACAAG | AAGTAGTTTC | AGTCAAACCG | GTTTTTTGAG | 180
| ATATACAACC | AAGTGGTGGT | GGAGGTAATA | TAGGAGCTTC | TGGTGAAAGC | TGTGATGGAT | 240
| AAAATAATCT | GTCTATTATA | TCAAAAAATT | TGGTTTTTAA | ACCTTTGGGT | GTATTTATTT | 300
| TCATAATATC | ATCAGCCAAT | CCCCGGAGAG | CTATAAATGG | ATTAACCCAA | AATACATCAT | 360
| TCGTTGATTT | GAACCATAAA | ATGATTTCTA | TTGGGTTACA | ATCCGTCTT | ATTATAATTC | 420
| CAGAAAGGTT | TTTTATATCT | TTATTTATTT | TTTATATAT | ATTTTTTCT | ATTTGATGAT | 480
| TACGGCATGG | TCCTTGAAGT | AGTATATTAA | TGTTGTTATA | TTGATTTTA | CTCGACGGAA | 540
| GCATGGTTAA | AATATCTTTT | ATATACGAAG | AAACAATTAG | AATTATTAAT | GAATTTATTA | 600
| AACCCCATCT | TCTAAAATTG | TGGAGAATAT | GAAAAATATT | CCGTTTTATA | TACAA | 655

( 2 ) INFORMATION FOR SEQ ID NO:74:

( i ) SEQUENCE CHARACTERISTICS:
        ( A ) LENGTH: 655 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

| | | | | | |
|---|---|---|---|---|---|
| TTGTATATAA | AACGGAATAT | TTTTCATATT | CTCCACAATT | TTAGAAGATG | GGGTTTAATA | 60
| AATTCATTAA | TAATTCTAAT | TGTTTCTTCG | TATATAAAAG | ATATTTAAC | CATGCTTCCG | 120
| TCGAGTAAAA | ATCAATATAA | CAACATTAAT | ATACTACTTC | AAGGACCATG | CCGTAATCAT | 180
| CAAATAGAAA | AAAATATATA | TAAAAAAATA | AATAAGATA | TAAAAAACCT | TTCTGGAATT | 240
| ATAATAAGAA | CGGATTGTAA | CCCAATAGAA | ATCATTTTAT | GGTTCAAATC | AACGAATGAT | 300
| GTATTTTGGG | TTAATCCATT | TATAGCTCTC | CGGGGATTGG | CTGATGATAT | TATGAAAATA | 360
| AATACACCCA | AAGGTTTAAA | AACCAAATTT | TTTGATATAA | TAGACAGATT | ATTTTATCCA | 420
| TCACAGCTTT | CACCAGAAGC | TCCTATATTA | CCTCCACCAC | CACTTGGTTG | TATATCTCAA | 480
| AAAACCGGTT | TGACTGAAAC | TACTTCTTGT | TTATGATGAC | TTCTAAACAC | AAACTCGAAA | 540
| ACAGGTATGA | CTCTACAGAC | AACAAAAATG | AGCCTGTTAT | TAAACGACCT | AGAGGAAGAC | 600
| CTAAGAATGT | TAATTTGTTA | AACAATTCTT | TAACTTTAAT | CAACAAGTCA | AGCTT | 655

( 2 ) INFORMATION FOR SEQ ID NO:75:

( i ) SEQUENCE CHARACTERISTICS:
        ( A ) LENGTH: 516 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..513

( x i ) SEQUENCE DESCRIPTION: SEQ ID NO:75:

| | | | | | | | | | | | | | | | | |
|---|---|---|---|---|---|---|---|---|---|---|---|---|---|---|---|---|
| TTG | TAT | ATA | AAA | CGG | AAT | ATT | TTT | CAT | ATT | CTC | CAC | AAT | TTT | AGA | AGA | | 48 |
| Leu | Tyr | Ile | Lys | Arg | Asn | Ile | Phe | His | Ile | Leu | His | Asn | Phe | Arg | Arg | | |
| 1 | | | | 5 | | | | | 10 | | | | | 15 | | | |
| TGG | GGT | TTA | ATA | AAT | TCA | TTA | ATA | ATT | CTA | ATT | GTT | TCT | TCG | TAT | ATA | | 96 |
| Trp | Gly | Leu | Ile | Asn | Ser | Leu | Ile | Ile | Leu | Ile | Val | Ser | Ser | Tyr | Ile | | |
| | | | 20 | | | | | 25 | | | | | 30 | | | | |
| AAA | GAT | ATT | TTA | ACC | ATG | CTT | CCG | TCG | AGT | AAA | AAT | CAA | TAT | AAC | AAC | | 144 |

```
Lys  Asp  Ile  Leu  Thr  Met  Leu  Pro  Ser  Ser  Lys  Asn  Gln  Tyr  Asn  Asn
          35                      40                      45

ATT  AAT  ATA  CTA  CTT  CAA  GGA  CCA  TGC  CGT  AAT  CAT  CAA  ATA  GAA  AAA        192
Ile  Asn  Ile  Leu  Leu  Gln  Gly  Pro  Cys  Arg  Asn  His  Gln  Ile  Glu  Lys
     50                      55                      60

AAT  ATA  TAT  AAA  AAA  ATA  AAT  AAA  GAT  ATA  AAA  AAC  CTT  TCT  GGA  ATT        240
Asn  Ile  Tyr  Lys  Lys  Ile  Asn  Lys  Asp  Ile  Lys  Asn  Leu  Ser  Gly  Ile
65                       70                      75                           80

ATA  ATA  AGA  ACG  GAT  TGT  AAC  CCA  ATA  GAA  ATC  ATT  TTA  TGG  TTC  AAA        288
Ile  Ile  Arg  Thr  Asp  Cys  Asn  Pro  Ile  Glu  Ile  Ile  Leu  Trp  Phe  Lys
               85                       90                           95

TCA  ACG  AAT  GAT  GTA  TTT  TGG  GTT  AAT  CCA  TTT  ATA  GCT  CTC  CGG  GGA        336
Ser  Thr  Asn  Asp  Val  Phe  Trp  Val  Asn  Pro  Phe  Ile  Ala  Leu  Arg  Gly
               100                      105                     110

TTG  GCT  GAT  GAT  ATT  ATG  AAA  ATA  AAT  ACA  CCC  AAA  GGT  TTA  AAA  ACC        384
Leu  Ala  Asp  Asp  Ile  Met  Lys  Ile  Asn  Thr  Pro  Lys  Gly  Leu  Lys  Thr
               115                      120                     125

AAA  TTT  TTT  GAT  ATA  ATA  GAC  AGA  TTA  TTT  TAT  CCA  TCA  CAG  CTT  TCA        432
Lys  Phe  Phe  Asp  Ile  Ile  Asp  Arg  Leu  Phe  Tyr  Pro  Ser  Gln  Leu  Ser
     130                      135                     140

CCA  GAA  GCT  CCT  ATA  TTA  CCT  CCA  CCA  CCA  CTT  GGT  TGT  ATA  TCT  CAA        480
Pro  Glu  Ala  Pro  Ile  Leu  Pro  Pro  Pro  Pro  Leu  Gly  Cys  Ile  Ser  Gln
145                      150                     155                          160

AAA  ACC  GGT  TTG  ACT  GAA  ACT  ACT  TCT  TGT  TTA  TGA                            516
Lys  Thr  Gly  Leu  Thr  Glu  Thr  Thr  Ser  Cys  Leu
                    165                     170
```

( 2 ) INFORMATION FOR SEQ ID NO:76:

( i ) SEQUENCE CHARACTERISTICS:
        ( A ) LENGTH: 171 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

```
Leu  Tyr  Ile  Lys  Arg  Asn  Ile  Phe  His  Ile  Leu  His  Asn  Phe  Arg  Arg
1                   5                   10                          15

Trp  Gly  Leu  Ile  Asn  Ser  Leu  Ile  Ile  Leu  Ile  Val  Ser  Ser  Tyr  Ile
               20                      25                      30

Lys  Asp  Ile  Leu  Thr  Met  Leu  Pro  Ser  Ser  Lys  Asn  Gln  Tyr  Asn  Asn
          35                      40                      45

Ile  Asn  Ile  Leu  Leu  Gln  Gly  Pro  Cys  Arg  Asn  His  Gln  Ile  Glu  Lys
     50                      55                      60

Asn  Ile  Tyr  Lys  Lys  Ile  Asn  Lys  Asp  Ile  Lys  Asn  Leu  Ser  Gly  Ile
65                       70                      75                           80

Ile  Ile  Arg  Thr  Asp  Cys  Asn  Pro  Ile  Glu  Ile  Ile  Leu  Trp  Phe  Lys
               85                       90                           95

Ser  Thr  Asn  Asp  Val  Phe  Trp  Val  Asn  Pro  Phe  Ile  Ala  Leu  Arg  Gly
               100                      105                     110

Leu  Ala  Asp  Asp  Ile  Met  Lys  Ile  Asn  Thr  Pro  Lys  Gly  Leu  Lys  Thr
               115                      120                     125

Lys  Phe  Phe  Asp  Ile  Ile  Asp  Arg  Leu  Phe  Tyr  Pro  Ser  Gln  Leu  Ser
     130                      135                     140

Pro  Glu  Ala  Pro  Ile  Leu  Pro  Pro  Pro  Pro  Leu  Gly  Cys  Ile  Ser  Gln
145                      150                     155                          160

Lys  Thr  Gly  Leu  Thr  Glu  Thr  Thr  Ser  Cys  Leu
                    165                     170
```

( 2 ) INFORMATION FOR SEQ ID NO:77:

( i ) SEQUENCE CHARACTERISTICS:
        ( A ) LENGTH: 1823 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

```
GCTTTGGACG  AGATTTAGGC  TGGGAAATTG  TTAGTTGAGC  ATATTGATTT  TCGCATAGTT        60
CATAAATATG  GTCTTCGTCA  TCATCATCAC  AAACTTGATC  ATACACATTT  TTATACTCAA       120
AAGTTGGAAT  AGTTCGTTCG  TAAATAGGAT  TTTCCCTTTC  AATTCGTTGA  GATGACTTTC       180
TTCTTACACC  GTTTTGTCTC  TTAATAGTAG  CATATATCGG  TTCATCTTCA  TATGATGAAA       240
TACGACGGCT  GGCCATAATT  CTATAAATAA  GAGAAGGTTA  AAAATAAGTT  GCTTAACTGG       300
TTTAGGCAAC  TAATAAAATA  TCTCTAAAAC  ATACCCCCTT  TTATATAAAT  CTGTGGATTA       360
GTTCGGATT   TCGAAACCCA  CCTTCTTATT  AGTGTTGCAT  CTGACGAAGT  TCCCGACTAA       420
CCATTCTCAA  ACAGGTTCTA  TAAGAATAAC  AAAATATCGC  AACCCCTACT  GTTACCAGGG       480
ATATATAAAA  CAAAATAGCG  GAAGTTGAAG  GCGTATTAAT  ATTGATACCC  CTAGCTGAAC       540
AACTAGAGCT  CCAAAACTGT  CTCCTAGCTT  CAGCTCTAGA  ATAATCTAAA  CGATCATCGT       600
CGAAGGCATA  AACTGAAAAA  ATAATGGATA  GTAAAAATAC  TATCTCCATT  GCTTTGATTG       660
AAAAACAAAA  ACCTTTTAAT  TGGACTATCA  ACAAATAAA   TGAAAGCCTT  CTGATGACCA       720
ACAACGAAGA  AATAAACTTG  ACTGAAAATT  TTAAAAATAC  GGGCACCTTT  TATAGCAAGA       780
TAATTGACCT  TGAAATCCGA  ACTGCTACAT  CTAGTCAATA  TGCAGTCTTT  GTTACACAAA       840
TGTGTTCTGA  TGACGAAAAT  ATGAATAATA  CAAATATTTT  TGTTATTAAT  GGTGTTATTG       900
ATTCTGGATA  TAGAGGAATA  GTTAAAGCGT  TAGTTTATTA  CCATCCAACT  GTAGAAAAAT       960
TAAATCCATA  CGATCTTAAA  ATTAAACTTC  CACTAATAGA  ACTTAGTAAA  GATTTAATAC      1020
CACTATCACC  TAGTTTACAT  AGTTATAGTG  AATTATATAA  TTTTTTTAAT  GTCTTTAATA      1080
AAAAACGTGA  TGAAGATGCT  GGTTATGATA  TACCATCTCC  AAATTTAGTT  CAAATAAAAC      1140
CGGGATATAG  TTACCTTTTT  TGTCTTCCTA  TTTTTCAATT  AGAAATGAAA  AACCCACCAA      1200
TCGCTTGTAT  TTTTGGTAGA  TCATCCTTAA  ATTCAAGCGG  AATAATTGTT  CTTCCAACTA      1260
TATGGAAACC  AAAAACAATT  TGTCAATTTT  TTATTAAAAA  TATATCCTCT  AAAACTGTAA      1320
CTATAGAAAA  AGGTCAGAGA  ATAGCTCAGT  TAGTTCTTTT  AAAAAACAAT  CAACCACTAT      1380
GGTTACAACC  ACAAATTAAT  TGTCATTCTT  TATTTCCAAA  GTCAAACTAT  TTAAGCTTAT      1440
CAAATCGAGA  ATGTGATATG  TGGAAGTTTA  CAGAAGATCT  GAATTTTGAA  GCACCGAAAA      1500
GTTACGAGG   AATAAATGGA  TTTGGATCCA  CGGGATTGTA  AAATTCGTTA  ATAAAGTTAT      1560
ATTTAAAGTG  CCAAACTTTC  ACGTGTCATT  TTTTTGGGAC  CGTTTCTTTT  TTGTTTAGTC      1620
GATAAAATAT  TTTCAGTTTC  CATAGAACTT  ATTAGAGGTT  CTGTATCTAG  TATATCTGTA      1680
GAATTATTTT  CATCATATTT  AACGGTTTGA  AGAGATAAGG  GTTTTGTTGT  ATTAGAATCT      1740
ATACCAAGGG  TTTTTTCTAA  AACCGCTACA  TCTGCCATAA  CAATATTATT  TTCTGAAGTC      1800
ATTTTTATGG  CTTGGGCACC  ACC                                                1823
```

( 2 ) INFORMATION FOR SEQ ID NO:78:

( i ) SEQUENCE CHARACTERISTICS:
        ( A ) LENGTH: 1823 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:78:

| | | | | | | |
|---|---|---|---|---|---|---|
| GGTGGTGCCC | AAGCCATAAA | AATGACTTCA | GAAAATAATA | TTGTTATGGC | AGATGTAGCG | 60 |
| GTTTTAGAAA | AAACCCTTGG | TATAGATTCT | AATACAACAA | AACCCTTATC | TCTTCAAACC | 120 |
| GTTAAATATG | ATGAAAATAA | TTCTACAGAT | ATACTAGATA | CAGAACCTCT | AATAAGTTCT | 180 |
| ATGGAAACTG | AAAATATTTT | ATCGACTAAA | CAAAAAGAA | ACGGTCCCAA | AAAAATGACA | 240 |
| CGTGAAAGTT | TGGCACTTTA | AATATAACTT | TATTAACGAA | TTTTACAATC | CCGTGGATCC | 300 |
| AAATCCATTT | ATTCCTCGTA | AACTTTTCGG | TGCTTCAAAA | TTCAGATCTT | CTGTAAACTT | 360 |
| CCACATATCA | CATTCTCGAT | TTGATAAGCT | TAAATAGTTT | GACTTTGGAA | ATAAAGAATG | 420 |
| ACAATTAATT | TGTGGTTGTA | ACCATAGTGG | TTGATTGTTT | TTTAAAAGAA | CTAACTGAGC | 480 |
| TATTCTCTGA | CCTTTTTCTA | TAGTTACAGT | TTTAGAGGAT | ATATTTTAA | TAAAAAATTG | 540 |
| ACAAATTGTT | TTTGGTTTCC | ATATAGTTGG | AAGAACAATT | ATTCCGCTTG | AATTTAAGGA | 600 |
| TGATCTACCA | AAAATACAAG | CGATTGGTGG | GTTTTCATT | TCTAATTGAA | AAATAGGAAG | 660 |
| ACAAAAAGG | TAACTATATC | CCGGTTTTAT | TTGAACTAAA | TTTGGAGATG | GTATATCATA | 720 |
| ACCAGCATCT | TCATCACGTT | TTTTATTAAA | GACATTAAAA | AAATTATATA | ATTCACTATA | 780 |
| ACTATGTAAA | CTAGGTGATA | GTGGTATTAA | ATCTTTACTA | AGTTCTATTA | GTGGAAGTTT | 840 |
| AATTTTAAGA | TCGTATGGAT | TTAATTTTTC | TACAGTTGGA | TGGTAATAAA | CTAACGCTTT | 900 |
| AACTATTCCT | CTATATCCAG | AATCAATAAC | ACCATTAATA | ACAAAAATAT | TTGTATTATT | 960 |
| CATATTTTCG | TCATCAGAAC | ACATTTGTGT | AACAAAGACT | GCATATTGAC | TAGATGTAGC | 1020 |
| AGTTCGGATT | TCAAGGTCAA | TTATCTTGCT | ATAAAAGGTG | CCCGTATTTT | TAAAATTTTC | 1080 |
| AGTCAAGTTT | ATTTCTTCGT | TGTTGGTCAT | CAGAAGGCTT | TCATTTATTT | TGTTGATAGT | 1140 |
| CCAATTAAAA | GGTTTTGTT | TTTCAATCAA | AGCAATGGAG | ATAGTATTTT | TACTATCCAT | 1200 |
| TATTTTTTCA | GTTTATGCCT | TCGACGATGA | TCGTTTAGAT | TATTCTAGAG | CTGAAGCTAG | 1260 |
| GAGACAGTTT | TGGAGCTCTA | GTTGTTCAGC | TAGGGGTATC | AATATTAATA | CGCCTTCAAC | 1320 |
| TTCCGCTATT | TTGTTTTATA | TATCCCTGGT | AACAGTAGGG | GTTGCGATAT | TTTGTTATTC | 1380 |
| TTATAGAACC | TGTTTGAGAA | TGGTTAGTCG | GGAACTTCGT | CAGATGCAAC | ACTAATAAGA | 1440 |
| AGGTGGGTTT | CGAAATCCGA | AACTAATCCA | CAGATTTATA | TAAAAGGGGG | TATGTTTTAG | 1500 |
| AGATATTTTA | TTAGTTGCCT | AAACCAGTTA | AGCAACTTAT | TTTTAACCTT | CTCTTATTTA | 1560 |
| TAGAATTATG | GCCAGCCGTC | GTATTTCATC | ATATGAAGAT | GAACCGATAT | ATGCTACTAT | 1620 |
| TAAGAGACAA | AACGGTGTAA | GAAGAAAGTC | ATCTCAACGA | ATTGAAAGGG | AAAATCCTAT | 1680 |
| TTACGAACGA | ACTATTCCAA | CTTTTGAGTA | TAAAAATGTG | TATGATCAAG | TTTGTGATGA | 1740 |
| TGATGACGAA | GACCATATTT | ATGAACTATG | CGAAAATCAA | TATGCTCAAC | TAACAATTTC | 1800 |
| CCAGCCTAAA | TCTCGTCCAA | AGC | | | | 1823 |

(2) INFORMATION FOR SEQ ID NO:79:

(i) SEQUENCE CHARACTERISTICS:
(A) LENGTH: 918 base pairs
(B) TYPE: nucleic acid
(C) STRANDEDNESS: single
(D) TOPOLOGY: linear (ii) MOLECULE TYPE: cDNA ( i x ) FEATURE:
    ( A ) NAME/KEY: CDS
    ( B ) LOCATION: 1..915

( x i ) SEQUENCE DESCRIPTION: SEQ ID NO:79:

```
ATG  GAT  AGT  AAA  AAT  ACT  ATC  TCC  ATT  GCT  TTG  ATT  GAA  AAA  CAA  AAA        48
Met  Asp  Ser  Lys  Asn  Thr  Ile  Ser  Ile  Ala  Leu  Ile  Glu  Lys  Gln  Lys
 1              5                        10                       15

CCT  TTT  AAT  TGG  ACT  ATC  AAC  AAA  ATA  AAT  GAA  AGC  CTT  CTG  ATG  ACC        96
Pro  Phe  Asn  Trp  Thr  Ile  Asn  Lys  Ile  Asn  Glu  Ser  Leu  Leu  Met  Thr
               20                        25                       30

AAC  AAC  GAA  GAA  ATA  AAC  TTG  ACT  GAA  AAT  TTT  AAA  AAT  ACG  GGC  ACC       144
Asn  Asn  Glu  Glu  Ile  Asn  Leu  Thr  Glu  Asn  Phe  Lys  Asn  Thr  Gly  Thr
          35                        40                       45

TTT  TAT  AGC  AAG  ATA  ATT  GAC  CTT  GAA  ATC  CGA  ACT  GCT  ACA  TCT  AGT       192
Phe  Tyr  Ser  Lys  Ile  Ile  Asp  Leu  Glu  Ile  Arg  Thr  Ala  Thr  Ser  Ser
     50                        55                       60

CAA  TAT  GCA  GTC  TTT  GTT  ACA  CAA  ATG  TGT  TCT  GAT  GAC  GAA  AAT  ATG       240
Gln  Tyr  Ala  Val  Phe  Val  Thr  Gln  Met  Cys  Ser  Asp  Asp  Glu  Asn  Met
 65                       70                       75                       80

AAT  AAT  ACA  AAT  ATT  TTT  GTT  ATT  AAT  GGT  GTT  ATT  GAT  TCT  GGA  TAT       288
Asn  Asn  Thr  Asn  Ile  Phe  Val  Ile  Asn  Gly  Val  Ile  Asp  Ser  Gly  Tyr
               85                        90                       95

AGA  GGA  ATA  GTT  AAA  GCG  TTA  GTT  TAT  TAC  CAT  CCA  ACT  GTA  GAA  AAA       336
Arg  Gly  Ile  Val  Lys  Ala  Leu  Val  Tyr  Tyr  His  Pro  Thr  Val  Glu  Lys
               100                       105                      110

TTA  AAT  CCA  TAC  GAT  CTT  AAA  ATT  AAA  CTT  CCA  CTA  ATA  GAA  CTT  AGT       384
Leu  Asn  Pro  Tyr  Asp  Leu  Lys  Ile  Lys  Leu  Pro  Leu  Ile  Glu  Leu  Ser
          115                       120                      125

AAA  GAT  TTA  ATA  CCA  CTA  TCA  CCT  AGT  TTA  CAT  AGT  TAT  AGT  GAA  TTA       432
Lys  Asp  Leu  Ile  Pro  Leu  Ser  Pro  Ser  Leu  His  Ser  Tyr  Ser  Glu  Leu
     130                       135                      140

TAT  AAT  TTT  TTT  AAT  GTC  TTT  AAT  AAA  AAA  CGT  GAT  GAA  GAT  GCT  GGT       480
Tyr  Asn  Phe  Phe  Asn  Val  Phe  Asn  Lys  Lys  Arg  Asp  Glu  Asp  Ala  Gly
145                       150                      155                      160

TAT  GAT  ATA  CCA  TCT  CCA  AAT  TTA  GTT  CAA  ATA  AAA  CCG  GGA  TAT  AGT       528
Tyr  Asp  Ile  Pro  Ser  Pro  Asn  Leu  Val  Gln  Ile  Lys  Pro  Gly  Tyr  Ser
               165                       170                      175

TAC  CTT  TTT  TGT  CTT  CCT  ATT  TTT  CAA  TTA  GAA  ATG  AAA  AAC  CCA  CCA       576
Tyr  Leu  Phe  Cys  Leu  Pro  Ile  Phe  Gln  Leu  Glu  Met  Lys  Asn  Pro  Pro
               180                       185                      190

ATC  GCT  TGT  ATT  TTT  GGT  AGA  TCA  TCC  TTA  AAT  TCA  AGC  GGA  ATA  ATT       624
Ile  Ala  Cys  Ile  Phe  Gly  Arg  Ser  Ser  Leu  Asn  Ser  Ser  Gly  Ile  Ile
          195                       200                      205

GTT  CTT  CCA  ACT  ATA  TGG  AAA  CCA  AAA  ACA  ATT  TGT  CAA  TTT  TTT  ATT       672
Val  Leu  Pro  Thr  Ile  Trp  Lys  Pro  Lys  Thr  Ile  Cys  Gln  Phe  Phe  Ile
     210                       215                      220

AAA  AAT  ATA  TCC  TCT  AAA  ACT  GTA  ACT  ATA  GAA  AAA  GGT  CAG  AGA  ATA       720
Lys  Asn  Ile  Ser  Ser  Lys  Thr  Val  Thr  Ile  Glu  Lys  Gly  Gln  Arg  Ile
225                       230                      235                      240

GCT  CAG  TTA  GTT  CTT  TTA  AAA  AAC  AAT  CAA  CCA  CTA  TGG  TTA  CAA  CCA       768
Ala  Gln  Leu  Val  Leu  Leu  Lys  Asn  Asn  Gln  Pro  Leu  Trp  Leu  Gln  Pro
               245                       250                      255

CAA  ATT  AAT  TGT  CAT  TCT  TTA  TTT  CCA  AAG  TCA  AAC  TAT  TTA  AGC  TTA       816
Gln  Ile  Asn  Cys  His  Ser  Leu  Phe  Pro  Lys  Ser  Asn  Tyr  Leu  Ser  Leu
          260                       265                      270

TCA  AAT  CGA  GAA  TGT  GAT  ATG  TGG  AAG  TTT  ACA  GAA  GAT  CTG  AAT  TTT       864
Ser  Asn  Arg  Glu  Cys  Asp  Met  Trp  Lys  Phe  Thr  Glu  Asp  Leu  Asn  Phe
     275                       280                      285

GAA  GCA  CCG  AAA  AGT  TTA  CGA  GGA  ATA  AAT  GGA  TTT  GGA  TCC  ACG  GGA       912
```

| Glu | Ala | Pro | Lys | Ser | Leu | Arg | Gly | Ile | Asn | Gly | Phe | Gly | Ser | Thr | Gly |
|---|---|---|---|---|---|---|---|---|---|---|---|---|---|---|---|
| | 290 | | | | | 295 | | | | 300 | | | | | |

TTG TAA  918
Leu
305

(2) INFORMATION FOR SEQ ID NO:80:

(i) SEQUENCE CHARACTERISTICS:
        (A) LENGTH: 305 amino acids
        (B) TYPE: amino acid
        (D) TOPOLOGY: linear (ii) MOLECULE TYPE: protein (xi) SEQUENCE DESCRIPTION: SEQ ID NO:80:

| Met | Asp | Ser | Lys | Asn | Thr | Ile | Ser | Ile | Ala | Leu | Ile | Glu | Lys | Gln | Lys |
|---|---|---|---|---|---|---|---|---|---|---|---|---|---|---|---|
| 1 | | | | 5 | | | | | 10 | | | | | 15 | |
| Pro | Phe | Asn | Trp | Thr | Ile | Asn | Lys | Ile | Asn | Glu | Ser | Leu | Leu | Met | Thr |
| | | | 20 | | | | 25 | | | | | | 30 | | |
| Asn | Asn | Glu | Glu | Ile | Asn | Leu | Thr | Glu | Asn | Phe | Lys | Asn | Thr | Gly | Thr |
| | | 35 | | | | | 40 | | | | | 45 | | | |
| Phe | Tyr | Ser | Lys | Ile | Ile | Asp | Leu | Glu | Ile | Arg | Thr | Ala | Thr | Ser | Ser |
| | 50 | | | | | 55 | | | | | 60 | | | | |
| Gln | Tyr | Ala | Val | Phe | Val | Thr | Gln | Met | Cys | Ser | Asp | Asp | Glu | Asn | Met |
| 65 | | | | | 70 | | | | | 75 | | | | | 80 |
| Asn | Asn | Thr | Asn | Ile | Phe | Val | Ile | Asn | Gly | Val | Ile | Asp | Ser | Gly | Tyr |
| | | | | 85 | | | | | 90 | | | | | 95 | |
| Arg | Gly | Ile | Val | Lys | Ala | Leu | Val | Tyr | Tyr | His | Pro | Thr | Val | Glu | Lys |
| | | | | 100 | | | | | 105 | | | | | 110 | |
| Leu | Asn | Pro | Tyr | Asp | Leu | Lys | Ile | Lys | Leu | Pro | Leu | Ile | Glu | Leu | Ser |
| | | | 115 | | | | | 120 | | | | | 125 | | |
| Lys | Asp | Leu | Ile | Pro | Leu | Ser | Pro | Ser | Leu | His | Ser | Tyr | Ser | Glu | Leu |
| | | 130 | | | | | 135 | | | | | 140 | | | |
| Tyr | Asn | Phe | Phe | Asn | Val | Phe | Asn | Lys | Lys | Arg | Asp | Glu | Asp | Ala | Gly |
| 145 | | | | | 150 | | | | | 155 | | | | | 160 |
| Tyr | Asp | Ile | Pro | Ser | Pro | Asn | Leu | Val | Gln | Ile | Lys | Pro | Gly | Tyr | Ser |
| | | | | 165 | | | | | 170 | | | | | 175 | |
| Tyr | Leu | Phe | Cys | Leu | Pro | Ile | Phe | Gln | Leu | Glu | Met | Lys | Asn | Pro | Pro |
| | | | 180 | | | | | 185 | | | | | 190 | | |
| Ile | Ala | Cys | Ile | Phe | Gly | Arg | Ser | Ser | Leu | Asn | Ser | Ser | Gly | Ile | Ile |
| | | 195 | | | | | 200 | | | | | 205 | | | |
| Val | Leu | Pro | Thr | Ile | Trp | Lys | Pro | Lys | Thr | Ile | Cys | Gln | Phe | Phe | Ile |
| | 210 | | | | | 215 | | | | | 220 | | | | |
| Lys | Asn | Ile | Ser | Ser | Lys | Thr | Val | Thr | Ile | Glu | Lys | Gly | Gln | Arg | Ile |
| 225 | | | | | 230 | | | | | 235 | | | | | 240 |
| Ala | Gln | Leu | Val | Leu | Leu | Lys | Asn | Asn | Gln | Pro | Leu | Trp | Leu | Gln | Pro |
| | | | | 245 | | | | | 250 | | | | | 255 | |
| Gln | Ile | Asn | Cys | His | Ser | Leu | Phe | Pro | Lys | Ser | Asn | Tyr | Leu | Ser | Leu |
| | | | 260 | | | | | 265 | | | | | 270 | | |
| Ser | Asn | Arg | Glu | Cys | Asp | Met | Trp | Lys | Phe | Thr | Glu | Asp | Leu | Asn | Phe |
| | | 275 | | | | | 280 | | | | | 285 | | | |
| Glu | Ala | Pro | Lys | Ser | Leu | Arg | Gly | Ile | Asn | Gly | Phe | Gly | Ser | Thr | Gly |
| | 290 | | | | | 295 | | | | 300 | | | | | |

Leu
305

( 2 ) INFORMATION FOR SEQ ID NO:81:

( i ) SEQUENCE CHARACTERISTICS:
        ( A ) LENGTH: 261 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..258

( x i ) SEQUENCE DESCRIPTION: SEQ ID NO:81:

```
ATG GAG ATA GTA TTT TTA CTA TCC ATT ATT TTT TCA GTT TAT GCC TTC     48
Met Glu Ile Val Phe Leu Leu Ser Ile Ile Phe Ser Val Tyr Ala Phe
 1               5                  10                  15

GAC GAT GAT CGT TTA GAT TAT TCT AGA GCT GAA GCT AGG AGA CAG TTT     96
Asp Asp Asp Arg Leu Asp Tyr Ser Arg Ala Glu Ala Arg Arg Gln Phe
             20                  25                  30

TGG AGC TCT AGT TGT TCA GCT AGG GGT ATC AAT ATT AAT ACG CCT TCA    144
Trp Ser Ser Ser Cys Ser Ala Arg Gly Ile Asn Ile Asn Thr Pro Ser
         35                  40                  45

ACT TCC GCT ATT TTG TTT TAT ATA TCC CTG GTA ACA GTA GGG GTT GCG    192
Thr Ser Ala Ile Leu Phe Tyr Ile Ser Leu Val Thr Val Gly Val Ala
     50                  55                  60

ATA TTT TGT TAT TCT TAT AGA ACC TGT TTG AGA ATG GTT AGT CGG GAA    240
Ile Phe Cys Tyr Ser Tyr Arg Thr Cys Leu Arg Met Val Ser Arg Glu
 65                  70                  75                  80

CTT CGT CAG ATG CAA CAC TAA                                        261
Leu Arg Gln Met Gln His
                 85
```

( 2 ) INFORMATION FOR SEQ ID NO:82:

( i ) SEQUENCE CHARACTERISTICS:
        ( A ) LENGTH: 86 amino acids
        ( B ) TYPE: amino acid
        ( D ) TOPOLOGY: linear ( i i ) MOLECULE TYPE: protein ( x i ) SEQUENCE DESCRIPTION: SEQ ID NO:82:

```
Met Glu Ile Val Phe Leu Leu Ser Ile Ile Phe Ser Val Tyr Ala Phe
 1               5                  10                  15

Asp Asp Asp Arg Leu Asp Tyr Ser Arg Ala Glu Ala Arg Arg Gln Phe
             20                  25                  30

Trp Ser Ser Ser Cys Ser Ala Arg Gly Ile Asn Ile Asn Thr Pro Ser
         35                  40                  45

Thr Ser Ala Ile Leu Phe Tyr Ile Ser Leu Val Thr Val Gly Val Ala
     50                  55                  60

Ile Phe Cys Tyr Ser Tyr Arg Thr Cys Leu Arg Met Val Ser Arg Glu
 65                  70                  75                  80

Leu Arg Gln Met Gln His
                 85
```

( 2 ) INFORMATION FOR SEQ ID NO:83:

( i ) SEQUENCE CHARACTERISTICS:
        ( A ) LENGTH: 255 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 1..255

( x i ) SEQUENCE DESCRIPTION: SEQ ID NO:83:

| ATG | GCC | AGC | CGT | CGT | ATT | TCA | TCA | TAT | GAA | GAT | GAA | CCG | ATA | TAT | GCT | 48 |
|---|---|---|---|---|---|---|---|---|---|---|---|---|---|---|---|---|
| Met | Ala | Ser | Arg | Arg | Ile | Ser | Ser | Tyr | Glu | Asp | Glu | Pro | Ile | Tyr | Ala | |
| 1 | | | | 5 | | | | | 10 | | | | | 15 | | |
| ACT | ATT | AAG | AGA | CAA | AAC | GGT | GTA | AGA | AGA | AAG | TCA | TCT | CAA | CGA | ATT | 96 |
| Thr | Ile | Lys | Arg | Gln | Asn | Gly | Val | Arg | Arg | Lys | Ser | Ser | Gln | Arg | Ile | |
| | | | 20 | | | | | 25 | | | | | 30 | | | |
| GAA | AGG | GAA | AAT | CCT | ATT | TAC | GAA | CGA | ACT | ATT | CCA | ACT | TTT | GAG | TAT | 144 |
| Glu | Arg | Glu | Asn | Pro | Ile | Tyr | Glu | Arg | Thr | Ile | Pro | Thr | Phe | Glu | Tyr | |
| | | 35 | | | | | 40 | | | | | 45 | | | | |
| AAA | AAT | GTG | TAT | GAT | CAA | GTT | TGT | GAT | GAT | GAT | GAC | GAA | GAC | CAT | ATT | 192 |
| Lys | Asn | Val | Tyr | Asp | Gln | Val | Cys | Asp | Asp | Asp | Asp | Glu | Asp | His | Ile | |
| | 50 | | | | 55 | | | | | 60 | | | | | | |
| TAT | GAA | CTA | TGC | GAA | AAT | CAA | TAT | GCT | CAA | CTA | ACA | ATT | TCC | CAG | CCT | 240 |
| Tyr | Glu | Leu | Cys | Glu | Asn | Gln | Tyr | Ala | Gln | Leu | Thr | Ile | Ser | Gln | Pro | |
| 65 | | | | | 70 | | | | | 75 | | | | | 80 | |
| AAA | TCT | CGT | CCA | AAG | | | | | | | | | | | | 255 |
| Lys | Ser | Arg | Pro | Lys | | | | | | | | | | | | |
| | | | | 85 | | | | | | | | | | | | |

( 2 ) INFORMATION FOR SEQ ID NO:84:

( i ) SEQUENCE CHARACTERISTICS:
        ( A ) LENGTH: 85 amino acids
        ( B ) TYPE: amino acid
        ( D ) TOPOLOGY: linear ( i i ) MOLECULE TYPE: protein ( x i ) SEQUENCE DESCRIPTION: SEQ ID NO:84:

| Met | Ala | Ser | Arg | Arg | Ile | Ser | Ser | Tyr | Glu | Asp | Glu | Pro | Ile | Tyr | Ala |
|---|---|---|---|---|---|---|---|---|---|---|---|---|---|---|---|
| 1 | | | | 5 | | | | | 10 | | | | | 15 | |
| Thr | Ile | Lys | Arg | Gln | Asn | Gly | Val | Arg | Arg | Lys | Ser | Ser | Gln | Arg | Ile |
| | | | 20 | | | | | 25 | | | | | 30 | | |
| Glu | Arg | Glu | Asn | Pro | Ile | Tyr | Glu | Arg | Thr | Ile | Pro | Thr | Phe | Glu | Tyr |
| | | 35 | | | | | 40 | | | | | 45 | | | |
| Lys | Asn | Val | Tyr | Asp | Gln | Val | Cys | Asp | Asp | Asp | Asp | Glu | Asp | His | Ile |
| | 50 | | | | 55 | | | | | 60 | | | | | |
| Tyr | Glu | Leu | Cys | Glu | Asn | Gln | Tyr | Ala | Gln | Leu | Thr | Ile | Ser | Gln | Pro |
| 65 | | | | | 70 | | | | | 75 | | | | | 80 |
| Lys | Ser | Arg | Pro | Lys | | | | | | | | | | | |
| | | | | 85 | | | | | | | | | | | |

( 2 ) INFORMATION FOR SEQ ID NO:85:

( i ) SEQUENCE CHARACTERISTICS:
        ( A ) LENGTH: 749 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:85:

| AAGCTTTCAA | AATGTGCCAA | GTAAATATAA | TTAATAAACT | CTCTATCAGA | AACTTTTAAA | 60 |
|---|---|---|---|---|---|---|
| CTCTGTCTAT | CAGCAGAAAT | ATAATTTCTC | AATACACCAA | CCTCTGAAAT | ATCGGCATTA | 120 |
| ATTCGATGTG | TTATATAATC | TTCTAGTTTA | ACAGCAATCT | TTCCTGTAGC | ATACCCACTT | 180 |

| | | | | | | |
|---|---|---|---|---|---|---|
| TGACAACAAA | ATTTTGATAA | CAAAGAAAAT | GATATTAAAT | CTATACATTT | AAGATTAGTT | 240 |
| TTGTTTTGTT | GTACAGGTAT | TTTATATGTT | TCGATAAAAT | CTTTTATAGC | TTGTAGGTCA | 300 |
| TAGGTATGAA | AAGGCTTTAA | ACTGTTTGTA | GCTTGAAATA | GATAAAATCT | TGTTGCTAAA | 360 |
| ACTAAAGTTT | TTTCTTCAGG | ACCAAATTTT | GAAGTAAACC | AAAACGGTGT | AGGATTTGTT | 420 |
| CCATATATTC | GTCTAAAGGC | TGCAAGTATT | TGTTGTTCGT | GATGAATATA | TAATAATGTT | 480 |
| AACCCATGGC | GTCCTTTATT | ACATTTCGAT | AAGCATGTTT | TTATAGATAA | TGTAGGGTCA | 540 |
| TATTTAGCAG | ATTCTAAAGT | TCTTCCAGAT | TTAGGAGTTA | GACGCTCTGT | CGTTATAGAT | 600 |
| AATATAGTTA | TTAAATCATC | ATGAATATTA | AACGTATGCT | GATCATCAAT | ACAAGAAAGT | 660 |
| ATTAATTTTG | TAGAGATTGG | GTTTCCATAT | AATAAAGATT | TAGCTATAAC | AGACGCTTCA | 720 |
| TAATTATTTT | TAATTGAACA | TATAAACAT | | | | 749 |

(2) INFORMATION FOR SEQ ID NO:86:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

| | | | | | | |
|---|---|---|---|---|---|---|
| ATGTTTATAT | GTTCAATTAA | AAATAATTAT | GAAGCGTCTG | TTATAGCTAA | ATCTTTATTA | 60 |
| TATGGAAACC | CAATCTCTAC | AAAATTAATA | CTTTCTTGTA | TTGATGATCA | GCATACGTTT | 120 |
| AATATTCATG | ATGATTTAAT | AACTATATTA | TCTATAACGA | CAGAGCGTCT | AACTCCTAAA | 180 |
| TCTGGAAGAA | CTTTAGAATC | TGCTAAATAT | GACCCTACAT | TATCTATAAA | AACATGCTTA | 240 |
| TCGAAATGTA | ATAAAGGACG | CCATGGGTTA | ACATTATTAT | ATATTCATCA | CGAACAACAA | 300 |
| ATACTTGCAG | CCTTTAGACG | AATATATGGA | ACAAATCCTA | CACCGTTTTG | GTTTACTTCA | 360 |
| AAATTTGGTC | CTGAAGAAAA | AACTTTAGTT | TTAGCAACAA | GATTTTATCT | ATTTCAAGCT | 420 |
| ACAAACAGTT | TAAAGCCTTT | TCATACCTAT | GACCTACAAG | CTATAAAAGA | TTTTATCGAA | 480 |
| ACATATAAAA | TACCTGTACA | ACAAAACAAA | ACTAATCTTA | AATGTATAGA | TTTAATATCA | 540 |
| TTTTCTTTGT | TATCAAAATT | TTGTTGTCAA | AGTGGGTATG | CTACAGGAAA | GATTGCTGTT | 600 |
| AAACTAGAAG | ATTATATAAC | ACATCGAATT | AATGCCGATA | TTTCAGAGGT | TGGTGTATTG | 660 |
| AGAAATTATA | TTTCTGCTGA | TAGACAGAGT | TTAAAAGTTT | CTGATAGAGA | GTTTATTAAT | 720 |
| TATATTTACT | TGGCACATTT | TGAAAGCTT | | | | 749 |

(2) INFORMATION FOR SEQ ID NO:87:

(i) SEQUENCE CHARACTERISTICS:
        (A) LENGTH: 747 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..747

(xi) SEQUENCE DESCRIPTION: SEQ ID NO:87:

| | | | | | | | | | | | | | | | | |
|---|---|---|---|---|---|---|---|---|---|---|---|---|---|---|---|---|
| ATG | TTT | ATA | TGT | TCA | ATT | AAA | AAT | AAT | TAT | GAA | GCG | TCT | GTT | ATA | GCT | 48 |
| Met | Phe | Ile | Cys | Ser | Ile | Lys | Asn | Asn | Tyr | Glu | Ala | Ser | Val | Ile | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AAA | TCT | TTA | TTA | TAT | GGA | AAC | CCA | ATC | TCT | ACA | AAA | TTA | ATA | CTT | TCT | 96 |
| Lys | Ser | Leu | Leu | Tyr | Gly | Asn | Pro | Ile | Ser | Thr | Lys | Leu | Ile | Leu | Ser | |
| | | | 20 | | | | | 25 | | | | | 30 | | | |
| TGT | ATT | GAT | GAT | CAG | CAT | ACG | TTT | AAT | ATT | CAT | GAT | GAT | TTA | ATA | ACT | 144 |
| Cys | Ile | Asp | Asp | Gln | His | Thr | Phe | Asn | Ile | His | Asp | Asp | Leu | Ile | Thr | |
| | | | 35 | | | | | 40 | | | | | 45 | | | |
| ATA | TTA | TCT | ATA | ACG | ACA | GAG | CGT | CTA | ACT | CCT | AAA | TCT | GGA | AGA | ACT | 192 |
| Ile | Leu | Ser | Ile | Thr | Thr | Glu | Arg | Leu | Thr | Pro | Lys | Ser | Gly | Arg | Thr | |
| | | 50 | | | | | 55 | | | | | 60 | | | | |
| TTA | GAA | TCT | GCT | AAA | TAT | GAC | CCT | ACA | TTA | TCT | ATA | AAA | ACA | TGC | TTA | 240 |
| Leu | Glu | Ser | Ala | Lys | Tyr | Asp | Pro | Thr | Leu | Ser | Ile | Lys | Thr | Cys | Leu | |
| 65 | | | | | 70 | | | | | 75 | | | | | 80 | |
| TCG | AAA | TGT | AAT | AAA | GGA | CGC | CAT | GGG | TTA | ACA | TTA | TTA | TAT | ATT | CAT | 288 |
| Ser | Lys | Cys | Asn | Lys | Gly | Arg | His | Gly | Leu | Thr | Leu | Leu | Tyr | Ile | His | |
| | | | | 85 | | | | | 90 | | | | | 95 | | |
| CAC | GAA | CAA | CAA | ATA | CTT | GCA | GCC | TTT | AGA | CGA | ATA | TAT | GGA | ACA | AAT | 336 |
| His | Glu | Gln | Gln | Ile | Leu | Ala | Ala | Phe | Arg | Arg | Ile | Tyr | Gly | Thr | Asn | |
| | | | 100 | | | | | 105 | | | | | 110 | | | |
| CCT | ACA | CCG | TTT | TGG | TTT | ACT | TCA | AAA | TTT | GGT | CCT | GAA | GAA | AAA | ACT | 384 |
| Pro | Thr | Pro | Phe | Trp | Phe | Thr | Ser | Lys | Phe | Gly | Pro | Glu | Glu | Lys | Thr | |
| | | 115 | | | | | 120 | | | | | 125 | | | | |
| TTA | GTT | TTA | GCA | ACA | AGA | TTT | TAT | CTA | TTT | CAA | GCT | ACA | AAC | AGT | TTA | 432 |
| Leu | Val | Leu | Ala | Thr | Arg | Phe | Tyr | Leu | Phe | Gln | Ala | Thr | Asn | Ser | Leu | |
| | 130 | | | | | 135 | | | | | 140 | | | | | |
| AAG | CCT | TTT | CAT | ACC | TAT | GAC | CTA | CAA | GCT | ATA | AAA | GAT | TTT | ATC | GAA | 480 |
| Lys | Pro | Phe | His | Thr | Tyr | Asp | Leu | Gln | Ala | Ile | Lys | Asp | Phe | Ile | Glu | |
| 145 | | | | | 150 | | | | | 155 | | | | | 160 | |
| ACA | TAT | AAA | ATA | CCT | GTA | CAA | CAA | AAC | AAA | ACT | AAT | CTT | AAA | TGT | ATA | 528 |
| Thr | Tyr | Lys | Ile | Pro | Val | Gln | Gln | Asn | Lys | Thr | Asn | Leu | Lys | Cys | Ile | |
| | | | | 165 | | | | | 170 | | | | | 175 | | |
| GAT | TTA | ATA | TCA | TTT | TCT | TTG | TTA | TCA | AAA | TTT | TGT | TGT | CAA | AGT | GGG | 576 |
| Asp | Leu | Ile | Ser | Phe | Ser | Leu | Leu | Ser | Lys | Phe | Cys | Cys | Gln | Ser | Gly | |
| | | | 180 | | | | | 185 | | | | | 190 | | | |
| TAT | GCT | ACA | GGA | AAG | ATT | GCT | GTT | AAA | CTA | GAA | GAT | TAT | ATA | ACA | CAT | 624 |
| Tyr | Ala | Thr | Gly | Lys | Ile | Ala | Val | Lys | Leu | Glu | Asp | Tyr | Ile | Thr | His | |
| | | 195 | | | | | 200 | | | | | 205 | | | | |
| CGA | ATT | AAT | GCC | GAT | ATT | TCA | GAG | GTT | GGT | GTA | TTG | AGA | AAT | TAT | ATT | 672 |
| Arg | Ile | Asn | Ala | Asp | Ile | Ser | Glu | Val | Gly | Val | Leu | Arg | Asn | Tyr | Ile | |
| | 210 | | | | | 215 | | | | | 220 | | | | | |
| TCT | GCT | GAT | AGA | CAG | AGT | TTA | AAA | GTT | TCT | GAT | AGA | GAG | TTT | ATT | AAT | 720 |
| Ser | Ala | Asp | Arg | Gln | Ser | Leu | Lys | Val | Ser | Asp | Arg | Glu | Phe | Ile | Asn | |
| 225 | | | | | 230 | | | | | 235 | | | | | 240 | |
| TAT | ATT | TAC | TTG | GCA | CAT | TTT | GAA | AGC | | | | | | | | 747 |
| Tyr | Ile | Tyr | Leu | Ala | His | Phe | Glu | Ser | | | | | | | | |
| | | | | 245 | | | | | | | | | | | | |

( 2 ) INFORMATION FOR SEQ ID NO:88:

( i ) SEQUENCE CHARACTERISTICS:
        ( A ) LENGTH: 249 amino acids
        ( B ) TYPE: amino acid
        ( D ) TOPOLOGY: linear ( i i ) MOLECULE TYPE: protein ( x i ) SEQUENCE DESCRIPTION: SEQ ID NO:88:

| | | | | | | | | | | | | | | | |
|---|---|---|---|---|---|---|---|---|---|---|---|---|---|---|---|
| Met | Phe | Ile | Cys | Ser | Ile | Lys | Asn | Asn | Tyr | Glu | Ala | Ser | Val | Ile | Ala |
| 1 | | | | 5 | | | | | 10 | | | | | 15 | |
| Lys | Ser | Leu | Leu | Tyr | Gly | Asn | Pro | Ile | Ser | Thr | Lys | Leu | Ile | Leu | Ser |
| | | | 20 | | | | | 25 | | | | | 30 | | |
| Cys | Ile | Asp | Asp | Gln | His | Thr | Phe | Asn | Ile | His | Asp | Asp | Leu | Ile | Thr |
| | | | 35 | | | | | 40 | | | | | 45 | | |

Ile Leu Ser Ile Thr Thr Glu Arg Leu Thr Pro Lys Ser Gly Arg Thr
          50                    55                  60

Leu Glu Ser Ala Lys Tyr Asp Pro Thr Leu Ser Ile Lys Thr Cys Leu
 65                  70                  75                      80

Ser Lys Cys Asn Lys Gly Arg His Gly Leu Thr Leu Leu Tyr Ile His
                 85                  90                  95

His Glu Gln Gln Ile Leu Ala Ala Phe Arg Arg Ile Tyr Gly Thr Asn
            100                 105                 110

Pro Thr Pro Phe Trp Phe Thr Ser Lys Phe Gly Pro Glu Glu Lys Thr
        115                 120                 125

Leu Val Leu Ala Thr Arg Phe Tyr Leu Phe Gln Ala Thr Asn Ser Leu
        130                 135             140

Lys Pro Phe His Thr Tyr Asp Leu Gln Ala Ile Lys Asp Phe Ile Glu
145                 150                 155                     160

Thr Tyr Lys Ile Pro Val Gln Gln Asn Lys Thr Asn Leu Lys Cys Ile
                165                 170                 175

Asp Leu Ile Ser Phe Ser Leu Leu Ser Lys Phe Cys Cys Gln Ser Gly
            180                 185                 190

Tyr Ala Thr Gly Lys Ile Ala Val Lys Leu Glu Asp Tyr Ile Thr His
        195                 200                 205

Arg Ile Asn Ala Asp Ile Ser Glu Val Gly Val Leu Arg Asn Tyr Ile
    210                 215                 220

Ser Ala Asp Arg Gln Ser Leu Lys Val Ser Asp Arg Glu Phe Ile Asn
225                 230                 235                     240

Tyr Ile Tyr Leu Ala His Phe Glu Ser
                245

( 2 ) INFORMATION FOR SEQ ID NO:89:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..30
        ( D ) OTHER INFORMATION: /label=primer ( x i ) SEQUENCE DESCRIPTION: SEQ ID NO:89:

GCCGGTACCA GGCTTTGGAC GAGATTTAGG      30

( 2 ) INFORMATION FOR SEQ ID NO:90:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..29
        ( D ) OTHER INFORMATION: /label=primer ( x i ) SEQUENCE DESCRIPTION: SEQ ID NO:90:

GCCGAATTCA ATATAATTAA TAAACTCTC      29

(2) INFORMATION FOR SEQ ID NO:91:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..28
(D) OTHER INFORMATION: /label=primer (xi) SEQUENCE DESCRIPTION: SEQ ID NO:91:

CCGGAATTCG CTTAGTGAGA GTATAAAC 28

(2) INFORMATION FOR SEQ ID NO:92:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..28
(D) OTHER INFORMATION: /label=primer (xi) SEQUENCE DESCRIPTION: SEQ ID NO:92:

CCGGAATTCC CTCATATTAT ATACTAAC 28